(12) United States Patent
Berra

(10) Patent No.: US 10,105,250 B2
(45) Date of Patent: *Oct. 23, 2018

(54) DUAL CAPTURE DEVICE FOR STENT GRAFT DELIVERY SYSTEM AND METHOD FOR CAPTURING A STENT GRAFT

(71) Applicant: Bolton Medical, Inc., Sunrise, FL (US)

(72) Inventor: Humberto Berra, Sunrise, FL (US)

(73) Assignee: Bolton Medical, Inc., Sunrise, FL (US)

( * ) Notice: Subject to any disclaimer, the term of this patent is extended or adjusted under 35 U.S.C. 154(b) by 405 days.

This patent is subject to a terminal disclaimer.

(21) Appl. No.: 14/924,102

(22) Filed: Oct. 27, 2015

(65) Prior Publication Data

US 2016/0045350 A1 Feb. 18, 2016

Related U.S. Application Data

(63) Continuation of application No. 14/300,647, filed on Jun. 10, 2014, now Pat. No. 9,220,617, which is a
(Continued)

(51) Int. Cl.
*A61F 2/95* (2013.01)
*A61F 2/966* (2013.01)
(Continued)

(52) U.S. Cl.
CPC ............... *A61F 2/966* (2013.01); *A61F 2/07* (2013.01); *A61F 2/915* (2013.01); *A61F 2/95* (2013.01);
(Continued)

(58) Field of Classification Search
CPC .. A61F 2/966; A61F 2/915; A61F 2/07; A61F 2/95; A61F 2230/0054; A61F 2/89;
(Continued)

(56) References Cited

U.S. PATENT DOCUMENTS 3,416,531 A 12/1968 Edwards
3,485,234 A 12/1969 Stevens
(Continued)

FOREIGN PATENT DOCUMENTS

CN 2451136 Y 10/2001
DE 197 53 123 A1 8/1999
(Continued)

OTHER PUBLICATIONS

Notification of Transmittal of the International Search Report and the Written Opinion or the International Searching Authority, or the Declaration for International Application No. PCT/US2009/039144, dated May 27, 2009.
(Continued)

*Primary Examiner* — Katherine M Shi
*Assistant Examiner* — Michael Mendoza
(74) *Attorney, Agent, or Firm* — Hamilton, Brook, Smith & Reynolds, P.C.

(57) ABSTRACT

A delivery system for delivering and deploying stents with proximal and distal apices includes a guidewire catheter, a nose cone assembly, a proximal capture portion and a stent graft with proximal and distal stents. The nose cone assembly is at the distal end of the guidewire catheter and includes a nose cone and a distal capture portion. The proximal capture portion is proximal to the distal capture portion of the nose cone assembly. The proximal stent is releasably secured to the distal capture portion and the distal stent is releasably secured to the proximal capture portion. The stent graft can be deployed by releasing the proximal stent and the distal stent from proximal and distal capture portions of the delivery system.

15 Claims, 72 Drawing Sheets

Related U.S. Application Data continuation of application No. 13/959,004, filed on Aug. 5, 2013, now abandoned, which is a continuation of application No. 12/415,728, filed on Mar. 31, 2009, now Pat. No. 8,500,792, and a continuation-in-part of application No. 11/701,867, filed on Feb. 1, 2007, now Pat. No. 9,198,786, said application No. 12/415,728 is a continuation-in-part of application No. 11/828,653, filed on Jul. 26, 2007, now abandoned, said application No. 12/415,728 is a continuation-in-part of application No. 11/828,675, filed on Jul. 26, 2007, now Pat. No. 8,062,345, said application No. 12/415,728 is a continuation-in-part of application No. 10/784,462, filed on Feb. 23, 2004, now Pat. No. 8,292,943, said application No. 12/415,728 is a continuation-in-part of application No. 10/884,136, filed on Jul. 2, 2004, now Pat. No. 7,763,063, said application No. 12/415,728 is a continuation-in-part of application No. 11/348,176, filed on Feb. 6, 2006, now Pat. No. 8,308,790, and a continuation-in-part of application No. 11/353,927, filed on Feb. 13, 2006, now Pat. No. 8,070,790, and a continuation-in-part of application No. 11/449,337, filed on Jun. 8, 2006, now Pat. No. 8,740,963, and a continuation-in-part of application No. 11/699,700, filed on Jan. 30, 2007, now abandoned, and a continuation-in-part of application No. 11/699,701, filed on Jan. 30, 2007, now Pat. No. 8,007,605, and a continuation-in-part of application No. 11/700,510, filed on Jan. 31, 2007, now Pat. No. 8,062,349, and a continuation-in-part of application No. 11/700,609, filed on Jan. 31, 2007, now Pat. No. 9,320,631, and a continuation-in-part of application No. 11/701,876, filed on Feb. 1, 2007, now abandoned.

(60) Provisional application No. 61/041,432, filed on Apr. 1, 2008, provisional application No. 60/765,449, filed on Feb. 3, 2006, provisional application No. 60/833,533, filed on Jul. 26, 2006, provisional application No. 60/833,533, filed on Jul. 26, 2006, provisional application No. 60/833,533, filed on Jul. 26, 2006, provisional application No. 60/499,652, filed on Sep. 3, 2003, provisional application No. 60/500,155, filed on Sep. 4, 2003, provisional application No. 60/499,652, filed on Sep. 3, 2003, provisional application No. 60/500,155, filed on Sep. 4, 2003, provisional application No. 60/851,282, filed on Oct. 12, 2006, provisional application No. 60/833,533, filed on Jul. 26, 2006, provisional application No. 60/765,449, filed on Feb. 3, 2006.

(51) Int. Cl.
| | |
|---|---|
| *A61F 2/07* | (2013.01) |
| *A61F 2/915* | (2013.01) |
| *A61F 2/86* | (2013.01) |
| *A61F 2/90* | (2013.01) |
| *A61F 2/82* | (2013.01) |
| *A61F 2/89* | (2013.01) |

(52) U.S. Cl.
CPC . *A61F 2/86* (2013.01); *A61F 2/89* (2013.01); *A61F 2/90* (2013.01); *A61F 2002/075* (2013.01); *A61F 2002/828* (2013.01); *A61F 2002/9505* (2013.01); *A61F 2002/9517* (2013.01); *A61F 2002/9528* (2013.01); *A61F 2230/0054* (2013.01)

(58) Field of Classification Search
CPC ........ A61F 2002/9505; A61F 2002/075; A61F 2002/828; A61F 2/90; A61F 2/86; A61F 2002/9528; A61F 2002/9517
See application file for complete search history.

(56) References Cited

U.S. PATENT DOCUMENTS

| | | |
|---|---|---|
| 3,502,069 A | 3/1970 | Silverman |
| 3,868,956 A | 3/1975 | Alfidi |
| 4,351,333 A | 9/1982 | Lazarus |
| 4,425,919 A | 1/1984 | Alston |
| 4,487,808 A | 12/1984 | Lambert |
| 4,515,593 A | 5/1985 | Norton |
| 4,516,972 A | 5/1985 | Samson |
| 4,534,363 A | 8/1985 | Gold |
| 4,572,186 A | 2/1986 | Gould |
| 4,580,568 A | 4/1986 | Gianturco |
| 4,634,432 A | 1/1987 | Kocak |
| 4,655,771 A | 4/1987 | Wallsten |
| 4,665,906 A | 5/1987 | Jervis |
| 4,665,918 A | 5/1987 | Garza et al. |
| 4,705,511 A | 11/1987 | Kocak |
| 4,787,899 A | 11/1988 | Lazarus |
| 4,817,613 A | 4/1989 | Jaraczewski |
| 4,990,151 A | 2/1991 | Wallsten et al. |
| 5,019,057 A | 5/1991 | Truckai |
| 5,041,126 A | 8/1991 | Gianturco |
| 5,057,092 A | 10/1991 | Webster |
| 5,067,957 A | 11/1991 | Jervis |
| 5,104,399 A | 4/1992 | Lazarus |
| 5,154,701 A | 10/1992 | Cheer et al. |
| 5,158,543 A | 10/1992 | Lazarus |
| 5,176,652 A | 1/1993 | Littrell |
| 5,176,660 A | 1/1993 | Truckai |
| 5,201,757 A | 4/1993 | Heyn et al. |
| 5,254,105 A | 10/1993 | Haaga |
| 5,282,824 A | 2/1994 | Gianturco |
| 5,290,295 A | 3/1994 | Querals et al. |
| 5,292,331 A | 3/1994 | Boneau |
| 5,306,263 A | 4/1994 | Voda |
| 5,324,306 A | 6/1994 | Makower et al. |
| 5,334,164 A | 8/1994 | Guy et al. |
| 5,334,168 A | 8/1994 | Hemmer |
| 5,338,295 A | 8/1994 | Cornelius |
| 5,342,384 A | 8/1994 | Sugarbaker |
| 5,358,493 A | 10/1994 | Schweich |
| 5,380,304 A | 1/1995 | Parker |
| 5,387,235 A | 2/1995 | Chuter |
| 5,397,345 A | 3/1995 | Lazarus |
| 5,405,377 A | 4/1995 | Cragg |
| 5,415,664 A | 5/1995 | Pinchuk |
| 5,433,723 A | 7/1995 | Lindenberg et al. |
| 5,456,713 A | 10/1995 | Chuter |
| 5,458,615 A | 10/1995 | Klemm et al. |
| 5,464,449 A | 11/1995 | Ryan et al. |
| 5,474,563 A | 12/1995 | Myler et al. |
| 5,480,423 A | 1/1996 | Ravenscroft et al. |
| 5,489,295 A | 2/1996 | Piplani et al. |
| 5,507,771 A | 4/1996 | Gianturco |
| 5,522,881 A | 6/1996 | Lentz |
| 5,522,882 A | 6/1996 | Gaterud et al. |
| 5,531,715 A | 7/1996 | Engelson |
| 5,533,987 A | 7/1996 | Pray |
| 5,534,007 A | 7/1996 | Germain |
| 5,540,712 A | 7/1996 | Kleshinski et al. |
| 5,545,210 A | 8/1996 | Hess et al. |
| 5,549,565 A | 8/1996 | Ryan et al. |
| 5,562,726 A | 10/1996 | Chuter |
| 5,562,728 A | 10/1996 | Lazarus et al. |
| 5,569,218 A | 10/1996 | Berg |
| 5,571,135 A | 11/1996 | Fraser et al. |
| 5,575,816 A | 11/1996 | Rudnick et al. |
| 5,575,817 A | 11/1996 | Martin |
| 5,582,614 A | 12/1996 | Feingold |
| 5,591,194 A | 1/1997 | Berthiaume |

(56) References Cited

U.S. PATENT DOCUMENTS

| | | |
|---|---|---|
| 5,591,195 A | 1/1997 | Taheri et al. |
| 5,597,378 A | 1/1997 | Jervis |
| 5,601,568 A | 2/1997 | Chevillon et al. |
| 5,607,442 A | 3/1997 | Fischell et al. |
| 5,609,625 A | 3/1997 | Piplani et al. |
| 5,609,627 A | 3/1997 | Goicoechea et al. |
| 5,613,974 A | 3/1997 | Andreas et al. |
| 5,618,270 A | 4/1997 | Orejola |
| 5,628,754 A | 5/1997 | Shevlin |
| 5,628,783 A | 5/1997 | Quiachon et al. |
| 5,632,763 A | 5/1997 | Glastra |
| 5,639,278 A | 6/1997 | Dereume et al. |
| 5,658,263 A | 8/1997 | Dang |
| 5,662,675 A | 9/1997 | Polanskyj Stockert et al. |
| 5,662,700 A | 9/1997 | Lazarus |
| 5,674,208 A | 10/1997 | Berg |
| 5,676,696 A | 10/1997 | Marcade |
| 5,683,449 A | 11/1997 | Marcade |
| 5,693,086 A | 12/1997 | Goicoechea et al. |
| 5,700,269 A | 12/1997 | Pinchuk et al. |
| 5,707,376 A | 1/1998 | Kavteladze et al. |
| 5,709,703 A | 1/1998 | Lukic et al. |
| 5,713,917 A | 2/1998 | Leonhardt et al. |
| 5,716,365 A | 2/1998 | Goicoechea et al. |
| 5,716,393 A | 2/1998 | Lindenberg et al. |
| 5,720,776 A | 2/1998 | Chuter et al. |
| 5,723,003 A | 3/1998 | Winston et al. |
| 5,730,733 A | 3/1998 | Mortier |
| 5,733,267 A | 3/1998 | Del Toro |
| 5,735,859 A | 4/1998 | Fischell et al. |
| 5,749,921 A | 5/1998 | Lenker et al. |
| 5,755,778 A | 5/1998 | Kleshinski |
| 5,776,142 A | 7/1998 | Gunderson |
| 5,782,811 A | 7/1998 | Samson |
| 5,782,904 A | 7/1998 | White et al. |
| 5,782,909 A | 7/1998 | Quiachon et al. |
| 5,788,707 A | 8/1998 | Del Toro et al. |
| 5,792,144 A | 8/1998 | Fischell et al. |
| 5,800,515 A | 9/1998 | Nadal et al. |
| 5,800,517 A | 9/1998 | Anderson et al. |
| 5,800,520 A | 9/1998 | Fogarty et al. |
| 5,824,036 A | 10/1998 | Lauterjung |
| 5,824,037 A | 10/1998 | Fogarty et al. |
| 5,824,039 A | 10/1998 | Piplani et al. |
| 5,824,040 A | 10/1998 | Cox et al. |
| 5,824,041 A | 10/1998 | Lenker et al. |
| 5,824,042 A | 10/1998 | Lombardi et al. |
| 5,824,044 A | 10/1998 | Quiachon et al. |
| 5,843,158 A | 12/1998 | Lenker et al. |
| 5,843,160 A | 12/1998 | Rhodes |
| 5,843,164 A | 12/1998 | Frantzen et al. |
| 5,843,167 A | 12/1998 | Dwyer et al. |
| 5,851,228 A | 12/1998 | Pinheiro |
| 5,860,998 A | 1/1999 | Robinson et al. |
| 5,871,536 A | 2/1999 | Lazarus |
| 5,891,110 A | 4/1999 | Larson |
| 5,891,114 A | 4/1999 | Chien |
| 5,893,868 A | 4/1999 | Hanson et al. |
| 5,899,892 A | 5/1999 | Mortier |
| 5,902,334 A | 5/1999 | Dwyer et al. |
| 5,904,713 A | 5/1999 | Leschinsky |
| 5,906,619 A | 5/1999 | Olson et al. |
| 5,910,101 A | 6/1999 | Andrews et al. |
| 5,911,715 A | 6/1999 | Berg |
| 5,916,263 A | 6/1999 | Goicoechea et al. |
| 5,938,696 A | 8/1999 | Goicoechea et al. |
| 5,944,726 A | 8/1999 | Blaeser et al. |
| 5,947,939 A | 9/1999 | Mortier |
| 5,951,495 A | 9/1999 | Berg |
| 5,954,651 A | 9/1999 | Berg |
| 5,957,949 A | 9/1999 | Leonhardt et al. |
| 5,961,511 A | 10/1999 | Mortier |
| 5,968,069 A | 10/1999 | Dusbabek et al. |
| 5,984,955 A | 11/1999 | Wisselink |
| 5,993,481 A | 11/1999 | Marcade et al. |
| 6,004,310 A | 12/1999 | Bardsley |
| 6,004,328 A | 12/1999 | Solar |
| 6,004,347 A | 12/1999 | McNamara et al. |
| 6,019,778 A | 2/2000 | Wilson et al. |
| 6,024,763 A | 2/2000 | Lenker et al. |
| 6,039,749 A | 3/2000 | Marin et al. |
| 6,039,758 A | 3/2000 | Quiachon et al. |
| 6,039,759 A | 3/2000 | Carpentier et al. |
| 6,045,557 A | 4/2000 | White et al. |
| 6,051,020 A | 4/2000 | Goicoechea et al. |
| 6,053,943 A | 4/2000 | Edwin et al. |
| 6,063,112 A | 5/2000 | Sgro |
| 6,071,307 A | 6/2000 | Rhee |
| 6,077,297 A | 6/2000 | Robinson et al. |
| 6,099,548 A | 8/2000 | Taheri |
| 6,099,558 A | 8/2000 | White et al. |
| 6,099,559 A | 8/2000 | Nolting |
| 6,110,191 A | 8/2000 | Dehdashtian et al. |
| 6,110,198 A | 8/2000 | Fogarty et al. |
| 6,117,167 A | 9/2000 | Goicoechea et al. |
| 6,120,480 A | 9/2000 | Zhang et al. |
| 6,123,723 A | 9/2000 | Konya et al. |
| 6,152,944 A | 11/2000 | Holman et al. |
| 6,165,163 A | 12/2000 | Chien |
| 6,165,213 A | 12/2000 | Goicoechea et al. |
| 6,168,616 B1 | 1/2001 | Brown, III |
| 6,168,623 B1 | 1/2001 | Fogarty et al. |
| 6,183,481 B1 | 2/2001 | Lee et al. |
| 6,183,505 B1 | 2/2001 | Mohn |
| 6,183,506 B1 | 2/2001 | Penn et al. |
| 6,193,705 B1 | 2/2001 | Mortier |
| 6,200,336 B1 | 3/2001 | Pavcnik et al. |
| 6,200,339 B1 | 3/2001 | Leschinsky et al. |
| 6,203,550 B1 | 3/2001 | Olson |
| 6,203,568 B1 | 3/2001 | Lombardi et al. |
| 6,210,435 B1 | 4/2001 | Piplani et al. |
| 6,212,422 B1 | 4/2001 | Berg |
| 6,213,976 B1 | 4/2001 | Trerotola |
| 6,214,038 B1 | 4/2001 | Piplani et al. |
| 6,221,079 B1 | 4/2001 | Magovern et al. |
| 6,221,102 B1 | 4/2001 | Baker et al. |
| 6,224,609 B1 | 5/2001 | Ressemann et al. |
| 6,228,063 B1 | 5/2001 | Aboul-Hosn |
| 6,231,601 B1 | 5/2001 | Myers et al. |
| 6,238,430 B1 | 5/2001 | Klumb et al. |
| 6,245,052 B1 | 6/2001 | Orth et al. |
| 6,248,112 B1 | 6/2001 | Gambale et al. |
| 6,248,116 B1 | 6/2001 | Chevillon |
| 6,251,132 B1 | 6/2001 | Ravenscroft et al. |
| 6,254,609 B1 | 7/2001 | Vrba et al. |
| 6,267,775 B1 | 7/2001 | Clerc et al. |
| 6,270,521 B1 | 8/2001 | Fischell et al. |
| 6,273,909 B1 | 8/2001 | Kugler et al. |
| 6,280,466 B1 | 8/2001 | Kugler et al. |
| 6,280,467 B1 | 8/2001 | Leonhardt |
| 6,285,903 B1 | 9/2001 | Rosenthal et al. |
| 6,287,315 B1 | 9/2001 | Wijeratne et al. |
| 6,302,906 B1 | 10/2001 | Goicoechea et al. |
| 6,302,907 B1 | 10/2001 | Hijlkema |
| 6,306,141 B1 | 10/2001 | Jervis |
| 6,312,458 B1 | 11/2001 | Golds |
| 6,319,275 B1 | 11/2001 | Lashinski et al. |
| 6,319,278 B1 | 11/2001 | Quinn |
| 6,322,585 B1 | 11/2001 | Khosravi et al. |
| 6,334,869 B1 | 1/2002 | Leonhardt et al. |
| 6,338,709 B1 | 1/2002 | Geoffrion et al. |
| 6,342,066 B1 | 1/2002 | Toro et al. |
| 6,344,044 B1 | 2/2002 | Fulkerson |
| 6,344,052 B1 | 2/2002 | Greenan et al. |
| 6,346,118 B1 | 2/2002 | Baker et al. |
| 6,350,278 B1 | 2/2002 | Lenker et al. |
| 6,355,056 B1 | 3/2002 | Pinheiro |
| 6,355,060 B1 | 3/2002 | Lenker et al. |
| 6,368,345 B1 | 4/2002 | Dehdashtian et al. |
| 6,375,675 B2 | 4/2002 | Dehdashtian et al. |
| 6,375,676 B1 | 4/2002 | Cox |
| 6,379,372 B1 | 4/2002 | Dehdashtian et al. |
| 6,389,946 B1 | 5/2002 | Frid et al. |
| 6,395,017 B1 | 5/2002 | Dwyer et al. |

(56) References Cited

U.S. PATENT DOCUMENTS

| | | |
|---|---|---|
| 6,395,022 B1 | 5/2002 | Piplani et al. |
| 6,402,781 B1 | 6/2002 | Langberg et al. |
| 6,416,490 B1 | 7/2002 | Ellis et al. |
| 6,416,542 B1 | 7/2002 | Marcade et al. |
| 6,419,686 B1 | 7/2002 | McLeod et al. |
| 6,425,898 B1 | 7/2002 | Wilson |
| 6,443,979 B1 | 9/2002 | Stalker et al. |
| 6,443,980 B1 | 9/2002 | Wang |
| 6,450,988 B1 | 9/2002 | Bradshaw |
| 6,451,053 B1 | 9/2002 | Dehdashtian et al. |
| 6,454,796 B1 | 9/2002 | Barkman et al. |
| 6,458,867 B1 | 10/2002 | Wang |
| 6,464,684 B1 | 10/2002 | Galdonik |
| 6,464,719 B2 | 10/2002 | Jayaraman |
| 6,464,721 B1 | 10/2002 | Marcade et al. |
| 6,478,818 B1 | 11/2002 | Taheri |
| 6,488,700 B2 | 12/2002 | Klumb et al. |
| 6,503,274 B1 | 1/2003 | Howanec, Jr. et al. |
| 6,505,066 B2 | 1/2003 | Berg |
| 6,514,282 B1 | 2/2003 | Inoue |
| 6,517,571 B1 | 2/2003 | Brauker et al. |
| 6,517,572 B2 | 2/2003 | Kugler et al. |
| 6,517,573 B1 | 2/2003 | Pollock et al. |
| 6,520,951 B1 | 2/2003 | Carrillo, Jr. et al. |
| 6,520,986 B2 | 2/2003 | Martin et al. |
| 6,524,335 B1 | 2/2003 | Hartley et al. |
| 6,524,336 B1 | 2/2003 | Papazolgou et al. |
| 6,533,753 B1 | 3/2003 | Haarstad et al. |
| 6,540,698 B1 | 4/2003 | Ishii |
| 6,540,778 B1 | 4/2003 | Quiachon et al. |
| 6,551,350 B1 | 4/2003 | Thornton et al. |
| 6,562,022 B2 | 5/2003 | Hoste |
| 6,565,596 B1 | 5/2003 | White et al. |
| 6,565,597 B1 | 5/2003 | Fearnot et al. |
| 6,575,994 B1 | 6/2003 | Marin et al. |
| 6,576,007 B2 | 6/2003 | Dehdashtian et al. |
| 6,582,458 B1 | 6/2003 | White et al. |
| 6,582,460 B1 | 6/2003 | Cryer |
| 6,592,526 B1 | 7/2003 | Lenker |
| 6,613,073 B1 | 9/2003 | White et al. |
| 6,616,626 B2 | 9/2003 | Crank et al. |
| 6,620,126 B2 | 9/2003 | Unsworth et al. |
| 6,641,606 B2 | 11/2003 | Ouriel et al. |
| 6,652,571 B1 | 11/2003 | White et al. |
| 6,652,572 B2 | 11/2003 | Kugler et al. |
| 6,660,033 B1 | 12/2003 | Marcade et al. |
| 6,676,666 B2 | 1/2004 | Vrba et al. |
| 6,682,536 B2 | 1/2004 | Vardi et al. |
| 6,682,537 B2 | 1/2004 | Ouriel et al. |
| 6,682,557 B1 | 1/2004 | Quiachon et al. |
| 6,685,736 B1 | 2/2004 | White et al. |
| 6,689,152 B2 | 2/2004 | Balceta et al. |
| 6,689,158 B1 | 2/2004 | White et al. |
| 6,692,458 B2 | 2/2004 | Forman et al. |
| 6,692,483 B2 | 2/2004 | Vardi et al. |
| 6,692,512 B2 | 2/2004 | Jang |
| 6,695,875 B2 | 2/2004 | Stelter et al. |
| 6,706,033 B1 | 3/2004 | Martinez et al. |
| 6,726,712 B1 | 4/2004 | Raeder-Devens |
| 6,733,519 B2 | 5/2004 | Lashinski et al. |
| 6,733,523 B2 | 5/2004 | Shaolian et al. |
| 6,755,856 B2 | 6/2004 | Fierens et al. |
| 6,761,731 B2 | 7/2004 | Majercak |
| 6,790,222 B2 | 9/2004 | Kugler et al. |
| 6,802,860 B2 | 10/2004 | Cosgrove et al. |
| 6,808,529 B2 | 10/2004 | Fulkerson |
| 6,811,559 B2 | 11/2004 | Thornton |
| 6,814,748 B1 | 11/2004 | Baker et al. |
| 6,821,291 B2 | 11/2004 | Bolea et al. |
| 6,827,710 B1 | 12/2004 | Mooney et al. |
| 6,827,711 B2 | 12/2004 | Sunseri |
| 6,830,575 B2 | 12/2004 | Stenzel et al. |
| 6,843,803 B2 | 1/2005 | Ryan et al. |
| 6,849,084 B2 | 2/2005 | Rabkin et al. |
| 6,849,088 B2 | 2/2005 | Dehdashtian et al. |
| 6,858,034 B1 | 2/2005 | Hijlkema et al. |
| 6,859,986 B2 | 3/2005 | Jackson |
| 6,860,901 B1 | 3/2005 | Baker et al. |
| 6,863,668 B2 | 3/2005 | Gillespie et al. |
| 6,866,660 B2 | 3/2005 | Garabedian |
| 6,871,085 B2 | 3/2005 | Sommer |
| 6,884,260 B2 | 4/2005 | Kugler et al. |
| 6,890,348 B2 | 5/2005 | Sydney et al. |
| 6,911,039 B2 | 6/2005 | Shiu et al. |
| 6,916,335 B2 | 7/2005 | Kanji |
| 6,918,925 B2 | 7/2005 | Tehrani |
| 6,932,829 B2 | 8/2005 | Majercak |
| 6,938,646 B2 | 9/2005 | Litton |
| 6,939,371 B2 | 9/2005 | Kugler et al. |
| 6,945,989 B1 | 9/2005 | Betelia et al. |
| 6,945,990 B2 | 9/2005 | Greenan |
| 6,964,679 B1 | 11/2005 | Marcade et al. |
| 6,989,024 B2 | 1/2006 | Hebert et al. |
| 6,994,722 B2 | 2/2006 | DiCarlo |
| 7,001,420 B2 | 2/2006 | Speck et al. |
| 7,011,647 B2 | 3/2006 | Purdy et al. |
| 7,014,653 B2 | 3/2006 | Ouriel |
| 7,025,773 B2 | 4/2006 | Gittings et al. |
| 7,052,511 B2 | 5/2006 | Weldon et al. |
| 7,070,582 B2 | 7/2006 | Freyman et al. |
| 7,105,016 B2 | 9/2006 | Shiu et al. |
| 7,112,217 B1 | 9/2006 | Kugler et al. |
| 7,115,134 B2 | 10/2006 | Chambers |
| 7,125,419 B2 | 10/2006 | Sequin et al. |
| 7,147,657 B2 | 12/2006 | Chiang et al. |
| 7,147,660 B2 | 12/2006 | Chobotov et al. |
| 7,160,318 B2 | 1/2007 | Greenberg et al. |
| 7,163,552 B2 | 1/2007 | Diaz |
| 7,166,125 B1 | 1/2007 | Baker et al. |
| 7,169,170 B2 | 1/2007 | Widenhouse |
| 7,195,639 B2 | 3/2007 | Quiachon et al. |
| 7,225,518 B2 | 6/2007 | Eidenschink et al. |
| 7,238,197 B2 | 7/2007 | Sequin et al. |
| 7,264,632 B2 | 9/2007 | Wright et al. |
| 7,294,147 B2 | 11/2007 | Hartley |
| 7,351,256 B2 | 4/2008 | Hojeibane et al. |
| 7,708,771 B2 | 5/2010 | Chuter et al. |
| 7,717,950 B2 | 5/2010 | Greenan |
| 7,722,663 B2 | 5/2010 | Austin |
| 7,763,063 B2 | 7/2010 | Arbefeuille et al. |
| 7,766,962 B1 | 8/2010 | Quinn |
| 7,837,724 B2 | 11/2010 | Keeble et al. |
| 8,043,354 B2 | 10/2011 | Greenberg et al. |
| 8,062,345 B2 | 11/2011 | Ouellette et al. |
| 8,062,349 B2 | 11/2011 | Moore et al. |
| 8,070,790 B2 | 12/2011 | Berra et al. |
| 8,292,943 B2 | 10/2012 | Berra et al. |
| 8,308,790 B2 | 11/2012 | Arbefeuille et al. |
| 8,449,595 B2 | 5/2013 | Ouellette et al. |
| 8,500,792 B2 | 8/2013 | Berra |
| 8,579,963 B2 | 11/2013 | Tabor |
| 8,636,788 B2 | 1/2014 | Arbefeuille et al. |
| 8,672,992 B2 | 3/2014 | Orr |
| 8,702,787 B2 | 4/2014 | Arbefeuille |
| 8,734,501 B2 | 5/2014 | Hartley et al. |
| 8,740,963 B2 | 6/2014 | Arbefeuille et al. |
| 8,998,970 B2 | 4/2015 | Arbefeuille et al. |
| 9,101,506 B2 | 8/2015 | Arbefeuille et al. |
| 9,173,755 B2 | 11/2015 | Berra et al. |
| 9,198,786 B2 | 12/2015 | Moore et al. |
| 9,220,617 B2 | 12/2015 | Berra |
| 9,320,631 B2 | 4/2016 | Moore et al. |
| 9,333,104 B2 | 5/2016 | Ouellette et al. |
| 9,364,314 B2 | 6/2016 | Berra et al. |
| 9,408,734 B2 | 8/2016 | Arbefeuille et al. |
| 9,408,735 B2 | 8/2016 | Arbefeuille et al. |
| 9,439,751 B2 | 9/2016 | White et al. |
| 9,554,929 B2 | 1/2017 | Arbefeuille et al. |
| 9,561,124 B2 | 2/2017 | Arbefeuille et al. |
| 9,592,112 B2 | 3/2017 | Arbefeuille et al. |
| 9,655,712 B2 | 5/2017 | Berra et al. |
| 9,827,123 B2 | 11/2017 | Arbefeuille et al. |
| 9,877,857 B2 | 1/2018 | Arbefeuille et al. |
| 9,907,686 B2 | 3/2018 | Ouellette et al. |

(56) References Cited

U.S. PATENT DOCUMENTS

| | | |
|---|---|---|
| 9,913,743 B2 | 3/2018 | Arbefeuille et al. |
| 9,925,080 B2 | 3/2018 | Arbefeuille et al. |
| 2001/0000801 A1 | 5/2001 | Miller et al. |
| 2001/0001833 A1 | 5/2001 | Ravenscroft et al. |
| 2001/0034549 A1 | 10/2001 | Bartholf et al. |
| 2001/0049547 A1 | 12/2001 | Moore |
| 2001/0053930 A1 | 12/2001 | Kugler |
| 2002/0007193 A1 | 1/2002 | Tanner et al. |
| 2002/0013617 A1 | 1/2002 | Matsutani et al. |
| 2002/0016597 A1 | 2/2002 | Dwyer et al. |
| 2002/0016627 A1 | 2/2002 | Golds |
| 2002/0035394 A1 | 3/2002 | Fierens |
| 2002/0045929 A1 | 4/2002 | Diaz |
| 2002/0052643 A1 | 5/2002 | Wholey et al. |
| 2002/0052660 A1 | 5/2002 | Geenhalgh |
| 2002/0072755 A1 | 6/2002 | Bigus et al. |
| 2002/0082523 A1 | 6/2002 | Kinsella et al. |
| 2002/0082674 A1 | 6/2002 | Anson et al. |
| 2002/0091439 A1 | 7/2002 | Baker et al. |
| 2002/0095140 A1 | 7/2002 | Lootz et al. |
| 2002/0107561 A1 | 8/2002 | Pinheiro |
| 2002/0108621 A1 | 8/2002 | Berg et al. |
| 2002/0138133 A1 | 9/2002 | Lenz et al. |
| 2002/0156518 A1 | 10/2002 | Tehrani |
| 2002/0156522 A1 | 10/2002 | Ivancev et al. |
| 2002/0161424 A1 | 10/2002 | Rapacki et al. |
| 2002/0165554 A1 | 11/2002 | Dworschak et al. |
| 2002/0188344 A1 | 12/2002 | Bolea et al. |
| 2002/0198587 A1 | 12/2002 | Greenberg et al. |
| 2003/0028237 A1 | 2/2003 | Sullivan et al. |
| 2003/0074049 A1 | 4/2003 | Hoganson et al. |
| 2003/0083734 A1 | 5/2003 | Friedrich et al. |
| 2003/0088305 A1 | 5/2003 | Van Schie et al. |
| 2003/0114910 A1 | 6/2003 | Juhani Laakso et al. |
| 2003/0120263 A1 | 6/2003 | Ouriel et al. |
| 2003/0120333 A1 | 6/2003 | Ouriel et al. |
| 2003/0135259 A1 | 7/2003 | Simso |
| 2003/0135269 A1 | 7/2003 | Swanstrom |
| 2003/0139803 A1 | 7/2003 | Sequin et al. |
| 2003/0163193 A1 | 8/2003 | Widenhouse |
| 2003/0176911 A1 | 9/2003 | Iancea et al. |
| 2003/0176912 A1 | 9/2003 | Chuter et al. |
| 2003/0191516 A1 | 10/2003 | Weldon et al. |
| 2003/0195614 A1 | 10/2003 | Ryan et al. |
| 2003/0199966 A1 | 10/2003 | Shiu et al. |
| 2003/0199967 A1 | 10/2003 | Hartley et al. |
| 2003/0212431 A1 | 11/2003 | Brady et al. |
| 2003/0220682 A1 | 11/2003 | Kujawski |
| 2003/0233140 A1 | 12/2003 | Hartley et al. |
| 2003/0236564 A1 | 12/2003 | Majercak |
| 2003/0236565 A1 | 12/2003 | DiMatteo et al. |
| 2004/0073284 A1 | 4/2004 | Bates et al. |
| 2004/0073289 A1 | 4/2004 | Hartley |
| 2004/0093063 A1 | 5/2004 | Wright et al. |
| 2004/0098084 A1 | 5/2004 | Hartley et al. |
| 2004/0106974 A1 | 6/2004 | Greenberg et al. |
| 2004/0117003 A1 | 6/2004 | Ouriel et al. |
| 2004/0148007 A1 | 7/2004 | Jackson et al. |
| 2004/0148009 A1 | 7/2004 | Buzzard et al. |
| 2004/0193141 A1 | 9/2004 | Leopold et al. |
| 2004/0193244 A1 | 9/2004 | Hartley et al. |
| 2004/0193245 A1 | 9/2004 | Deem et al. |
| 2004/0193252 A1 | 9/2004 | Perez |
| 2004/0199240 A1 | 10/2004 | Dorn |
| 2004/0230284 A1 | 11/2004 | Headley et al. |
| 2004/0230286 A1 | 11/2004 | Moore et al. |
| 2004/0236403 A1 | 11/2004 | Leonhardt et al. |
| 2004/0236407 A1 | 11/2004 | Fierens et al. |
| 2004/0267281 A1 | 12/2004 | Harari et al. |
| 2005/0021125 A1 | 1/2005 | Stack et al. |
| 2005/0027305 A1 | 2/2005 | Shiu et al. |
| 2005/0033406 A1 | 2/2005 | Barnhart et al. |
| 2005/0038495 A1 | 2/2005 | Greenan |
| 2005/0049667 A1 | 3/2005 | Arbefeuille et al. |
| 2005/0049674 A1 | 3/2005 | Berra et al. |
| 2005/0060016 A1 | 3/2005 | Wu et al. |
| 2005/0080476 A1 | 4/2005 | Gunderson et al. |
| 2005/0080477 A1 | 4/2005 | Sydney et al. |
| 2005/0096726 A1 | 5/2005 | Sequin et al. |
| 2005/0107862 A1 | 5/2005 | Ohlenschlaeger |
| 2005/0149166 A1 | 7/2005 | Schaeffer et al. |
| 2005/0159803 A1 | 7/2005 | Lad et al. |
| 2005/0159804 A1 | 7/2005 | Lad et al. |
| 2005/0171597 A1 | 8/2005 | Boatman et al. |
| 2005/0171598 A1 | 8/2005 | Schaeffer |
| 2005/0177222 A1 | 8/2005 | Mead |
| 2005/0183259 A1 | 8/2005 | Eidenschink et al. |
| 2005/0192659 A1 | 9/2005 | Dahl et al. |
| 2005/0222668 A1 | 10/2005 | Schaeffer et al. |
| 2005/0283223 A1 | 12/2005 | Greenan |
| 2005/0288764 A1 | 12/2005 | Snow et al. |
| 2006/0004433 A1 | 1/2006 | Greenberg et al. |
| 2006/0020319 A1 | 1/2006 | Kim et al. |
| 2006/0020320 A1 | 1/2006 | Shaolian et al. |
| 2006/0058864 A1 | 3/2006 | Schaeffer et al. |
| 2006/0127439 A1 | 6/2006 | Mattes et al. |
| 2006/0129169 A1 | 6/2006 | Fogarty et al. |
| 2006/0129224 A1 | 6/2006 | Arbefeuille et al. |
| 2006/0135961 A1 | 6/2006 | Rosenman et al. |
| 2006/0178726 A1 | 8/2006 | Douglas |
| 2006/0178733 A1 | 8/2006 | Pinchuk et al. |
| 2006/0188408 A1 | 8/2006 | Arbefeuille et al. |
| 2006/0195172 A1 | 8/2006 | Luo et al. |
| 2006/0200110 A1 | 9/2006 | Lentz et al. |
| 2006/0212105 A1 | 9/2006 | Dorn et al. |
| 2006/0265047 A1 | 11/2006 | Dorn |
| 2006/0276872 A1 | 12/2006 | Arbefeuille et al. |
| 2006/0282150 A1 | 12/2006 | Olson et al. |
| 2007/0021822 A1 | 1/2007 | Boatman |
| 2007/0048348 A1 | 3/2007 | Atanasoska et al. |
| 2007/0053952 A1 | 3/2007 | Chen et al. |
| 2007/0055338 A1 | 3/2007 | Dorn |
| 2007/0055340 A1 | 3/2007 | Pryor |
| 2007/0055341 A1 | 3/2007 | Edoga et al. |
| 2007/0055345 A1 | 3/2007 | Arbefeuille |
| 2007/0055347 A1 | 3/2007 | Arbefeuille |
| 2007/0083252 A1 | 4/2007 | McDonald |
| 2007/0100422 A1 | 5/2007 | Shumer et al. |
| 2007/0100425 A1 | 5/2007 | Sequin et al. |
| 2007/0123972 A1 | 5/2007 | Greenberg et al. |
| 2007/0135818 A1 | 6/2007 | Moore et al. |
| 2007/0135889 A1 | 6/2007 | Moore et al. |
| 2007/0142894 A1 | 6/2007 | Moore et al. |
| 2007/0156228 A1 | 7/2007 | Majercak et al. |
| 2007/0162109 A1 | 7/2007 | Davila et al. |
| 2007/0163668 A1 | 7/2007 | Arbefeuille et al. |
| 2007/0168014 A1 | 7/2007 | Jimenez et al. |
| 2007/0173929 A1 | 7/2007 | Boucher et al. |
| 2007/0179592 A1 | 8/2007 | Schaeffer |
| 2007/0179593 A1 | 8/2007 | Fierens et al. |
| 2007/0179601 A1 | 8/2007 | Fierens et al. |
| 2007/0198078 A1 | 8/2007 | Berra et al. |
| 2007/0203566 A1 | 8/2007 | Arbefeuille et al. |
| 2007/0207186 A1 | 9/2007 | Scanlon et al. |
| 2007/0213800 A1 | 9/2007 | Fierens et al. |
| 2007/0219620 A1 | 9/2007 | Eells et al. |
| 2007/0244545 A1 | 10/2007 | Birdsall et al. |
| 2008/0021538 A1 | 1/2008 | Wright et al. |
| 2008/0027528 A1 | 1/2008 | Jagger et al. |
| 2008/0046065 A1 | 2/2008 | Hartley |
| 2008/0065011 A1 | 3/2008 | Marchand et al. |
| 2008/0071343 A1 | 3/2008 | Mayberry et al. |
| 2008/0077226 A1 | 3/2008 | Ouellette et al. |
| 2008/0077227 A1 | 3/2008 | Ouellette et al. |
| 2008/0082158 A1 | 4/2008 | Tseng et al. |
| 2008/0114441 A1 | 5/2008 | Rust et al. |
| 2008/0132996 A1 | 6/2008 | Drasler et al. |
| 2008/0172122 A1 | 7/2008 | Mayberry et al. |
| 2008/0195191 A1 | 8/2008 | Luo et al. |
| 2008/0208175 A1 | 8/2008 | Beckman et al. |
| 2008/0262590 A1 | 10/2008 | Murray |
| 2008/0264102 A1 | 10/2008 | Berra |
| 2008/0269865 A1 | 10/2008 | Snow et al. |
| 2009/0163951 A1 | 6/2009 | Simmons et al. |

(56) References Cited

U.S. PATENT DOCUMENTS

| | | |
|---|---|---|
| 2009/0254165 A1 | 10/2009 | Tabor et al. |
| 2010/0030255 A1 | 2/2010 | Berra et al. |
| 2010/0030318 A1 | 2/2010 | Berra |
| 2010/0234932 A1 | 9/2010 | Arbefeuille et al. |
| 2010/0274340 A1 | 10/2010 | Hartley et al. |
| 2011/0071614 A1 | 3/2011 | Majercak |
| 2011/0208288 A1 | 8/2011 | Arbefeuille et al. |
| 2011/0218607 A1 | 9/2011 | Arbefeuille et al. |
| 2011/0251664 A1 | 10/2011 | Acosta de Acevedo |
| 2011/0307049 A1 | 12/2011 | Kao |
| 2011/0313503 A1 | 12/2011 | Berra et al. |
| 2012/0123517 A1 | 5/2012 | Ouellette et al. |
| 2012/0143305 A1 | 6/2012 | Berra et al. |
| 2012/0296413 A1 | 11/2012 | Arbefeuille et al. |
| 2013/0274856 A1 | 10/2013 | Arbefeuille et al. |
| 2013/0325099 A1 | 12/2013 | Berra |
| 2014/0039597 A9 | 2/2014 | Arbefeuille et al. |
| 2014/0135890 A9 | 5/2014 | Berra |
| 2014/0135892 A1 | 5/2014 | Arbefeuille et al. |
| 2014/0135896 A1 | 5/2014 | Arbefeuille et al. |
| 2014/0148890 A9 | 5/2014 | Ouellette et al. |
| 2014/0243952 A1 | 8/2014 | Parodi et al. |
| 2014/0277340 A1 | 9/2014 | White et al. |
| 2014/0288627 A1 | 9/2014 | Ouellette et al. |
| 2014/0316510 A1 | 10/2014 | Berra |
| 2015/0173922 A1 | 6/2015 | Arbefeuille et al. |
| 2015/0202066 A1 | 7/2015 | Berra |
| 2015/0202068 A1 | 7/2015 | Arbefeuille et al. |
| 2015/0272755 A1 | 10/2015 | Arbefeuille et al. |
| 2016/0081787 A1 | 3/2016 | Parodi |
| 2016/0270901 A1 | 9/2016 | Berra et al. |
| 2016/0270936 A1 | 9/2016 | Berra et al. |
| 2016/0310301 A1 | 10/2016 | Moore et al. |
| 2016/0338867 A1 | 11/2016 | White et al. |
| 2017/0000600 A1 | 1/2017 | Berra et al. |
| 2017/0100232 A1 | 4/2017 | Arbefeuille et al. |
| 2017/0100271 A1 | 4/2017 | Arbefeuille et al. |
| 2017/0135807 A1 | 5/2017 | Arbefeuille et al. |
| 2017/0151076 A9 | 6/2017 | Arbefeuille et al. |
| 2017/0165090 A1 | 6/2017 | Arbefeuille et al. |
| 2017/0165091 A1 | 6/2017 | Arbefeuille et al. |
| 2017/0281332 A1 | 10/2017 | Lostetter |
| 2017/0281382 A1 | 10/2017 | Lostetter |
| 2017/0340433 A1 | 11/2017 | Berra |
| 2017/0340462 A1 | 11/2017 | Lostetter |
| 2018/0071123 A1 | 3/2018 | Arbefeuille |

FOREIGN PATENT DOCUMENTS

| | | |
|---|---|---|
| DE | 10 2006 053748 B3 | 4/2008 |
| EP | 0 510 851 A1 | 10/1992 |
| EP | 0 873 733 A1 | 10/1998 |
| EP | 0 960 607 A1 | 12/1999 |
| EP | 0 696 447 B1 | 1/2000 |
| EP | 0 990 426 A1 | 4/2000 |
| EP | 1 177 779 A2 | 2/2002 |
| EP | 1 302 178 A2 | 4/2003 |
| EP | 1 358 903 A2 | 11/2003 |
| EP | 1 369 098 A1 | 12/2003 |
| EP | 1522277 A2 | 4/2005 |
| EP | 1 772 120 A2 | 4/2007 |
| EP | 1 923 024 A2 | 5/2008 |
| EP | 1 929 979 A2 | 6/2008 |
| EP | 1 440 673 B1 | 9/2008 |
| EP | 1 982 677 A2 | 10/2008 |
| EP | 1 508 313 B1 | 12/2008 |
| FR | 2 714 816 | 7/1995 |
| FR | 2 722 678 | 1/1996 |
| FR | 2 779 939 A1 | 12/1999 |
| WO | WO 95/23008 | 8/1995 |
| WO | WO 96/09013 | 3/1996 |
| WO | WO 96/23455 | 8/1996 |
| WO | WO 96/31174 | 10/1996 |
| WO | WO 96/38101 | 12/1996 |
| WO | WO 97/10778 A1 | 3/1997 |
| WO | WO 97/33532 | 9/1997 |
| WO | WO 98/20811 | 5/1998 |
| WO | WO 98/23242 | 6/1998 |
| WO | WO 98/42276 | 10/1998 |
| WO | WO 98/53761 A1 | 12/1998 |
| WO | WO 99/25273 | 5/1999 |
| WO | WO 99/37242 | 7/1999 |
| WO | WO 99/65420 | 12/1999 |
| WO | WO 00/02615 | 1/2000 |
| WO | WO 00/30562 | 6/2000 |
| WO | WO 00/78248 A1 | 12/2000 |
| WO | WO 01/17602 A1 | 3/2001 |
| WO | WO 01/21102 A1 | 3/2001 |
| WO | WO 02/28316 A2 | 4/2002 |
| WO | WO 03/015662 A1 | 2/2003 |
| WO | WO 2004/000169 A1 | 12/2003 |
| WO | WO 2004/002370 A1 | 1/2004 |
| WO | WO 2004/071352 A1 | 8/2004 |
| WO | WO 2005/023149 A2 | 3/2005 |
| WO | WO 2005/034808 A1 | 4/2005 |
| WO | WO 2005/058409 A1 | 6/2005 |
| WO | WO 2005/067819 A1 | 7/2005 |
| WO | WO 2005/081936 A2 | 9/2005 |
| WO | WO 2005/112821 A2 | 12/2005 |
| WO | WO 2006/019551 A1 | 2/2006 |
| WO | WO 2006/088638 A1 | 8/2006 |
| WO | WO 2006/125382 A1 | 11/2006 |
| WO | WO 2007/008533 A1 | 1/2007 |
| WO | WO 2007/028086 A2 | 3/2007 |
| WO | WO 2007/092276 A2 | 8/2007 |
| WO | WO 2007/123956 A2 | 11/2007 |
| WO | WO 2008/031103 A2 | 3/2008 |
| WO | 2008066923 A1 | 6/2008 |
| WO | WO 2008/098252 A2 | 8/2008 |
| WO | WO 2009/023221 A1 | 2/2009 |
| WO | WO 2009/124124 A1 | 10/2009 |
| WO | WO 2010/005524 A2 | 1/2010 |
| WO | 2010/027485 A1 | 3/2010 |
| WO | 2010/105195 A2 | 9/2010 |
| WO | 2013/154749 A1 | 10/2013 |

OTHER PUBLICATIONS

Notification Concerning Transmittal of International Preliminary Report on Patentability for International Application No. PCT/US2009/039144, dated Oct. 14, 2010.
Office Action, U.S. Appl. No. 12/415,728, dated May 9, 2012.
Notice of Allowance, U.S. Appl. No. 12/415,728, dated Jan. 17, 2013.
Office Action, U.S. Appl. No. 13/959,004, dated Dec. 17, 2013.
Office Action, U.S. Appl. No. 14/300,647, dated Dec. 19, 2014.
Office Action, U.S. Appl. No. 14/300,647, dated Aug. 4, 2015.
Notice of Allowance, U.S. Appl. No. 14/300,647, dated Sep. 21, 2015.

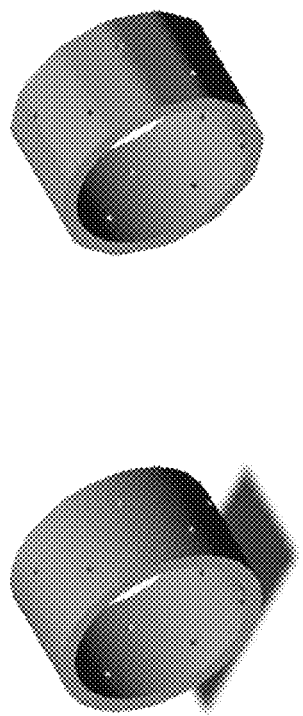
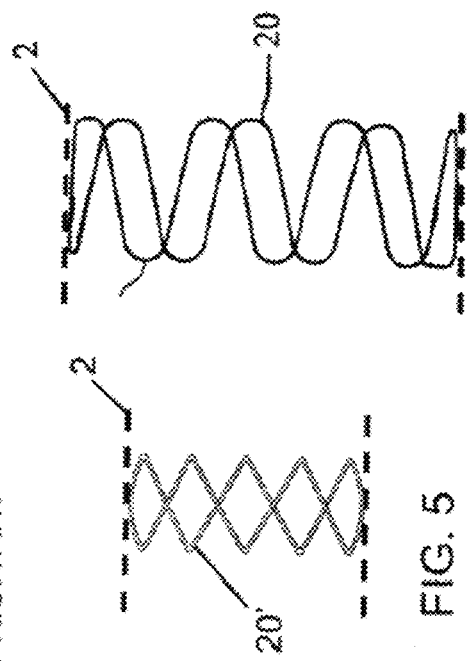
FIG. 4 PRIOR ART
FIG. 5 PRIOR ART
FIG. 6
FIG. 7

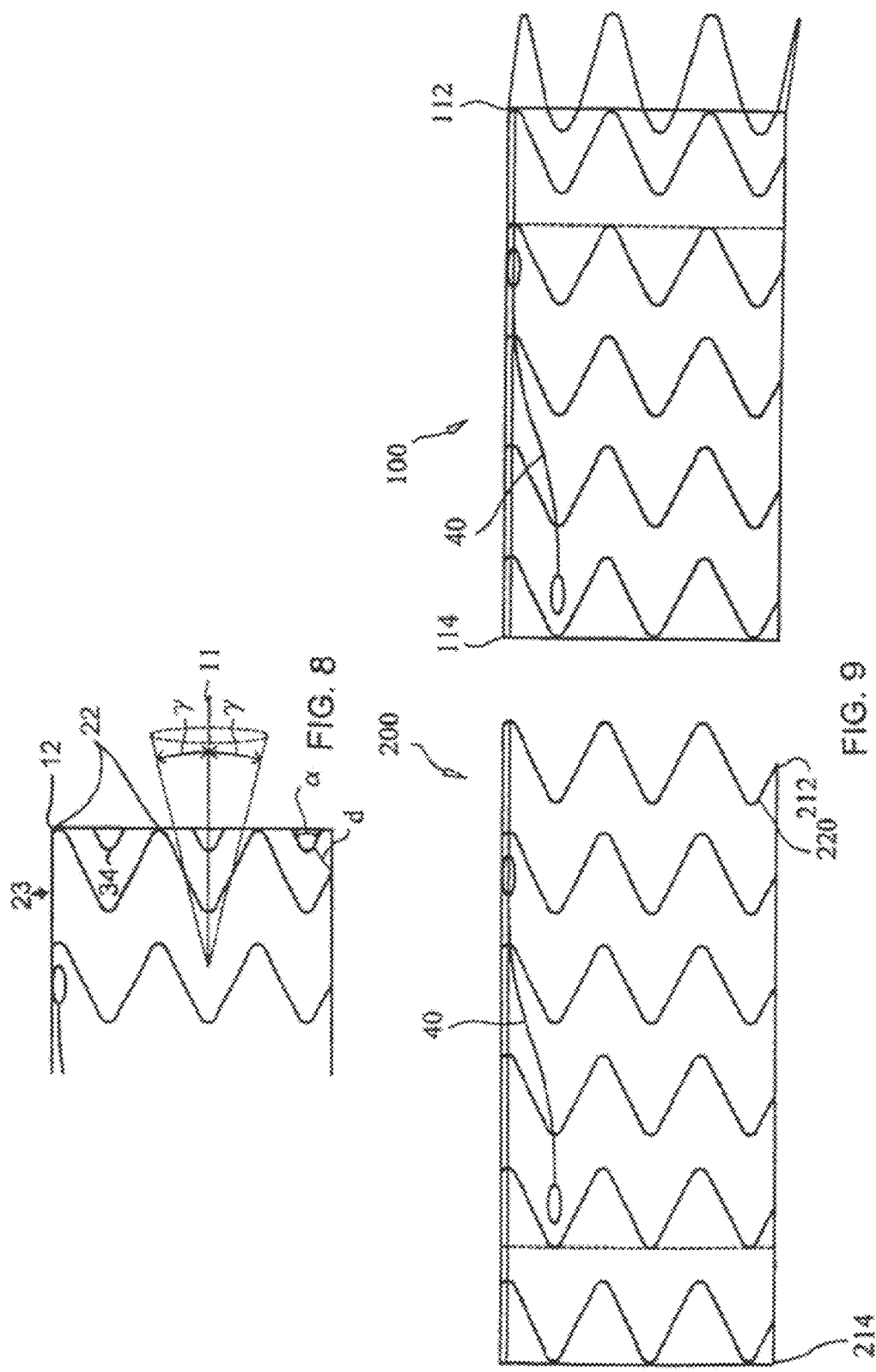

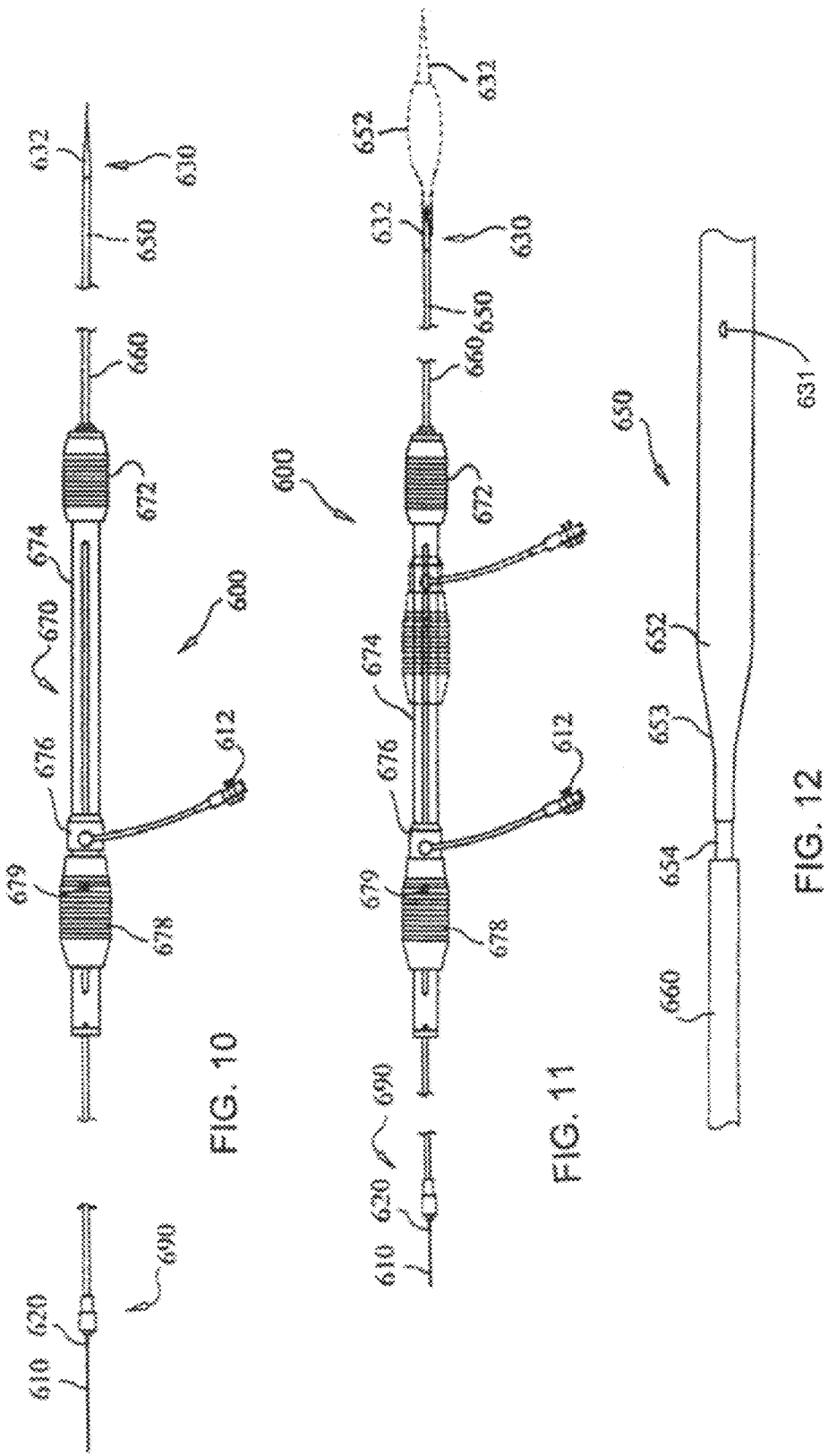

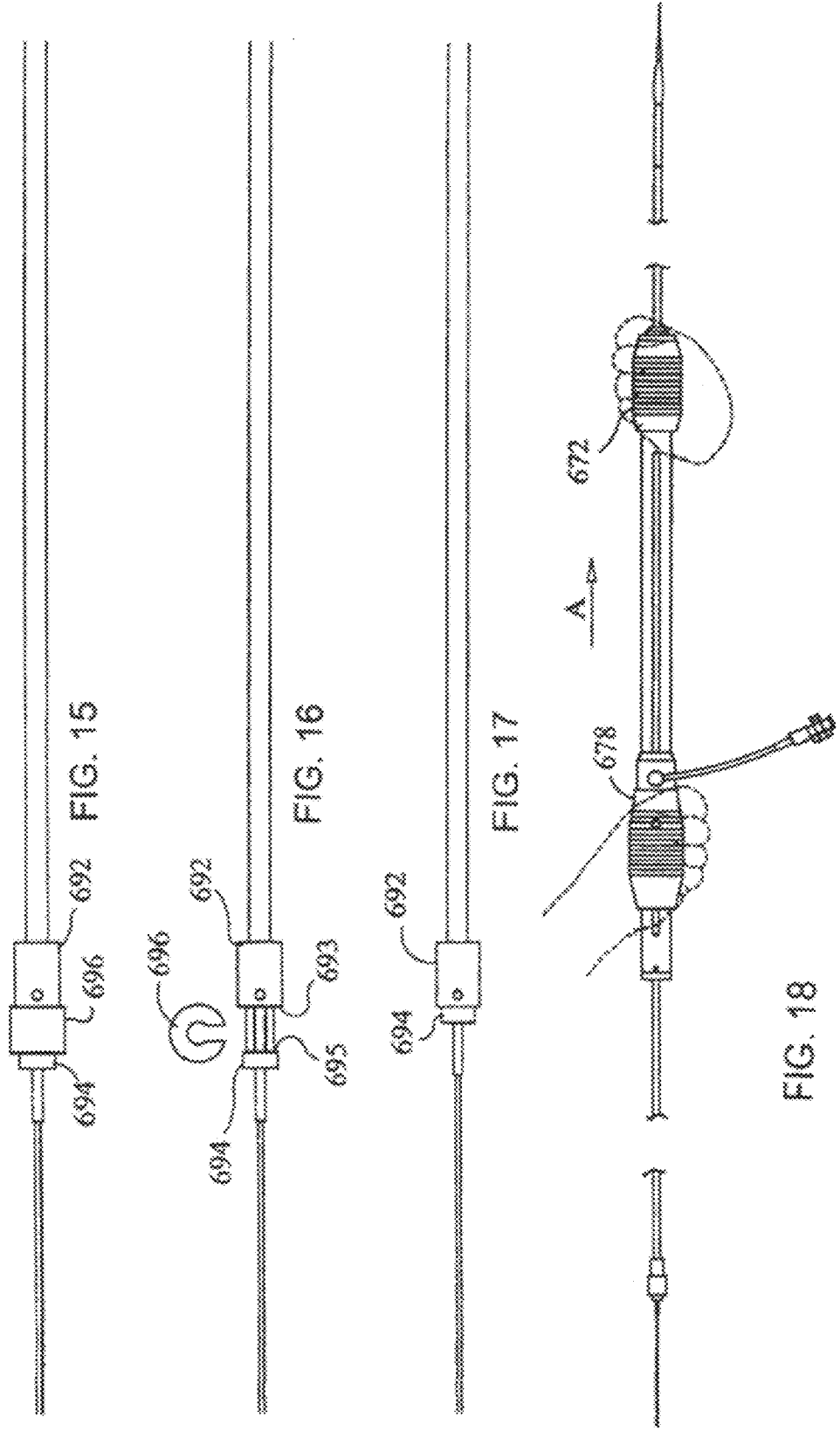

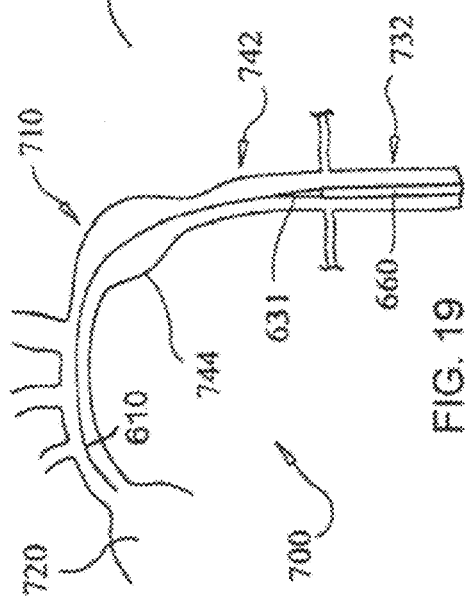
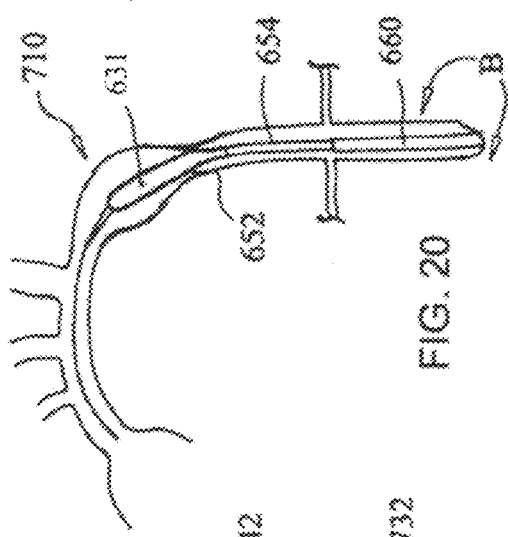
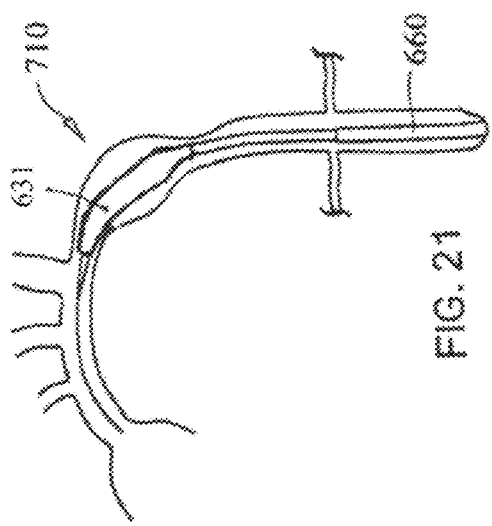
FIG. 19
FIG. 20
FIG. 21
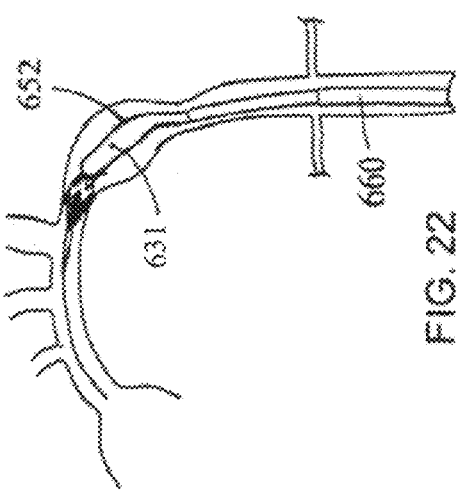
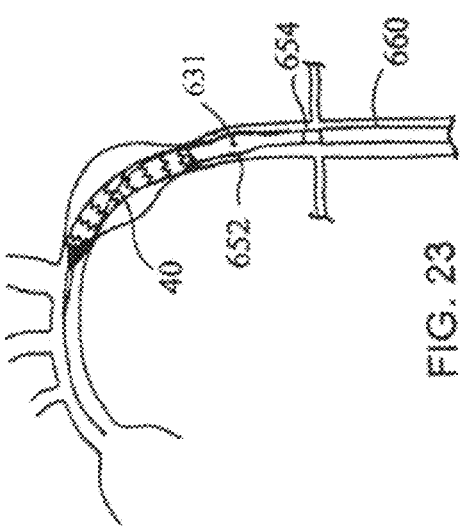
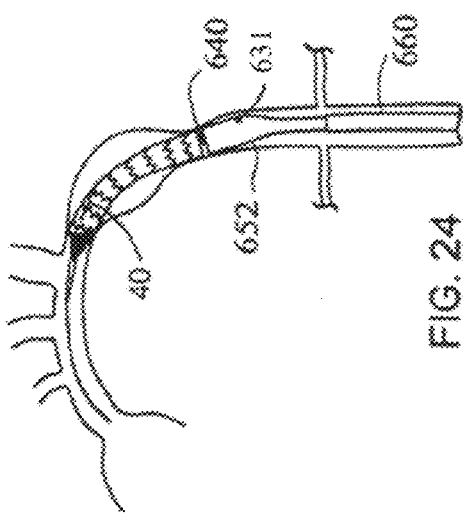
FIG. 22
FIG. 23
FIG. 24

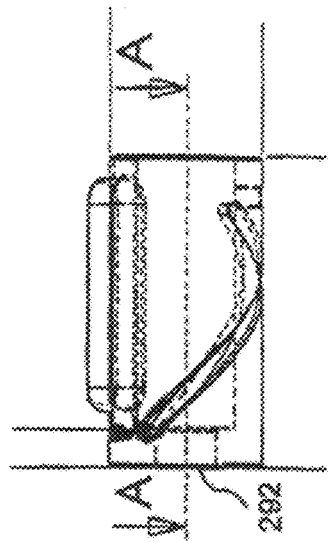
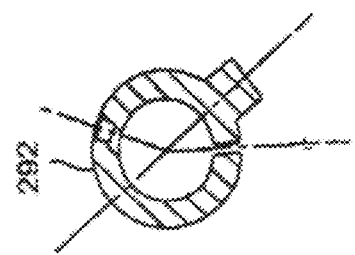
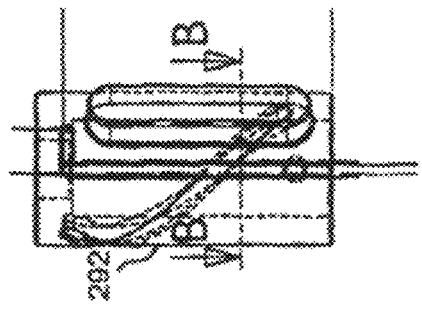
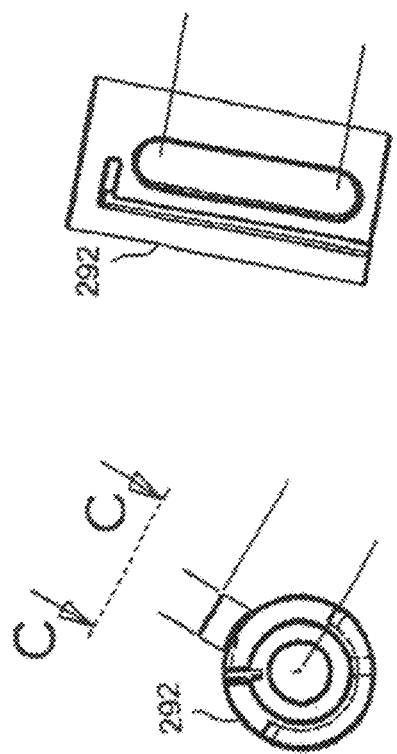
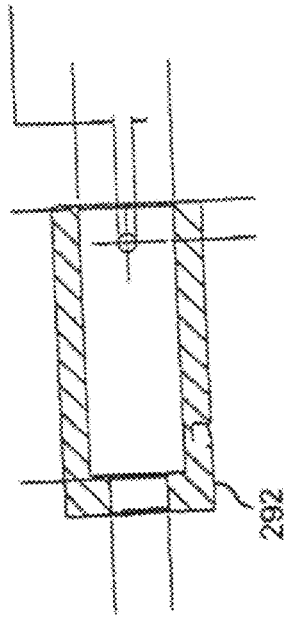

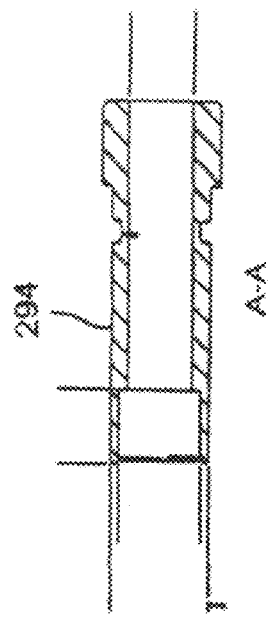
FIG. 40
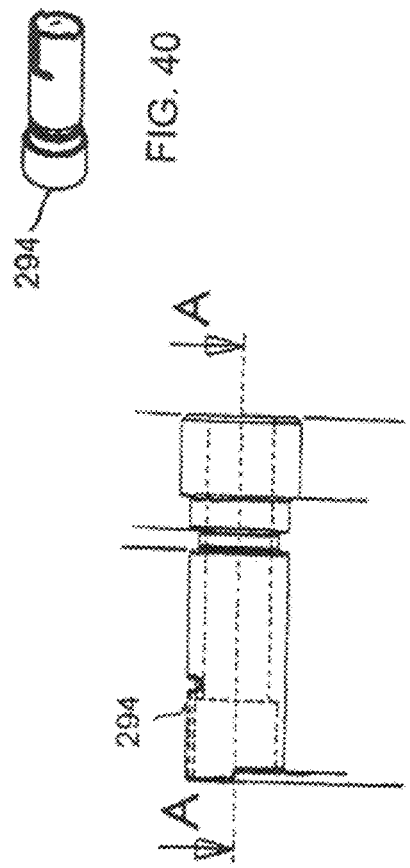
FIG. 41
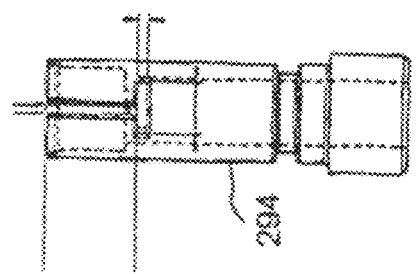
FIG. 42
FIG. 43

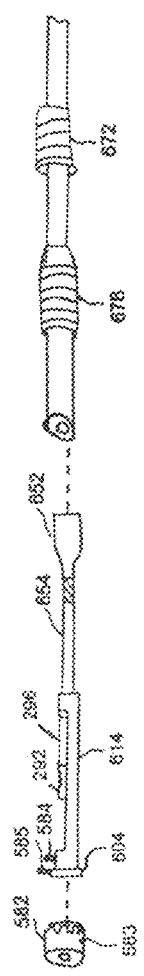
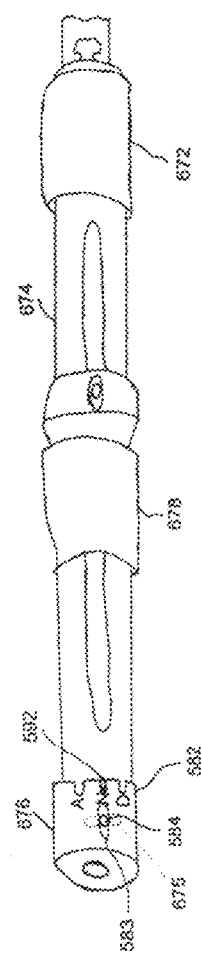

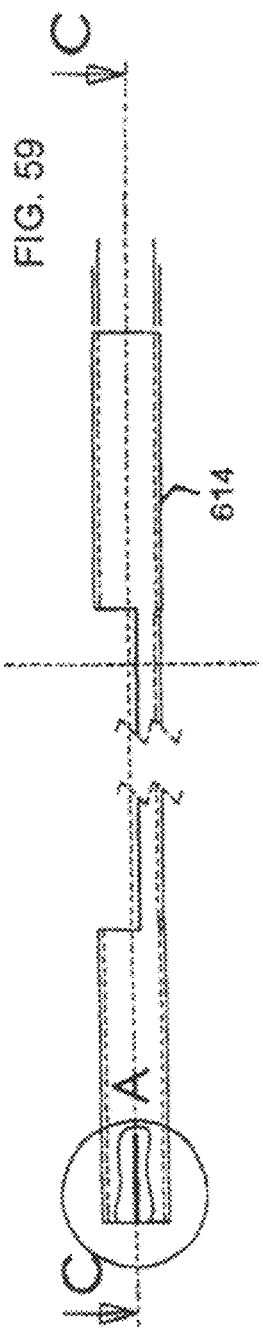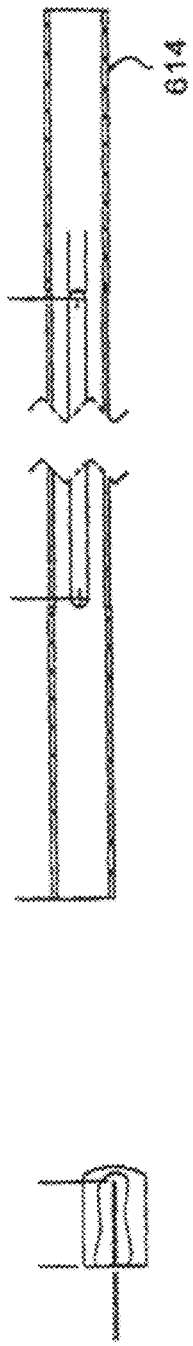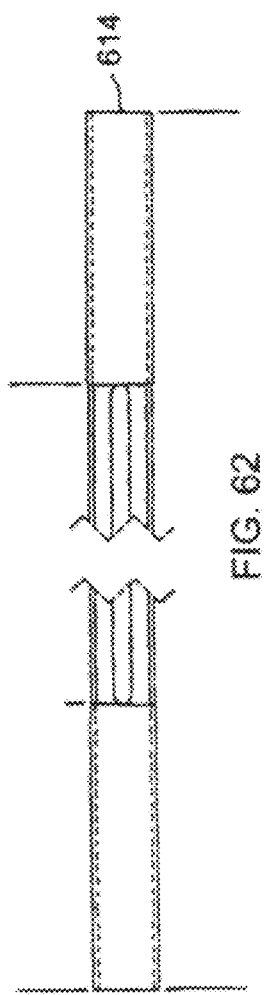

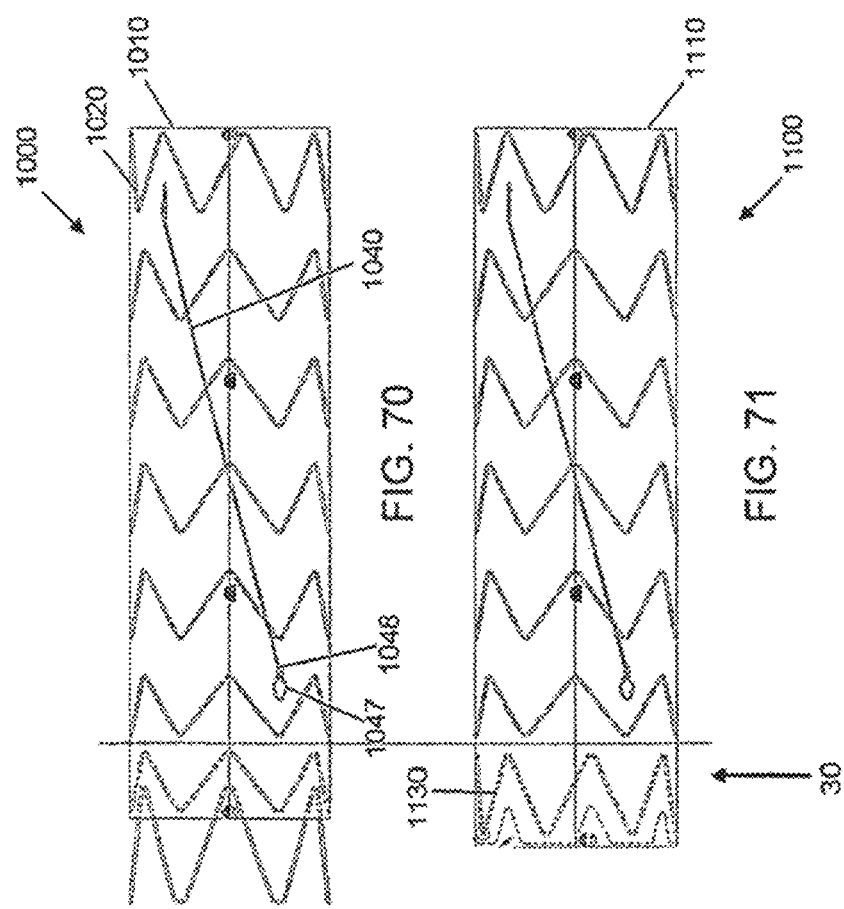

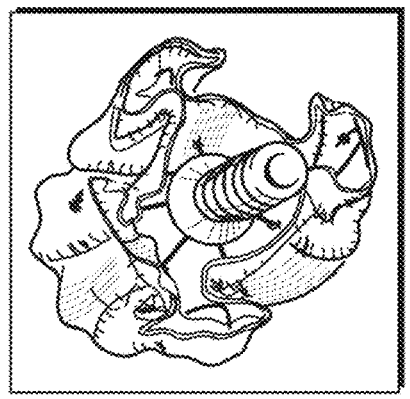
FIG. 75
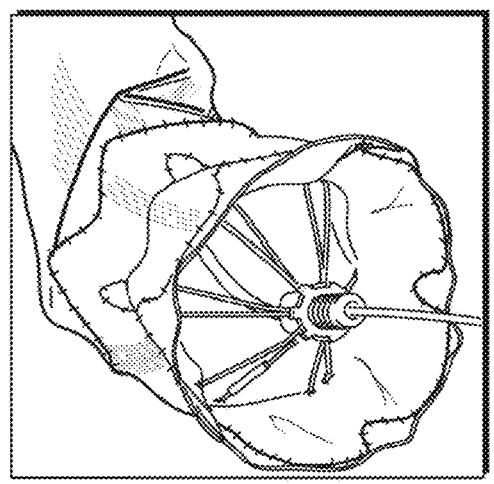
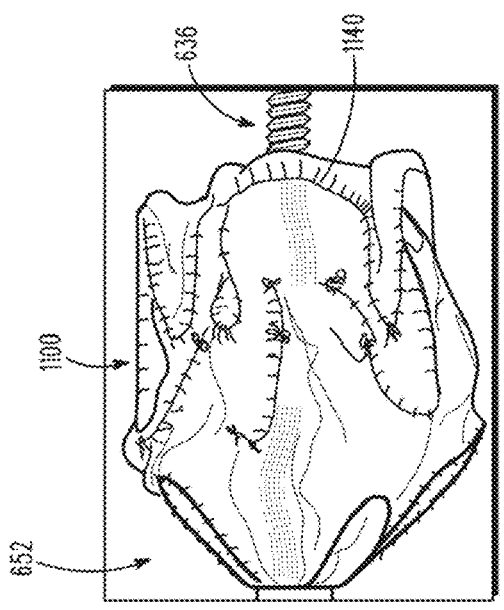
FIG. 76
FIG. 77

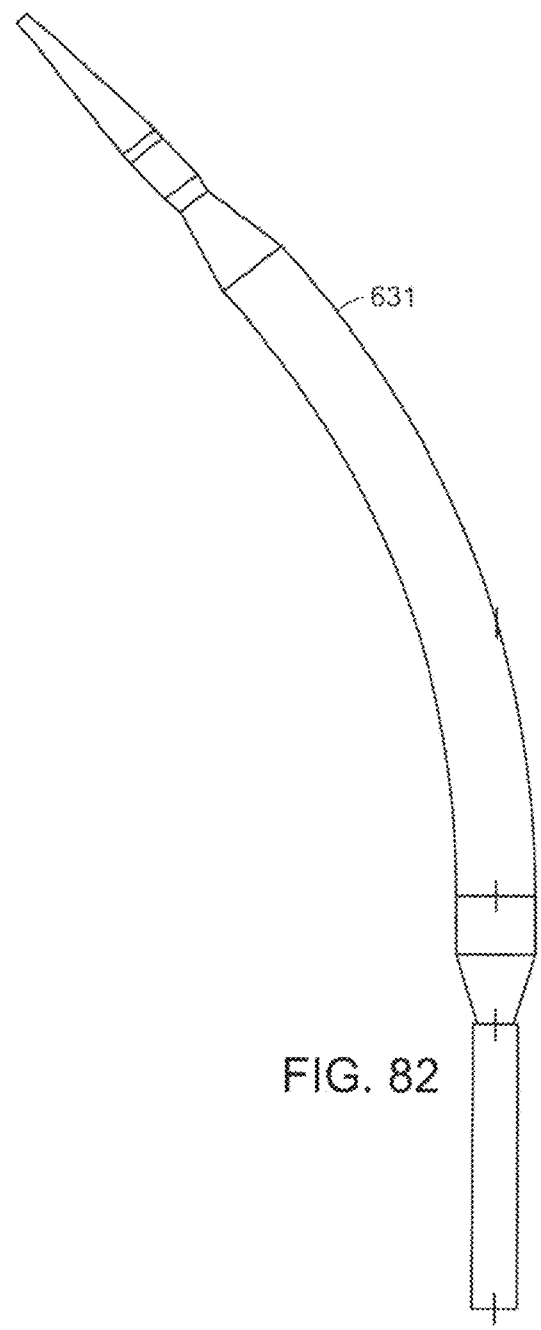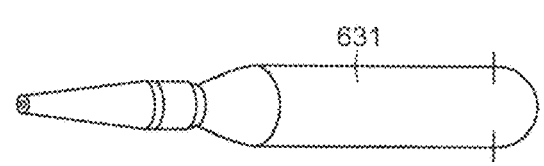
FIG. 83
FIG. 82
FIG. 84
FIG. 85

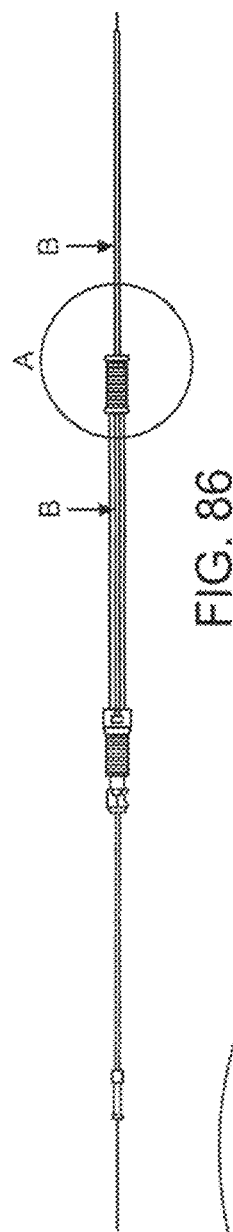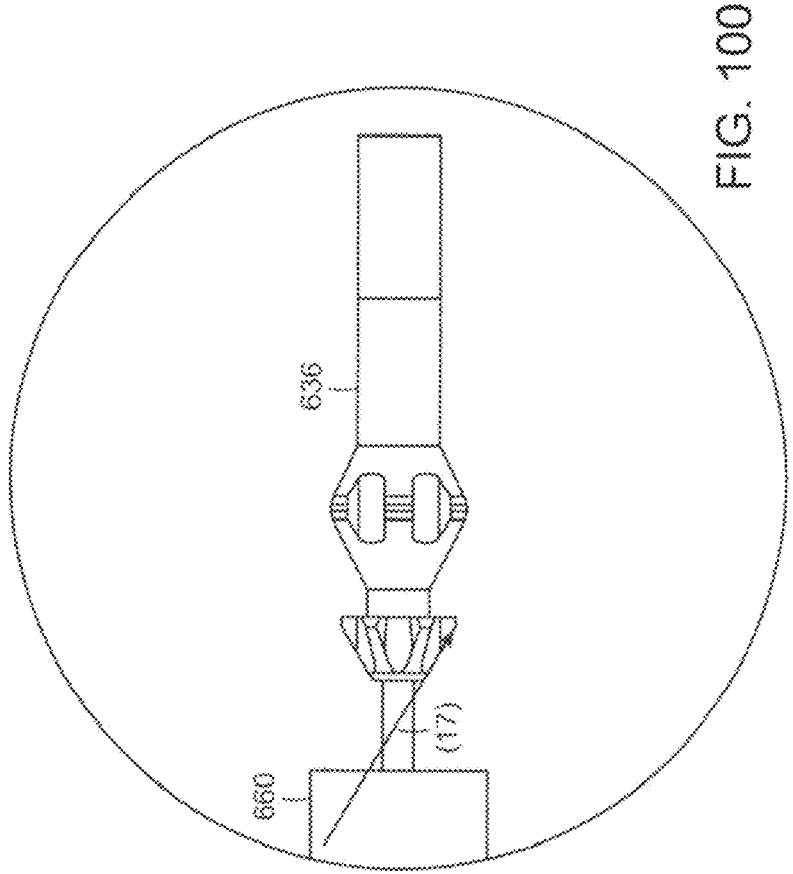

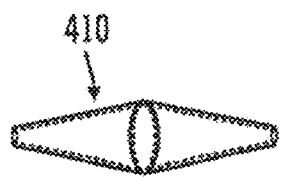
FIG. 127
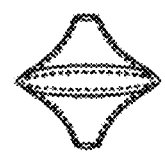
FIG. 128
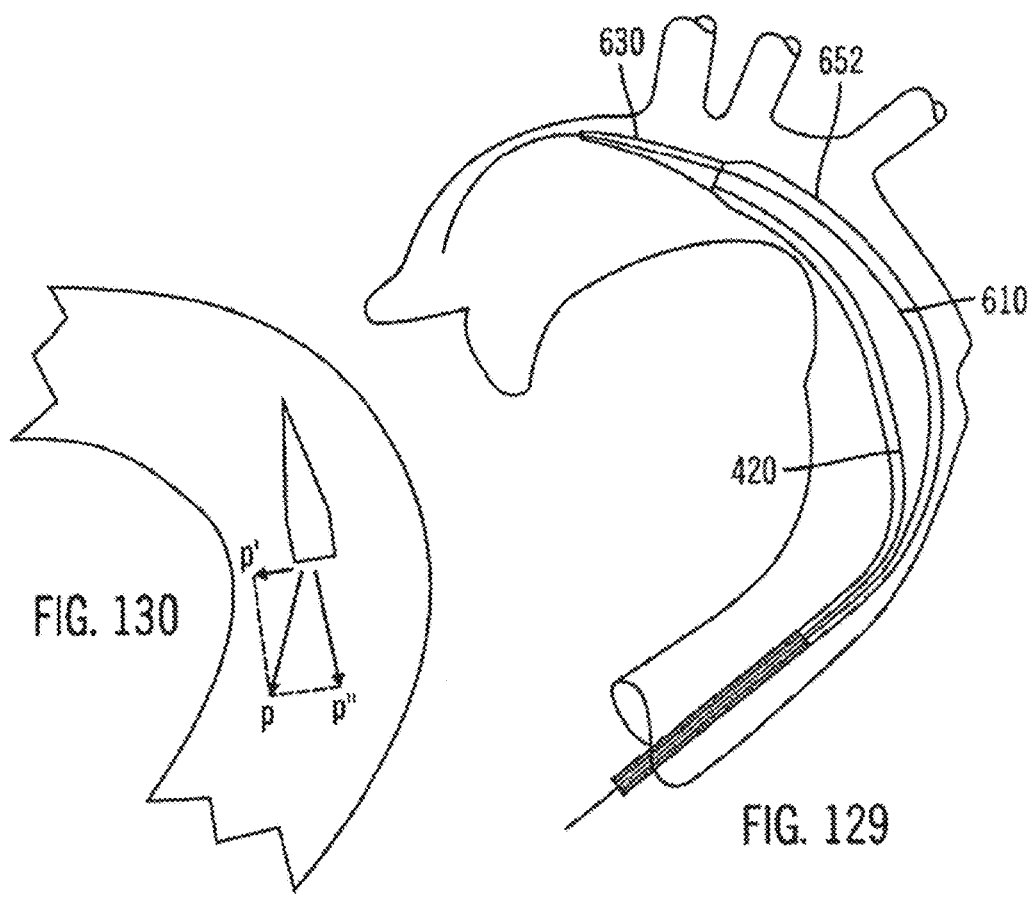
FIG. 130
FIG. 129

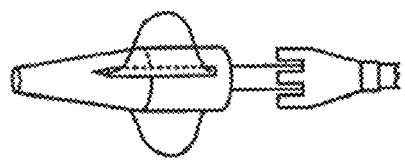
FIG. 136  FIG. 137
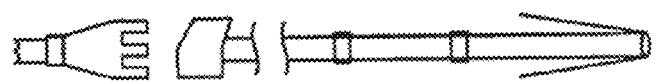
FIG. 138
 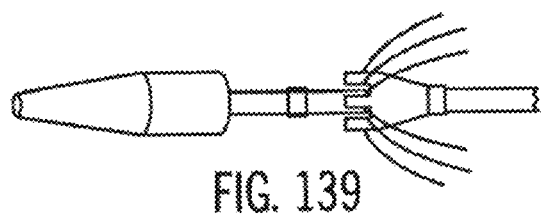
FIG. 140  FIG. 139
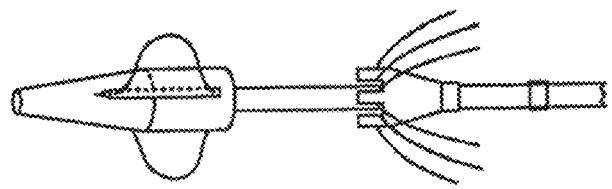
FIG. 141

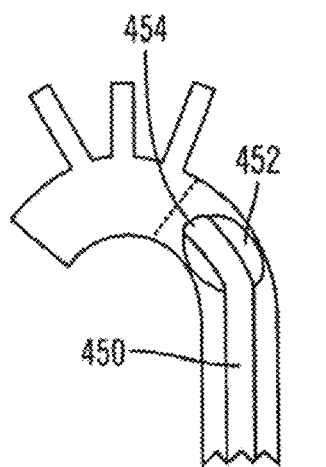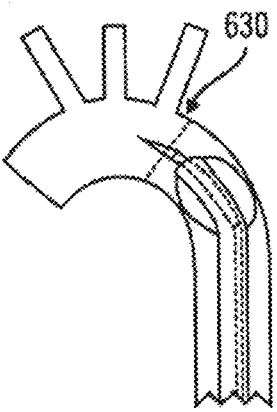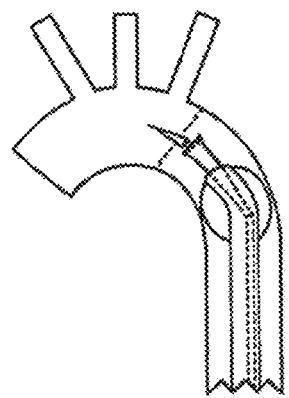
FIG. 147  FIG. 148  FIG. 149
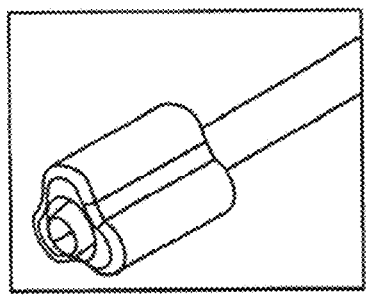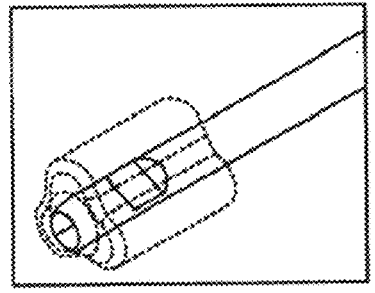
FIG. 150A  FIG. 150B
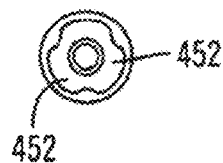
FIG. 151

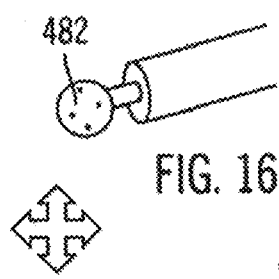
FIG. 161
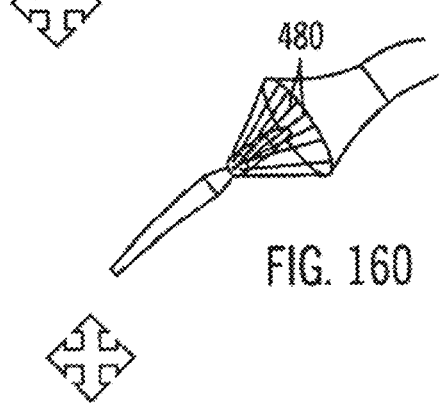
FIG. 160
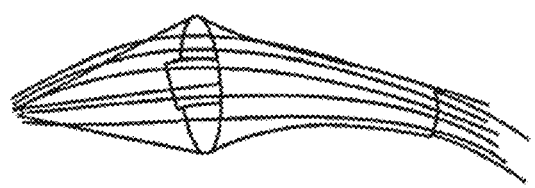
FIG. 162
FIG. 163

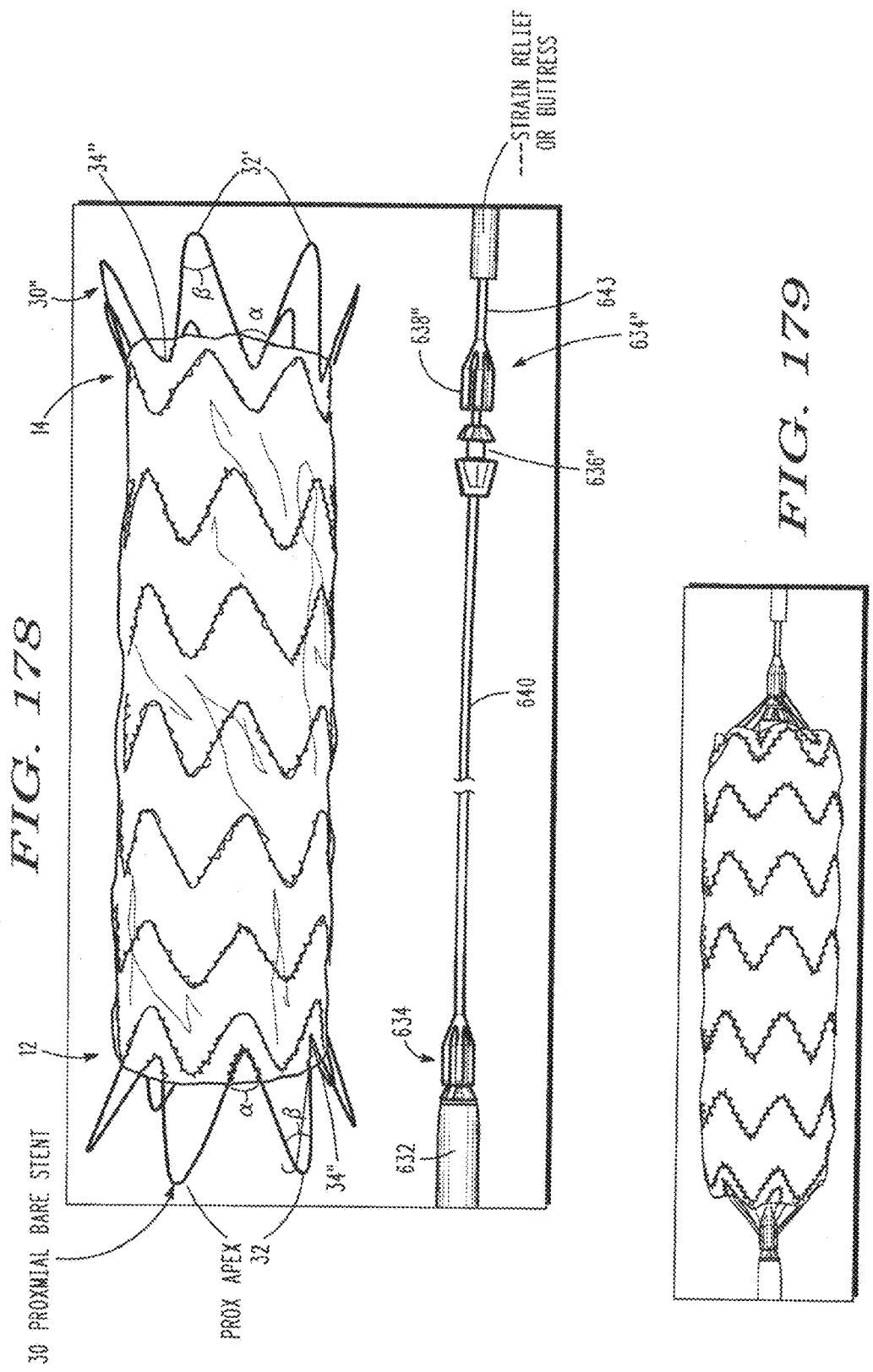

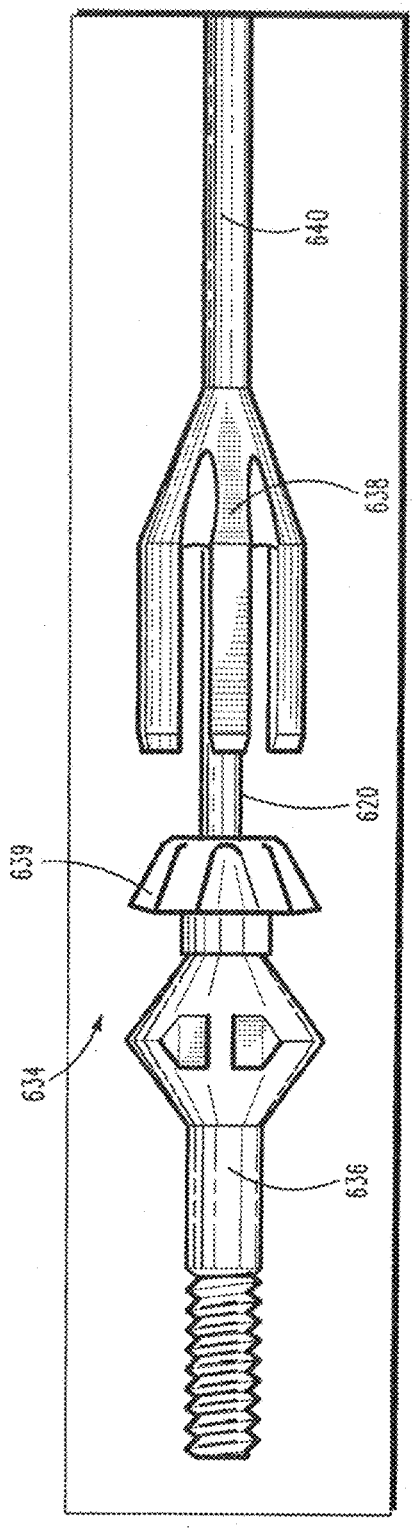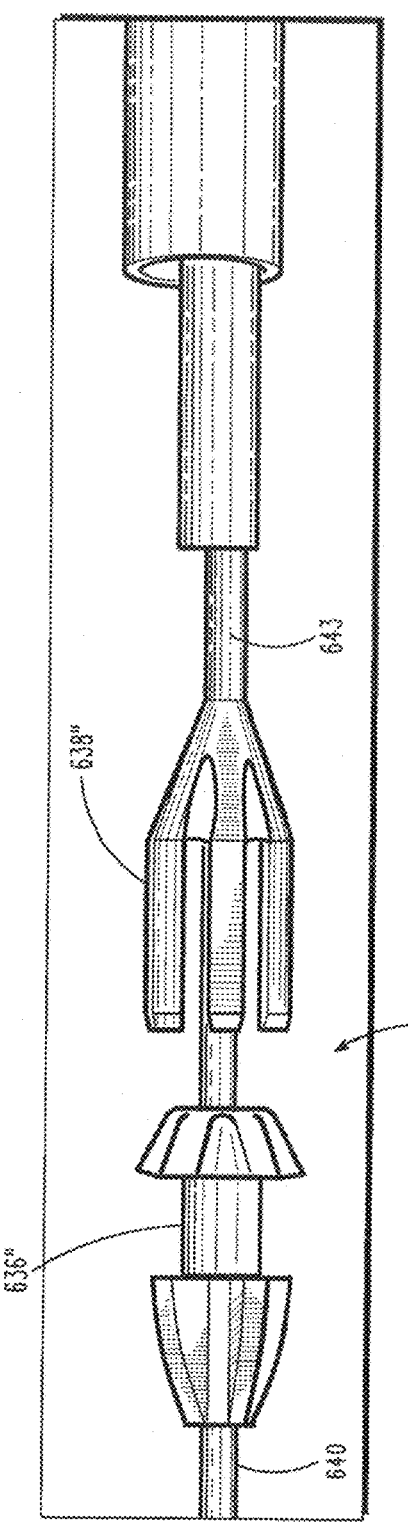

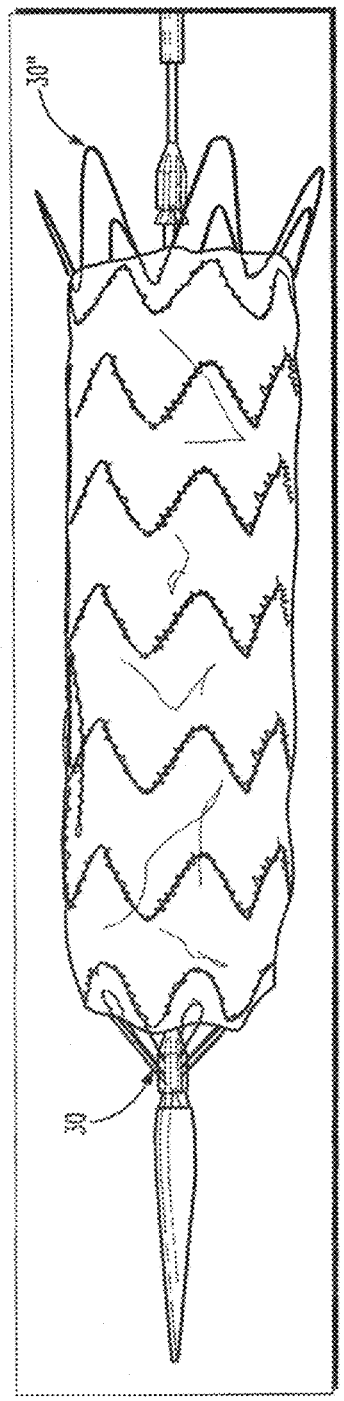
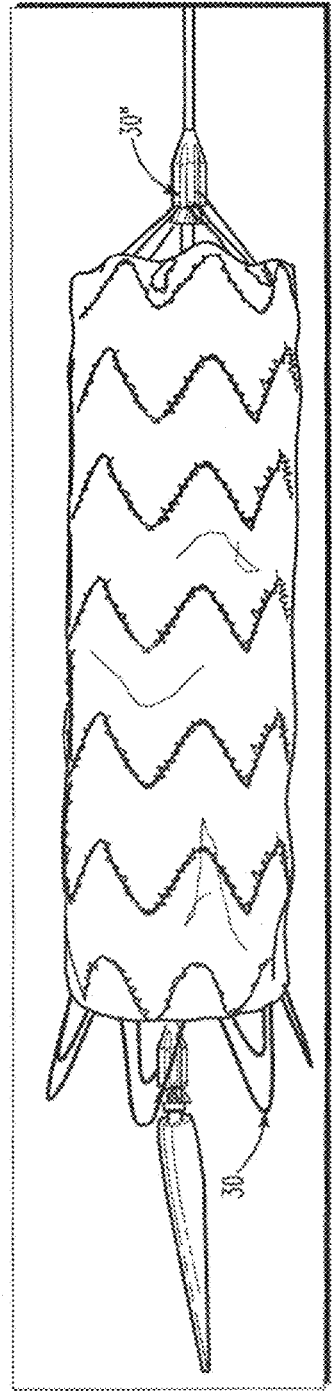
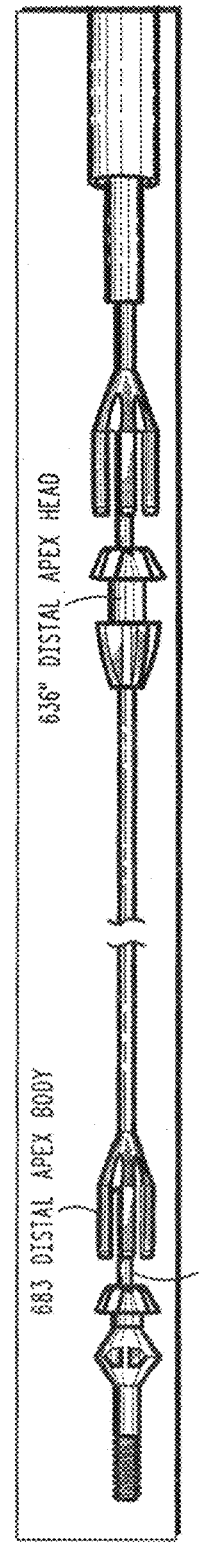
FIG. 182
FIG. 183
FIG. 184

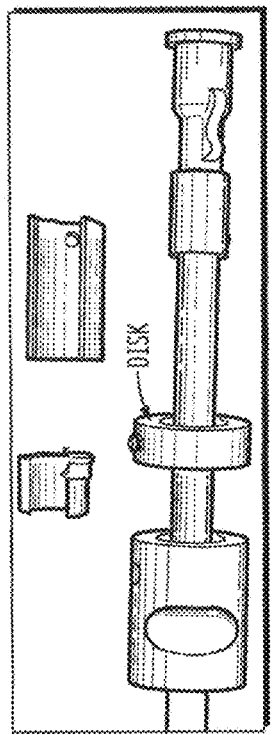
FIG. 186
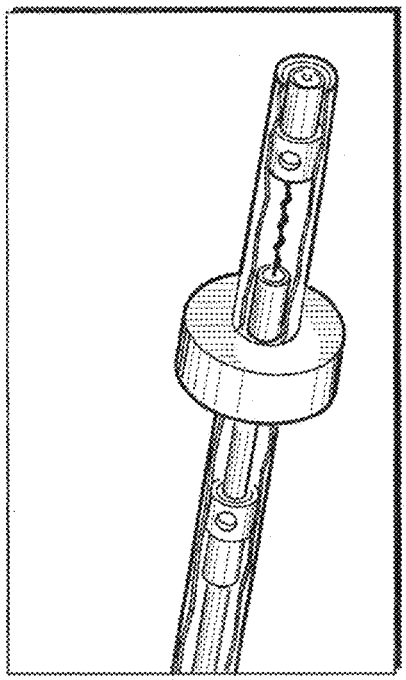
FIG. 187
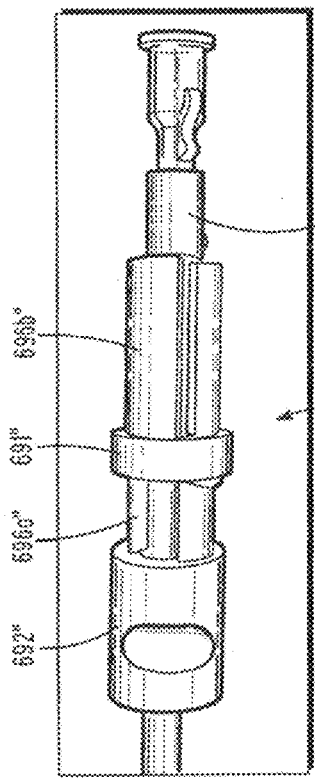
FIG. 185
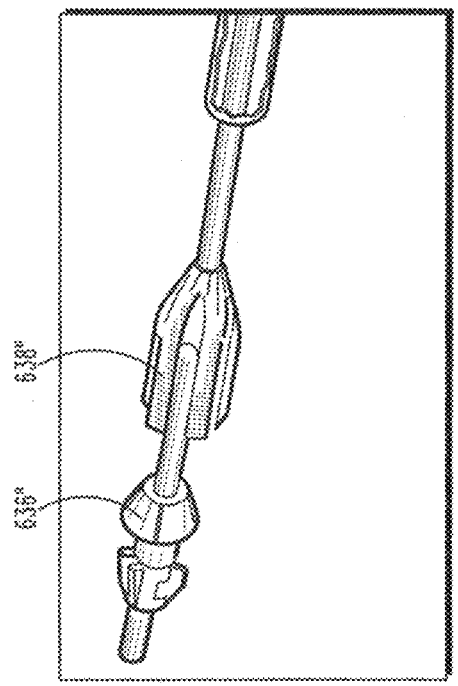

DUAL CAPTURE DEVICE FOR STENT GRAFT DELIVERY SYSTEM AND METHOD FOR CAPTURING A STENT GRAFT

RELATED APPLICATIONS

This application is a continuation of U.S. application Ser. No. 14/300,647, filed Jun. 10, 2014, which is a continuation of U.S. application Ser. No. 13/959,004, filed Aug. 5, 2013, now abandoned, which is a continuation of U.S. application Ser. No. 12/415,728, filed Mar. 31, 2009, now U.S. Pat. No. 8,500,792, which claims the benefit of U.S. Provisional Application No. 61/041,432, filed Apr. 1, 2008. U.S. application Ser. No. 12/415,728 is a continuation-in-part of U.S. application Ser. No. 11/701,867, filed Feb. 1, 2007, which claims the benefit of U.S. Provisional Application Nos. 60/765,449, filed Feb. 3, 2006 and 60/833,533, filed Jul. 26, 2006. U.S. application Ser. No. 12/415,728 is also a continuation-in-part of U.S. application Ser. No. 11/828,653, filed Jul. 26, 2007, now abandoned, which claims the benefit of U.S. Provisional Application No. 60/833,533, filed Jul. 26, 2006. U.S. application Ser. No. 12/415,728 is also a continuation-in-part of U.S. application Ser. No. 11/828,675, filed Jul. 26, 2007, now U.S. Pat. No. 8,062,345, which claims the benefit of U.S. Provisional Application No. 60/833,533, filed Jul. 26, 2006. U.S. application Ser. No. 12/415,728 is also a continuation-in-part of U.S. application Ser. No. 10/784,462, filed Feb. 23, 2004, now U.S. Pat. No. 8,292,943, which claims the benefit of U.S. Provisional Application Nos. 60/499,652, filed Sep. 3, 2003 and 60/500,155, filed Sep. 4, 2003. U.S. application Ser. No. 12/415,728 is also a continuation-in-part of U.S. application Ser. No. 10/884,136, filed Jul. 2, 2004, now U.S. Pat. No. 7,763,063, which claims the benefit of U.S. Provisional Application Nos. 60/499,652, filed Sep. 3, 2003 and 60/500,155, filed Sep. 4, 2003. U.S. application Ser. No. 12/415,728 is also a continuation-in-part of U.S. application Ser. No. 11/348,176, filed Feb. 6, 2006, now U.S. Pat. No. 8,308,790; Ser. No. 11/353,927, filed Feb. 13, 2006, now U.S. Pat. No. 8,070,790; Ser. No. 11/449,337, filed Jun. 8, 2006, now U.S. Pat. No. 8,740,963; Ser. No. 11/699,700, filed Jan. 30, 2007, now abandoned; Ser. No. 11/699,701, filed Jan. 30, 2007, now U.S. Pat. No. 8,007,605; Ser. No. 11/700,510, filed Jan. 31, 2007, now U.S. Pat. No. 8,062,349; Ser. No. 11/700,609, filed Jan. 31, 2007; and Ser. No. 11/701,876, filed Feb. 1, 2007, now abandoned. U.S. application Ser. No. 11/701,876 claims the benefit of U.S. Provisional Application Nos. 60/851,282, filed Oct. 12, 2006; 60/833,533, filed Jul. 26, 2006 and 60/765,449, filed Feb. 3, 2006.

The entire teachings of the above applications are incorporated herein by reference.

BACKGROUND OF THE INVENTION

Field of the Invention

The invention lies in the field of endoluminal blood vessel repairs. The invention specifically relates to a delivery system and method for self-centering a proximal end of a stent graft, for example, for endoluminally repairing aneurysm and/or dissections of the thoracic transverse aortic arch, thoracic posterior aortic arch, and the descending thoracic portion of the aorta. The present invention lies in the field of prosthesis delivery systems, in particular, to a stent capture device for releasably holding a stent graft in an endovascular stent graft delivery system and methods for capturing the stent graft in a delivery system for implantation.

Description of the Related Art

A stent graft is an implantable device made of a tube-shaped surgical graft covering and an expanding or self-expanding frame. The stent graft is placed inside a blood vessel to bridge, for example, an aneurismal, dissected, or other diseased segment of the blood vessel, and, thereby, exclude the hemodynamic pressures of blood flow from the diseased segment of the blood vessel.

In selected patients, a stent graft advantageously eliminates the need to perform open thoracic or abdominal surgical procedures to treat diseases of the aorta and eliminates the need for total aortic reconstruction. Thus, the patient has less trauma and experiences a decrease in hospitalization and recovery times. The time needed to insert a stent graft is substantially less than the typical anesthesia time required for open aortic bypass surgical repair, for example.

Use of surgical and/or endovascular grafts have widespread use throughout the world in vascular surgery. There are many different kinds of vascular graft configurations. Some have supporting framework over their entirety, some have only two stents as a supporting framework, and others simply have the tube-shaped graft material with no additional supporting framework, an example that is not relevant to the present invention.

One of the most commonly known supporting stent graft frameworks is that disclosed in U.S. Pat. Nos. 5,282,824 and 5,507,771 to Gianturco (hereinafter collectively referred to as "Gianturco"). Gianturco describes a zig-zag-shaped, self-expanding stent commonly referred to as a z-stent. The stents are, preferably, made of nitinol, but also have been made from stainless steel and other biocompatible materials.

There are various features characterizing a stent graft. The first significant feature is the tube of graft material. This tube is commonly referred to as the graft and forms the tubular shape that will, ultimately, take the place the diseased portion of the blood vessel. The graft is, preferably, made of a woven sheet (tube) of polyester or PTFE. The circumference of the graft tube is, typically, at least as large as the diameter and/or circumference of the vessel into which the graft will be inserted so that there is no possibility of blood flowing around the graft (also referred to as endoleak) to either displace the graft or to reapply hemodynamic pressure against the diseased portion of the blood vessel. Accordingly, to so hold the graft, self-expanding frameworks are attached typically to the graft material, whether on the interior or exterior thereof. Because blood flow within the lumen of the graft could be impaired if the framework was disposed on the interior wall of the graft, the framework is connected typically to the exterior wall of the graft. The ridges formed by such an exterior framework help to provide a better fit in the vessel by providing a sufficiently uneven outer surface that naturally grips the vessel where it contacts the vessel wall and also provides areas around which the vessel wall can endothelialize to further secure the stent graft in place.

One of the significant dangers in endovascular graft technology is the possibility of the graft migrating from the desired position in which it is installed. Therefore, various devices have been created to assist in anchoring the graft to the vessel wall.

One type of prior art prosthetic device is a stent graft made of a self-expanding metallic framework. For delivery, the stent graft is, first, radially compressed and loaded into an introducer system that will deliver the device to the target area. When the introducer system holding the stent graft positioned in an appropriate location in the vessel and allowed to open, the radial force imparted by the self-expanding framework is helpful, but, sometimes, not entirely sufficient, in endoluminally securing the stent graft within the vessel.

U.S. Pat. No. 5,824,041 to Lenker et al. (hereinafter "Lenker") discloses an example of it stent graft delivery system. Lenker discloses various embodiments in which a sheath is retractable proximally over a prosthesis to be released. With regard to FIGS. 7 and 8, Lenker names components 72 and 76, respectively, as "sheath" and "prosthesis-containment sheath." However, the latter is merely the catheter in which the prosthesis 74 and the sheath 72 are held. With regard to FIGS. 9 and 10, the sheath 82 has inner and outer layers 91, 92 fluid-tightly connected to one another to form a ballooning structure around the prosthesis P. This ballooning structure inflates when liquid is inflated with a non-compressible fluid medium and flares radially outward when inflated. With regard to FIGS. 13 to 15, Lenker discloses the "sheath" 120, which is merely the delivery catheter, and an eversible membrane 126 that "folds back over itself (everts) as the sheath 120 is refracted so that there are always two layers of the membrane between the distal end of the sheath [120] and the prosthesis P." Lenker at col. 9, lines 63 to 66. The eversion (peeling back) is caused by direct connection of the distal end 130 to the sheath 120. The Lenker delivery system shown in FIGS. 19A to 19D holds the prosthesis P at both ends 256, 258 while an outer catheter 254 is retracted over the prosthesis P and the inner sheath 260. The inner sheath 260 remains inside the outer catheter 254 before, during, and after retraction. Another structure for holding the prosthesis P at both ends is illustrated in FIGS. 23A and 23B. Therein, the proximal holder having resilient axial members 342 is connected to a proximal ring structure 346. FIGS. 24A to 24C also show an embodiment for holding the prosthesis at both ends inside thin-walled tube 362.

To augment radial forces of stents, some prior art devices have added proximal and/or distal stents that are not entirely covered by the graft material. By not covering with graft material a portion of the proximal/distal ends of the stent, these stents have the ability to expand further radially than those stents that are entirely covered by the graft material. By expanding further, the proximal/distal stent ends better secure to the interior wall of the vessel and, in doing so, press the extreme cross-sectional surface of the graft ends into the vessel wall to create a fixated blood-tight seal.

One example of such a prior art exposed stent can be found in United States Patent Publication US 2002/0198587 to Greenberg et al. The modular stent graft assembly therein has a three-part stent graft: a two-part graft having an aortic section 12 and an iliac section 14 (with four sizes for each) and a contralateral iliac occluder 80. FIGS. 1, 2, and 4 to 6 show the attachment stent 32. As illustrated in FIGS. 1, 2, and 4, the attachment stent 32, while rounded, is relatively sharp and, therefore, increases the probability of puncturing the vessel.

A second example of a prior art exposed stent can be found in U.S. Patent Publication 2003/0074049 to Hoganson et al. (hereinafter "Hoganson"), which discloses a covered stent 10 in which the elongated portions or sections 24 of the ends 20a and 20b extend beyond the marginal edges of the cover 22. See Hoganson at FIGS. 1, 3, 9, 11a, 11b, 12a, 12b, and 13. However, these extending exposed edges are triangular, with sharp apices pointing both upstream and downstream with regard to a graft placement location. Such a configuration of the exposed stent 20a, 20b increases the possibility of puncturing the vessel. In various embodiments shown in FIGS. 6a, 6b, 6c, 10, 14a, Hoganson teaches completely covering the extended stent and, therefore, the absence of a stent extending from the cover 22. It is noted that the Hoganson stent is implanted by inflation of a balloon catheter.

Another example of a prior art exposed stent can be found in U.S. Pat. No. 6,565,596 to White et al. (hereinafter "White I"), which uses a proximally extending stent to prevent twisting or kinking and to maintain graft against longitudinal movement. The extending stent is expanded by a balloon and has a sinusoidal amplitude greater than the next adjacent one or two sinusoidal wires. White I indicates that it is desirable to space wires adjacent upstream end of graft as close together as is possible. The stent wires of White I are actually woven into graft body by piercing the graft body at various locations. See White I at FIGS. 6 and 7. Thus, the rips in the graft body can lead to the possibility of the exposed stent moving with respect to the graft and of the graft body ripping further. Between the portions of the extending stent 17, the graft body has apertures.

The stent configuration of U.S. Pat. No. 5,716,393 to Lindenberg et al. is similar to White I in that the outermost portion of the one-piece stent—made from a sheet that is cut/punched and then rolled into cylinder—has a front end with a greater amplitude than the remaining body of the stent.

A further example of a prior art exposed stent can be found in U.S. Pat. No. 6,524,335 to Hartley et al. (hereinafter "Hartley"). FIGS. 1 and 2 of Hartley particularly disclose a proximal first stent 1 extending proximally from graft proximal end 4 with both the proximal and distal apices narrowing to pointed ends.

Yet another example of a prior art exposed stent can be found in U.S. Pat. No. 6,355,056 to Pinheiro (hereinafter "Pinheiro I"). Like the Hartley exposed stent, Pinheiro discloses exposed stents having triangular, sharp proximal apices.

Still a further example of a prior art exposed stent can be found in U.S. Pat. No. 6,099,558 to White et al. (hereinafter "White II"). The White II exposed stent is similar to the exposed stent of White I and also uses a balloon to expand the stent.

An added example of a prior art exposed stent can be found in U.S. Pat. No. 5,871,536 to Lazarus, which discloses two support members 68 longitudinally extending from proximal end to a rounded point. Such points, however, create a very significant possibility of piercing the vessel.

An additional example of a prior art exposed stent can be found in U.S. Pat. No. 5,851,228 to Pinheiro (hereinafter "Pinheiro II"). The Pinheiro II exposed stents are similar to the exposed stents of Pinheiro I and, as such, have triangular, sharp, proximal apices.

Still another example of a prior art exposed stent can be found in Lenker (U.S. Pat. No. 5,824,041), which shows a squared-off end of the proximal and distal exposed band members 14. A portion of the exposed members 14 that is attached to the graft material 18, 20 is longitudinally larger than a portion of the exposed members 14 that is exposed and extends away from the graft material 18, 20. Lenker et al. does not describe the members 14 in any detail.

Yet a further example of a prior art exposed stent can be found in U.S. Pat. No. 5,824,036 to Lauterjung, which, of all of the prior art embodiments described herein, shows the most pointed of exposed stents. Specifically, the proximal ends of the exposed stent are apices pointed like a minaret. The minaret points are so shaped intentionally to allow forks 300 (see Lauterjung at FIG. 5) external to the stent 154 to pull the stent 154 from the sheath 302, as opposed to being pushed.

A final example of a prior art exposed stent can be found in U.S. Pat. No. 5,755,778 to Kleshinski. The Kleshinski exposed stents each have two different shaped portions, a triangular base portion and a looped end portion. The totality of each exposed cycle resembles a castellation. Even though the end-most portion of the stent is curved, because it is relatively narrow, it still creates the possibility of piercing the vessel wall.

All of these prior art stents suffer from the disadvantageous characteristic that the relatively sharp proximal apices of the exposed stents have a shape that is likely to puncture the vessel wall.

Devices other than exposed stents have been used to inhibit graft migration. A second of such devices is the placement of a relatively stiff longitudinal support member longitudinally extending along the entirety of the graft.

The typical stent graft has a tubular body and a circumferential framework. This framework is not usually continuous. Rather, it typically takes the form of a series of rings along the tubular graft. Some stent grafts have only one or two of such rings at the proximal and/or distal ends and some have many stents tandemly placed along the entirety of the graft material. Thus, the overall stent graft has an "accordion" shape. During the systolic phase of each cardiac cycle, the hemodynamic pressure within the vessel is substantially parallel with the longitudinal plane of the stent graft. Therefore, a device having unsecured stents, could behave like an accordion or concertina with each systolic pulsation, and may have a tendency to migrate downstream. (A downstream migration, to achieve forward motion, has a repetitive longitudinal compression and extension of its cylindrical body.) Such movement is entirely undesirable. Connecting the stents with support along the longitudinal extent of the device thereof can prevent such movement. To provide such support, a second anti-migration device can be embodied as a relatively stiff longitudinal bar connected to the framework.

A clear example of a longitudinal support bar can be found in Pinheiro I (U.S. Pat. No. 6,355,056) and Pinheiro II (U.S. Pat. No. 5,851,228). Each of these references discloses a plurality of longitudinally extending struts 40 extending between and directly interconnecting the proximal and distal exposed stents 20a, 20b. These struts 40 are designed to extend generally parallel with the inner lumen 15 of the graft 10, in other words, they are straight.

Another example of a longitudinal support bar can be found in U.S. Pat. No. 6,464,719 to Jayaraman. The Jayaraman stent is formed from a graft tube 21 and a supporting sheet 1 made of nitinol. This sheet is best shown in FIG. 3. The end pieces 11, 13 of the sheet are directly connected to one another by wavy longitudinal connecting pieces 15 formed by cutting the sheet 1. To form the stent graft, the sheet 1 is coiled with or around the cylindrical tube 21. See FIGS. 1 and 4. Alternatively, a plurality of connecting pieces 53 with holes at each end thereof can be attached to a cylindrical fabric tube 51 by stitching or sutures 57, as shown in FIG. 8. Jayaraman requires more than one of these serpentine shaped connecting pieces 53 to provide longitudinal support.

United States Patent Publication 2002/0016627 and U.S. Pat. No. 6,312,458 to Golds each disclose a variation of a coiled securing member 20. A different kind of supporting member is disclosed in FIG. 8 of U.S. Pat. No. 6,053,943 to Edwin et al.

Like Jayaraman, U.S. Pat. No. 5,871,536 to Lazarus discloses a plurality of straight, longitudinal support structures 38 attached to the circumferential support structures 36, see FIGS. 1, 6, 7, 8, 10, 11, 12, 14. FIG. 8 of Lazarus illustrates the longitudinal support structures 38 attached to a distal structure 36 and extending almost all of the way to the proximal structure 36. The longitudinal structures 38, 84, 94 can be directly connected to the body 22, 80 and can be telescopic 38, 64.

United States Patent Publication 2003/0088305 to Van Schie et al. (hereinafter "Van Schie") does not disclose a support bar. Rather, it discloses a curved stent graft using an elastic material 8 connected to stents at a proximal end 2 and at a distal end 3 (see FIGS. 1, 2) thereof to create a curved stent graft. Because Van Schie needs to create a flexible curved graft, the elastic material 8 is made of silicone rubber or another similar material. Thus, the material 8 cannot provide support in the longitudinal extent of the stent graft. Accordingly, an alternative to the elastic support material 8 is a suture material 25 shown in FIGS. 3 to 6.

SUMMARY OF THE INVENTION

Briefly, in accordance with the present invention, disclosed is a delivery system for delivering and deploying stents with proximal and distal apices includes first and second hollow lumens and a hollow apex release lumen, the first lumen having a distal end and an interior extending along a longitudinal axis, the second lumen having a distal end and being slidably disposed about the first lumen, and the apex release lumen having a distal end and being slidably disposed about the second lumen. A proximal apex capture device of the delivery system includes a first distal capture portion fixedly connected to the first lumen, the first distal capture portion having a first distal portion with a proximal end and a proximal stopper having a distal side disposed in a plane approximately perpendicular to the longitudinal axis being disposed at a first proximal distance from the proximal end of the first distal portion, and defining first stopping surface portions. A first proximal capture portion is fixedly connected to the distal end of the apex release lumen and has fingers extending toward the first distal capture portion in a distal direction, the fingers defining a first interior cavity shaped to receive the first proximal stopper therein, the first distal capture portion and the first proximal capture portion being formed to hold the distal apices there between and, together, defining a first stent captured state in which the first proximal stopper is received in the first interior cavity and the first proximal capture portion approximately closes off the first interior cavity along the longitudinal axis.

In accordance with another feature, an embodiment of the present invention includes a distal apex capture device with a second distal capture portion fixedly connected to the distal end of the second lumen, the distal capture portion having both a second distal portion with a second proximal end and a second proximal stopper having a distal side disposed in a plane approximately perpendicular to the longitudinal axis, being disposed at a proximal distance from the proximal end of the second distal portion, and defining second stopping surface portions. A second proximal capture portion is fixedly connected to the distal end of the second lumen and has fingers extending toward the second distal capture portion in a distal direction, the fingers defining a second interior cavity shaped to receive the second proximal stopper therein, the proximal and distal capture portions being formed to hold the proximal apices there between and, together, defining a second stent captured state in which the second proximal stopper is received in the second interior cavity and the second distal capture portion approximately closes off the second interior cavity along the longitudinal axis.

In accordance with a further feature of the present invention, the proximal end of the first distal portion and the first stopper define a first stent apex cavity and the first proximal and the first distal capture portions are formed to hold the proximal apices in the first stent apex cavity.

In accordance with a further feature of the present invention, the proximal end of the second distal portion and the second stopper define a second stent apex cavity and the second proximal and the second distal capture portions are formed to hold the distal apices in the second stent apex cavity.

In accordance with the present invention, the proximal end of the second distal portion and the second stopper define a second stent apex cavity, the second proximal and the second distal capture portions are formed to hold the second proximal apices in the second stent apex cavity, and relative movement of the second and said apex release lumen moves the second proximal and the second distal capture portions with respect to one another to substantially close the second stent apex cavity and, thereby, place the second proximal and the second distal capture portions in the second captured state.

BRIEF DESCRIPTION OF THE DRAWINGS

The features of the present invention, which are believed to be novel, are set forth with particularity in the appended claims. The invention, together with further objects and advantages thereof, may best be understood by reference to the following description, taken in conjunction with the accompanying drawings, in the several figures of which like reference numerals identify like elements, and in which:

FIG. 4 is a perspective view of a prior art round mandrel for forming prior art stents;

FIG. 5 is a fragmentary, side elevational view of a prior art stent in a portion of a vessel;

FIG. 6 is a perspective view of a dodecahedral-shaped mandrel for forming stents in FIGS. 1 to 3;

FIG. 7 is a fragmentary, side elevational view of the stent of FIGS. 1 to 3 in a portion of a vessel;

FIG. 8 is a fragmentary, enlarged side elevational view of the proximal end of the stent graft of FIG. 1 illustrating movement of a gimbaled end;

FIG. 9 is a side elevational view of a two-part stent graft according to the invention;

FIG. 10 is a fragmentary, side elevational view of a delivery system according to the invention with a locking ring in a neutral position;

FIG. 11 is a fragmentary, side elevational view of the delivery system of FIG. 10 with the locking ring in an advancement position and, as indicated by dashed lines, a distal handle and sheath assembly in an advanced position;

FIG. 12 is a fragmentary, enlarged view of a sheath assembly of the delivery system of FIG. 10;

FIG. 15 is a fragmentary, enlarged view of an apex release assembly of the delivery system of FIG. 10 in the captured position;

FIG. 16 is a fragmentary, enlarged view of the apex release assembly of FIG. 15 in the captured position with an intermediate part removed;

FIG. 17 is a fragmentary, enlarged view of the apex release assembly of FIG. 16 in the released position;

FIG. 18 is a fragmentary, side elevational view of the delivery system of FIG. 11 showing how a user deploys the prosthesis;

FIG. 19 is a fragmentary cross-sectional view of human arteries including the aorta with the assembly of the present invention in a first step of a method for inserting the prosthesis according to the invention;

FIG. 20 is a fragmentary cross-sectional view of the arteries of FIG. 19 with the assembly in a subsequent step of the method for inserting the prosthesis;

FIG. 21 is a fragmentary cross-sectional view of the arteries of FIG. 20 with the assembly in a subsequent step of the method for inserting the prosthesis;

FIG. 22 is a fragmentary cross-sectional view of the arteries of FIG. 21 with the assembly in a subsequent step of the method for inserting the prosthesis;

FIG. 23 is a fragmentary cross-sectional view of the arteries of FIG. 22 with the assembly in a subsequent step of the method for inserting the prosthesis;

FIG. 24 is a fragmentary cross-sectional view of the arteries of FIG. 23 with the assembly in a subsequent step of the method for inserting the prosthesis;

FIG. 34 is a cross-sectional view of a pusher clasp rotator of the handle assembly of FIG. 33;

FIG. 35 is a plan view of the pusher clasp rotator of FIG. 34 viewed along line C-C;

FIG. 36 is a plan and partially hidden view of the pusher clasp rotator of FIG. 34 with a helix groove for a first embodiment of the handle assembly of FIGS. 10, 11, and 18;

FIG. 37 is a cross-sectional view of the pusher clasp rotator of FIG. 36 along section line A-A;

FIG. 38 is a plan and partially hidden view of the pusher clasp rotator of FIG. 36;

FIG. 39 is a cross-sectional view of the pusher clasp rotator of FIG. 38 along section line B-B;

FIG. 40 is a perspective view of a rotator body of the handle assembly of FIG. 33;

FIG. 41 is an elevational and partially hidden side view of the rotator body of FIG. 40;

FIG. 42 is a cross-sectional view of the rotator body of FIG. 41 along section line A-A;

FIG. 43 is an elevational and partially hidden side view of the rotator body of FIG. 40;

FIG. 50 is a fragmentary, exploded side elevational view of a portion of a second embodiment of the handle assembly according to the invention;

FIG. 51 is a fragmentary, side elevational view of the portion of FIG. 50 in a neutral position;

FIG. 59 is a fragmentary and partially hidden side elevational view of a clasp sleeve of the second embodiment of the handle assembly;

FIG. 60 is a fragmentary, cross-sectional view of a portion the clasp sleeve of FIG. 59 along section line A;

FIG. 61 is a fragmentary, cross-sectional view of the clasp sleeve of FIG. 59 along section line C-C;

FIG. 62 is a fragmentary and partially hidden side elevational view of the clasp sleeve of FIG. 59 rotated with respect to FIG. 59;

FIG. 70 is a side elevational view of a stent graft according to the invention;

FIG. 71 is a side elevational view of an alternative embodiment of the stent graft with a clasping stent and a crown stent;

FIG. 75 is a photograph of a perspective view from a distal end of the stent graft of FIG. 71 with an alternative embodiment of the crown stent where less of the stent is attached to the graft;

FIG. 76 is a photograph of a side view of the stent graft of FIG. 71 partially withdrawn from a flexible sheath of the delivery system according to the invention with some of the capture stent apices releasably held within the apex capture device of the delivery system;

FIG. 77 is a photograph of a perspective view of the captured stent graft of FIG. 76 from the proximal end thereof and with some of the capture stent apices releasably held within the apex capture device of the delivery system;

FIG. 82 is a fragmentary, side elevational view of a distal end of the delivery system according to the invention with the inner sheath in a curved orientation and having an alternative embodiment of a D-shaped marker thereon;

FIG. 83 is a fragmentary, plan view of the distal end of FIG. 82 viewed from above;

FIG. 84 is a fragmentary, plan and partially hidden view of the distal end of FIG. 82 viewed from below with the D-shaped marker on the opposite top side;

FIG. 85 is a fragmentary, elevational view of the distal end of FIG. 82 viewed from the top of FIG. 82 and parallel to the longitudinal axis of the catheter of the delivery system;

FIG. 86 is a side elevational view of the delivery system according to the invention with an alternative embodiment of a rotating distal handle;

FIG. 100 is a fragmentary, enlarged, side elevational view of the distal end of the delivery system of FIG. 90;

FIG. 119 is a fragmentary, shaded, cross-sectional view of a distal portion of the handle assembly of FIG. 90 without the proximal handle;

FIG. 120 is a fragmentary, diagrammatic cross-sectional view of the thoracic aorta with a prior art stent graft having an inflow plane at an angle to an implant plane;

FIG. 121 is a fragmentary, diagrammatic cross-sectional view of the thoracic aorta with a stent graft placed according to the invention with the inflow plane aligned with the implant plane;

FIG. 122 is a diagrammatic, side elevational view of a first exemplary embodiment of a stent graft centering device according to the invention;

FIG. 123 is a fragmentary, diagrammatic, cross-sectional view of the stent graft centering device of FIG. 122 in an aorta;

FIG. 124 is a fragmentary, diagrammatic, perspective view of a second exemplary embodiment of a stent graft centering device according to the invention;

FIG. 125 is a fragmentary, diagrammatic, cross-sectional view of the stent graft centering device of FIG. 124 with one balloon inflated in an aorta;

FIG. 126 is a diagrammatic, plan view of the stent graft centering device of FIG. 124 with three balloons inflated;

FIG. 127 is a diagrammatic, hidden, perspective view of a fourth exemplary embodiment of a stent graft centering device according to the invention in a first position;

FIG. 128 is a diagrammatic, hidden, perspective view of the stent graft centering device of FIG. 127 in a second position;

FIG. 129 is a fragmentary, diagrammatic, cross-sectional view of a fifth exemplary embodiment of a stent graft centering device according to the invention;

FIG. 130 is a fragmentary, diagrammatic, cross-sectional illustration forces acting upon the stent graft centering device of FIG. 129;

Figure 131:
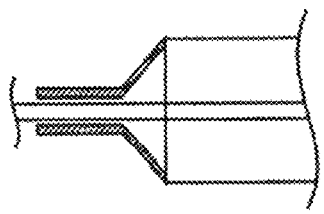
Figure 132:
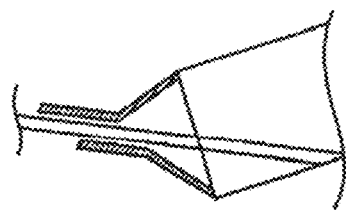
Figure 133:
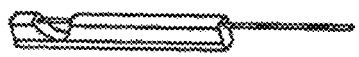
Figure 134:
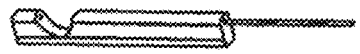
Figure 135:
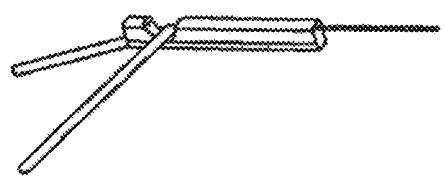
Figure 142:
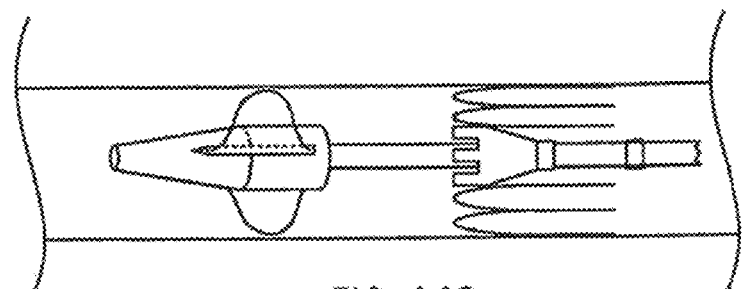
Figure 143:
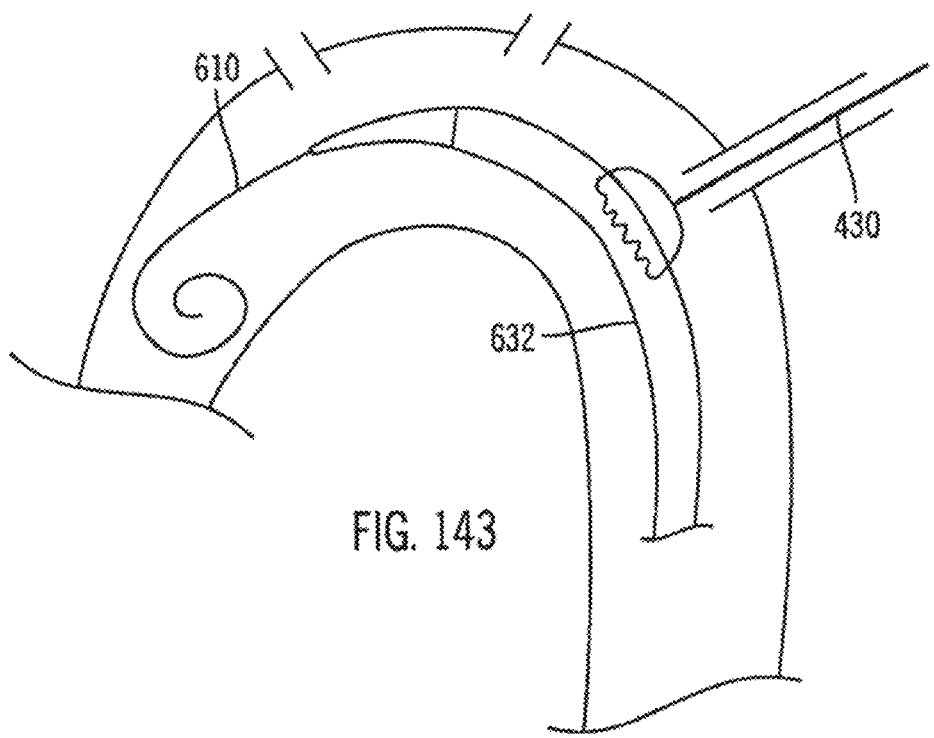
Figure 144:
Figure 145:
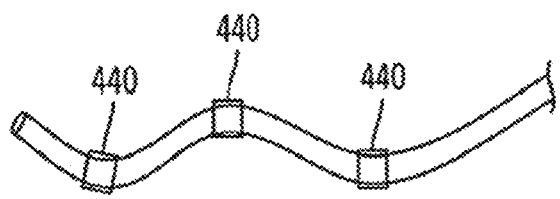
Figure 146:
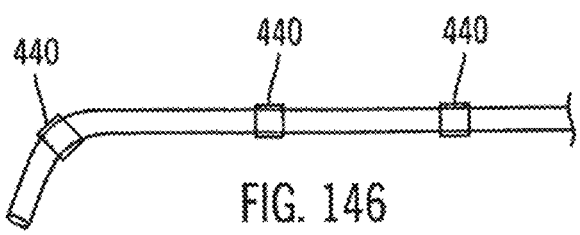
Figures 152, 153, 154:
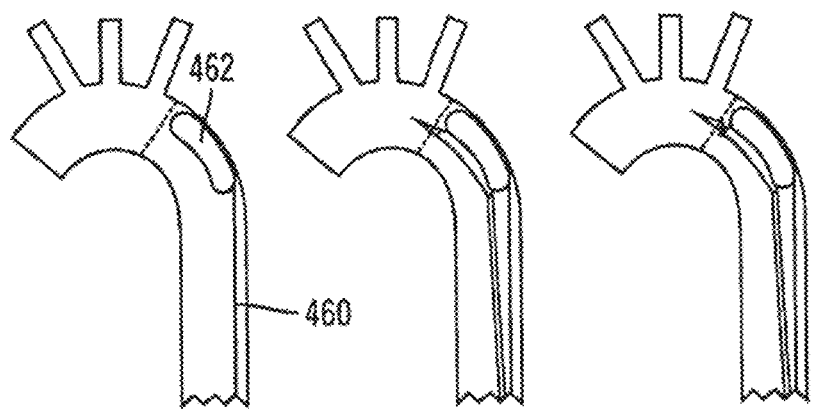
Figure 155:
Figure 156:
Figure 157:
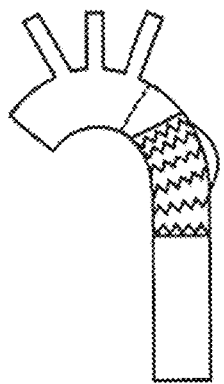
Figure 158:
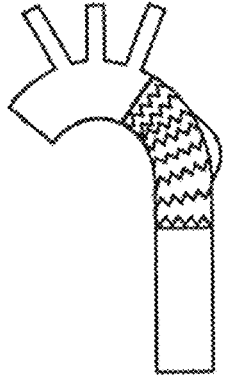
Figure 159:
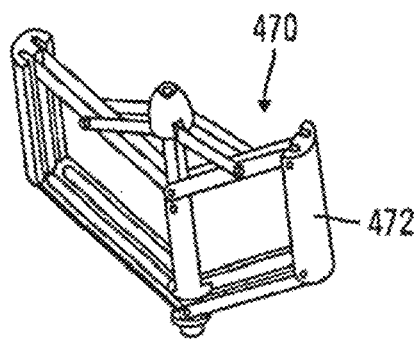
Figure 164:
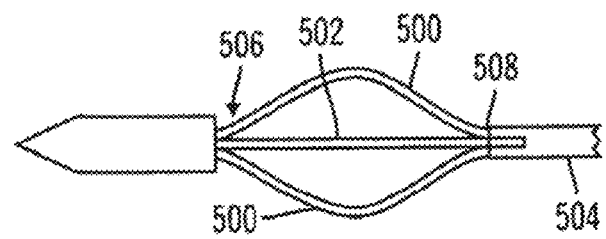
Figure 165:
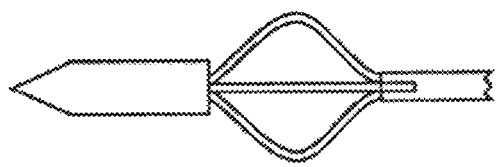
Figure 166:
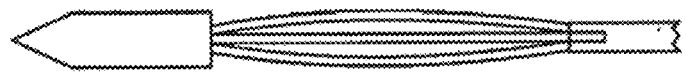
Figure 167:
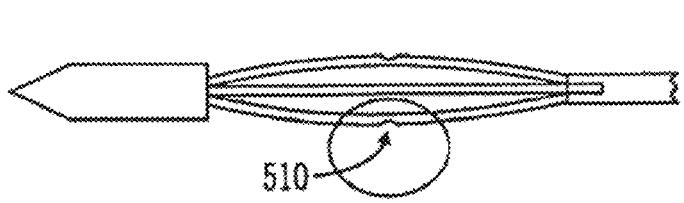
Figure 167A:
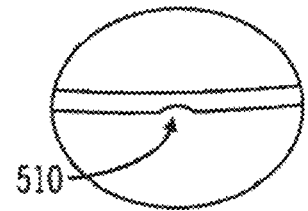
Figure 168:
Figure 169:
Figure 170:
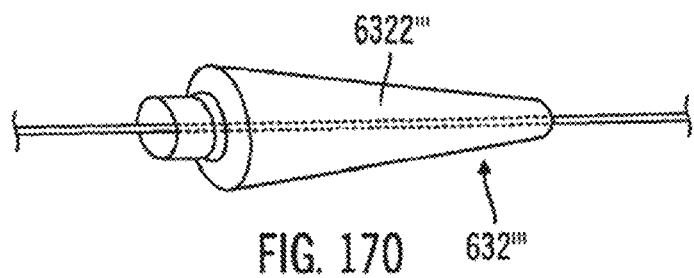
Figure 171:
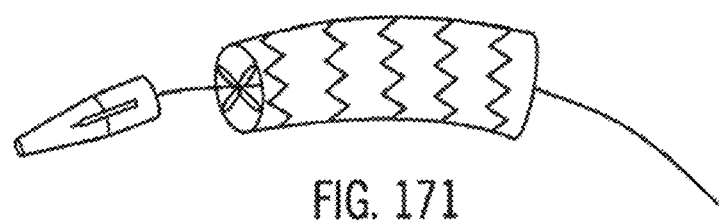
Figure 172:
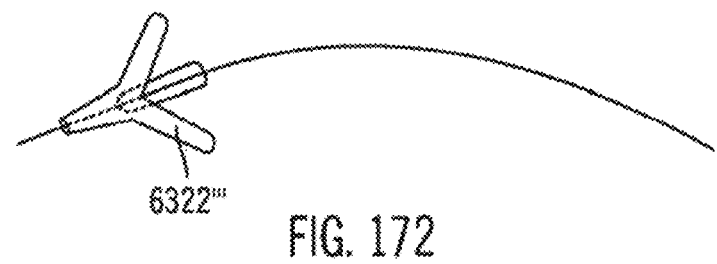
Figure 173:
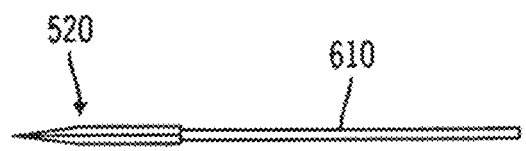
Figure 174:
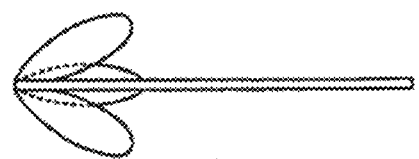
Figure 175:
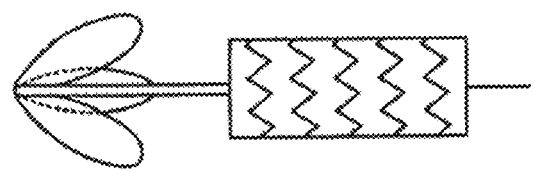
Figure 176:
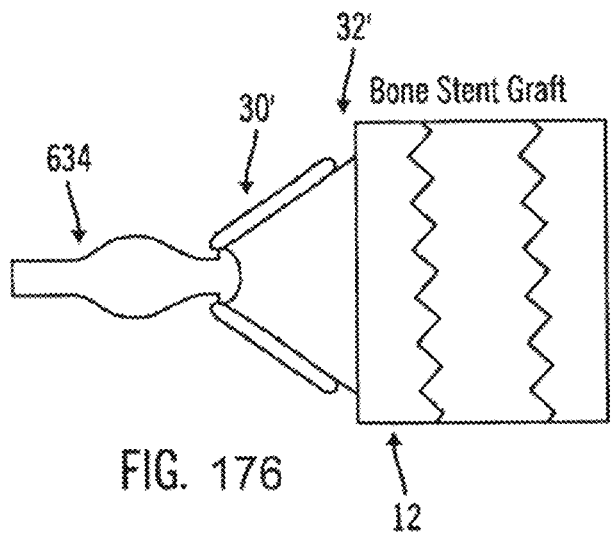
Figure 177:
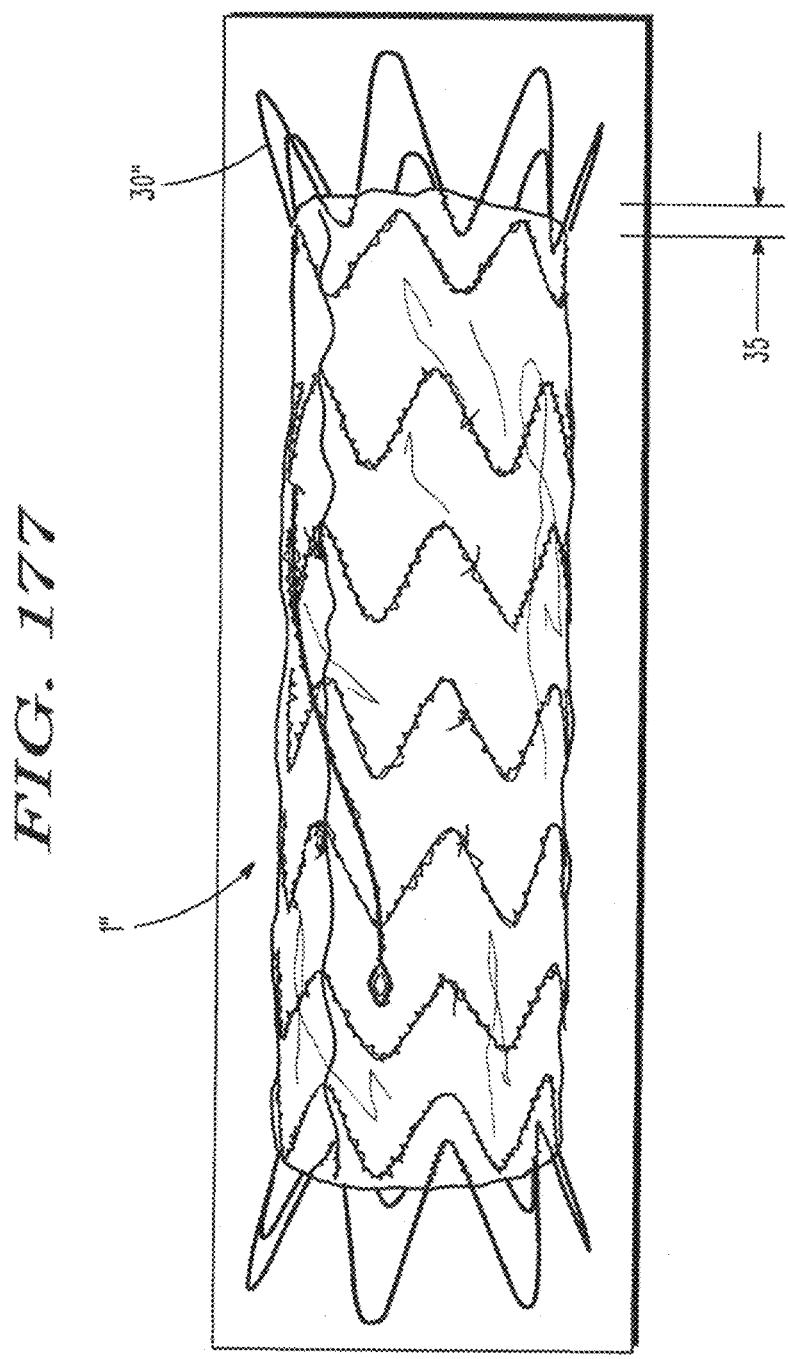

FIG. 131 is a fragmentary, diagrammatic, cross-sectional view of a sixth exemplary embodiment of a stent graft centering device according to the invention in a first position;

FIG. 132 is a fragmentary, diagrammatic, cross-sectional view of the stent graft centering device of FIG. 131 in a second position;

FIG. 133 is a fragmentary, diagrammatic, perspective view of a seventh exemplary embodiment of a stent graft centering device according to the invention in a closed position;

FIG. 134 is a fragmentary, diagrammatic, perspective view of the stent graft centering device of FIG. 133 in an open position;

FIG. 135 is a fragmentary, diagrammatic, perspective view of the stent graft centering device of FIG. 133 in captured state;

FIG. 136 is a fragmentary, diagrammatic, side elevational view of an eighth exemplary embodiment of a stent graft centering device according to the invention;

FIG. 137 is a fragmentary; diagrammatic, side elevational view of the stent graft centering device of FIG. 136 in an extended state;

FIGS. 138 and 140 is a fragmentary, diagrammatic, exploded view the stent graft centering device of FIG. 136;

FIG. 139 is a fragmentary, diagrammatic, side elevational view the stent graft centering device of FIG. 136 in a retracted state with a stent captured;

FIG. 141 is a fragmentary, diagrammatic, side elevational view the stent graft centering device of FIG. 136 in an extended centering state with a stent captured;

FIG. 142 is a fragmentary, diagrammatic, side elevational view the stent graft centering device of FIG. 136 in an extended centering state with a stent released;

FIG. 143 is a fragmentary, diagrammatic, cross-sectional view of an ninth exemplary embodiment of a stent graft centering device according to the invention in an aorta;

FIG. 144 is a fragmentary, diagrammatic, side elevational view of a tenth exemplary embodiment of a stent graft centering device according to the invention in a straight orientation;

FIG. 145 is a fragmentary, diagrammatic, side elevational view of the stent graft centering device of FIG. 144 in a crooked orientation;

FIG. 146 is a fragmentary, diagrammatic, side elevational view of the stent graft centering device of FIG. 144 in a bent orientation;

FIG. 147 is a fragmentary, diagrammatic, cross-sectional view of an eleventh exemplary embodiment of a stent graft centering device according to the invention in a centered orientation;

FIG. 148 is a fragmentary, diagrammatic, cross-sectional view of the stent graft centering device of FIG. 147 with a delivery system therein and a stent graft closed;

FIG. 149 is a fragmentary, diagrammatic, cross-sectional view of the stent graft centering device of FIG. 147 with a delivery system therein and a stent graft open;

FIGS. 150A and 150B are fragmentary, diagrammatic, perspective views of the stent graft centering device of FIG. 147 with balloons inflated;

FIG. 151 is a fragmentary, diagrammatic, perspective view of the stent graft centering device of FIG. 147 with balloons deflated;

FIG. 152 is a fragmentary, diagrammatic, cross-sectional view of a twelfth exemplary embodiment of a stent graft centering device according to the invention in an aorta;

FIG. 153 is a fragmentary, diagrammatic, cross-sectional view of the stent graft centering device of FIG. 152 centering a stent graft delivery device with the stent graft closed;

FIG. 154 is a fragmentary, diagrammatic, cross-sectional view of the stent graft centering device of FIG. 152 centering a stent graft delivery device with the stent graft open;

FIG. 155 is a fragmentary, diagrammatic, cross-sectional view of the stent graft centering device of FIG. 152;

FIG. 156 is a fragmentary, diagrammatic, side elevational view of a thirteenth exemplary embodiment of a stent graft centering device according to the invention;

FIG. 157 is a fragmentary, diagrammatic, side elevational view of a prior art stent graft in an aorta having the inflow plane at an angle to the implant plane;

FIG. 158 is a fragmentary, diagrammatic, side elevational view of the stent graft centering device of FIG. 156 in an aorta having the inflow plane aligned with the implant plane;

FIG. 159 is a fragmentary, diagrammatic, perspective view of a fourteenth exemplary embodiment of a stent graft centering device according to the invention;

FIG. 160 is a fragmentary, diagrammatic, perspective view of a fifteenth exemplary embodiment of a stent graft centering device according to the invention;

FIG. 161 is a fragmentary, diagrammatic, perspective view of a control assembly of the stent graft centering device of FIG. 160;

FIG. 162 is a fragmentary, diagrammatic, perspective view of a sixteenth exemplary embodiment of a stent graft centering device according to the invention in a first configuration;

FIG. 163 is a fragmentary, diagrammatic, perspective view of the stent graft centering device of FIG. 162 in a second configuration;

FIG. 164 is a fragmentary, diagrammatic, side elevational view of a seventeenth exemplary embodiment of a stent graft centering device according to the invention in an expanded orientation;

FIG. 165 is a fragmentary, diagrammatic, side elevational view of the stent graft centering device of FIG. 164 in a further expanded orientation;

FIG. 166 is a fragmentary, diagrammatic, side elevational view of the stent graft centering device of FIG. 164 in a contracted orientation;

FIG. 167 is a fragmentary, diagrammatic, side elevational view of the stent graft centering device of FIG. 164 in an open position;

FIG. 167A is a fragmentary, diagrammatic, enlarged side elevational view of a portion of the stent graft centering device of FIG. 167 in the open position;

FIG. 168 is a fragmentary, diagrammatic, enlarged, side elevational view of a portion of the stent graft centering device of FIG. 164 in a captured position;

FIG. 169 is a fragmentary, diagrammatic, side elevational view of the stent graft centering device of FIG. 167 in a captured position of a stent;

FIG. 170 is a fragmentary, diagrammatic, perspective view of an eighteenth exemplary embodiment of a stent graft centering device according to the invention in a closed orientation;

FIG. 171 is a fragmentary, diagrammatic, perspective view of the stent graft centering device of FIG. 170 through a stent graft;

FIG. 172 is a fragmentary, diagrammatic, perspective view of the stent graft centering device of FIG. 171 in an open orientation without the stent graft;

FIG. 173 is a fragmentary, diagrammatic, side elevational view of a nineteenth exemplary embodiment of a stent graft centering device according to the invention in a closed orientation;

FIG. 174 is a fragmentary, diagrammatic, side elevational view of the stent graft centering device of FIG. 173 in an open orientation;

FIG. 175 is a fragmentary, diagrammatic, side elevational view of the stent graft centering device of FIG. 174 through a stent graft;

FIG. 176 is a fragmentary, diagrammatic, side elevational view of a twentieth exemplary embodiment of a stent graft centering device according to the invention;

FIG. 177 is a is a side elevational view of an alternative embodiment of a stent graft according to the invention;

FIG. 178 is a is a fragmentary, side elevational view of the stent graft of FIG. 177 adjacent an alternative embodiment of a stent graft apex capture assembly according to the invention;

FIG. 179 is a fragmentary, side elevational view of the stent graft of FIG. 177 captured within the stent graft apex capture assembly of FIG. 178;

FIG. 180 is a fragmentary, enlarged, side elevational view of a distal portion of the stent graft apex capture assembly of FIG. 178;

FIG. 181 is a fragmentary, enlarged, side elevational view of a proximal portion of the stent graft apex capture assembly of FIG. 178;

FIG. 182 is a fragmentary, side elevational view of the stent graft of FIG. 177 partially captured within the stent graft apex capture assembly of FIG. 178;

FIG. 183 is a fragmentary, side elevational view of the stent graft of FIG. 177 partially captured within the stent graft apex capture assembly of FIG. 178;

FIG. 184 is a fragmentary, side elevational view of the stent graft apex capture assembly of FIG. 178 with the nose cone removed;

FIG. 185 is a fragmentary, enlarged, side elevational view of an apex capture control assembly in a locked state according to the invention for the stent graft apex capture assembly of FIG. 178;

FIG. 186 is a fragmentary. enlarged, side elevational view of the apex capture control assembly of FIG. 185 in an unlocked state; and FIG. 187 is a fragmentary, enlarged, perspective and partially transparent view of a proximal portion of the stent graft apex capture and release assemblies of FIGS. 178 and 185.

DESCRIPTION OF EXEMPLARY EMBODIMENTS

While the specification concludes with claims defining the features of the invention that are regarded as novel, it is believed that the invention will be better understood from a consideration of the following description in conjunction with the drawing figures, in which like reference numerals are carried forward.

The present invention provides a stent graft, delivery system, and method for implanting a prosthesis with a two-part expanding delivery system that treats, in particular, thoracic aortic defects from the brachiocephalic level of the aortic arch distally to a level just superior to the celiac axis and provides an endovascular foundation for an anastomosis with the thoracic aorta, while providing an alternative method for partial/total thoracic aortic repair by excluding the vessel defect and making surgical repair of the aorta unnecessary. The stent graft of the present invention, however, is not limited to use in the aorta. It can be endoluminally inserted in any accessible artery that could accommodate the stent graft's dimensions.

Stent Graft

The stent graft according to the present invention provides various features that, heretofore, have not been applied in the art and, thereby, provide a vessel repair device that implants/conforms more efficiently within the natural or diseased course of the aorta, decreases the likelihood of vessel puncture, and increases the blood-tight vascular connection, and decreases the probability of graft mobility.

The stent graft is implanted endovascularly before or during or in place of an open repair of the vessel (i.e., an arch, in particular, the ascending and/or descending portion of the aorta) through a delivery system described in detail below. The typical defects treated by the stent graft are aortic aneurysms, aortic dissections, and other diseases such as penetrating aortic ulcer, coarctation, and patent ductus arteriosus, related to the aorta. When endovascularly placed in the aorta, the stent graft forms a seal in the vessel and automatically affixes itself to the vessel with resultant effacement of the pathological lesion.

Figure 1:
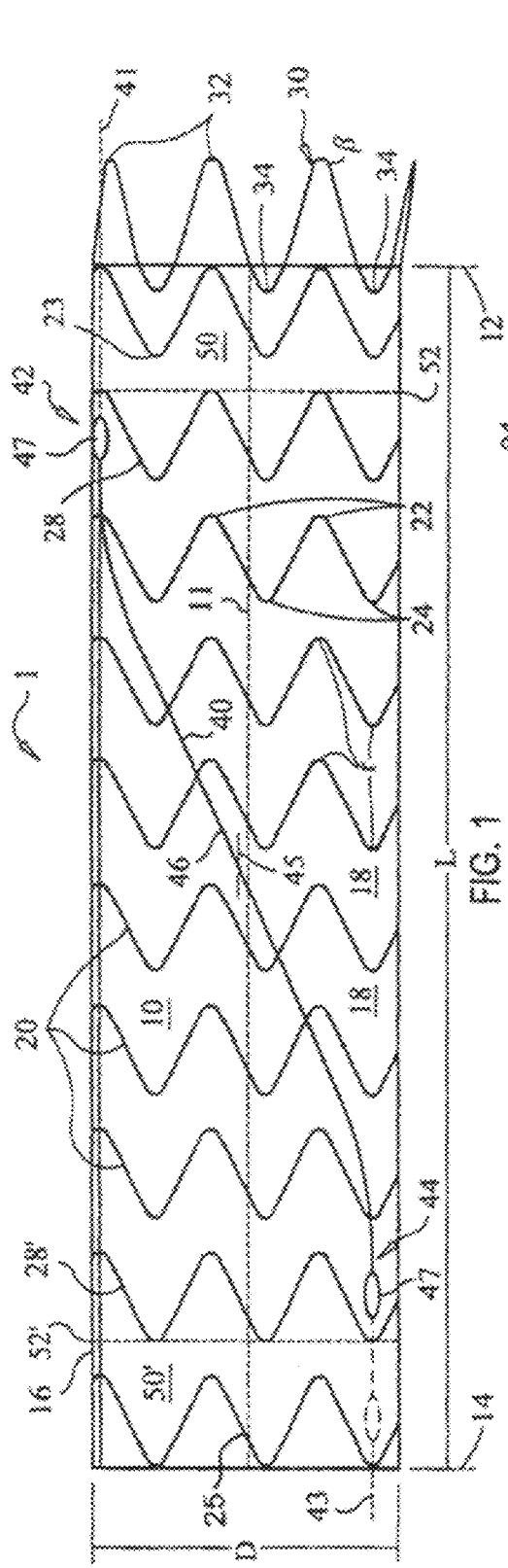
FIG. 1 is a side elevational view of a stent graft according to the invention.

Referring now to the figures of the drawings in detail and first, particularly to FIG. 1 thereof, there is shown an improved stent graft 1 having a graft sleeve 10 and a number of stents 20. These stents 20 are, preferably, made of nitinol, an alloy having particularly special properties allowing it to rebound to a set configuration after compression, the rebounding property being based upon the temperature at which the alloy exists. For a detailed explanation of nitinol and its application with regard to stents, see, e.g., U.S. Pat. Nos. 4,665,906, 5,067,957, and 5,597,378 to Jervis and to Gianturco.

The graft sleeve 10 is cylindrical in shape and is made of a woven graft material along its entire length. The graft material is, preferably, polyester, in particular, polyester referred to under the name DACRON® or other material types like Expanded Polytetrafluoroethylene ("EPTFE"), or other polymeric based coverings. The tubular graft sleeve 10 has a framework of individual lumen-supporting wires each referred to in the art as a stent 20. Connection of each stent 20 is, preferably, performed by sewing a polymeric (nylon, polyester) thread around an entirety of the stent 20 and through the graft sleeve 10. The stitch spacings are sufficiently close to prevent any edge of the stent 20 from extending substantially further from the outer circumference of the graft sleeve 10 than the diameter of the wire itself. Preferably, the stitches have a 0.5 mm to 5 mm spacing.

The stents 20 are sewn either to the exterior or interior surfaces of the graft sleeve 10. FIG. 1 illustrates all stents 20, 30 on the exterior surface 16 of the graft sleeve 10. In an exemplary non-illustrated embodiment, the most proximal 23 and distal stents and a bare stent 30 are connected to the interior surface of the graft sleeve 10 and the remainder of the stents 20 are connected to the exterior surface 16. Another possible non-illustrated embodiment alternates connection of the stents 20, 30 to the graft sleeve 10 from the graft exterior surface to the graft interior surface, the alternation having any periodic sequence.

A stent 20, when connected to the graft sleeve 10, radially forces the graft sleeve 10 open to a predetermined diameter D. The released radial force creates a seal with the vessel wall and affixes the graft to the vessel wall when the graft is implanted in the vessel and is allowed to expand.

Typically, the stents 20 are sized to fully expand to the diameter D of the fully expanded graft sleeve 10. However, a characteristic of the present invention is that each of the stents 20 and 30 has a diameter larger than the diameter D of the fully expanded graft sleeve 10. Thus, when the stent graft 1 is fully expanded and resting on the internal surface of the vessel where it has, been placed, each stent 20 is imparting independently a radially directed force to the graft sleeve 10. Such pre-compression, as it is referred to herein, is applied (1) to ensure that the graft covering is fully extended, (2) to ensure sufficient stent radial force to make sure sealing occurs, (3) to affix the stent graft and prevent it from kinking, and (4) to affix the stent graft and prevent migration.

Preferably, each of the stents 20 is fanned with a single nitinol wire. Of course other biocompatible materials can be used, for example, stainless steel, biopolymers, cobalt chrome, and titanium alloys.

Figure 2:
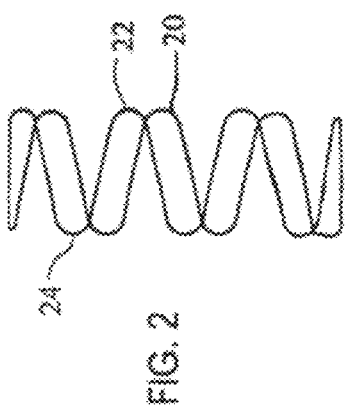
FIG. 2 is a side elevational view of a stent of the stent graft of FIG. 1.

An exemplary shape of each stent 20 corresponds to what is referred in the art as a Z-stent, see, e.g., Gianturco (although the shape of the stents 20 can be in any form that satisfies the functions of a self-expanding stent). Thus, the wire fanning the stent 20 is a ring having a wavy or sinusoidal shape. In particular, an elevational view orthogonal to the center axis 21 of the stent 20, reveals a shape somewhere between a triangular wave and a sinusoidal wave as shown in FIG. 2. In other words, the view of FIG. 2 shows that the stents 20 each have alternating proximal 22 and distal 24 apices. Preferably, the apices have a radius r that does not present too great of a point towards a vessel wall to prevent any possibility of puncturing the vessel, regardless of the complete circumferential connection to the graft sleeve 10. In particular, the radius r of curvature of the proximal 22 and distal 24 apices of the stent 20 are, preferably, equal. The radius of curvature r is between approximately 0.1 mm and approximately 3.0 mm, in particular, approximately 0.5 mm.

Another advantageous feature of a stent lies in extending the longitudinal profile along which the stent contacts the inner wall of a vessel. This longitudinal profile can be explained with reference to FIGS. 3 to 7.

Prior art stents and stents according to the present invention are fanned on mandrels 29, 29' by winding the wire around the mandrel 29, 29' and forming the apexes 22, 24, 32, 34 by wrapping the wire over non-illustrated pins that protrude perpendicular from the axis of the mandrel. Such pins, if illustrated, would be located in the holes illustrated in the mandrels 29, 29' of FIGS. 4 and 6. Prior art stents are formed on a round mandrel 29 (also referred to as a bar). A stent 20 formed on a round mandrel 29 has a profile that is rounded (see FIG. 5). Because of the rounded profile, the stent 20' does not conform evenly against the inner wall of the vessel 2 in which it is inserted. This disadvantage is critical in the area of stent graft 1 seal zones—areas where the ends of the graft 10 need to be laid against the inner wan of the vessel 2. Clinical experience reveals that stents 20' formed with the round mandrel 29 do not lie against the vessel 2; instead, only a midsection of the stent 20' rests against the vessel 2, as shown in FIG. 5. Accordingly, when such a stent 20' is present at either of the proximal 12 or distal 14 ends of the stent graft 1, the graft material flares away from the wall of the vessel 2 into the lumen—a condition that is to be avoided. An example of this flaring can be seen by comparing the upper and lower portions of the curved longitudinal profile of the stent 20' in FIG. 5 with the linear longitudinal profile of the vessel 2.

Figure 3:
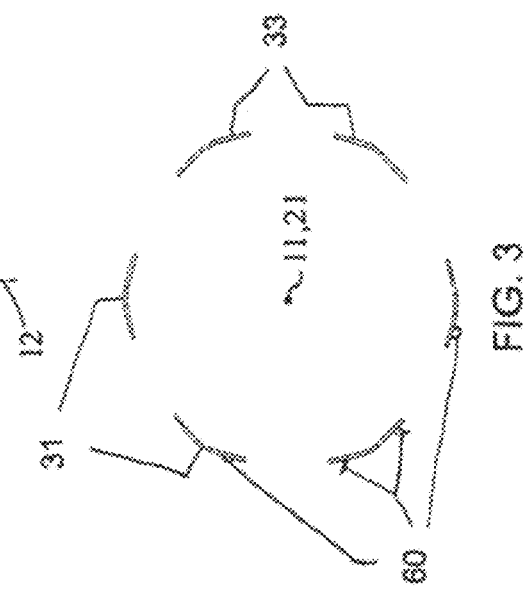
FIG. 3 is a cross-sectional view of the stent of FIG. 2 with different embodiments of protrusions.

To remedy this problem and ensure co-columnar apposition of the stent and vessel, stents 20 of the present invention are formed on a multiple-sided mandrel. In particular, the stents 20 are formed on a polygonal-shaped mandrel 29'. The mandrel 29' does not have sharp edges. Instead, it has flat sections and rounded edge portions between the respective flat sections. Thus, a stent formed on the mandrel 29' will have a cross-section that is somewhat round but polygonal, as shown in FIG. 3. The cross-sectional view orthogonal to the center axis 21 of such a stent 20 will have beveled or rounded edges 31 (corresponding to the rounded edge portions of the mandrel 29') disposed between flat sides or struts 33 (corresponding to the flat sections of the mandrel 29').

To manufacture the stent 20, apexes of the stents 20 are formed by winding the wire over non-illustrated pins located on the rounded portions of the mandrel 29'. Thus, the struts 33 lying between the apexes 22, 24, 32, 34 of the stents 20 lie flat against the flat sides of the mandrel 29'. When so formed on the inventive mandrel 29', the longitudinal profile is substantially less rounded than the profile of stent 20' and, in practice, is substantially linear.

For stents 20 having six proximal 22 and six distal 24 apices, the stents 20 are formed on a dodecahedron-shaped mandrel 29' (a mandrel having twelve sides), which mandrel 29' is shown in FIG. 6. A stent 20 formed on such a mandrel 29' will have the cross-section illustrated in FIG. 3.

The fourteen-apex stent 20 shown in FIG. 7 illustrates a stent 20 that has been formed on a fourteen-sided mandrel. The stent 20 in FIG. 7 is polygonal in cross-section (having fourteen sides) and, as shown in FIG. 7, has a substantially linear longitudinal profile. Clinically, the linear longitudinal profile improves the stent's 20 ability to conform to the vessel 2 and press the graft sleeve 10 outward in the sealing zones at the extremities of the individual stent 20.

Another way to improve the performance of the stent graft 1 is to provide the distal-most stent 25 on the graft 10 (i.e., downstream) with additional apices and to give it a longer longitudinal length (i.e., greater amplitude) and/or a longer circumferential length. When a stent 25 having a longer circumferential length is sewn to a graft, the stent graft 1 will perform better clinically. The improvement, in part, is due to a need for the distal portion of the graft material 10 to be pressed firmly against the wan of the vessel The additional apices result in additional points of contact between the stent graft 1 and vessel wall, thus ensuring better apposition to the wall of the vessel and better sealing of the graft material 10 to the vessel. The increased apposition and sealing substantially improves the axial alignment of the distal end 14 of the stent graft 1 to the vessel. As set forth above, each of the stents 20 and 30 has a diameter larger than the diameter D of the fully expanded graft sleeve 10. Thus, if the distal stent 25 also has a diameter larger than the diameter D, it will impart a greater radial bias on all 360 degrees of the corresponding section of the graft than stents not having such an oversized configuration.

A typical implanted stent graft 1 typically does not experience a lifting off at straight portions of a vessel because the radial bias of the stents acting upon the graft sleeve give adequate pressure to align the stent and graft sleeve with the vessel wall. However, when a typical stent graft is implanted in a curved vessel (such as the aorta), the distal end of the stent graft 1 does experience a lift off from the vessel wall. The increased apposition and sealing of the stent graft 1 according to the present invention substantially decreases the probability of lift off because the added height and additional apices enhance the alignment of the stent graft perpendicular to the vessel wall as compared to prior art stent grafts (no lift off occurs).

The number of total apices of a stent is dependent upon the diameter of the vessel in which the stent graft 1 is to be implanted. Vessels having a smaller diameter have a smaller total number of apices than a stent to be implanted in a vessel having a larger diameter. Table 1 below indicates exemplary stent embodiments for vessels having different diameters. For example, if a vessel has a 26 or 27 mm diameter, then an exemplary diameter of the graft sleeve 10 is 30 mm. For a 30 mm diameter graft sleeve, the intermediate stents 20 will have 5 apices on each side (proximal and distal) for a total of 10 apices. In other words, the stent defines 5 periodic "waves." The distal-most stent 25, in comparison, defines 6 periodic "waves" and, therefore, has 12 total apices. It is noted that the distal-most stent 25 in FIG. 1 does not have the additional apex. While Table 1 indicates exemplary embodiments, these configurations can be adjusted or changed as needed.

TABLE 1

| Vessel Diameter (mm) | Graft Diameter (mm) | Stent Apices/Side (Distal-most Stent #) |
|---|---|---|
| 19 | 22 | 5(5) |
| 20-21 | 24 | 5(5) |
| 22-23 | 26 | 5(5) |
| 24-25 | 28 | 5(6) |
| 26-27 | 30 | 5(6) |
| 28-29 | 32 | 6(7) |
| 30-31 | 34 | 6(7) |
| 32-33 | 36 | 6(7) |
| 34 | 38 | 6(7) |
| 35-36 | 40 | 7(8) |
| 37-38 | 42 | 7(8) |
| 39-40 | 44 | 7(8) |
| 41-42 | 46 | 7(8) |

To increase the security of the stent graft 1 in a vessel, an exposed or bare stent 30 is provided on the stent graft 1, preferably, only at the proximal end 12 of the graft sleeve 10—proximal meaning that it is attached to the portion of the graft sleeve 10 from which the blood flows into the sleeve, i.e., blood flows from the bare stent 30 and through the sleeve 10 to the left of FIG. 1. The bare stent 30 is not limited to being attached at the proximal end 12. Another non-illustrated bare stent can be attached similarly to the distal end 14 of the graft sleeve 10.

Significantly, the bare stent 30 is only partially attached to the graft sleeve 10. Specifically, the bare stent 30 is fixed to the graft sleeve 10 only at the distal apices 34 of the bare stent 30. Thus, the bare stent 30 is partially free to extend the proximal apices 32 away from the proximal end of the graft sleeve 10.

The bare stent 30 has various properties, the primary one being to improve the apposition of the graft material to the contour of the vessel wall and to align the proximal portion of the graft covering in the lumen of the arch and provide a blood-tight closure of the proximal end 12 of the graft sleeve 10 so that blood does not pass between the vascular inside wall and outer surface 16 of the sleeve 10 (endoleak).

An exemplary configuration for the radius of curvature a of the distal apices 34 is substantially equal to the radius r of the proximal 22 and distal 24 apices of the stent 20, in particular, it is equal at least to the radius of curvature r of the proximal apices of the stent 20 directly adjacent the bare stent 30. Thus, as shown in FIG. 8, a distance between the proximal apices 22 of the most proximal stent 23 and crossing points of the exposed portions of the bare stent 30 are substantially at a same distance from one another all the way around the circumference of the proximal end 12 of the graft sleeve 10. Preferably, this distance varies based upon the graft diameter. Accordingly, the sinusoidal portion of the distal apices 34 connected to the graft sleeve 10 traverse substantially the same path as that of the stent 23 closest to the bare stent 30. Thus, the distance d between the stent 22 and all portions of the bare stent 30 connected to the graft sleeve 10 remain constant. Such a configuration is advantageous because it maintains the symmetry of radial force of the device about the circumference of the vessel and also aids in the synchronous, simultaneous expansion of the device, thus increasing apposition of the graft material to the vessel wall to induce a proximal seal—and substantially improve the proximal seal—due to increasing outward force members in contact with the vessel wall.

Inter-positioning the stents 23, 30 in phase with one another, creates an overlap, i.e., the apices 34 of the bare stent 30 are positioned within the troughs of the stent 23. A further advantage of such a configuration is that the overlap provides twice as many points of contact between the proximal opening of the graft 10 and the vessel in which the stent graft 1 is implanted. The additional apposition points keep the proximal opening of the graft sleeve 10 open against the vessel wall, which substantially reduces the potential for endoleaks. In addition, the overlap of the stents 23, 30 increases the radial load or resistance to compression, which functionally increases fixation and reduces the potential for device migration.

In contrast to the distal apices 34 of the bare stent 30, the radius of curvature $\beta$ of the proximal apices 32 (those apices that are not sewn into the graft sleeve 10) is significantly larger than the radius of curvature a of the distal apices 34. An exemplary configuration for the bare stent apices has a radius approximately equal to 1.5 mm for the proximal apices 32 and approximately equal to 0.5 mm for the distal apices 34. Such a configuration substantially prevents perforation of the blood vessel by the proximal apices 32, or, at a minimum, makes is much less likely for the bare stent 30 to perforate the vessel because of the less-sharp curvature of the proximal apices 32.

The bare stent 30 also has an amplitude greater than the other stents 20. Preferably, the peak-to-peak amplitude of the stents 20 is approximately 1.3 cm to 1.5 cm, whereas the peak-to-peak amplitude of the bare stent 30 is approximately 2.5 cm to 4.0 cm. Accordingly, the force exerted by the bare stent 30 on the inner wall of the aorta (due to the bare stent 30 expanding to its native position) is spread over a larger surface area. Thus, the bare stent 30 of the present invention presents a less traumatic radial stress to the interior of the vessel wall—a characteristic that, while less per square mm than an individual one of the stents 20 would be, is sufficient, nonetheless, to retain the proximal end 12 in position. Simultaneously, the taller configuration of the bare stent 30 guides the proximal opening of the stent graft in a more "squared-off" manner. Thus, the proximal opening of the stent graft is more aligned with the natural curvature of the vessel in the area of the proximal opening.

As set forth above, because the vessel moves constantly, and due to the constantly changing pressure imparted by blood flow, any stent graft placed in the vessel has the natural tendency to migrate downstream. This is especially true when the stent graft 1 has graft sleeve segments 18 with lengths defined by the separation of the stents on either end of the segment 18, giving the stent graft 1 an accordion, concertina, or caterpillar-like shape. When such a shape is pulsating with the vessel and while hemodynamic pressure is imparted in a pulsating manner along the stent graft from the proximal end 12 to the downstream distal end 14, the stent graft 1 has a tendency to migrate downstream in the vessel. It is desired to have such motion be entirely prohibited.

Support along a longitudinal extent of the graft sleeve 10 assists in preventing such movement. Accordingly, as set forth above, prior art stent grafts have provided longitudinal rods extending in a straight line from one stent to another.

The present invention, however, provides a longitudinal, spiraling/helical support member 40 that, while extending relatively parallel to the longitudinal axis 11 of the graft sleeve 10, is not aligned substantially parallel to a longitudinal extent of the entirety of the stent graft 1 as done in the prior art. "Relatively parallel" is referred to herein as an extent that is more along the longitudinal axis 11 of the stent graft 1 than along an axis perpendicular thereto.

Specifically, the longitudinal support member 40 has a somewhat S-turn shape, in that, a proximal portion 42 is relatively parallel to the axis 11 of the graft sleeve 10 at a first degree 41 (being defined as a degree of the 360 degrees of the circumference of the graft sleeve 10), and a distal portion 44 is, also, relatively parallel to the axis 11 of the tube graft, but at a different second degree 43 on the circumference of the graft sleeve 10. The difference between the first and second degrees 41, 43 is dependent upon the length L of the graft sleeve 10. For an approximately 20 cm (approx. 8") graft sleeve, for example, the second degree 43 is between 80 and 110 degrees away from the first degree 41, in particular, approximately 90 degrees away. In comparison, for an approximately 9 cm (approx. 3.5") graft sleeve, the second degree 43 is between 30 and 60 degrees away from the first degree 41, in particular, approximately 45 degrees away. As set forth below, the distance between the first and second degrees 41, 43 is also dependent upon the curvature and the kind of curvature that the stent graft 1 will be exposed to when in vivo.

The longitudinal support member 40 has a curved intermediate portion 46 between the proximal and distal portions 42, 44. By using the word "portion" it is not intended to mean that the rod is in three separate parts (of course, in a particular configuration, a multi-part embodiment is possible). An exemplary embodiment of the longitudinal support member 40 is a single, one-piece rod made of stainless steel, cobalt chrome, nitinol, or polymeric material that is shaped as a fully curved helix 42, 44, 46 without any straight portion. In an alternative stent graft embodiment, the proximal and distal portions 42, 44 can be substantially parallel to the axis 11 of the stent graft 1 and the central portion 46 can be helically curved.

One way to describe an exemplary curvature embodiment of the longitudinal support member 40 can be using an analogy of asymptotes. If there are two asymptotes extending parallel to the longitudinal axis 11 of the graft sleeve 10 at the first and second degrees 41, 43 on the graft sleeve 10, then the proximal portion 42 can be on the first degree 41 or extend approximately asymptotically to the first degree 41 and the distal portion 44 can be on the second degree 43 or extend approximately asymptotically to the second degree 43. Because the longitudinal support member 40 is one piece in an exemplary embodiment, the curved portion 46 follows the natural curve formed by placing the proximal and distal portions 42, 44 as set forth herein.

In such a position, the curved longitudinal support member 40 has a centerline 45 (parallel to the longitudinal axis 11 of the graft sleeve 10 halfway between the first and second degrees 41, 43 on the graft sleeve 10). In this embodiment, therefore, the curved portion intersects the centerline 45 at approximately 20 to 40 degrees in magnitude, preferably at approximately 30 to 35 degrees.

Another way to describe the curvature of the longitudinal support member can be with respect to the centerline 45. The portion of the longitudinal support member 40 between the first degree 41 and the centerline 45 is approximately a mirror image of the portion of the longitudinal support member 40 between the second degree 43 and the centerline 45, but rotated one-hundred eighty degrees (180°) around an axis orthogonal to the centerline 45. Such symmetry can be referred to herein as "reverse-mirror symmetrical."

The longitudinal support member 40 is, preferably, sewn to the graft sleeve 10 in the same way as the stents 20. However, the longitudinal support member 40 is not sewn directly to any of the stents 20 in the proximal portions of the graft. In other words, the longitudinal support member 40 is independent of the proximal skeleton formed by the stents 20. Such a configuration is advantageous because an independent proximal end creates a gimbal that endows the stent graft with additional flexibility. Specifically, the gimbaled proximal end allows the proximal end to align better to the proximal point of apposition, thus reducing the chance for endoleak. The additional independence from the longitudinal support member allows, the proximal fixation point to be independent from the distal section that is undergoing related motion due to the physiological motion of pulsatile flow of blood. Also in an exemplary embodiment, the longitudinal support member 40 is pre-formed in the desired spiral/helical shape (counter-clockwise from proximal to distal), before being attached to the graft sleeve 10.

Because vessels receiving the stent graft 1 are riot typically straight (especially the aortic arch), the final implanted position of the stent graft 1 will, most likely, be curved in some way. In prior art stent grafts (which only provide longitudinally parallel support rods), there exist, inherently, a force that urges the rod, and, thereby, the entire stent graft, to the straightened, natural shape of the rod. This force is disadvantageous for stent grafts that are to be installed in an at least partly curved manner.

The curved shape of the longitudinal support member 40 according to the present invention eliminates at least a majority, or substantially all, of this disadvantage because the longitudinal support member's 40 natural shape is curved. Therefore, the support member 40 imparts less of a force, or none at all, to straighten the longitudinal support member 40, and, thereby, move the implanted stent graft in an undesirable way. At the same time, the curved longitudinal support member 40 negates the effect of the latent kinetic force residing in the aortic wall that is generated by the propagation of the pulse wave and systolic blood pressure in the cardiac cycle, which is, then, released during diastole. As set forth in more detail below, the delivery system of the present invention automatically aligns the stent graft 1 to the most optimal position while traversing the curved vessel in which it is to be implanted, specifically, the longitudinal support member 40 is placed substantially at the superior longitudinal surface line of the curved aorta (with respect to anatomical position).

In an exemplary embodiment, the longitudinal support member 40 can be curved in a patient-customized way to accommodate the anticipated curve of the actual vessel in which the graft will be implanted. Thus, the distance between the first and second degrees 41, 43 will be dependent upon the curvature and the kind of curvature that the stent graft 1 will be exposed to when in vivo. As such, when implanted, the curved longitudinal support member 40 will, actually, exhibit an opposite force against any environment that would alter its conformance to the shape of its resident vessel's existing course(es).

Preferably, the support member 40 is sewn, in a similar manner as the stents 20, on the outside surface 16 of the graft sleeve 10.

In prior art support rods, the ends thereof are merely a terminating end of a steel or nitinol rod and are, therefore, sharp. Even though these ends are sewn to the tube graft in the prior art, the possibility of tearing the vessel wall still exists. It is, therefore, desirable to not provide the support rod with sharp ends that could puncture the vessel in which the stent graft is placed.

The two ends of the longitudinal support member 40 of the present invention do not end abruptly. Instead, each end of the longitudinal support member loops 47 back upon itself such that the end of the longitudinal support member along the axis of the stent graft is not sharp and, instead, presents an exterior of a circular or oval shape when viewed from the ends 12, 14 of the graft sleeve 10. Such a configuration substantially prevents the possibility of tearing the vessel wall and also provides additional longitudinal support at the oval shape by having two longitudinally extending sides of the oval 47.

In addition, in another embodiment, the end of the longitudinal support member may be connected to the second proximal stent 28 and to the most distal stent. This configuration would allow the longitudinal support member to be affixed to stent 28 (see FIG. 1) and the most distal stent for support while still allowing for the gimbaled feature of the proximal end of the stent graft to be maintained.

A significant feature of the longitudinal support member 40 is that the ends of the longitudinal support member 40 may not extend all the way to the two ends 12, 14 of the graft sleeve 10. Instead, the longitudinal support member 40 terminates at or prior to the second-to-last stent 28 at the proximal end 12 and, if desired, prior to the second-to-last stent 28 at the distal end 14 of the graft sleeve 10. Such an ending configuration (whether proximal only or both proximal and distal) is chosen for a particular reason—when the longitudinal support member 40 ends before either of the planes defined by cross-sectional lines 52, 52', the sleeve 10 and the stents 20 connected thereto respectively form gimbaled portions 50, 50'. In other words, when a grasping force acting upon the gimbaled ends 50, 50' moves or pivots the cross-sectional plane defining each end opening of the graft sleeve 10 about the longitudinal axis 11 starting from the planes defined by the cross-sectional lines 52, 52', then the moving portions 50, 50' can be oriented at any angle y about the center of the circular opening in all directions (360 degrees), as shown in FIG. 8. The natural gimbal, thus, allows the ends 50, 50' to be inclined in any radial direction away from the longitudinal axis 11.

Among other things, the gimbaled ends 50, 50' allow each end opening to dynamically align naturally to the curve of the vessel in which it is implanted. A significant advantage of the gimbaled ends 50, 50' is that they limit propagation of the forces acting upon the separate parts. Specifically, a force that, previously, would act upon the entirety of the stent graft 1, in other words, both the end portions 50, 50' and the middle portion of the stent graft 1 (i.e., between planes 52, 52'), now principally acts upon the portion in which the force occurs. For example, a force that acts only upon one of the end portions 50, 50' substantially does not propagate into the middle portion of the stent graft 1 (i.e., between planes 52, 52'). More significantly, however, when a force acts upon the middle portion of the stent graft 1 (whether moving longitudinally, axially (dilation), or in a torqued manner), the ends 50, 50', because they are gimbaled, remain relatively completely aligned with the natural contours of the vessel surrounding the respective end 50, 50' and have virtually none of the force transferred thereto, which force could potentially cause the ends to grate, rub, or shift from their desired fixed position in the vessel. Accordingly, the stent graft ends 50, 50' remain fixed in the implanted position arid extend the seating life of the stent graft 1.

Another advantage of the longitudinal support member 40 is that it increases the columnar strength of the graft stent 1. Specifically, the material of the graft sleeve can be compressed easily along the longitudinal axis 11, a property that remains true even with the presence of the stents 20 so long as the stents 20 are attached to the graft sleeve 10 with a spacing between the distal apices 24 of one stent 20 and the proximal apices 22 of the next adjacent stent 20. This is especially true for the amount of force imparted by the flow of blood along the extent of the longitudinal axis 11. However, with the longitudinal support member 40 attached according to the present invention, longitudinal strength of the stent graft 1 increases to overcome the longitudinal forces imparted by blood flow.

Another benefit imparted by having such increased longitudinal strength is that the stent graft 1 is further prevented from migrating in the vessel because the tube graft is not compressing and expanding in an accordion-like manner—movement that would, inherently, cause graft migration.

A further measure for preventing migration of the stent graft 1 is to equip at least one of any of the individual stents 20, 30 or the longitudinal support member 40 with protuberances 60, such as barbs or hooks (FIG. 3). See, e.g., United States Patent Publication 2002/0052660 to Greenhalgh. In an exemplary embodiment of the present invention, the stents 20, 30 are secured to the outer circumferential surface 16 of the graft sleeve 10. Accordingly, if the stents 20 (or connected portions of stent 30) have protuberances 60 protruding outwardly, then such features would catch the interior wall of the vessel and add to the prevention of stent graft 1 migration. Such an embodiment can be preferred for aneurysms but is not preferred for the fragile characteristics of dissections because such protuberances 60 can excoriate the inner layer(s) of the vessel and cause leaks between layers, for example.

As shown in FIG. 9, the stent graft 1 is not limited to a single graft sleeve 10. Instead, the entire stent graft can be a first stent graft 100 having all of the features of the stent graft 1 described above and a second stent graft 200 that, instead of having a circular extreme proximal end 12, as set forth above, has a proximal end 212 with a shape following the contour of the most proximal stent 220 and is slightly larger in circumference than the distal circumference of the first stent graft 100. Therefore, an insertion of the proximal end 212 of the second stent graft 200 into the distal end 114 of the first stent graft 100 results, in total, in a two-part stent graft. Because blood flows from the proximal end 112 of the first stent graft 100 to the distal end 214 of the second stent graft 200, it is preferable to have the first stent graft 100 fit inside the second stent graft 200 to prevent blood from leaking out there between. This configuration can be achieved by implanting the devices in reverse order (first implant graft 200 and, then, implant graft 100. Each of the stent grafts 100, 200 can have its own longitudinal support member 40 as needed.

It is not significant if the stent apices of the distal-most stent of the first stent graft 100 are not aligned with the stent apices of the proximal-most stent 220 of the second stent graft 200. What is important is the amount of junctional overlap between the two grafts 100, 200.

Delivery System

As set forth above, the prior art includes many different systems for endoluminally delivering a prosthesis, in particular, a stent graft, to a vessel. Many of the delivery systems have similar parts and most are guided along a guidewire that is inserted, typically, through an insertion into the femoral artery near a patient's groin prior to use of the delivery system. To prevent puncture of the arteries leading to and including the aorta, the delivery system is coaxially connected to the guidewire and tracks the course of the guidewire up to the aorta. The parts of the delivery system that will track over the wire are, therefore, sized to have an outside diameter smaller than the inside diameter of the femoral artery of the patient. The delivery system components that track over the guidewire include the stent graft and are made of a series of coaxial lumens referred to as catheters and sheaths. The stent-graft is constrained, typically, by an outer catheter, requiring the stent graft to be compressed to fit inside the outer catheter. Doing so makes the portion of the delivery system that constrains the stent graft very stiff, which, therefore, reduces that portion's flexibility and makes it difficult for the delivery system to track over the guidewire, especially along curved vessels such as the aortic arch. In addition, because the stent graft exerts very high radial forces on the constraining catheter due to the amount that it must be compressed to fit inside the catheter, the process of deploying the stent graft by sliding the constraining catheter off of the stent graft requires a very high amount of force, typically referred to as a deployment force. Also, the catheter has to be strong enough to constrain the graft, requiring it to be made of a rigid material. If the rigid material is bent, such as when tracking into the aortic arch, the rigid material tends to kink, making it difficult if not impossible to deploy the stent graft.

Common features of vascular prosthesis delivery systems include a tapered nose cone fixedly connected to a guidewire lumen, which has an inner diameter substantially corresponding to an outer diameter of the guidewire such that the guidewire lumen slides easily over and along the guidewire. A removable, hollow catheter covers and holds a compressed prosthesis in its hollow and the catheter is fixedly connected to the guidewire lumen. Thus, when the prosthesis is in a correct position for implantation, the physician withdraws the hollow catheter to gradually expose the self-expanding prosthesis from its proximal end towards its distal end. When the catheter has withdrawn a sufficient distance from each portion of the expanding framework of the prosthesis, the framework can expand to its native position, preferably, a position that has a diameter at least as great as the inner diameter of the vessel wall to, thereby, tightly affix the prosthesis in the vessel. When the catheter is entirely withdrawn from the prosthesis and, thereby, allows the prosthesis to expand to the diameter of the vessel, the prosthesis is fully expanded and connected endoluminally to the vessel along the entire extent of the prosthesis, e.g., to treat a dissection. When treating an aneurysm, for example, the prosthesis is in contact with the vessel's proximal and distal landing zones when completely released from the catheter. At such a point in the delivery, the delivery system can be withdrawn from the patient. The prosthesis, however, cannot be reloaded in the catheter if implantation is not optimal.

The aorta usually has a relatively straight portion in the abdominal region and in a lower part of the thoracic region. However, in the upper part of the thoracic region, the aorta is curved substantially, traversing an upside-down U-shape from the back of the heart over to the front of the heart. As explained above, prior art delivery systems are relatively hard and inflexible (the guidewire/catheter portion of the prior art delivery systems). Therefore, if the guidewire/catheter must traverse the curved portion of the aorta, it will kink as it is curved or it will press against the top portion of the aortic curve, possibly puncturing the aorta if the diseased portion is located where the guidewire/catheter is exerting its force. Such a situation must be avoided at all costs because the likelihood of patient mortality is high. The prior art does not provide any way for substantially reducing the stress on the curved portion of the aorta or for making the guidewire/catheter sufficiently flexible to traverse the curved portion without causing damage to the vessel.

The present invention, however, provides significant features not found in the prior art that assist in placing a stent graft in a curved portion of the aorta in a way that substantially reduces the stress on the curved portion of the aorta and substantially reduces the insertion forces needed to have the compressed graft traverse the curved portion of the aorta. As set forth above, the longitudinal support member 40 is pre-formed in a desired spiral/helical shape before being attached to the graft sleeve 10 and, in an exemplary embodiment, is curved in a patient-customized way to accommodate the anticipated curve of the actual vessel in which the graft will be implanted. As such, optimal positioning of the stent graft 1 occurs when the longitudinal support member 40 is placed substantially at the superior longitudinal surface line of the curved aorta (with respect to anatomical position). Such placement can be effected in two ways. First, the stent graft 1, the support member 40, or any portion of the delivery system that is near the target site can be provided with radiopaque markers that are monitored by the physician and used to manually align the support member 40 in what is perceived as an optimal position. The success of this alignment technique, however, is dependent upon the skill of the physician. Second, the delivery system can be made to, automatically align the support member 40 at the optimal position. No such system existed in the prior art. However, the delivery system of the present invention provides such an alignment device, thereby, eliminating the need for physician guesswork as to the three-dimensional rotational position of the implanted stent graft 1. This alignment device is explained in further detail below with respect to FIGS. 64 to 67.

The delivery system of the present invention also has a very simple to use handle assembly. The handle assembly takes advantage of the fact that the inside diameter of the aorta is substantially larger that the inside diameter of the femoral arteries. The present invention, accordingly, uses a two-stage approach in which, after the device is inserted in through the femoral artery and tracks up into the abdominal area of the aorta (having a larger diameter (see FIG. 19) than the femoral artery), a second stage is deployed (see FIG. 20) allowing a small amount of expansion of the stent graft while still constrained in a sheath; but this sheath, made of fabric/woven polymer or similar flexible material, is very flexible. Such a configuration gives the delivery system greater flexibility for tracking, reduces deployment forces because of the larger sheath diameter, and easily overcome kinks because the sheath is made of fabric.

To describe the delivery system of the present invention, the method for operating the delivery assembly 600 will be described first in association with FIGS. 10, 11, and 12. Thereafter, the individual components will be described to allow a better understanding of how each step in the process is effected for delivering the stent graft 1 to any portion of the aorta 700 (see FIGS. 19 to 24), in particular, the curved portion 710 of the aorta.

Figure 25:
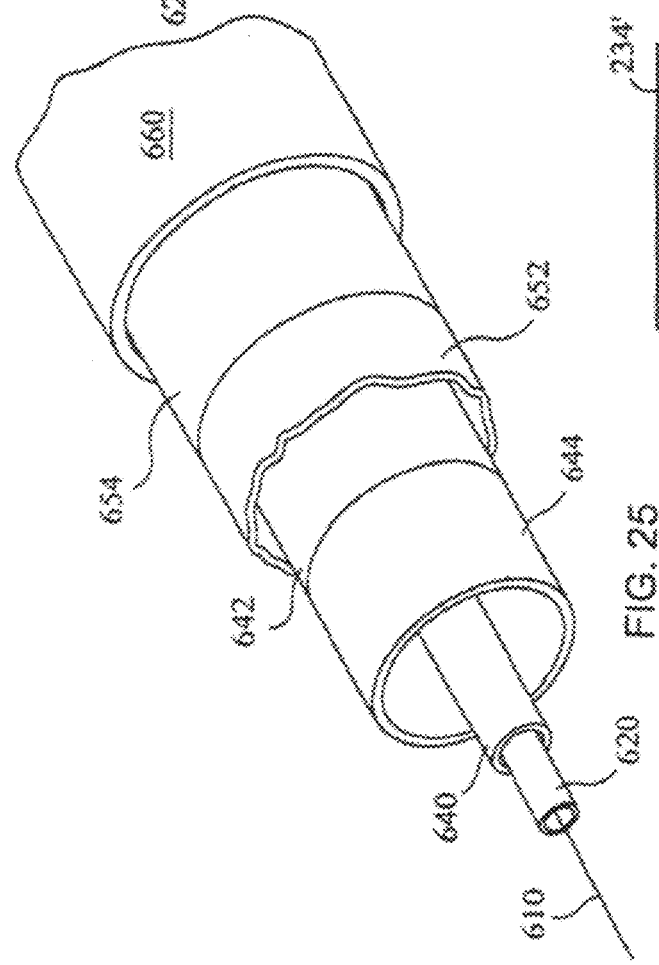
FIG. 25 is a fragmentary, diagrammatic, perspective view of the coaxial relationship of delivery system lumen according to the invention.
Figure 29:
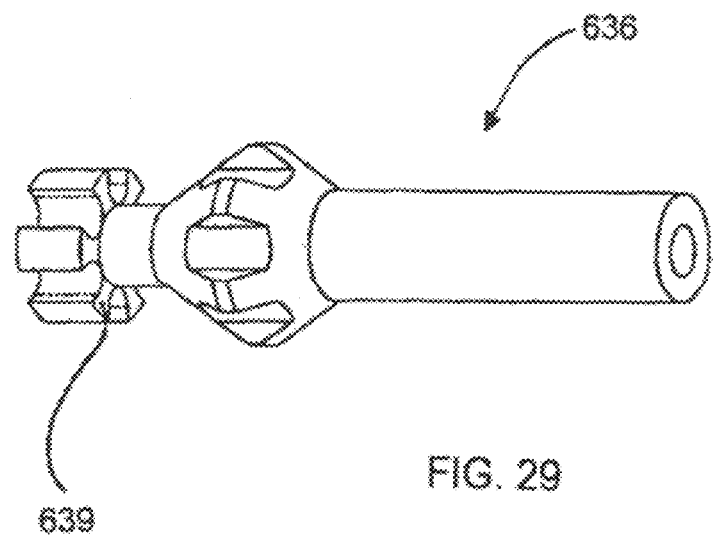
FIG. 29 is a perspective view of a distal apex head of the apex capture device of FIG. 13.
Figure 30:
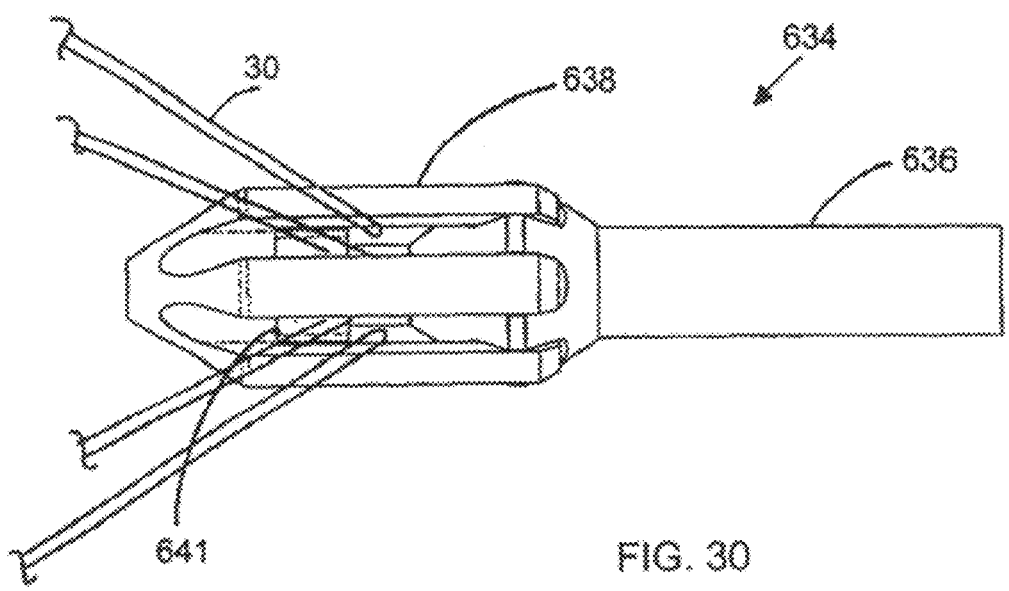
FIG. 30 is a fragmentary side elevational view of the distal apex head of FIG. 29 and a proximal apex body of the apex capture device of FIG. 13 with portions of a bare stent in the captured position.
Figure 31:
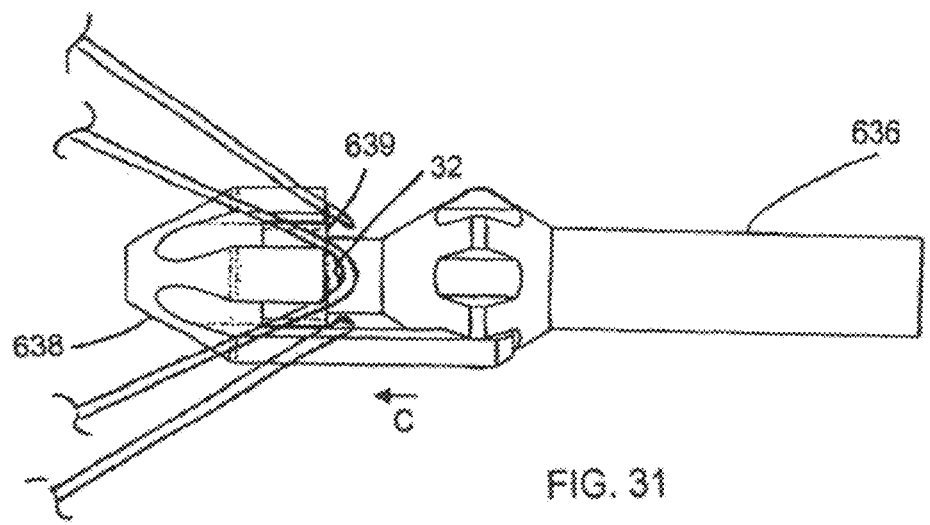
FIG. 31 is a fragmentary, side elevational view of the distal apex head and proximal apex body of FIG. 30 with a portion of the proximal apex body cut away to illustrate the bare stent in the captured position.

Initially, the distal end 14 of the stent graft is compressed and placed into a hollow, cup-shaped, or tubular-shaped graft holding device, in particular, the distal sleeve 644 (see, e.g., FIG. 25). At this point, it is noted that the convention for indicating direction with respect to delivery systems is opposite that of the convention for indicating direction with respect to stent grafts. Therefore, the proximal direction of the delivery system is that portion closest to the user/physician employing the system and the distal direction corresponds to the portion farthest away from the user/ physician, i.e., towards the distal-most nose cone 632.

Figure 68:
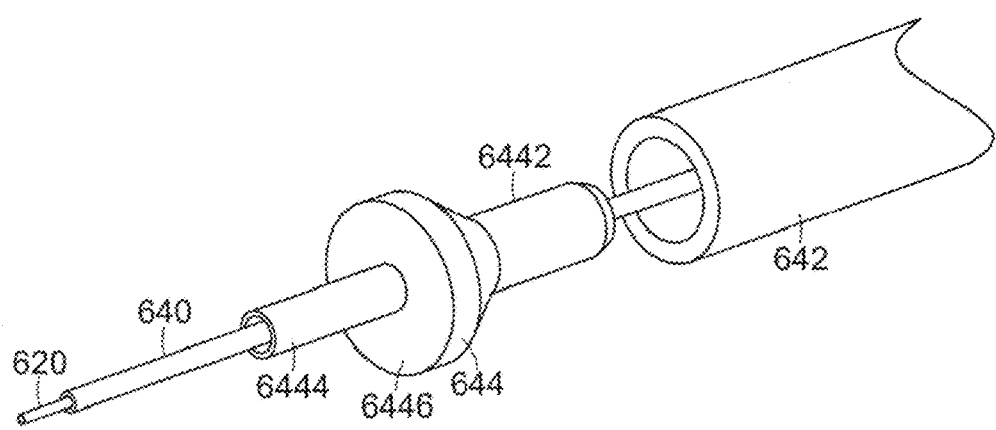
FIG. 68 is a fragmentary, enlarged, partially exploded perspective view of an alternative embodiment of a distal end of the graft push lumen of FIG. 25.

The distal sleeve 644 is fixedly connected to the distal end of the graft push lumen 642, which lumen 642 provides an end face for the distal end 14 of the stent graft 1. Alternatively, the distal sleeve 644 can be removed entirely. In such a configuration, as shown in FIG. 12, for example, the proximal taper of the inner sheath 652 can provide the measures for longitudinally holding the compressed distal end of the graft 1. If the sleeve 644 is removed, it is important to prevent the distal end 14 of the stent graft 1 from entering the space between the interior surface of the hollow sheath lumen 654 and the exterior surface of the graft push lumen 642 slidably disposed in the sheath lumen 654. Selecting a radial thickness of the space to be less than the diameter of the wire making up the stent 20, 30 (in particular, no greater than half a diameter thereof) insures reliable movement of the distal end 14 of the stent graft 1. In another alternative configuration shown in FIG. 68, the distal sleeve 644 can be a disk-shaped buttress 644 present at the distal end of the graft push lumen 642. An example configuration can provide the buttress 644 with a hollow proximal insertion peg 6442, a hollow distal stiffening tube 6444, and an intermediate buttress wall 6446. The buttress 644 is concentric to the center axis of the delivery system 600 and allows the co-axial guidewire lumen 620 and apex release lumen 640 to pass therethrough. The peg 6442 allows for easy connection to the graft push lumen 642. The stiffening tube 64 creates a transition in stiffness from the graft push lumen 642 to the guidewire lumen 620 and apex release lumen 640 and provides support to the lumen 620, 640 located therein. Such a transition in stiffness reduces any possibility of kinking at the distal end of the graft push lumen 642 and aids in transferring force from the graft push lumen 642 to the lumen therein 620, 640 when all are in a curved orientation. The buttress wall 6446 provides a flat surface that will contact the distal-end-facing side of the stent graft 1 and can be used to push the stent graft distally when the graft push lumen 642 is moved distally. The alternative configuration of the buttress 644 insures that the stent graft 1 does not become impinged within the graft push lumen 642 and the lumen therein 620, 640 when these components are moved relative to each other.

As set forth in more detail below, each apex 32 of the bare stent 30 is, then, loaded into the apex capture device 634 so that the stent graft 1 is held at both its proximal and distal ends. The loaded distal end 14, along with the distal sleeve 644 and the graft push lumen 642, are, in turn, loaded into the inner sheath 652, thus, further compressing the entirety of the stent graft 1. The captured bare stent 30, along with the nose cone assembly 630 (including the apex capture device 634), is loaded until the proximal end of the nose cone 632 rests on the distal end of the inner sheath 652. The entire nose cone assembly 630 and sheath assembly 650 is, then, loaded proximally into the rigid outer catheter 660, further compressing the stent graft 1 (resting inside the inner sheath 652) to its fully compressed position for later insertion into a patient. See FIG. 63.

The stent graft 1 is, therefore, held both at its proximal and distal ends and, thereby, is both pushed and pulled when moving from a first position (shown in FIG. 19 and described below) to a second position (shown in FIG. 21 and described below). Specifically, pushing is accomplished by the non-illustrated interior end face of the hollow distal sleeve 644 (or the taper 653 of the inner sheath 652) and pulling is accomplished by the hold that the apex capture device 634 has on the apices 32 of the bare stent 30.

The assembly 600 according to the present invention tracks along a guidewire 610 already inserted in the patient and extending through the aorta and up to, but not into, the left ventricle of the heart 720. Therefore, a guidewire 610 is inserted through the guidewire lumen 620 starting from the nose cone assembly 630, through the sheath assembly 650, through the handle assembly 670, and through the apex release assembly 690. The guidewire 610 extends out the proximal-most end of the assembly 600. The guidewire lumen 620 is coaxial with the nose cone assembly 630, the sheath assembly 650, the handle assembly 670, and the apex release assembly 690 and is the innermost lumen of the assembly 600 immediately surrounding the guidewire 610.

Before using the delivery system assembly 600, all air must be purged from inside the assembly 600. Therefore, a liquid, such as sterile U.S.P. saline, is injected through a non-illustrated tapered luer fitting to flush the guidewire lumen at a non-illustrated purge port located near a proximal end of the guidewire lumen. Second, saline is also injected through the luer fitting 612 of the lateral purge-port (see FIG. 11), which liquid fills the entire internal co-axial space of the delivery system assembly 600. It may be necessary to manipulate the system to facilitate movement of the air to be purged to the highest point of the system.

After purging all air, the system can be threaded onto the guidewire and inserted into the patient. Because the outer catheter 660 has a predetermined length, the fixed front handle 672 can be disposed relatively close to the entry port of the femoral artery. It is noted, however, that the length of the outer catheter 660 is sized such that it will not have the fixed proximal handle 672 directly contact the entry port of the femoral artery in a patient who has the longest distance between the entry port and the thoracic/abdominal junction 742, 732 of the aorta expected in a patient (this distance is predetermined). Thus, the delivery assembly 600 of the present invention can be used with typical anatomy of the patient. Of course, the assembly 600 can be sized to any usable length.

The nose cone assembly 630 is inserted into a patient's femoral artery and follows the guidewire 610 until the nose cone 632 reaches the first position at a level of the celiac axis. The first position is shown in FIG. 19. The nose cone assembly 630 is radiopaque, whether wholly or partially, to enable the physician to determine fluoroscopically, for example, that the nose cone assembly 630 is in the first position. For example, the nose cone 632 can have a radiopaque marker 631 anywhere thereon or the nose cone 632 can be entirely radiopaque.

FIGS. 19 to 24 illustrate the catheter 660 extending approximately up to the renal arteries. However, the catheter 660 of the present invention is configured to travel up to the celiac axis (not shown in FIGS. 19 to 24). As used herein, the celiac axis is to be defined according to common medical terms. In a simplistic definition, the celiac axis is a plane that intersects and is parallel to a central axis of a patient's celiac at the intersection of the celiac and the aorta and, therefore, this plane is approximately orthogonal to the longitudinal axis of the abdominal/thoracic aorta at the point where the celiac intersects the aorta. Therefore, with respect to extension of the catheter 660 into the aorta, it is extended into the aorta up to but not past the celiac axis. After arriving at this distal-most position, the distal end of the catheter 660 remains substantially steady along the longitudinal axis of the aorta until after the stent graft 1 is implanted (see FIG. 24) and the entire delivery system is to be removed from the patient. While the delivery system of the present invention can be retracted in the orientation shown in FIG. 24 except for one difference (the bare stent 32 is open and the apex release device 634 is released from compressing the bare stent 32), the preferred embodiment for removal of the catheter 660 from the aorta after implantation of the stent graft 1 occurs with reference to the condition shown in FIG. 19—where all of the interior lumens 620, 640, 642, 654 are refracted inside the catheter 660 and the nose cone 631 is in contact with the distal end of the catheter 660.

After the nose cone assembly 630 is in the first position shown in FIG. 19, the locking knob or ring 676 is placed from its neutral position into its advancement position. As will be described below, placing the locking knob 676 into its advancement position A allows both the nose cone assembly 630 and the internal sheath assembly 650 to move as one when the proximal handle 678 is moved in either the proximal or distal directions because the locking knob 676 radially locks the graft push lumen 642 to the lumens of the apex release assembly 690 (including the guidewire lumen 620 and an apex release lumen 640). The locking knob 676 is fixedly connected to a sheath lumen 654.

Before describing how various embodiments of the handle assembly 670 function, a summary of the multi-lumen connectivity relationships; throughout the neutral, advancement, and deployment positions, is described.

Figure 48:
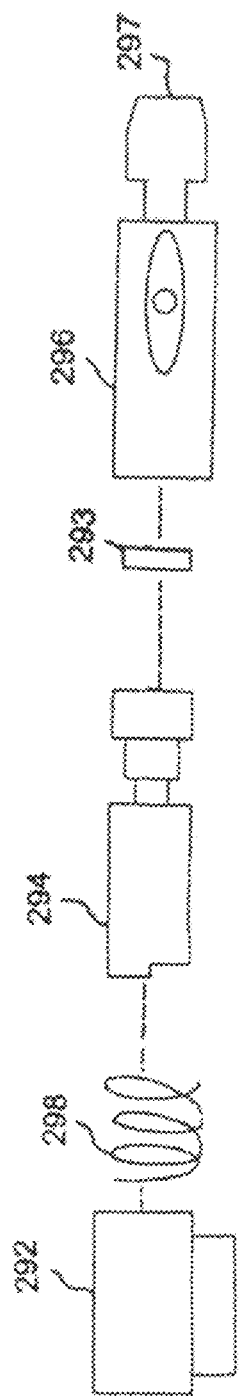
FIG. 48 is an exploded side elevational view of a portion of the handle assembly of FIG. 47.
Figure 52:
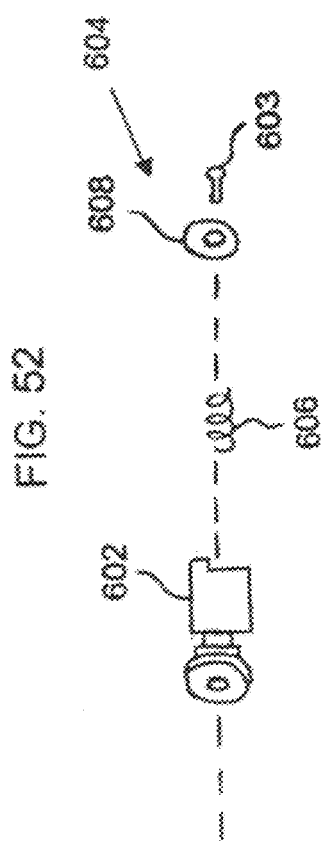
FIG. 52 is an exploded view of a first portion of the second embodiment of the handle assembly.

When the locking ring is in the neutral position, the pusher clasp spring 298 shown in FIG. 48 and the distal clasp body spring 606 shown in FIG. 52 are both disengaged. This allows free movement of the graft push lumen 642 with the guidewire lumen 620 and the apex release lumen 640 within the handle body 674.

When the locking knob 676 is moved into the advancement position, the pusher clasp spring 298 shown in FIG. 48 is engaged and the distal clasp body spring 606 shown in FIG. 52 is disengaged. The sheath lumen 654 (fixedly attached to the inner sheath 652) is, thereby, locked to the graft push lumen 642 (fixedly attached to the distal sleeve 644) so that, when the proximal handle 678 is moved toward the distal handle 672, both the sheath lumen 654 and the graft push lumen 642 move as one. At this point, the graft push lumen 642 is also locked to both the guidewire lumen 620 and the apex release lumen 640 (which are locked to one another through the apex release assembly 690 as set forth in more detail below). Accordingly, as the proximal handle 678 is moved to the second position, shown with dashed lines in FIG. 11, the sheath assembly 650 and the nose cone assembly 630 progress distally out of the outer catheter 660 as shown in FIGS. 20 and 21 and with dashed lines in FIG. 11.

At this point, the sheath lumen 654 needs to be withdrawn from the stent graft 1 to, thereby, expose the stent graft 1 from its proximal end 12 to its distal end 14 and, ultimately, entirely off of its distal end 14. Therefore, movement of the locking knob 676 into the deployment position D will engage the distal clasp body spring 606 shown in FIG. 52 and disengage the pusher clasp spring 298 shown in FIG. 48. Accordingly, the graft push lumen 642 along with the guidewire lumen 620 and the apex release lumen 640 are locked to the handle body 674 so as not to move with respect to the handle body 674. The sheath lumen 654 is unlocked from the graft push lumen 642. Movement of the distal handle 678 back to the third position (proximally), therefore, pulls the sheath lumen 654 proximally, thus, proximally withdrawing the inner sheath 652 from the stent graft 1.

At this point, the delivery assembly 600 only holds the bare stent 30 of the stent graft 1. Therefore, final release of the stent graft 1 occurs by releasing the bare stent 30 from the nose cone assembly 630, which is accomplished using the apex release assembly 690 as set forth below.

In order to explain how the locking and releasing of the lumen occur as set forth above, reference is made to FIGS. 33 to 62.

Figure 33:
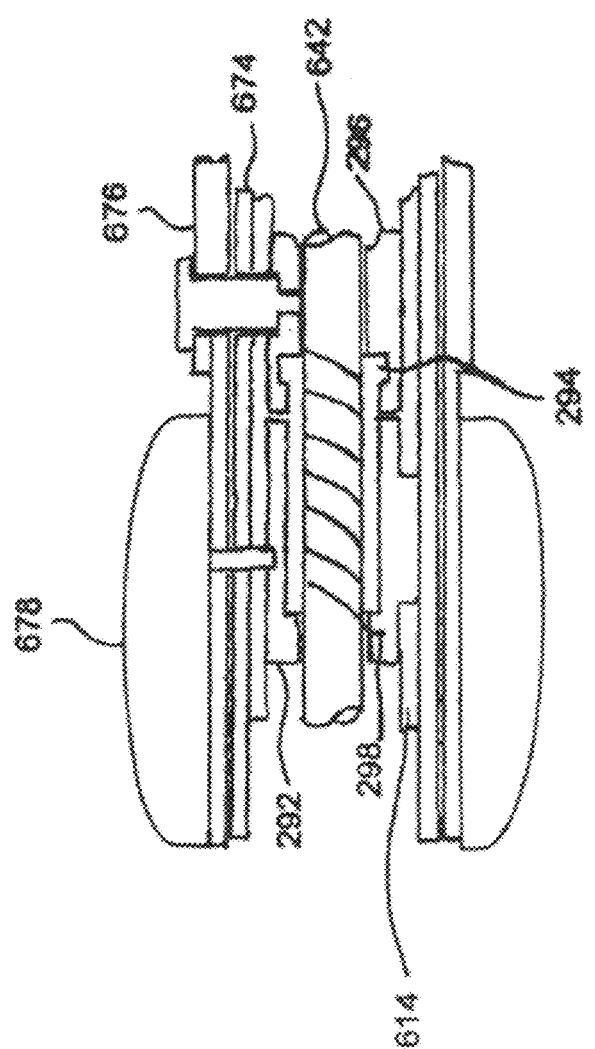
FIG. 33 is a fragmentary, cross-sectional view of an embodiment of handle assemblies according to the invention.
Figure 44:
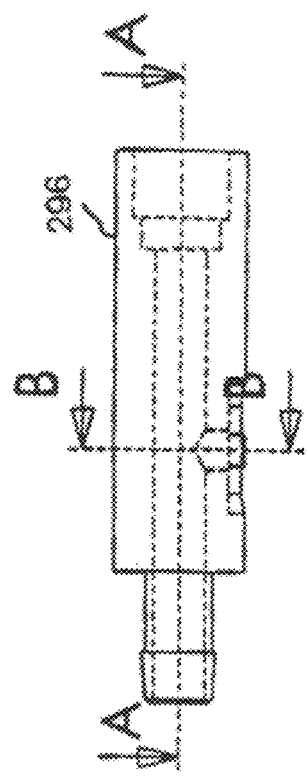
FIG. 44 is an elevational and partially hidden side view of a pusher clasp body of the handle assembly of FIG. 33.
Figure 46:
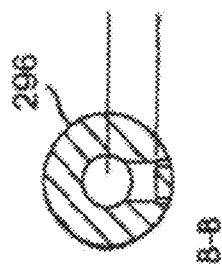
FIG. 46 is a cross-sectional view of the pusher clasp body of FIG. 44 along section line B-B.
Figure 45:
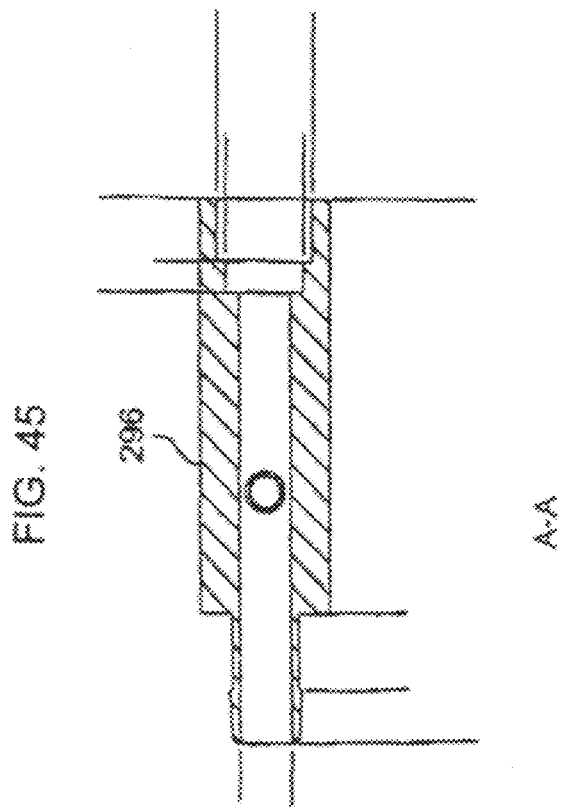
FIG. 45 is a cross-sectional view of the pusher clasp body of FIG. 44 along section line A-A.
Figure 47:
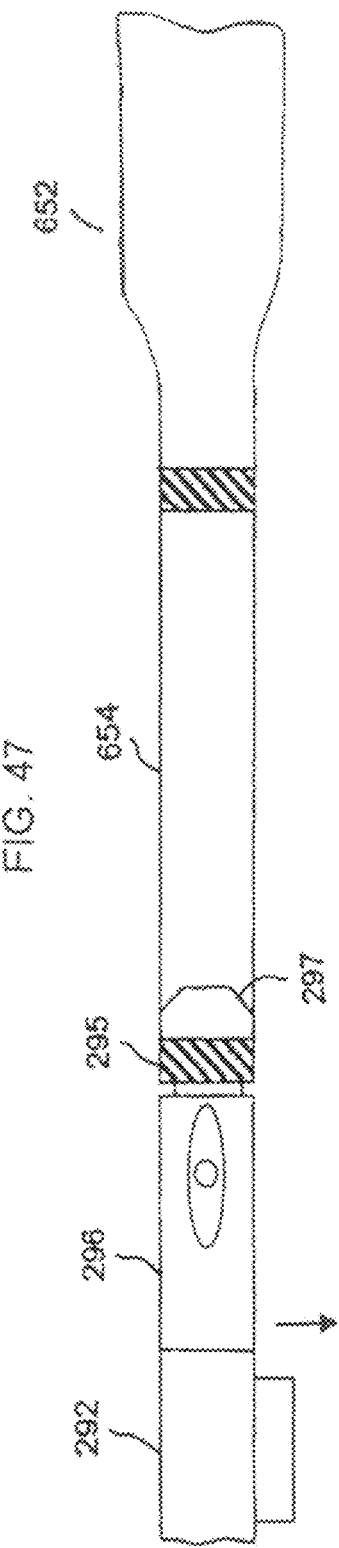
FIG. 47 is a fragmentary, side elevational view of a portion of the handle assembly of FIG. 33 with a sheath assembly according to the invention.

FIG. 33 is a cross-sectional view of the proximal handle 678 and the locking knob 676. A pusher clasp rotator 292 is disposed between a clasp sleeve 614 and the graft push lumen 642. A specific embodiment of the pusher clasp rotator 292 is illustrated in FIGS. 34 through 39. Also disposed between the clasp rotator 292 and the graft push lumen 642 is a rotator body 294, which is directly adjacent the graft push lumen 642. A specific embodiment of the rotator body 294 is illustrated in FIGS. 40 through 43. Disposed between the rotator body 294 and the sheath lumen 654 is a pusher clasp body 296, which is fixedly connected to the rotator body 294 and to the locking knob 676. A specific embodiment of the pusher clasp body 296 is illustrated in FIGS. 44 through 46. A pusher clasp spring 298 operatively connects the pusher clasp rotator 292 to the rotator body 294 (and, thereby, the pusher clasp body 296).

Figure 49:
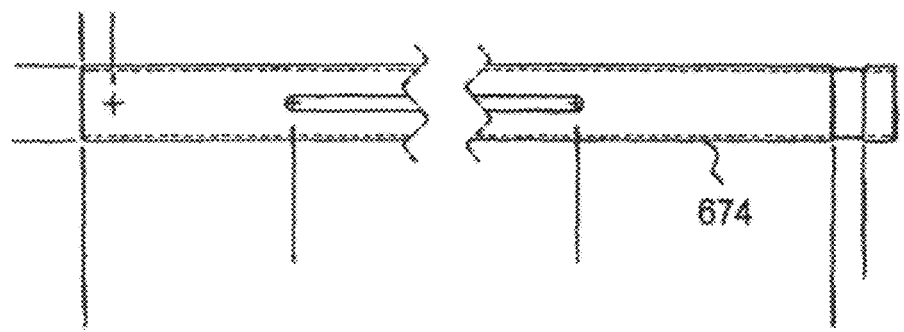
FIG. 49 is a fragmentary elevational and partially hidden side view of a handle body of the handle assembly of FIG. 33.

An exploded view of these components is presented in FIG. 48, where an O-ring 293 is disposed between the rotator body 294 and the pusher clasp body 296. As shown in the plan view of FIG. 47, a crimp ring 295 connects the sheath lumen 654 to the distal projection 297 of the pusher clasp body 296. A hollow handle body 674 (see FIGS. 10, 11, and 33), on which the proximal handle 678 and the locking knob 676 are slidably mounted, holds the pusher clasp rotator 292, the rotator body 294, the pusher clasp body 296, and the pusher clasp spring 298 therein. This entire assembly is rotationally mounted to the distal handle 672 for rotating the stent graft 1 into position (see FIGS. 23 and 24 and the explanations thereof below). A specific embodiment of the handle body 674 is illustrated in FIG. 49.

A setscrew 679 extends from the proximal handle 678 to contact a longitudinally helixed groove in the pusher clasp rotator 292 (shown in FIGS. 36 and 38). Thus, when moving the proximal handle 678 proximally or distally, the pusher clasp rotator 292 rotates clockwise or counter-clockwise.

An alternative embodiment of the locking knob 676 is shown in FIG. 50 et seq. in which, instead of applying a longitudinal movement to rotate the pusher clasp spring 298 through the cam/follower feature of the proximal handle 678 and pusher clasp rotator 292, a rotating locking knob 582 is located at the proximal end of the handle body 674. The knob 582 has three positions that are clearly shown in FIG. 51: a neutral position N, an advancement position A, and a deployment position D. The functions of these positions N, A, D correspond to the positions N, A, D of the locking knob 676 and the proximal handle 678 as set forth above.

In the alternative embodiment, a setscrew or pin 584 is threaded into the clasp sleeve 614 through a slot 675 in the handle body 674 and through a slot 583 in the knob 582 to engage the locking knob 582. The depth of the pin 584 in the clasp sleeve 614 is small because of the relatively small thickness of the clasp sleeve 614. To provide additional support to the pin 584 and prevent it from coming out of the clasp sleeve 614, an outer ring 6144 is disposed on the exterior surface of the proximal end of the clasp sleeve 614. Because of the x-axis orientation of the slot 583 in the knob 582 and the y-axis orientation of the slot 675 in the handle body 674, when the knob 582 is slid over the end of the handle body 674 and the setscrew 584 is screwed into the clasp sleeve 614, the knob 582 is connected fixedly to the handle body 674. When the locking knob 582 is, thereafter, rotated between the neutral N, advancement A, and deployment D positions, the clasp sleeve 614 rotates to actuate the spring lock (see FIGS. 48 and 52).

Figure 53:
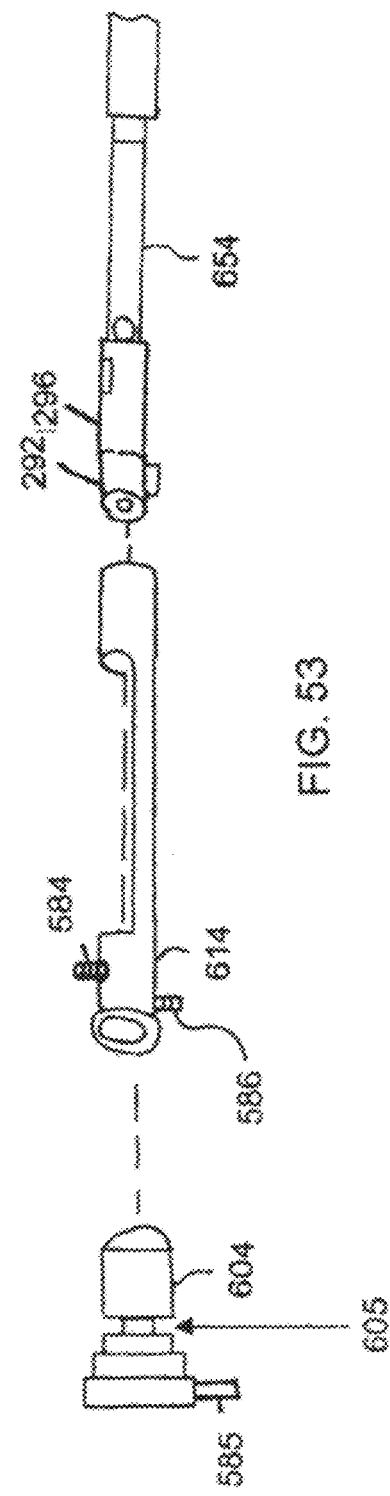
FIG. 53 is a fragmentary, exploded view of a larger portion of the second embodiment of the handle assembly as compared to FIG. 52 with the first portion and the sheath assembly.
Figure 56:
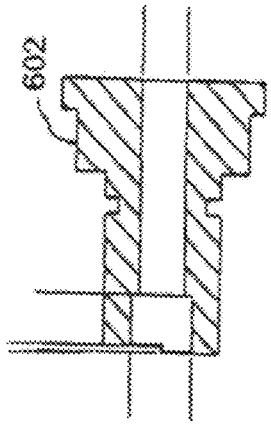
FIG. 56 is a cross-sectional view of the clasp body of FIG. 55 along section line A-A.
Figure 54:
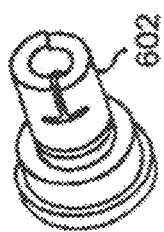
FIG. 54 is perspective view of a clasp body of the second embodiment of the handle assembly.
Figure 58:
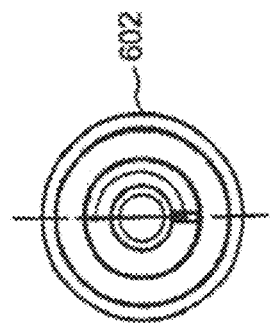
FIG. 58 is a plan view of the clasp body of FIG. 57 viewed from section line B-B.
Figure 55:
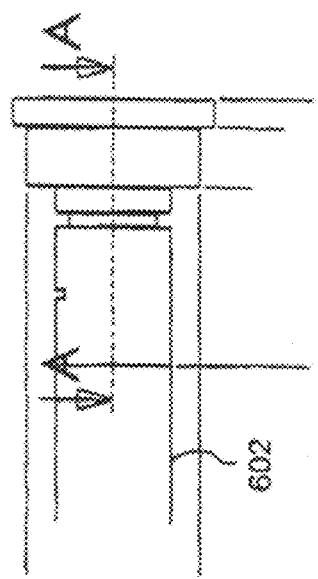
FIG. 55 is an elevational side view of the clasp body of FIG. 54.
Figure 57:
FIG. 57 is a plan view of the clasp body of FIG. 54.

A setscrew 586, shown in FIG. 53, engages a groove 605 in the proximal clasp assembly 604 to connect the proximal clasp assembly 604 to the clasp sleeve 614 but allows the clasp sleeve 614 to rotate around the clasp body 602. The clasp sleeve 614 is shown in FIGS. 50 and 53 and, in particular, in FIGS. 59 to 62. The proximal clasp assembly 604 of FIG. 53 is more clearly shown in the exploded view of FIG. 52. The proximal clasp assembly 604 is made of the components including a distal clasp body spring 606, a locking washer 608, a fastener 603 (in particular, a screw fitting into internal threads of the proximal clasp body 602), and a proximal clasp body 602. The proximal clasp body 602 is shown, in particular, in FIGS. 54 through 58. The proximal clasp assembly 604 is connected fixedly to the handle body 674, preferably, with a screw 585 shown in FIG. 50 and hidden from view in FIG. 51 under knob 582.

The handle body 674 has a position pin 592 for engaging in position openings at the distal end of the locking knob 582. The position pin 592 can be a setscrew that only engages the handle body 674. When the locking knob 582 is pulled slightly proximally, therefore, the knob can be rotated clockwise or counter-clockwise to place the pin 592 into the position openings corresponding to the advancement A, neutral N, and deployment D positions.

As shown in FIG. 18, to begin deployment of the stent graft 1, the user/physician grasps both the distal handle 672 and the proximal handle 678 and slides the proximal handle 678 towards the distal handle 672 in the direction indicated by arrow A. This movement, as shown in FIGS. 19 to 21, causes the flexible inner sheath 652, holding the compressed stent graft 1 therein, to emerge progressively from inside the outer catheter 660. Such a process allows the stent graft 1, while constrained by the inner sheath 652, to expand to a larger diameter shown in FIG. 12, this diameter being substantially larger than the inner diameter of the outer catheter 660 but smaller than the inner diameter of the vessel in which it is to be inserted. Preferably, the outer catheter 660 is made of a polymer (co-extrusions or teflons) and the inner sheath 652 is made of a material, such as a fabric/woven polymer or other similar material. Therefore, the inner sheath 652 is substantially more flexible than the outer catheter 660.

It is noted, at this point, that the inner sheath 652 contains a taper 653 at its proximal end, distal to the sheath's 652 connection to the sheath lumen 654 (at which connection the inner sheath 652 has a similar diameter to the distal sleeve 644 and works in conjunction with the distal sleeve 644 to capture the distal end 14 of the stent graft 1. The taper 653 provides a transition that substantially prevents any kinking of the outer catheter 660 when the stent graft 1 is loaded into the delivery assembly 600 (as in the position illustrated in FIGS. 10 and 11) and, also, when the outer catheter 660 is navigating through the femoral and iliac vessels. One specific embodiment of the sheath lumen 654 has a length between approximately 30 and approximately 40 inches, in particular, 36 inches, an outer diameter of between approximately 0.20 and approximately 0.25 inches, in particular 0.238 inches, and an inner diameter between approximately 0.18 and approximately 0.22 inches, in particular, 0.206 inches.

When the proximal handle 678 is moved towards its distal position, shown by the dashed lines in FIG. 11, the nose cone assembly 630 and the sheath assembly 650 move towards a second position where the sheath assembly 650 is entirely out of the outer catheter 660 as shown in FIGS. 20 and 21.

As can be seen most particularly in FIGS. 20 and 21, as the nose cone assembly 630 and the sheath assembly 650 are emerging out of the outer catheter 660, they are traversing the curved portion 710 of the descending aorta. The tracking is accomplished visually by viewing radiopaque markers on various portions of the delivery system and/or the stent graft 1 with fluoroscopic measures. Such markers will be described in further detail below, The delivery system can be made visible, for example, by the nose cone 630 being radiopaque or containing radiopaque materials.

It is noted that if the harder outer catheter 660 was to have been moved through the curved portion 710 of the aorta 700, there is a great risk of puncturing the aorta 700, and, particularly, a diseased portion 744 of the proximal descending aorta 710 because the outer catheter 660 is not as flexible as the inner sheath 652. But, because the inner sheath 652 is so flexible, the nose cone assembly 630 and the sheath assembly 650 can be extended easily into the curved portion 710 of the aorta 700 with much less force on the handle than previously needed with prior art systems while, at the same time, imparting harmless forces to the intraluminal surface of the curved aorta 710 due to the flexibility of the inner sheath 652.

At the second position shown in FIG. 21, the user/physician, using fluoroscopic tracking of radiopaque markers (e.g., marker 631) on any portion of the nose cone or on the stent graft 1 and/or sheath assemblies 630, 650, for example; makes sure that the proximal end 112 of the stent graft 1 is in the correct longitudinal position proximal to the diseased portion 744 of the aorta 700. Because the entire inserted assembly 630, 650 in the aorta 700 is still rotationally connected to the portion of the handle assembly 670 except for the distal handle 672 (distal handle 672 is connected with the outer sheath 660 and rotates independently of the remainder of the handle assembly 670), the physician can rotate the entire inserted assembly 630, 650 clockwise or counterclockwise (indicated in FIG. 20 by arrow B) merely by rotating the proximal handle 678 in the desired direction. Such a feature is extremely advantageous because the non-rotation of the outer catheter 660 while the inner sheath 652 is rotating eliminates stress on the femoral and iliac arteries when the rotation of the inner sheath 652 is needed and performed.

Accordingly, the stent graft 1 can be pre-aligned by the physician to place the stent graft 1 in the optimal circumferential position. FIG. 23 illustrates the longitudinal support member 40 not in the correct superior position and FIG. 24 illustrates the longitudinal support member 40 in the correct superior position. The optimal superior surface position is, preferably, near the longest superior longitudinal line along the circumference of the curved portion of the aorta as shown in FIGS. 23 and 24. As set forth above, when the longitudinal support member 40 extends along the superior longitudinal line of the curved aorta, the longitudinal support member 40 substantially eliminates any possibility of forming a kink in the inferior radial curve of the stent graft 1 during use and also allows transmission of longitudinal forces exerted along the inside lumen of the stent graft 1 to the entire longitudinal extent of the stent graft 1, thereby allowing the entire outer surface of the stent graft 1 to resist longitudinal migration. Because of the predefined curvature of the support member 40, the support member 40 cannot align exactly and entirely along the superior longitudinal line of the curved aorta. Accordingly, an optimal superior surface position of the support member 40 places as much of the central portion of the support member 40 (between the two ends 47 thereof) as possible close to the superior longitudinal line of the curved aorta. A particularly desirable implantation position has the superior longitudinal line of the curved aorta intersecting the proximal half of the support member 40—the proximal half being defined as that portion of the support member 40 located between the centerline 45 and the proximal support member loop 47. However, for adequate implantation purposes, the centerline 45 of the support member 40 can be as much as seventy circumferential degrees away from either side of the superior longitudinal line of the curved aorta. Adequate implantation can mean that the stent graft 1 is at least approximately aligned. When implantation occurs with the stent graft I being less than seventy degrees, for example, less than forty degrees, away from either side of the superior longitudinal line of the curved aorta, then it is substantially aligned.

In prior art stent grafts and stent graft delivery systems, the stent graft is, typically, provided with symmetrically-shaped radiopaque markers along one longitudinal line and at least one other symmetrically-shaped radiopaque marker disposed along another longitudinal line on the opposite side (one-hundred eighty degrees (180°) of the stent graft. Thus, using two-dimensional fluoroscopic techniques, the only way to determine if the stent graft is in the correct rotational position is by having the user/physician rotate the stent graft in both directions until it is determined that the first longitudinal line is superior and the other longitudinal line is anterior. Such a procedure requires more work by the physician and is therefore, undesirable.

Figure 28:
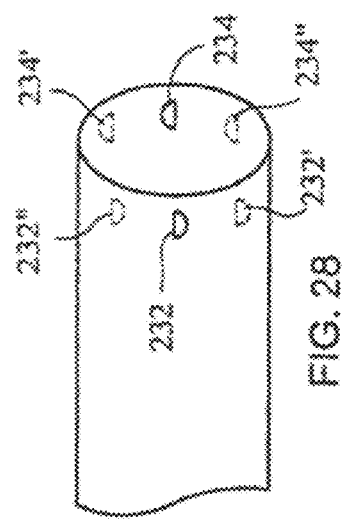
FIG. 28 is a fragmentary perspective view of the stent graft of FIG. 1 with various orientations of radiopaque markers according to the invention.
Figure 27:
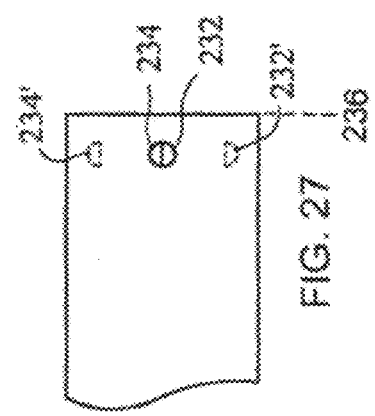
FIG. 27 is a fragmentary, side elevational view of the stent graft of FIG. 1 with various orientations of radiopaque markers according to the invention.

According to an exemplary embodiment of the invention illustrated in FIGS. 27 and 28, unique radiopaque markers 232, 234 are positioned on the stent graft 1 to assist the user/physician in correctly positioning the longitudinal support member 40 in the correct aortic superior surface position with only one directional rotation, which corresponds to the minimal rotation needed to place the stent graft 1 in the rotationally correct position.

Specifically, the stent graft 1 is provided with a pair of symmetrically shaped but diametrically opposed markers 232, 234 indicating to the user/physician which direction the stent graft 1 needs to be rotated to align the longitudinal support member 40 to the superior longitudinal line of the curved aorta (with respect to anatomical position). Preferably, the markers 232, 234 are placed at the proximate end 12 of the graft sleeve 10 on opposite sides (one-hundred eighty degrees (180°)) of the graft sleeve 10.

The angular position of the markers 232, 234 on the graft sleeve 10 is determined by the position of the longitudinal support member 40. In an exemplary embodiment, the support member 40 is between the two markers 232, 234. To explain such a position, if the marker 232 is at a 0 degree position on the graft sleeve 10 and the marker 234 is at a one-hundred eighty degree (1800) position, then the centerline 45 of the support member 40 is at a ninety degree position. However, an alternative position of the markers can place the marker 234 ninety degrees away from the first degree 41 (see FIG. 1). Such a positioning is dependent somewhat upon the way in which the implantation is to be viewed by the user/physician and can be varied based on other factors. Thus, the position can be rotated in any beneficial way.

Exemplary ancillary equipment in endovascular placement of the stent graft 1 is a fluoroscope with a high-resolution image intensifier mounted on a freely angled C-arm. The C-arm can be portable, ceiling, or pedestal mounted. It is important that the C-arm have a complete range of motion to achieve AP to lateral projections without moving the patient or contaminating the sterile field. Capabilities of the C-arm should include: Digital Subtraction Angiography, High-resolution Angiography, and Roadmapping.

For introduction of the delivery system into the groin access arteries, the patient is, first, placed in a sterile field in a supine position. To determine the exact target area for placement of the stent graft 1, the C-arm is rotated to project the patient image into a left anterior oblique projection, which opens the radial curve of the thoracic aortic arch for optimal visualization without superimposition of structures. The degree of patient rotation will vary, but is usually 40 to 50 degrees. At this point, the C-arm is placed over the patient with the central ray of the fluoroscopic beam exactly perpendicular to the target area. Such placement allows for the markers 232, 234 to be positioned for correct placement of the stent graft 1. Failure to have the central ray of the fluoroscopic beam perpendicular to the target area can result in parallax, leading to visual distortion to the patient anatomy due to the divergence of the fluoroscopic x-ray beam, with a resultant misplacement of the stent graft 1. An angiogram is performed and the proposed stent graft landing zones are marked on the visual monitor. Once marked, neither the patient, the patient table, nor the fluoroscopic C-arm can be moved, otherwise, the reference markers become invalid. The stent graft 1 is, then, placed at the marked landing zones.

In an exemplary embodiment, the markers 232, 234 are hemispherical, in other words, they have the approximate shape of a "D", This shape is chosen because it provides special, easy-to-read indicators that instantly direct the user/physician to the correct placement position for the longitudinal support member 40. FIG. 27, for example, illustrates a plan view of the markers 232, 234 when they are placed in the upper-most superior longitudinal line of the curved aorta. The correct position is indicated clearly because the two hemispheres have the flat diameters aligned on top of or immediately adjacent to one another such that a substantially complete circle is formed by the two hemispherically rounded portions of the markers 232, 234. This position is also indicated in the perspective view of FIG. 28.

Each of FIGS. 27 and 28 have been provided with examples where the markers 232, 234 are not aligned and, therefore, the stent graft 1 is not in the correct insertion position. For example, in FIG. 27, two markers 232', 234' indicate a misaligned counter-clockwise-rotated stent graft 1 when viewed from the plane 236 at the right end of the stent graft 1 of FIG. 23 looking toward the left end thereof and down the axis 11. Thus, to align the markers 232', 234' in the most efficient way possible (the shortest rotation), the user/physician sees that the distance between the two flat diameters is closer than the distance between the highest points of the hemispherical curves. Therefore, it is known that the two flat diameters must be joined together by rotating the stent graft 1 clockwise.

FIG. 28 has also been provided with two markers 232", 234" indicating a misaligned clockwise-rotated stent graft 1 when viewed from the plane 236 at the right end of the stent graft 1 of FIG. 27 looking toward the left end thereof and down the axis 11. Thus, to align the markers 232", 234" in the most efficient way possible (the shortest rotation), the user/physician sees that the distance between the highest points of the hemispherical curves is smaller than the distance between the two flat diameters. Therefore, it is known that the two flat diameters must be joined together by rotating the stent graft 1 in the direction that the highest points of the hemispherical curves point; in other words, the stent graft 1 must be rotated counter-clockwise.

A significant advantage provided by the diametrically opposed symmetric markers 232, 234 is that they can be used for migration diagnosis throughout the remaining life of a patient after the stent graft 1 has been placed inside the patient's body. If fluoroscopic or radiographic techniques are used any time after the stent graft 1 is inserted in the patient's body, and if the stent graft 1 is viewed from the same angle as it was viewed when placed therein, then the markers' 232, 234 relative positions observed should give the examining individual a very clear and instantaneous determination as to whether or not the stent graft 1 has migrated in a rotational manner.

The hemispherical shape of the markers 232, 234 are only provided as an example shape. The markers 232, 234 can be any shape that allows a user/physician to distinguish alignment and direction of rotation for alignment. For example, the markers 232, 234 can be triangular, in particular, an isosceles triangle having the single side be visibly longer or shorter than the two equal sides.

As set forth above, alignment to the optimal implantation position is dependent upon the skill of the physician(s) performing the implantation. The present invention improves upon the embodiments having longitudinal and rotational radiopaque markers 232, 234 and substantially eliminates the need for rotational markers. Specifically, it is noted that the guidewire 610 travels through a curve through the aortic arch towards the heart 720. It is, therefore, desirable to pre-shape the delivery system to match the aorta of the patient.

Figure 64:
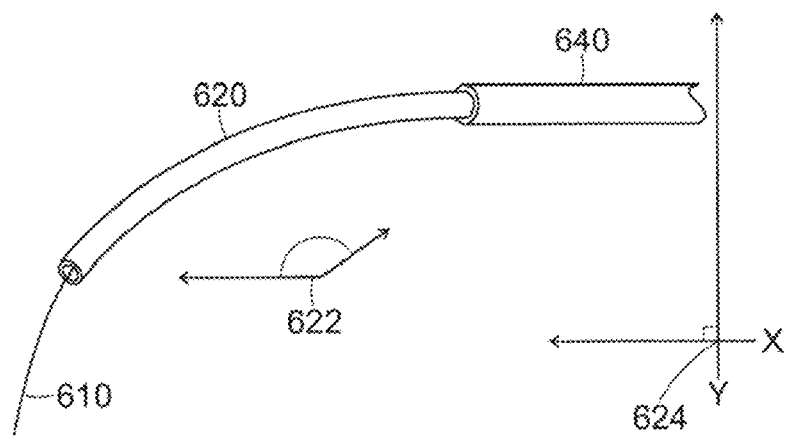
FIG. 64 is a fragmentary, perspective view of a portion of self-alignment configuration according to the invention.

The guidewire lumen 620 is formed from a metal, preferably, stainless steel Thus, the guidewire lumen 620 can be deformed plastically into any given shape. In contrast, the apex release lumen 640 is formed from a polymer, which tends to retain its original shape and cannot plastically deform without an external force, e.g., the use of heat. Therefore, to effect the pre-shaping of the delivery assembly 600, the guidewire lumen 620, as shown in FIG. 64, is pre-shaped with a curve at a distal-most area 622 of the lumen 620. The pre-shape can be determined, for example; using the fluoroscopic pre-operative techniques described above, in which the guidewire lumen 620 can be customized to the individual patient's aortic shape. Alternatively, the guidewire lumen 620 can be pre-shaped in. a standard manner that is intended to fit an average patient. Another alternative is to provide a kit that can be used to pre-shape the guidewire lumen 620 in a way that is somewhat tailored to the patient, for example, by providing a set of delivery systems 600 or a set of different guidewire lumens 620 that have different radii of curvature.

With the pre-curved guidewire lumen 620, when the nose cone 632 and inner sheath 652 exit the outer catheter 660 and begin to travel along the curved guidewire 610, the natural tendency of the pre-curved guidewire lumen 620 will be to move in a way that will best align the two curves to one another (see FIGS. 20 and 21). The primary factor preventing the guidewire lumen 620 from rotating itself to cause such an alignment is the torque generated by rotating the guidewire lumen 620 around the guidewire 610. The friction between the aorta and the device also resists rotational motion. The delivery system 600, however, is configured naturally to minimize such torque. As set forth above with respect to FIGS. 15 to 17, the guidewire lumen 620 freely rotates within the apex release lumen 640 and is only connected to the apex release lumen 640 at the proximal-most area of both lumen 620, 640. While the inner sheath 652 advances through the aortic arch, the two lumen 620, 640 are rotationally connected only at the apex release assembly 690. This means that rotation of the guidewire lumen 620 about the guidewire 610 and within the apex release lumen 640 occurs along the entire length of the guidewire lumen 620. Because the metallic guidewire lumen 620 is relatively rotationally elastic along its length, rotation of the distal-most portion (near the nose cone assembly 630) with respect to the proximal-most portion (near the apex release assembly 690) requires very little force. In other words, the torque resisting rotation of the distal-most portion to conform to the curve of the guidewire 610 is negligible. Specifically, the torque is so low that the force resisting the alignment of the guidewire lumen 620 to the guidewire 610 causes little, negligible, or no damage to the inside of the aorta, especially to a dissecting inner wall of a diseased aorta.

Due to the configuration of the delivery system 600 of the present invention, when the guidewire lumen 620 is extended from the outer catheter 660 (along with the apex release lumen 640, the stent graft 1, the inner sheath 652 as shown in FIGS. 20 and 21, for example), the pre-shape of the guidewire lumen 620 causes automatic and natural rotation of the entire distal assembly—including the stent graft 1—along its longitudinal axis. This means that the length and connectivity of the guidewire lumen 620, and the material from of which the guidewire lumen 620 is made, allow the entire distal assembly (1, 620, 630, 640, 650) to naturally rotate and align the pre-curved guidewire lumen 620 with the curve of the guidewire 610—this is true even if the guidewire lumen 620 is inserted into the aorta entirely opposite the curve of the aorta (one-hundred eighty degrees (180°)). In all circumstances, the curved guidewire lumen 620 will cause rotation of the stent graft 1 into an optimal implantation position, that is, aligning the desired portion of the support member 40 within ±70 degrees of the superior longitudinal line of the curved aorta. Further, the torque forces acting against rotation of the guidewire lumen 620 will not be too high to cause damage to the aorta while carrying out the rotation.

The self-aligning feature of the invention begins with a strategic loading of the stent graft 1 in the inner sleeve 652. To describe the placement of the supporting member 40 of the stent graft 1 relative to the curve 622 of the guidewire lumen 620, an X-Y coordinate curve plane is defined and shown in FIG. 64. In particular, the guidewire lumen 620 is curved and that curve 622 defines the curve plane 624.

To insure optimal implantation, when loading the stent graft 1 into the inner sheath 652, a desired point 'on the supporting member 40 between the centerline 45 of the stent graft 1 and the proximal support member loop 47 is aligned to intersect the curve plane 624. An exemplary, but not required, location of the desired point on the supporting member 40 is located forty-five (45) degrees around the circumference of the stent graft 1 shown in FIG. 1 beginning from the first degree 41 in line with the proximal support member loop 47. When the stent graft 1 is loaded in an exemplary orientation, it is ready for insertion into the inner sleeve 652. During the loading process, the stent graft 1 and the guidewire lumen 620 are held constant rotationally. After such loading, the inner sleeve 652 is refracted into the outer catheter 660 and the delivery system 600 is ready for purging with saline and use with a patient.

Figure 65:
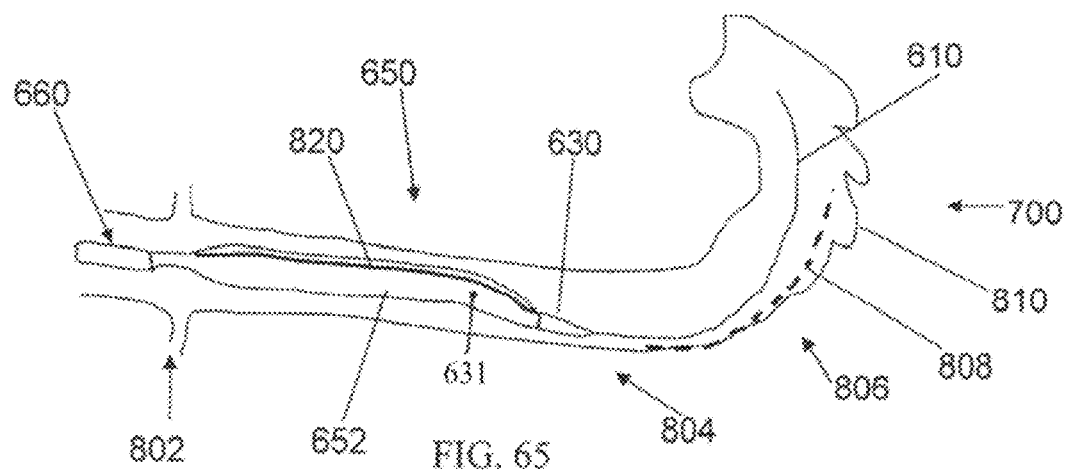
FIG. 65 is a diagrammatic, fragmentary, cross-sectional view of a distal portion of the delivery system with the self-alignment configuration according to the invention inside the descending thoracic aorta and with the self-alignment configuration in an orientation opposite a desired orientation.
Figure 66:
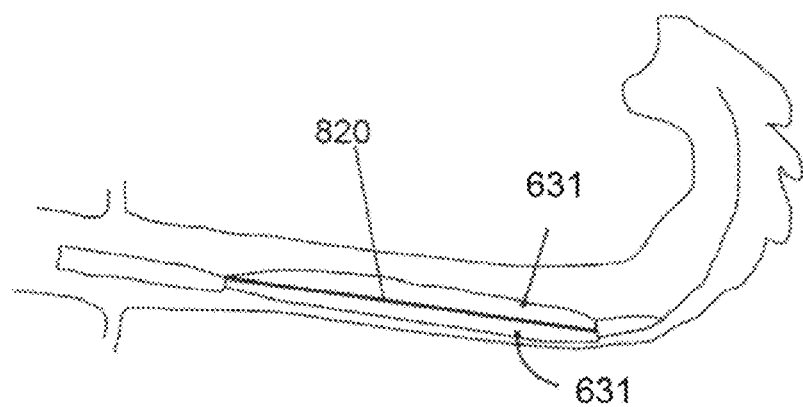
FIG. 66 is a diagrammatic, fragmentary, cross-sectional view of the distal portion of the delivery system of FIG. 65 with the self-alignment configuration partially inside the descending thoracic aorta and partially inside the aortic arch and with the self-alignment configuration in an orientation closer to the desired orientation.
Figure 67:
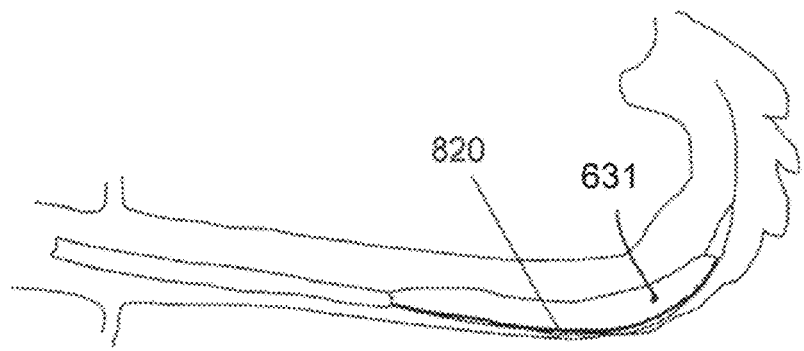
FIG. 67 is a diagrammatic, fragmentary, cross-sectional view of the distal portion of the delivery system of FIG. 65 with the self-alignment configuration primarily inside the aortic arch and with the self-alignment configuration substantially in the desired orientation.

FIGS. 65 to 67 illustrate self-alignment of the distal assembly 620, 630, 640, 650 after it is pushed out from the distal end of the outer catheter 660 (see FIGS. 20 and 21). FIG. 65 shows an aorta 700 and the distal assembly after it has traversed the iliac arteries 802 and enters the descending thoracic portion 804 of the aorta. The nose cone assembly 630 is positioned just before the aortic arch 806 and the stent graft 1 is contained within the inner sheath 652. A reference line 820 is placed on the stent graft 1 at a longitudinal line of the stent graft 1 that is intended to align with the superior longitudinal line 808 (indicated with dashes) of the aortic arch 806. In FIG. 65, the reference line 820 also lies on the curved plane 624 defined by the pre-curved guidewire lumen 620. As can be clearly seen from FIG. 65, the reference line 820 is positioned almost on or on the inferior longitudinal line of the curved aorta—thus, the stent graft 1 is one-hundred eighty degrees (180°) out of alignment. FIG. 66 shows the nose cone assembly 630 fully in the aortic arch 806 and the inner sleeve 652 at the entrance of the aortic arch 806. With the self-aligning configuration of the pre-curved guidewire lumen 620, movement of the distal assembly from the position shown in FIG. 65 to the position shown in FIG. 66 causes a rotation of the reference line 820 almost ninety degrees (90°) clockwise (with respect to a view looking upward within the descending aorta) towards the superior longitudinal line 808. In FIG. 67, the nose cone assembly 630 has reached, approximately, the left subclavian artery 810. Rotational movement of the distal assembly is, now, complete, with the reference line 820 almost aligned with the superior longitudinal line 808 of the aortic arch 806. From the views of FIGS. 65 to 67, also shown is the fact that the pre-curved guidewire lumen 620 has not caused any portion of the inner sleeve 652 to push against the inner surface of the aortic arch 806 with force—force that might exacerbate an aortic dissection.

It is noted that the guidewire lumen 620 need not be rotationally fixedly connected to the apex release lumen 640 when the apex release assembly 690 is in the locked position shown in FIGS. 15 and 16. Instead, a non-illustrated, freely rotatable coupling can be interposed anywhere along the guidewire lumen 620 (but, preferably, closer to the apex release assembly 690). This coupling would have a proximal portion rotationally fixedly connected to the to the apex release lumen 640 when the apex release assembly 690 is in the locked position shown in FIGS. 15 and 16 and a freely-rotatable distal portion that is fixedly connected to all of the guidewire lumen 620 disposed distal thereto. Thus, the guidewire lumen 620 near the sheath assembly 650 will always be freely rotatable and, thereby, allow easy and torque-free rotation of the guidewire lumen 620 about the guidewire 610.

Figure 69:
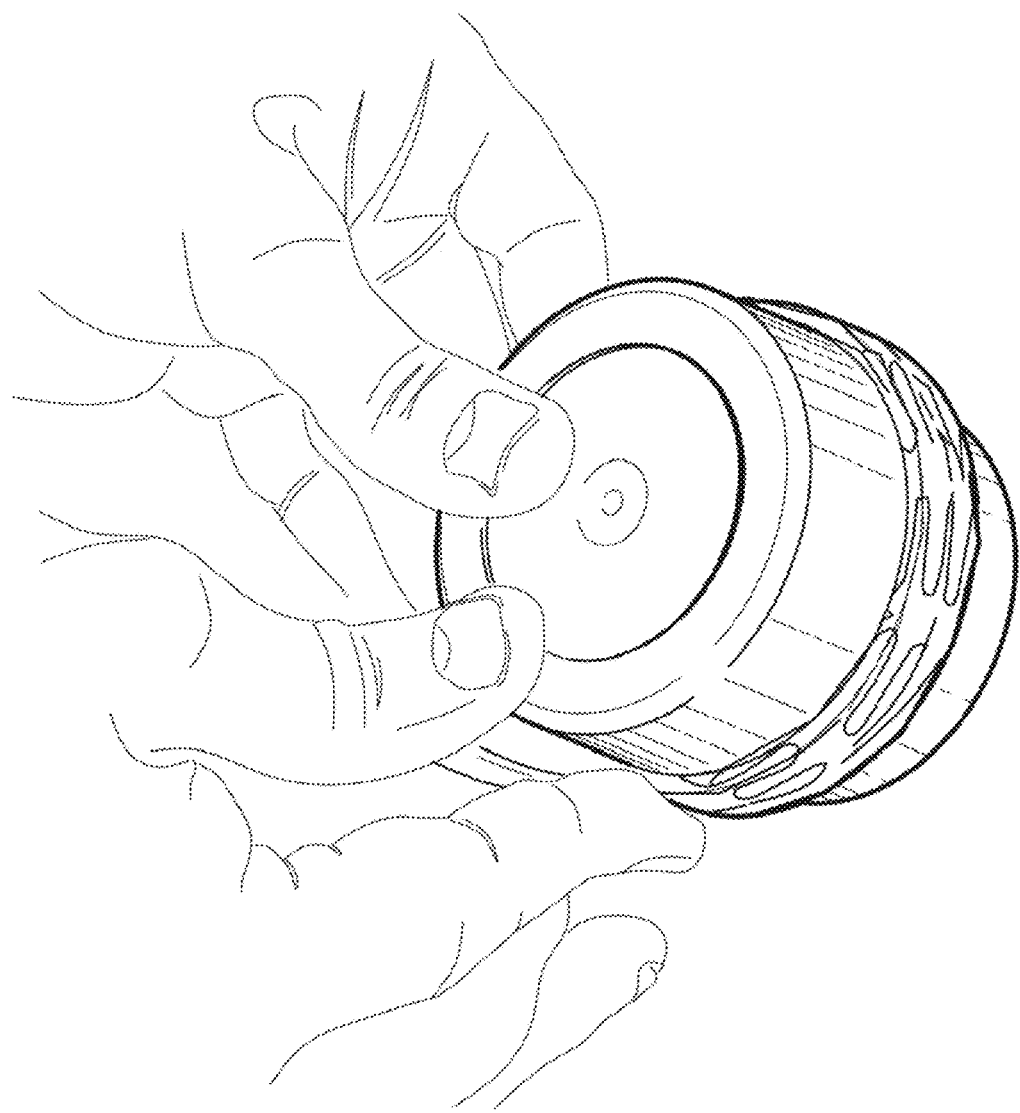
FIG. 69 depicts a user bending a stent graft assembly around a curving device to impart a curve to a guidewire lumen therein.

It is also noted that the pre-curved section 622 of the guidewire lumen need not be made at the manufacturer. As shown in FIG. 69, a curving device can be provided with the delivery system 600 to allow the physician performing the implantation procedure to tailor-fit the curve 622 to the actual curve of the vessel in which the stent graft 1 is to be implanted. Because different patients can have different aortic arch curves, a plurality of these curving devices can be provided with the delivery system 600, each of the curving devices having a different curved shape. Each device can also have two sides with each side having a different curved shape, thus, reducing the number of devices if a large number of curves are required. Further, the curving devices can all be rotationally connected on a common axle or spindle for each of transport, storage, arid use.

For tailoring the curve to the patient's curved vessel, the physician can, for example, fluoroscopically view the vessel (e.g., aortic arch) and, determine therefrom the needed curve by, for example, holding up the curving device to the display. Any kind of curving device can be used to impart a bend to the guidewire lumen 620 when the guidewire lumen 620 is bent around the circumference.

Because of the predefined curvature of the support member 40, the support member 40 cannot align exactly and entirely along the superior longitudinal line of the curved aorta. Accordingly, an optimal superior surface position of the support member 40 places as much of the central portion of the support member 40 (between the two ends 47 thereof) as possible close to the superior longitudinal line 808 of the curved aorta. A particularly desirable implantation position has the superior longitudinal line 808 of the curved aorta intersecting the proximal half of the support member 40—the proximal half being defined as that portion of the support member 40 located between the centerline 45 and the proximal support member loop 47. However, for adequate implantation purposes, the centerline 45 of the support member 40 can be as much as seventy circumferential degrees away from either side of the superior longitudinal line of the curved aorta.

When the stent graft 1 is in place both longitudinally and circumferentially (FIG. 21), the stent graft 1 is ready to be removed from the inner sheath 652 and implanted in the vessel 700. Because relative movement of the stent graft 1 with respect to the vessel is no longer desired, the inner sheath 652 needs to be retracted while the stent graft 1 remains in place, i.e., no longitudinal or circumferential movement. Such immovability of the stent graft 1 is insured by, first, the apex capture device 634 of the nose cone assembly 630 holding the front of the stent graft 1 by its bare stent 30 (see FIGS. 13, 22, and 23) and, second, by unlocking the locking knob 676/placing the locking ring/knob in the D position—which allows the sheath lumen 654 to move independently from the guidewire lumen 620, apex release lumen 640, and graft push lumen 642. The apex capture device 634, as shown in FIGS. 13, 14, 30 and 311 (and as will be described in more detail below), is holding each individual distal apex 32 of the bare stent 30 in a secure manner—both rotationally and longitudinally.

Figure 13:
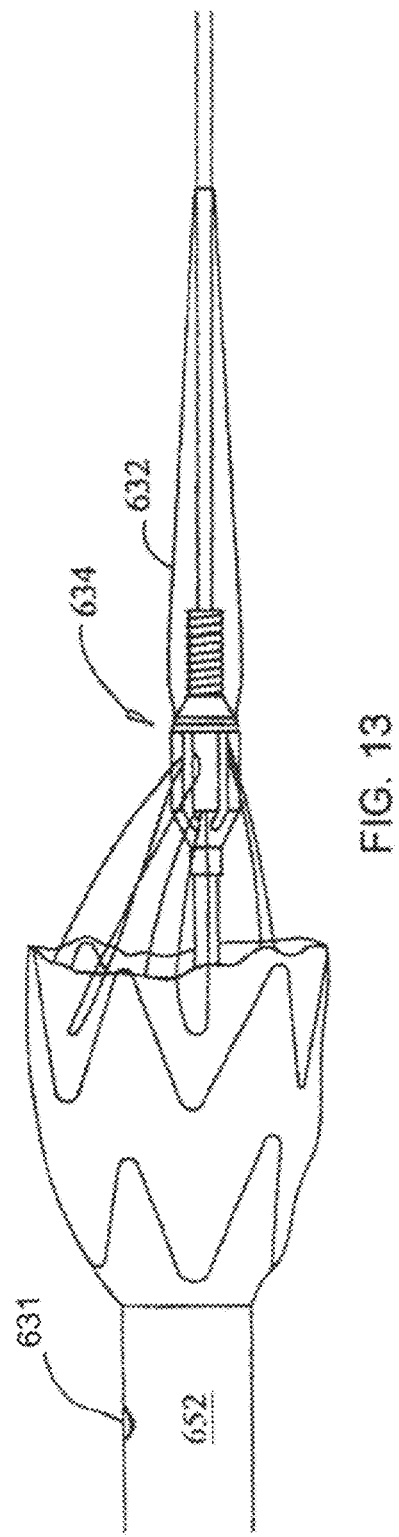
FIG. 13 is a fragmentary, enlarged view of an apex capture device of the delivery system of FIG. 10 in a captured position.

The nose cone assembly 630, along with the apex capture device 634, is securely attached to the guidewire lumen 620 (and the apex release lumen 640 at least until apex release occurs). The inner sheath 652 is securely attached to a sheath lumen 654, which is coaxially disposed around the guidewire lumen 620 and fixedly attached to the proximal handle 678. The stent graft 1 is also supported at its distal end by the graft push lumen 642 and the distal sleeve 644 or the taper 653 of the inner sheath 652. (The entire coaxial relationship of the various lumens 610, 620, 640, 642, 654, and 660 is illustrated for exemplary purposes only in FIG. 25, and a portion of which can also be seen in the exploded view of the handle assembly in FIG. 50) Therefore, when the proximal handle 678 is moved proximally with the locking knob 676 in the deployment position D, the sheath lumen 654 moves proximally as shown in FIGS. 13, 22, and 23, taking the sheath 652 proximally along with it while the guidewire lumen 620, the apex release lumen 640, the graft push lumen 642, and the distal sleeve 644 remain substantially motionless and, therefore, the stent graft 1 remains both rotationally and longitudinally steady.

The stent graft 1 is, now, ready to be finally affixed to the aorta 700. To perform the implantation, the bare stent 30 must be released from the apex capture device 634. As will be described in more detail below, the apex capture device 634 shown in FIGS. 13, 14, and 29 to 32, holds the proximal apices 32 of the bare stent 30 between the distal apex head 636 and the proximal. apex body 638. The distal apex head 636 is fixedly connected to the guidewire lumen 620. The proximal apex body 638, however, is fixedly connected to the apex release lumen 640, which is coaxial with both the guidewire lumen 620 and the sheath lumen 654 and disposed therebetween, as illustrated diagrammatically in FIG. 25. (As. will be described in more detail below, the graft push lumen 642 is also fixedly connected to the apex release lumen 640.) Therefore, relative movement of the apex release lumen 640 and the guidewire lumen 620 separates the distal apex head 636 and a proximal apex body 638 from one another.

Figure 26:
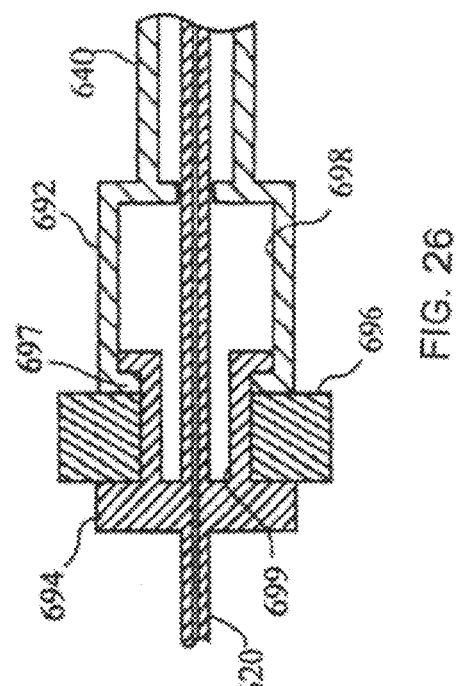
FIG. 26 is a fragmentary, cross-sectional view of the apex release assembly according to the invention.

To cause such relative movement, the apex release assembly 690 has, in an exemplary embodiment, three parts, a distal release part 692, a proximal release part 694, and an intermediate part 696 (which is shown in the form of a clip in FIGS. 16 and 26). To insure that the distal apex head 636 and the proximal apex body 638 always remain fixed with respect to one another until the bare stent 30 is ready to be released, the proximal release part 694 is formed with a distal surface 695, the distal release part 692 is formed with a proximal surface 693, and the intermediate part 696 has proximal and distal surfaces corresponding to the surfaces 695, 693 such that, when the intermediate part 696 is inserted removably between the distal surface 695 and the proximal surface 693, the intermediate part 696 fastens the distal release part 692 and the proximal release part 694 with respect to one another in a form-locking connection. A form-locking connection is one that connects two elements together due to the shape of the elements themselves, as opposed to a force-locking connection, which locks the elements together by force external to the elements. Specifically, as shown in FIG. 26, the clip 696 surrounds a distal plunger 699 of the proximal release part 694 that is inserted slidably within a hollow 698 of the distal release part 692. The plunger 699 of the proximal release part 694 can slide within the hollow 698, but a stop 697 inside the hollow 698 prevents the distal plunger 699 from withdrawing from the hollow 698 more than the longitudinal span of the clip 696.

Figure 14:
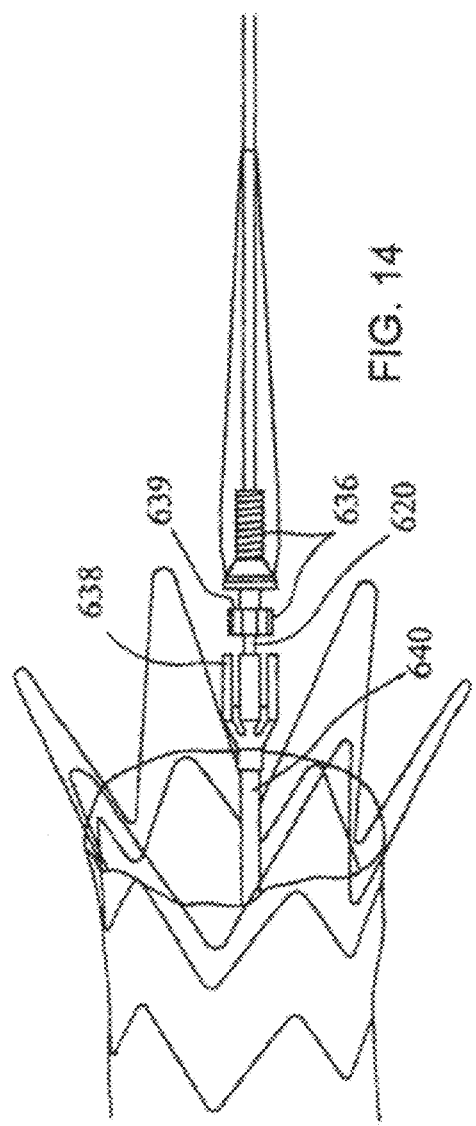
FIG. 14 is a fragmentary, enlarged view of the apex capture device of FIG. 13 in a released position.

To allow relative movement between the distal apex head 636 and the proximal apex body 638, the intermediate part 696 is removed easily with one hand and, as shown from the position in FIG. 16 to the position in FIG. 17, the distal release part 692 and the proximal release part 694 are moved axially towards one another (preferably, the former is moved towards the latter). Such movement separates the distal apex head 636 and the proximal apex body 638 as shown in FIG. 14. Accordingly, the distal apices 32 of the bare stent 30 are free to expand to their natural position in which the bare stent 30 is released against the vessel 700.

Of course, the apex release assembly 690 can be formed with any kind of connector that moves the apex release lumen 640 and the guidewire lumen 620 relative to one another. In an exemplary alternative embodiment, for example, the intermediate part 696 can be a selectable lever that is fixedly connected to either one of the distal release part 692 or the proximal release part 694 and has a length equal to the width of the clip 696 shown in FIG. 26. Thus, when engaged by pivoting the lever between the distal release part 692 and the proximal release part 694, for example, the parts 692, 694 cannot move with respect to one another and, when disengaged by pivoting the lever out from between the parts 692, 694, the distal release part 692 and the proximal release part 694 are free to move towards one another.

The apex capture device 634 is unique to the present invention in that it incorporates features that allow the longitudinal forces subjected on the stent graft 1 to be fully supported, through the bare stent 30) by both the guidewire lumen 620 and apex release lumen 640. Support occurs by providing the distal apex head 636 with a distal surface 639—which surface 639 supports the proximal apices 32 of the bare stent 30 (shown in the enlarged perspective view of the distal apex head 636 in FIG. 29). When captured, each proximal apex 32 of the bare stent 30 separately rests on a distal surface 639, as more clearly shown in FIGS. 30 and 31 The proximal spokes of the distal apex head 636 slide within the fingers of the proximal apex body 638 as these parts moves towards one another. A slight space, therefore, exists between the fingers and the outer circumferential surfaces of the spokes. To insure that the bare stent 30 does not enter this space (which would prevent a proper release of the bare stent 30 from the apex capture device 634, a radial thickness of the space must be less than the diameter of the wire making up the bare stent 30. Preferably, the space is no greater than half a diameter of the wire.

Figure 32:
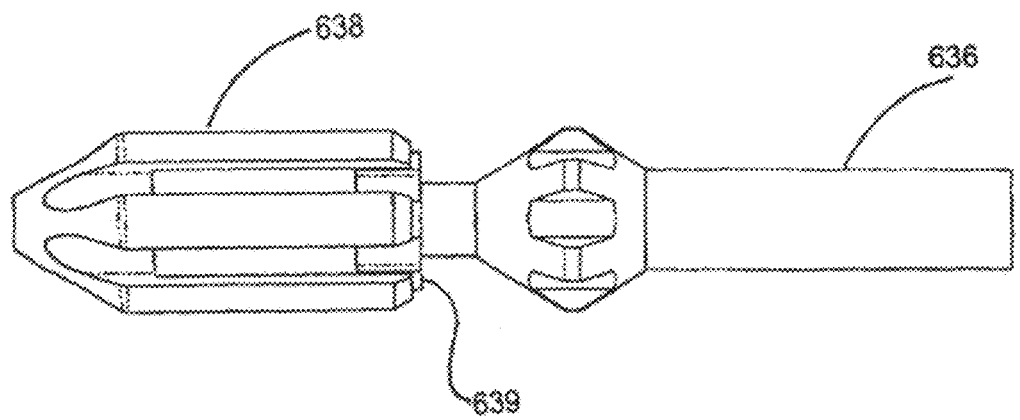
FIG. 32 is a fragmentary side elevational view of the distal apex head and proximal apex body of FIG. 30 in the released position.

Having the distal surface 639 be the load-bearing surface of the proximal apices 32 ensures expansion of each and every one of the distal apices 32 from the apex release assembly 690. The proximal surface 641 of the distal apex head 636 (see FIG. 30) meets with the interior surfaces of the proximal apex body 638 to help carry the apex load because the apices of the bare stent 30 are captured therebetween when the apex capture device 634 is closed. Complete capture of the bare stent 30, therefore, fully transmits any longitudinal forces acting on the bare stent 30 to both the guidewire lumen 620 and apex release lumen 640, making the assembly much stronger. Such capture can be clearly seen in the cut-away view of the proximal apex body 638 in FIG. 31. For release of the apices 32 of the bare stent 30, the proximal apex body 638 moves leftward with respect to FIGS. 30 to 33 (compare FIGS. 30 and 31 with FIG. 32). Because friction exists between the apices 32 and the "teeth" of the proximal apex body 638 when the apices 32 are captured, the apices 32 will also try to move to the left along with the proximal apex body 638 and, if allowed to do so, possibly would never clear the "teeth" to allow each apex 32 to expand. However, as the proximal apex body 638 disengages (moves in the direction of arrow C in FIG. 31), direct contact with the distal surface 639 entirely prevents the apices 32 from sliding in the direction of arrow C along with the proximal apex body 638 to ensure automatic release of every captured apex 32 of the bare stent 30. Because the proximal apex body 638 continues to move in the direction of arrow C, eventually the "teeth" will clear their respective capture of the apices 32 and the bare stent 30 will expand entirely. The release position of the distal apex head 636 and the proximal apex body 638 is shown in FIGS. 14 and 32, and corresponds to the position of the apex release assembly 690 in FIG. 17. As can be seen, tapers on the distal outer surfaces of the proximal apex body 638 further assist in the prevention of catching the proximal apices 32 of the bare stent 30 on any part of the apex capture device 634. In this configuration, the distal surfaces 639 bear all the load upon the bare stent 30 and the fingers of the proximal apex body 638.

Simply put, the apex capture device 634 provides support for load placed on the stent graft 1 during advancement A of the inner sheath 652 and during withdrawal of the inner sheath 652 (i.e., during deployment D). Such a configuration benefits the apposition of the bare stent 30 by releasing the bare stent 30 after the entire graft sleeve 10 has been deployed, thus reducing the potential for vessel perforation at the point of initial deployment.

When the stent graft 1 is entirely free from the inner sheath 652 as shown in FIG. 24, the proximal handle 678 is, then, substantially at or near the third position (deployment position) shown in FIG. 10.

The stent graft 1 is, now, securely placed within the vessel 700 and the entire portion 630, 650, 660 of the assembly 600 may be removed from the patient.

FIGS. 70 and 71 illustrate alternative configurations of the stent graft 1 of FIG. 1, The stent graft 1000 of FIG. 70 is similar to the stent graft 1 of FIG. 1. The stent graft 1000 has a graft 1010 and a number of stents 1020. The stents 1020 are attached either to the exterior or interior surfaces of the graft sleeve 1010. Preferably, the stents 1020 are sewn to the graft 1010. The stent graft 1000 shown in FIG. 70 has been discussed above with respect to FIG. 1, for example, and, therefore, the discussion relevant to features already discussed will not be repeated for the sake of brevity.

FIG. 70 shows an exemplary embodiment of the curved ends 1047 of the connecting rod 1040. In particular, the rod 1040 forms a loop (whether, polygonal, ovular, or circular) and has an end portion 1048 that continues back parallel and next to the rod 1040 for a short distance, This end portion 1048, along with the adjacent portion of the rod 1040 allows, for example, connective stitching to cover two lengths of the rod 1040 and better secures the end portion 1048 to the graft sleeve 1010. In such configuration, there is limited or even no chance of a sharp end of the rod 1040 to be exposed to harm the graft sleeve 1010 or the vessel wall in which the stent graft 1000 is placed.

An alternative embodiment of the stent graft 1000 is shown as stent graft 1100 in FIG. 71. This stent graft 1100 contains a graft sleeve 1110 that completely covers the bare stent 30 shown in FIGS. 1 and 70 and is hereinafter referred to with respect to FIGS. 71 to 78 as a clasping stent 1130. As shown particularly well in FIGS. 72 and 74, the clasping stent 1130 is entirely covered by the graft 1110 but is not attached to the material of the graft 1110 along its entirety.

Figure 72:
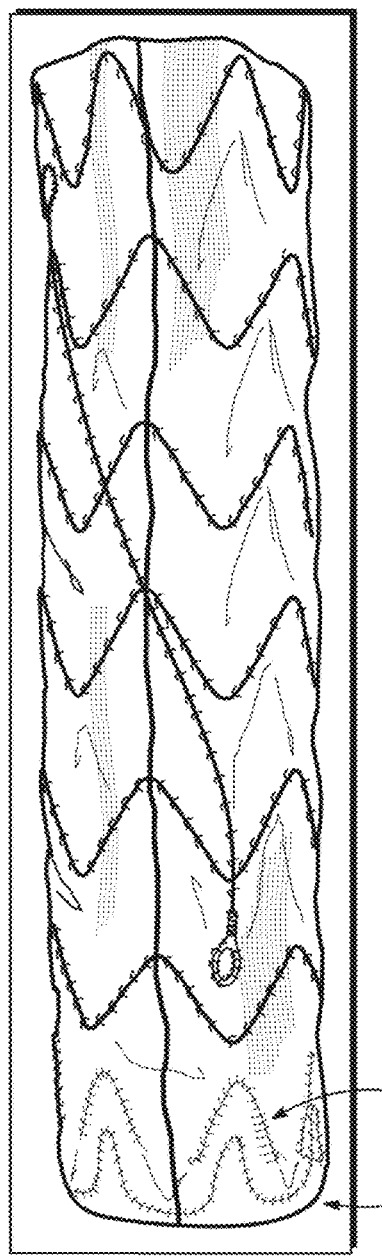
FIG. 72 is a photograph depicting a side view of the stent graft of FIG. 71.
Figure 74:
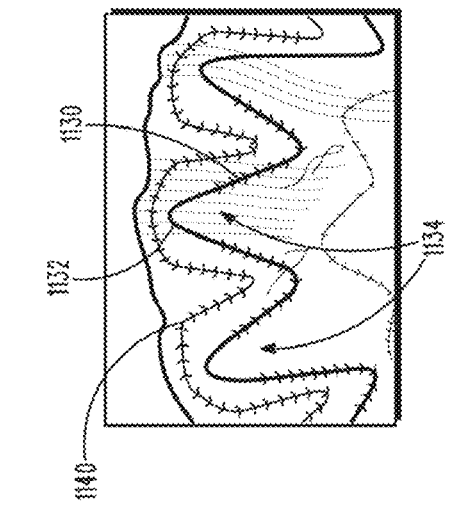
FIG. 74 is a photograph of an enlarged, perspective view from the interior of the proximal end of the stent graft of FIG. 71.
Figure 73:
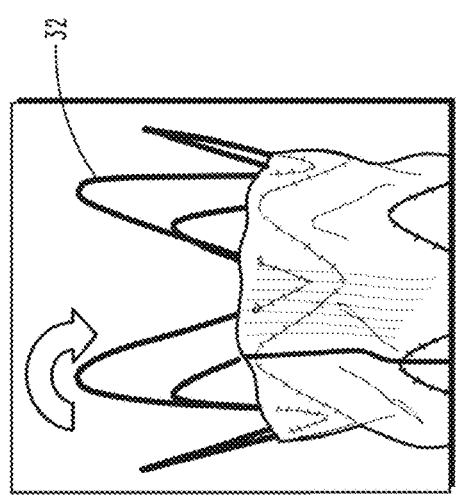
FIG. 73 is a photograph of a perspective view from a side of a proximal end of the stent graft of FIGS. 1 and 70 with a bare stent protruding from the proximal end thereof.
Figure 79:
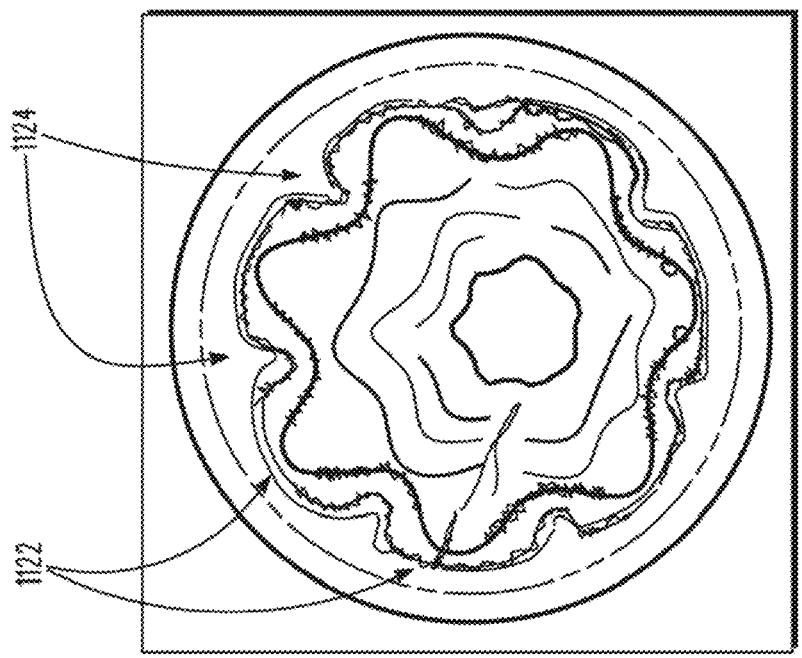
FIG. 79 is a photograph of a perspective view from the proximal end of the stent graft of FIG. 71 deployed in an exemplary vessel.
Figure 78:
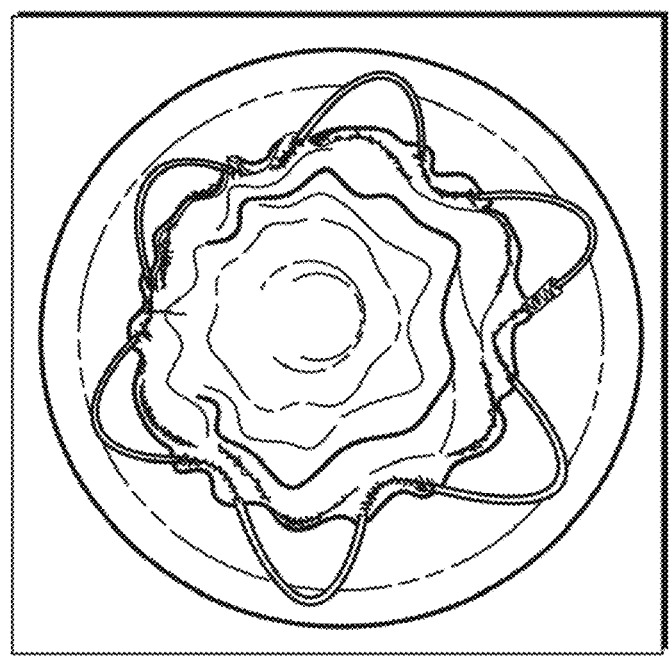
FIG. 78 is a photograph of a perspective view from the proximal end of the stent graft of FIGS. 1 and 70 deployed in an exemplary vessel.

At least some of the proximal apices 1132, preferably, at least three or four, are left unconnected to permit a releasable connection with the fingers of the proximal apex body 638 when the fingers are extended through the apex openings 1134. Of course, in certain applications, it may be beneficial to only leave one apex 1132 unconnected. The unconnected portion of each the apices 1132 has a minimal longitudinal length of about 10 percent of the longitudinal length of the stent and a maximum longitudinal length of up to approximately 90 percent of the length of the stent. Preferably, the longitudinal length of the unconnected portion is between approximately 30 to 40 percent as shown in FIGS. 72 and 74, which show the clasping stent 1130 sewn to the interior of the graft 1110. For ease of comparison, FIG. 73 illustrating the proximal end of the stent graft of FIGS. 1 and 70 is included next to FIG. 74. The unconnected portions of apices 1132 need not have the same longitudinal lengths. Depending on the application, one or some of the unconnected portions of apices 1132 can have a longitudinal length different from other ones of the unconnected portions of apices 1132. FIG. 75, for example, illustrates an embodiment near the maximum longitudinal length of the unconnected portion of the clasping stent 1130.

FIGS. 76 and 77 illustrate a proximal end of the stent graft 1100 of FIG. 71 partially deployed from the flexible inner sheath 652, As can be seen in FIG. 76, the entire capturing assemblies of the apex capture device 634 reside inside the stent graft 1100 when the apices are captured. Only the distal-most portion of the distal apex head 636 extends out from the interior of the stent graft 1100. With regard to the view of FIG. 77, it can be seen that only a few of the apices 1132 of the clasping stent 1130 are actually held by the apex capture device 634.

It is noted at this point that implantation of the stent graft 1, 1000, 1100 of the present invention occurs while blood is flowing from the heart of the patient. Accordingly, the stent graft 1100 cannot occlude the vessel in which it is to be implanted and, in order to do so, there must exist a lumen for passing blood throughout the time after the stent graft 1100 has partially or fully expanded within the vessel. If all of the apices 1132 of the clasping stent 1130 were held within the apex capture device 634, then there is a possibility of occluding the vessel if the unattached portion of the apices 1132 are too short to provide such a lumen. To avoid this condition, if only some apices 1132 of the clasping stent 1130 are captured, as illustrated in FIG. 77, then a sufficiently large lumen exists to allow blood flow through the vessel in which the stent graft is to be implanted. Alternatively, if a large percentage of the apices 1132 are left unconnected, as shown, for example, in FIG. 75, then all of the apices 1132 can be releasably held by the apex capture device 634 while the graft sleeve 1110 remains entirely open to allow blood flow through the stent graft 1100 during the stent graft 1100 implantation process.

There exists a drawback to placing the clasping stent 1130 as the proximal stent of the stent graft 1100 because material of the graft 1110 is proximal of the clasping stent 1130. If unsupported, this material could move disadvantageously toward the interior of the stent graft 1100 after implantation and decrease or occlude blood flow. To prevent such movement, the stent graft 1100 also includes a crown stent 1140. Like the clasping stent 1130, the crown stent 1140 is shown in FIGS. 71, 72, 74 to 76, and 78 as being attached to the inside of the graft 1120 and, in this exemplary embodiment, is sewn to the material of the graft using the same polyester suture as the other stents. Of course, the crown stent 1140 can be attached to the exterior of the graft 1010. In such a configuration, the crown stent 1140 augments the rigidity of the material of the graft 1120 to reduce enfolding thereof at the proximal end of the stent graft 1100.

Alternatively and/or additionally, a non-illustrated distal crown stent can be attached to the inside or outside of the graft 1120 at the opposite distal end of the stent graft 1100. In such a configuration, this distal crown stent 1140 augments the rigidity of the material at the distal end of the graft 1120 to reduce enfolding thereof.

The material of the graft 1120 can extend and bridge the entire distance between two proximal crown apices 1122. It is noted, however, that, alternatively or additionally, the material of the graft 1120 may be partially cut out between crown apices 1122 of the crown stent 1140 to define a plurality of a radially distensible flange portions 1124 at the proximal end of the stent graft 1100, as shown in FIG. 74.

There are various advantages provided by the stent graft 1100 over the prior art. First, the clasping and crown stents 1130, 1140 improve the apposition of the material of the graft to the intima of the vessel in which the stent graft 1100 is placed, in particular, in the aorta. Second, by better aligning the proximal portion of the stent graft 1110 in the lumen of the arch, the clasping and crown stents 1130, 1140 provide an improved blood-tight closure of the proximal end of the stent graft 1110 so that blood does not pass between the intima of the vasculature and the outer surface of the stent graft 1110.

As set forth above, if the apex capture device 634 captures less than all of the apices of the clasping stent 1130. The resulting openings allow blood flow during implantation. It is illustrated particularly well in FIGS. 1, 13, 14, and 70 that the material of the graft 10 of stent graft 1, 1000 begins only distal of the center of the bare stent 32. In comparison, as shown in FIGS. 71 and 73, the material of the graft 1120 begins well proximal of the proximal-most apices of the clasping stent 1130. Thus, this embodiment allows the material of the graft 1120 to extend much further into a vessel (i.e., further into the curved arch of the aorta). Therefore, a physician can repair a vessel further upstream in the aorta than the embodiment of the stent graft 1, 1000 of FIGS. 1 and 70.

In the prosthesis embodiment of FIGS. 1 and 70, there is direct contact between the metal of the bare stent 32 and the intima of the blood vessel. In contrast thereto, the configuration of the stent graft 1100 with the clasping stent 1130 places material of the graft 1120 between the metal of the clasping stent 1130 and the intima. Such a configuration provides a more atraumatic connection between the vessel and the proximal end of the stent graft 1100 than the configuration of FIGS. 1 and 70. This advantage is especially important for treating dissections—where the intima is in a weakened condition.

Figure 63:
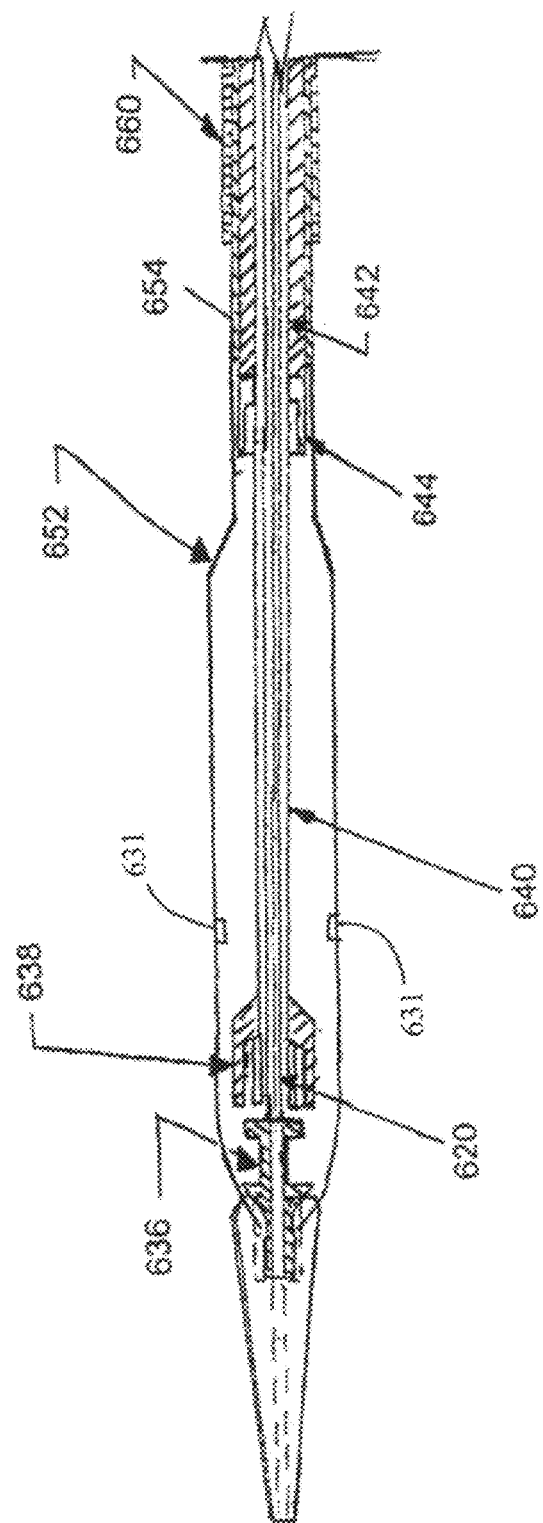
FIG. 63 is a fragmentary, cross-sectional view of the nose cone and sheath assemblies of FIG. 10.

FIG. 63 illustrates interaction between the catheter 660, the inner sheath 652, and the nose cone assembly 630 (including the nose cone 632, the distal apex head 636, and the proximal apex body 638). In this illustration, first, the catheter 660 is in a proximal position that does not cover the inner sheath 652 in any way. For example, this position of the catheter 660 occurs when the inner sheath 652 has extended out of the catheter 660 as shown in FIGS. 20 and 21.

Next, the inner sheath 652 is clearly shown in its expanded state (caused by the non-illustrated prosthesis disposed therein and expanding outward). The distal-most end of the inner sheath 652 is disposed between the distal apex head 636 and the nose cone 632. In such an orientation, the inner sheath 652 is in the position that occurs during extension out of the catheter 660 as shown for example, in FIGS. 20 and 21. Because the nose cone 632 screws onto the distal end of the distal apex head 636, the distal-most end of the inner sheath 652 is releasably captured between the two parts 632, 636 until it is removed. Refraction of the sheath lumen 654 proximally pulls the distal-most captured end of the inner sheath 652 out from the capturing interface.

Finally, the proximal apex body 638 is in a retracted position proximal of the distal apex head 636. This orientation is for illustrative purposes only to show the interaction of the distal apex head 636 and the proximal apex body 638 because the separation would not occur in use until, as set forth above, the inner sheath 652 is fully retracted from over the stent graft 1 and the proximal, apices 32 of the stent 30 have been released as shown in FIG. 14.

Figure 81:
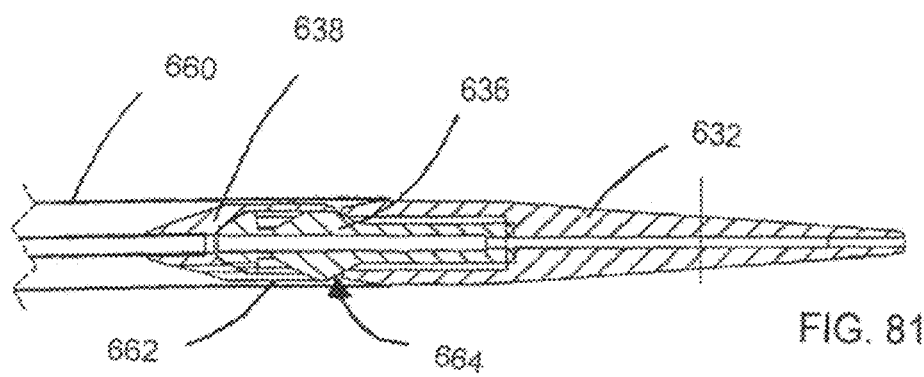
FIG. 81 is a fragmentary, cross-sectional view of the apex capture assembly of FIG. 80 along a plane orthogonal to the view plane of FIG. 80 and through the longitudinal axis of the delivery system according to the invention without the inner sheath.
Figure 80:
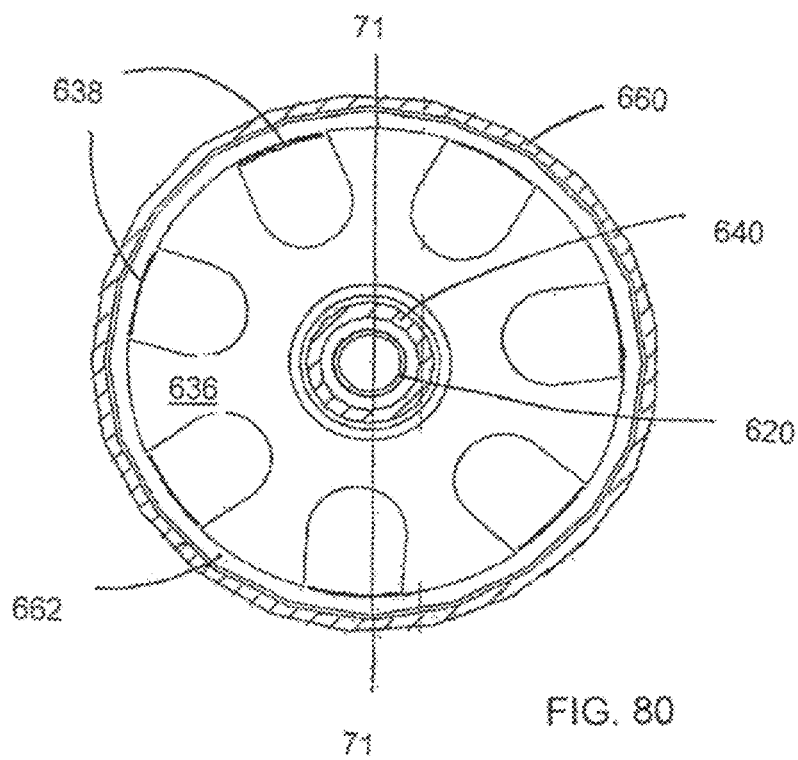
FIG. 80 is a cross-sectional view of the apex capture assembly of FIGS. 13, 14, 29 to 32, and 63 along a plane orthogonal to the longitudinal axis of the delivery system according to the invention without the inner sheath.
Figure 87:
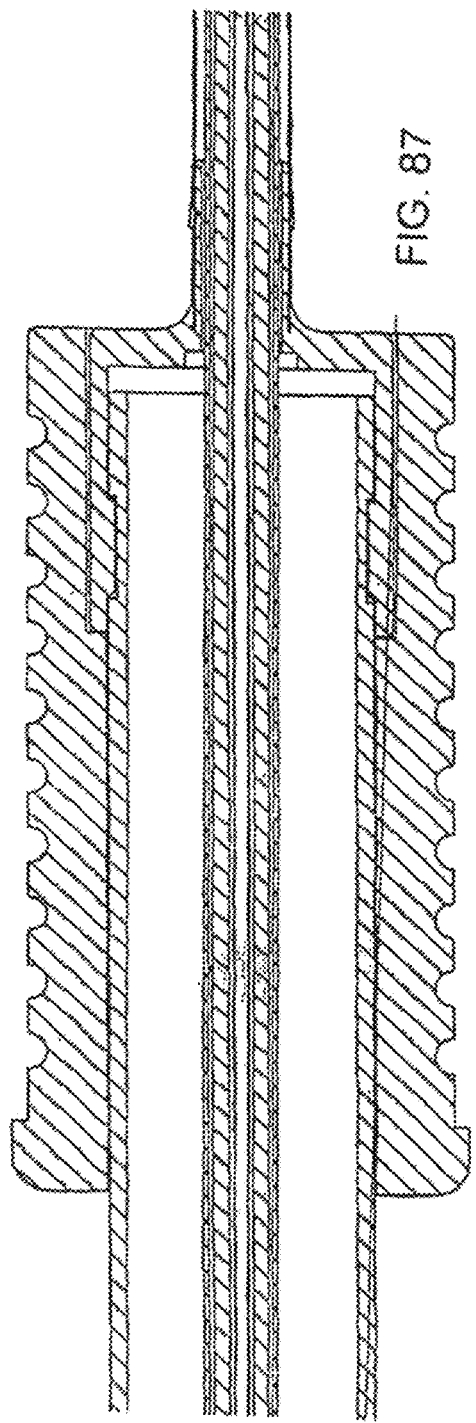
FIG. 87 is a fragmentary, cross-sectional view of the rotating distal handle of FIG. 86.
Figure 88:
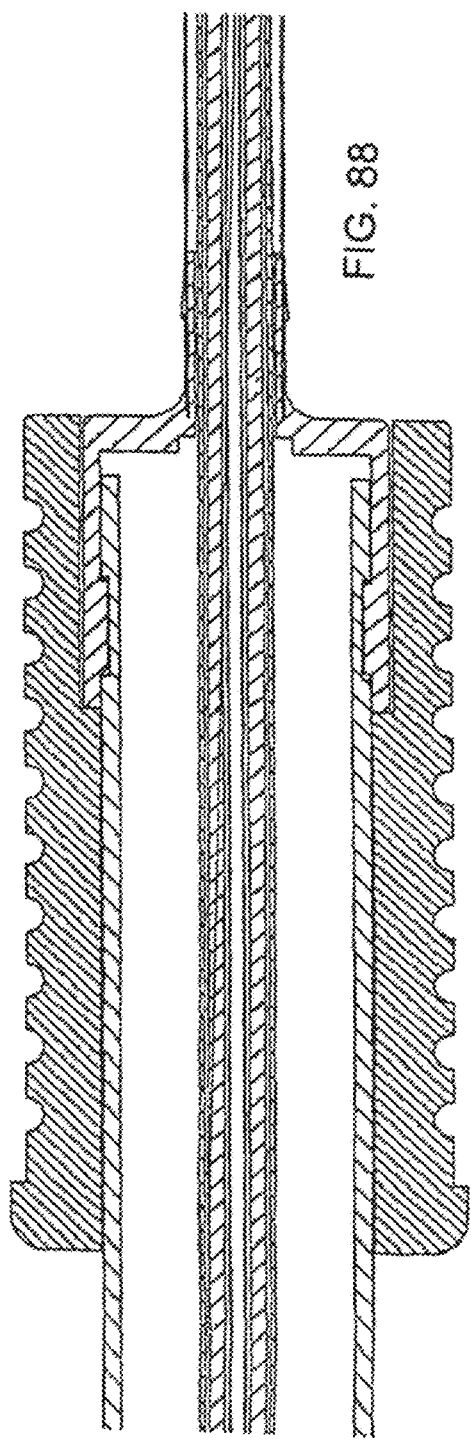
FIG. 88 is a is a fragmentary, cross-sectional view of an alternative embodiment of the rotating distal handle of FIG. 86.
Figure 89:
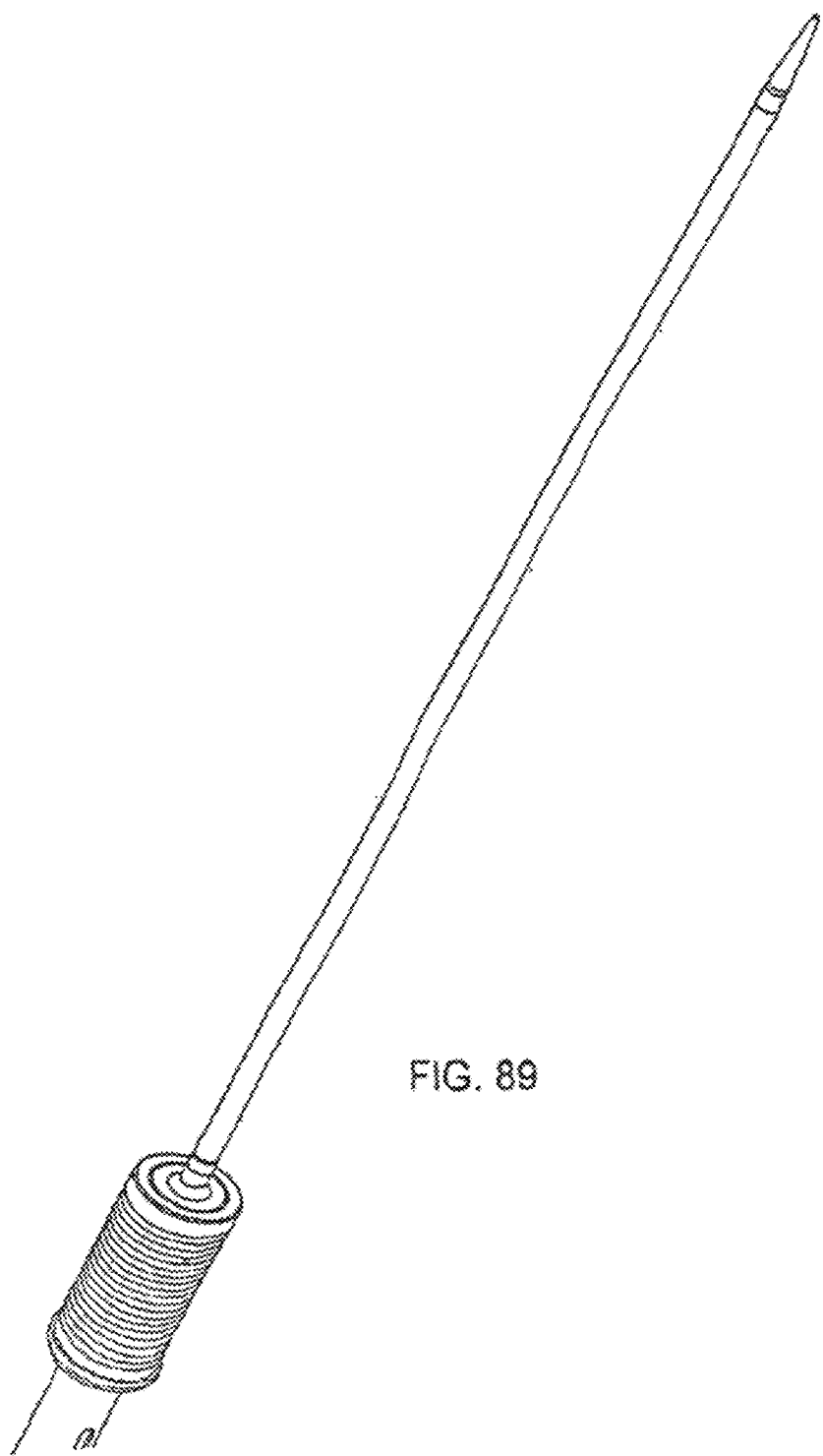
FIG. 89 is a fragmentary, perspective view of the distal end of the delivery system of FIG. 86.

FIG. 80 is a cross-section through the catheter 660, the fingers of the proximal apex body 638, the distal apex head 636, the apex release lumen 640, and the guidewire 620. FIG. 81 is a cross-section of the distal end of the delivery system along the longitudinal axis of the delivery system. These two figures illustrate the space 662 that exists between the catheter 660 and both of the proximal apex body 638 and the distal apex head 636 to make room for the inner sheath 652 to surround the parts 636, 638 and pass between the nose cone 632 and the distal apex head 636 and enter the pass 664 that allows the inner sheath 652 to be releasably held there as shown in FIG. 63 until it is desired to remove the inner sheath 652 therefrom.

FIG. 82 shows a distal end of the delivery system according to the invention in the orientation of FIGS. 20 and 21, for example. The inner sheath 652 is curved and has an alternative embodiment of a D shaped marker 234 thereon. In contrast to the configuration of two markers 234 on the stent graft 1 as shown in FIGS. 27 and 28, there is only one marker 234 on the inner sheath 652. As illustrated in the orientations of FIGS. 83, 84, and 85, the marker 234 allows the user to see how the inner sheath 652 should be oriented prior to implantation.

FIGS. 86, 87, 88, and 89 illustrate an alternative embodiment of the front handle 672 that is rotatably attached to the handle 674 and rotatably fixed to the catheter 660.

FIGS. 90 to 119 depict another exemplary embodiment of various features of the delivery assembly 600.

Figure 90:
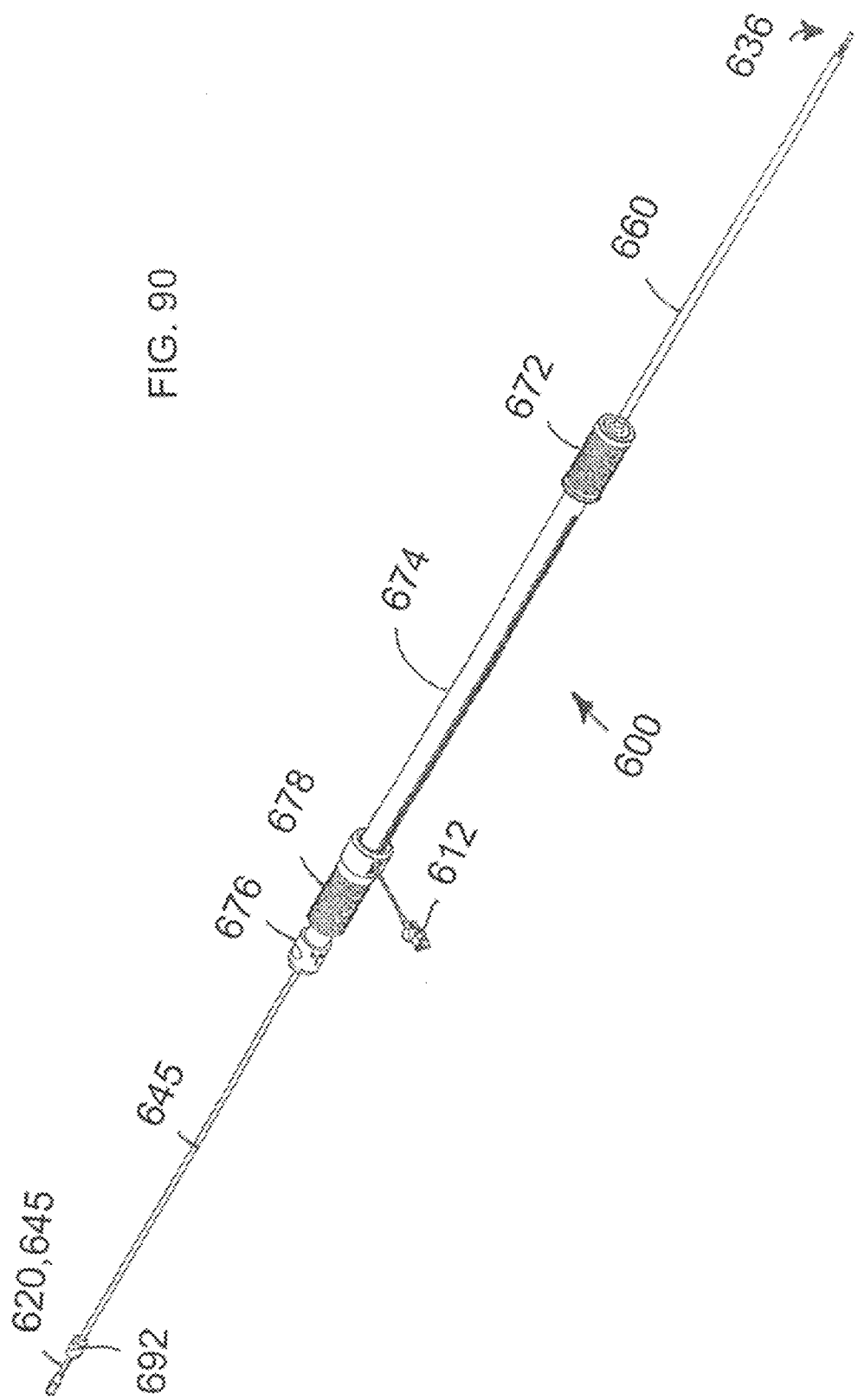
FIG. 90 is a perspective view from the distal side of another embodiment of the delivery system of the invention.

FIG. 90 shows the entire delivery assembly 600 with a portion of nose cone assembly 630 removed to reveal the distal apex head 636.

Figure 91:
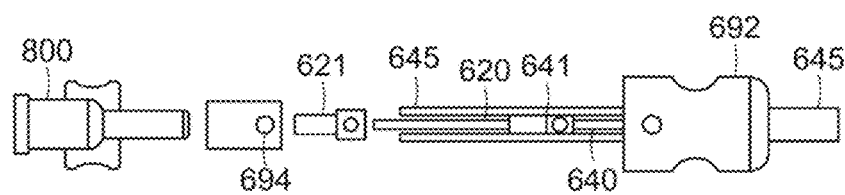
FIG. 91 is a fragmentary, enlarged, exploded, side elevational view of the apex release assembly of the delivery system of FIG. 90.

On the proximal end of the delivery assembly 600, the enlarged view of FIG. 91 depicts an alternative embodiment of the apex release assembly 690. In FIG. 91, a proximal pusher support tube 645 surrounds two coaxial lumens, the guidewire lumen 620 and the apex release lumen 640. The proximal pusher support tube 645 is longitudinally fixed to the proximal end of the graft push lumen 642 and has substantially the same diameter as the graft push lumen 642. Because the proximal pusher support tube 645 is used for pushing/pulling the combination lumen 642, 645, and due to the fact that the proximal pusher support tube 645 only resides within the handle body or proximal thereof, the proximal pusher support tube 645 can be made of a relatively stiff material, such as stainless steel, for example. In contrast, the graft push lumen 642 needs to flex and bend when extending out of the outer catheter 660 and. into vasculature. Thus, the graft push lumen 642 is made from a relatively flexible material, such as a plastic. In FIG. 91, the proximal portion of the proximal pusher support tube 645 is cut away to reveal the features therein, including the guidewire lumen 620 and the apex release lumen 640.

The apex release lumen 640 is axially fixed to the proximal apex body 638. The guidewire lumen 620, on the other hand, is axially fixed to the distal apex head 636. Thus, distal movement of the apex release lumen 640 with respect to the guidewire lumen 620 separates the tines of the proximal apex body 638 extending over the spokes of the distal apex head 636. To effect this relative movement, proximal and distal crimping devices 621 and 641 are respectively attached to the guidewire 620 and the apex release lumen 640. The distal release part 692 is connected, through a non-illustrated set screw to the distal crimping device 641. The proximal release part 694 is connected, also through a non-illustrated set screw, to the proximal crimping device 621. Finally, a proximal luer connector 800 is connected to the proximal-most end of the proximal pusher support tube 645 so that all of the lumen 620, 640, 645 can be filled and/or drained with a liquid, such as saline.

Figure 92:
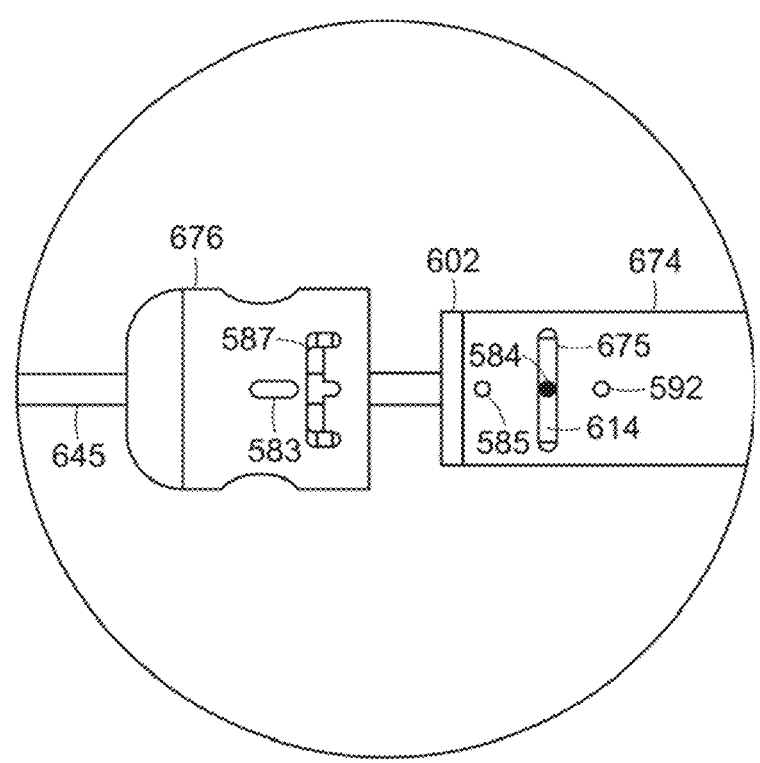
FIG. 92 is a fragmentary, enlarged. partially exploded, side elevational view of the locking knob assembly of the delivery system of FIG. 90.
Figure 93:
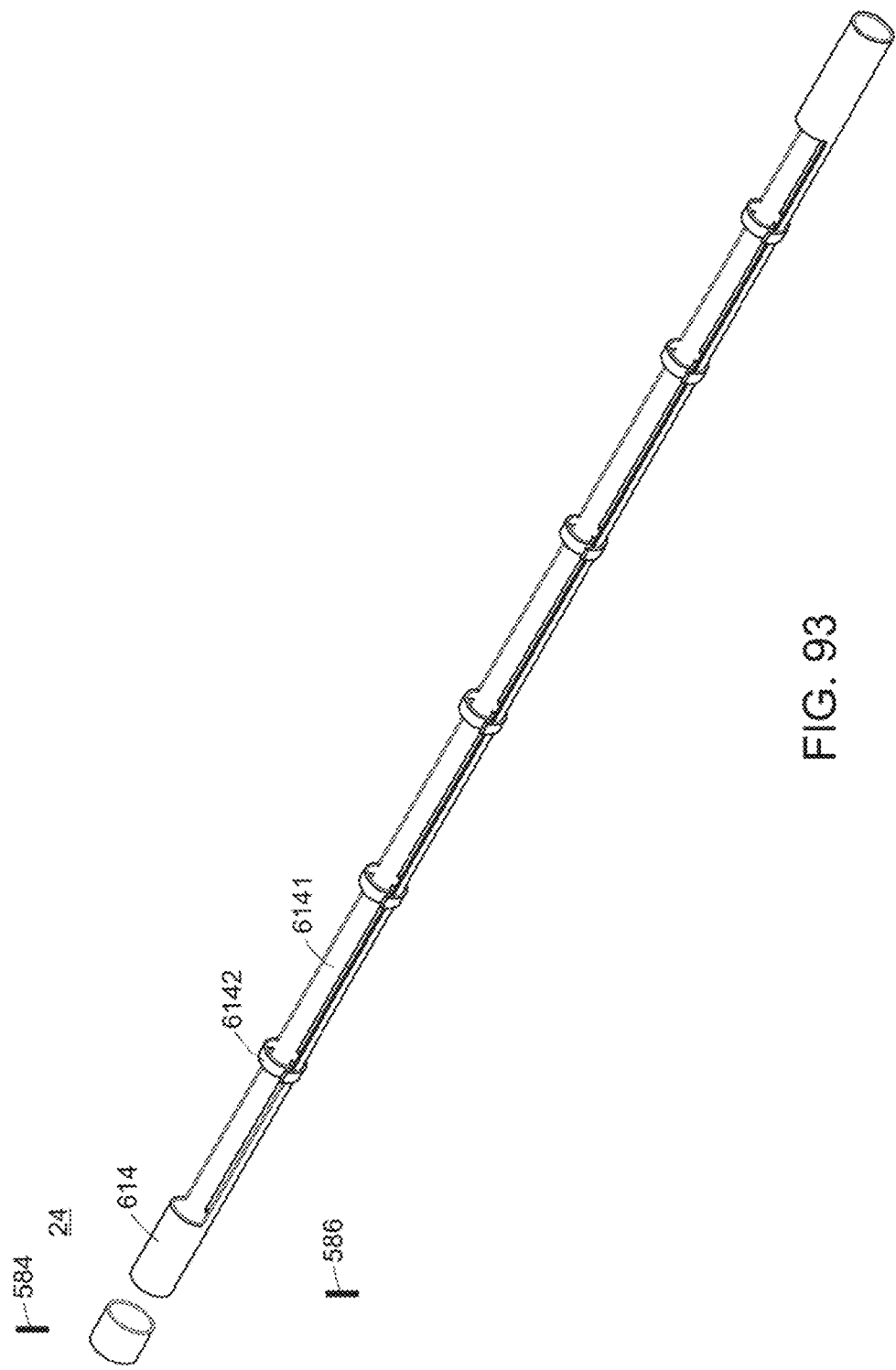
FIG. 93 is a perspective view of a clasp sleeve of a handle assembly of the delivery system of FIG. 90.

FIG. 92 is an enlarged view of the alternative embodiment of the locking knob 582 first shown in FIGS. 50 and 51. To better explain the features of FIG. 92, reference is made to the separated clasp sleeve 614 of FIG. 93, which was first depicted in FIGS. 50, 53, and 59 to 62. This clasp sleeve 614 is longitudinally fixedly and rotationally freely connected to the handle body 674 through the setscrew 584 that protrudes into the slot 675 of the handle body 674. The setscrew 584 is screwed into but not through the proximal end of the clasp sleeve as shown in FIG. 93. for example. This setscrew 584 protrudes into the slot 675 in the handle body 674. When so connected. the clasp sleeve 614 cannot move longitudinally with respect to the handle body 674 but can rotationally move along the arc defined by the length of the slot 675. The setscrew 584 protrudes from the outer circumference of the handle body 674 because it enters into the longitudinal slot 583 in the locking knob 582. Thus, the setscrew 584 also controls the longitudinal movement distance of the locking knob 582. When the knob 582 is at rest, the setscrew 584 resides 'in the distal end of the slot 583 because of the bias caused by spring 607 (see FIG. 94).

The second setscrew 592 (also referred to as a position pin) starts from the handle body 674 but does not extend inside the handle body 674. The setscrew 592 does, however, protrude out from the handle body 674 and into the three-position slot 587 of the locking knob 582. Thus, the setscrew 592 controls the rotation of the knob 582 within the three positions.

The third setscrew 585 is screwed through a threaded hole in the handle body 674 and into a co-axial threaded hole 6021 of the clasp body 602 until the setscrew 585. is even with the exterior surface of the handle body 674. Thus, the setscrew 585 does not protrude from the outer circumference of the handle body 674.

Figure 94:
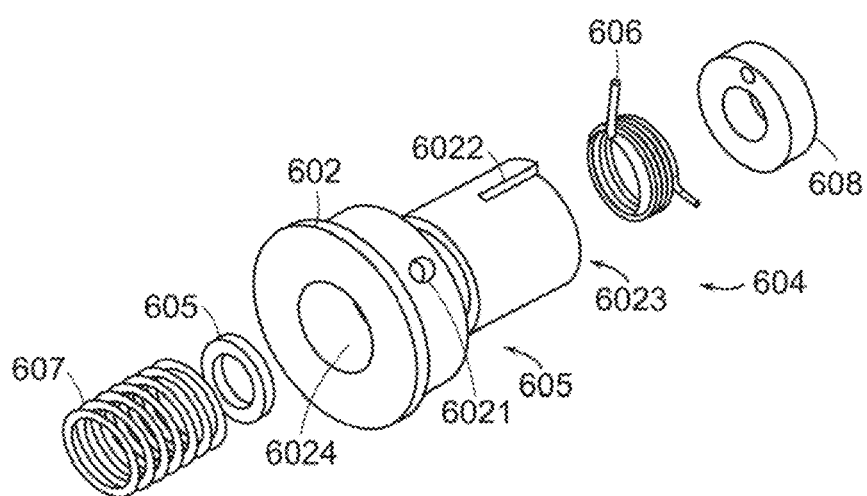
FIG. 94 is an exploded, perspective view of a clasp body assembly of the handle assembly of FIG. 90.
Figure 101:
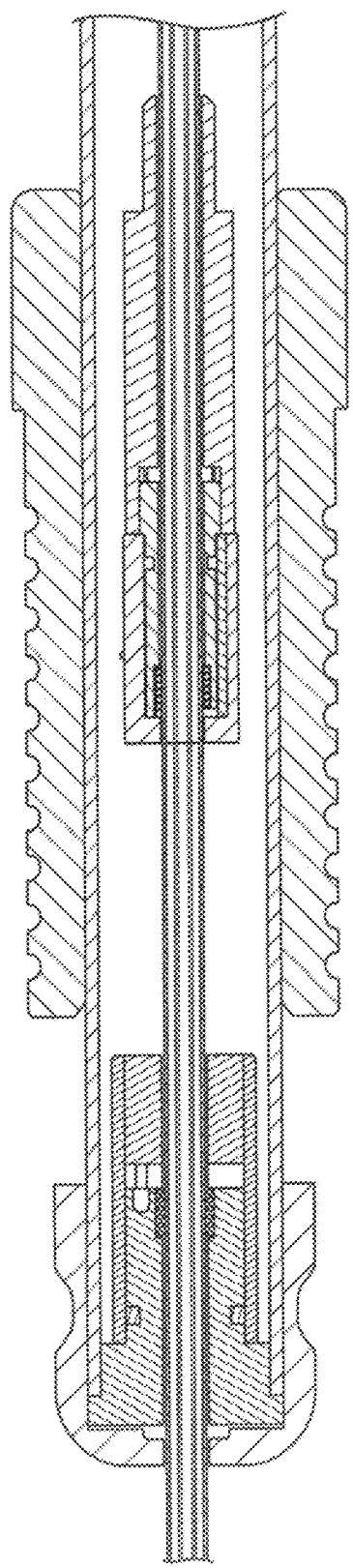
FIG. 101 is a fragmentary, partially hidden side elevational view and partially cross-sectional view of the proximal end of the handle assembly of FIG. 90 with the sheath lumen removed.
Figure 102:
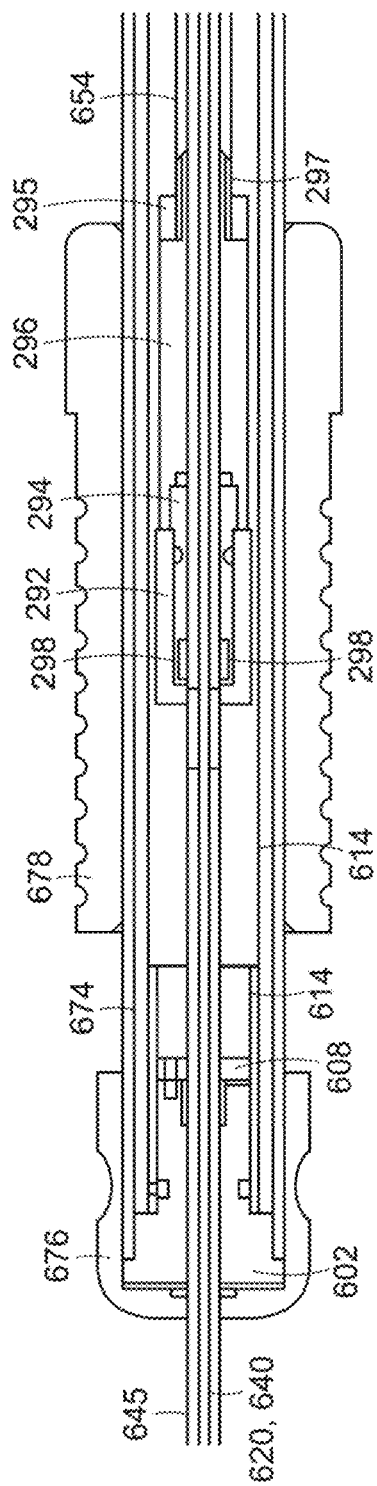
FIG. 102 is a fragmentary, cross-sectional view of the proximal end of the handle assembly of FIG. 101.

The proximal clasp assembly 604 was first illustrated in FIG. 52. In FIG. 94, the proximal clasp assembly 604 is illustrated with different detail. The clasp body 602 has a distal interior cavity 6023 shaped to receive therein the distal clasp body spring 606, which is a torsion spring in this exemplary embodiment. The locking washer 608 is connected to the distal end of the clasp body 602 by a non-illustrated setscrew that, for example, runs through the bore illustrated at the 12 O'clock position on the locking washer 608 in FIG. 94. To keep the clasp body assembly pressed into the clasp sleeve 614, as shown in FIGS. 101 and 102 for example, a distal spring washer 605 and a proximal compression spring 607 are inserted into a proximal interior cavity 6024. Placement of the locking knob 676 onto the handle body 674, as shown in FIG. 92 for example, compresses the compression spring 607 between the locking knob 676 and the proximal surface of the spring washer 605 residing inside the proximal interior cavity 6023 of the clasp body 602. This compression forces the knob 676 proximally to keep the spring 592 inside the three-position slot 675. The spring washer 605 is present to prevent the spring 607 from binding when the locking knob 676 is rotated between the three rotational positions. The smooth surface of the washer 605 does not catch the distal end of the compression spring 607 when the spring 607 rotates.

Figure 95:
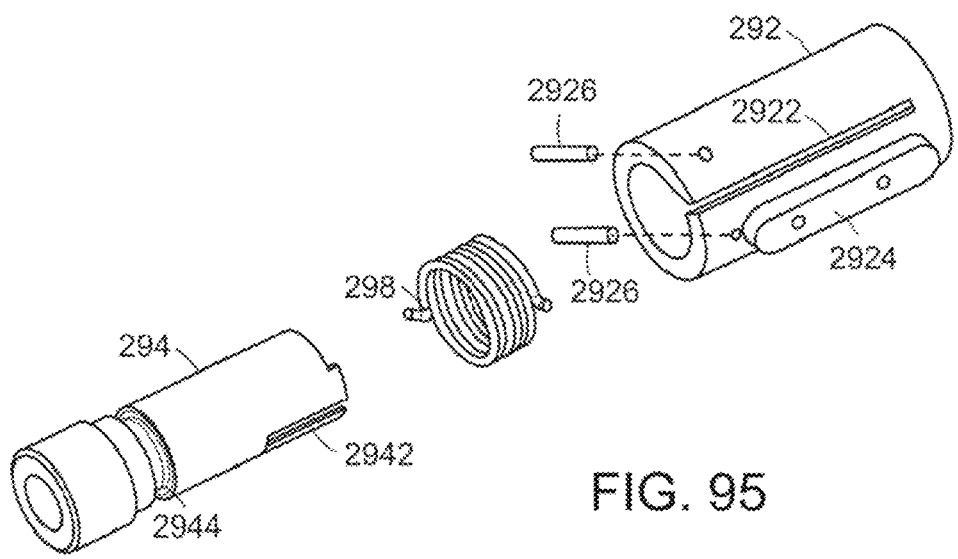
FIG. 95 is an exploded, perspective view of a rotator assembly of the handle assembly of FIG. 90.
Figure 96:
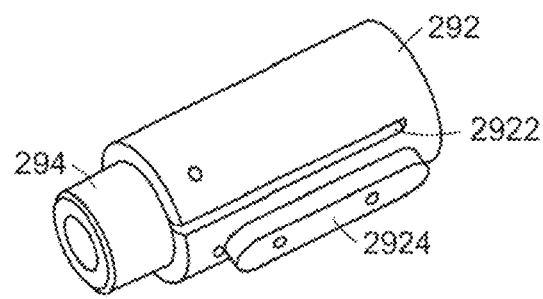
FIG. 96 is a perspective view of the rotator assembly of FIG. 95 in an assembled state.

The rotator assembly includes the pusher clasp rotator 292, the pusher clasp spring 298, and the rotator body 294. These parts are first depicted in FIGS. 34 to 43 and 47 to 48 and are next depicted in FIGS. 95 and 96. In FIG. 95, the rotator assembly is illustrated in an exploded, unassembled state and FIG. 96 shows the assembly in an assembled state. When assembled, the two protruding ends of the pusher clasp spring 298 are respectively inserted into the longitudinal slots 2942 and 2922 of each of the rotator body 294 and the pusher clasp rotator 292. Because the distal end of the rotator body 294 is smaller in diameter than the cavity of the pusher clasp rotator 292, the end of the spring that fits inside the slot 2922 must be longer than the end of the spring 298 that fits inside the slot 2942 of the rotator body 294.

The rotator body 294 is secured inside the pusher clasp rotator 292 by two dowels 2926 that are press fit through a first orifice in the clasp rotator 292 after the rotator body 294 is inside the clasp rotator 292. These dowels 2926, then, pass through a circumferential groove 2944 substantially without touching the walls of the groove 2944 and, then, through a second orifice in the clasp rotator 292 directly opposite the first orifice. In such a configuration, the rotator body 294 is longitudinally fixed but rotationally free inside the clasp rotator 292. The first and second orifices and the groove 2944 are clearly shown in FIG. 113 (with the dowels 2926 removed for clarity).

Figure 97:
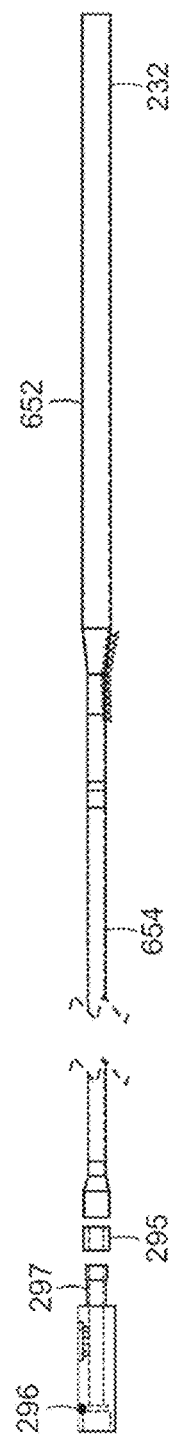
FIG. 97 is a fragmentary, exploded, side elevational view of a delivery sheath of the delivery system of FIG. 90.
Figure 98:
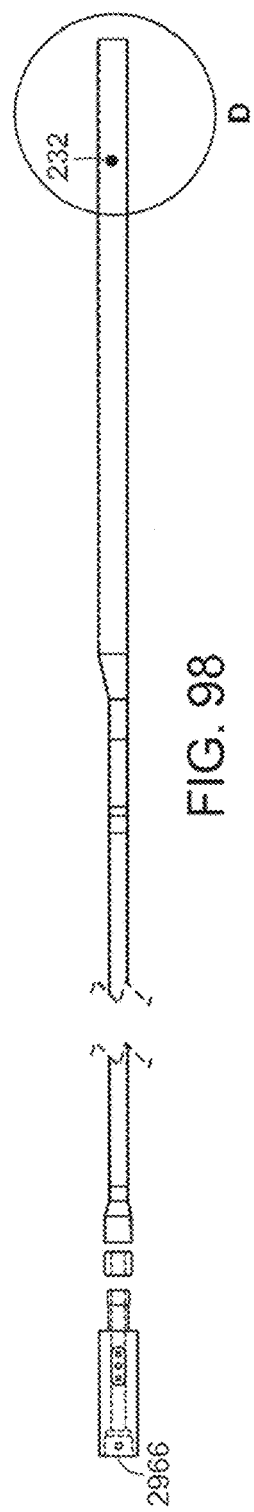
FIG. 98 is a fragmentary, exploded, side elevational view of the delivery sheath of FIG. 97 rotated approximately 90 degrees.
Figure 99:
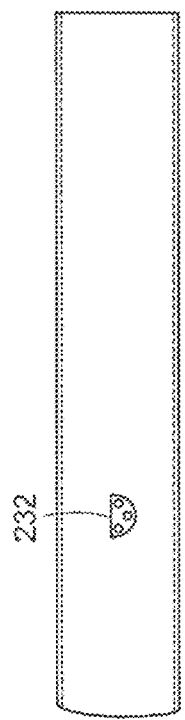
FIG. 99 is an enlarged, side elevational view of a portion of the delivery sheath of FIG. 98.

FIGS. 44 to 48 illustrated the pusher clasp body 296 and its relationship with the sheath lumen 654. FIGS. 97 and 98 further illustrate two views of the pusher clasp body 296 and its distal projection 297. The proximal end of the sheath lumen 654 passes through the crimp ring 295 and over the distal projection 297. Then, to secure the sheath lumen 654 to the pusher clasp body 296, the crimp ring 295 is compressed/crimped. Such a connection both longitudinally and rotationally stabilizes the sheath lumen 654 with respect to the pusher clasp body 296. Two pins 2962 hold the pusher clasp body 296 to the proximal handle 678 so that longitudinal movement of the proximal handle 678 translates into a corresponding longitudinal movement of the pusher clasp body 296 within the handle body 674. These pins 2962 pass through a plug 2964, shown in FIG. 114, and then into the pusher clasp body 296. The length of the pins that exist through the plug 2964 and also through the pusher clasp body 296 gives enough support to prevent movement of the handle 678 from breaking the pins 2962, which might occur if the plug 2964 were not present.

It is noted that the conical expansion of the proximal end of the inner sheath 652 is different in FIGS. 97 and 98. This is because the embodiment shown in FIGS. 97 and 98 illustrates an expansion portion of the inner sheath 652 that is sutured on only one side thereof. Accordingly, when viewed along the suture line (as in FIG. 98), the cone has one flat side. In contrast, when viewed in an elevation 90 degrees turned from that suture line (as in FIG. 97), the expansion portion has a conical elevational view.

Also shown in FIG. 98 on the inner sheath 652 is a D-shaped radiopaque marker 232. This marker 23215 enlarged in FIG. 99 and can be, for example, secured to the inner sheath 652 by three sutures, diagrammatically indicated with an "X."

FIG. 100 is an enlarged view of the distal end of the handle assembly 670 shown in FIG. 90. This embodiment of the distal apex head 636 shows an alternative embodiment of the proximal portion that was first shown in FIG. 29. As can be seen in the drawing, the proximal side of the distal apex head 636 is tapered. This tapered shape allows the distal apex head 636 to enter further into the interior cavity between the prongs of the proximal apex body 638 than the distal apex head 636 shown in FIG. 29. It is noted that the portion of the delivery system at the distal end is to be flexible so that this portion can traverse curved vessels. Thus, it is desirable for the length of the distal apex head 636 and the proximal apex body 638 (semi-rigid parts) to be as short as possible. By allowing the distal apex head 636 to travel further into the proximal apex body 638, the longitudinal length of the two parts 636 can be shorter.

Now that the various parts of the handle assembly 670 have been shown and described separately, the interactions and orientations when assembled can now be further understood with reference to the following description and to FIGS. 101 to 105.

FIGS. 101 to 102 show the proximal half of the handle assembly 670 from just proximal of the locking knob 676 to just distal of the distal end of the proximal handle 678 (when the handle 678 is in a proximal position). The hidden lines shown in FIG. 101 aid in the understanding of this portion. It is noted that the sheath lumen 654 is not illustrated in FIG. 101 for clarity.

FIG. 102 clearly shows the components that are involved in the proximal half of the handle assembly 670. The handle body 674 is surrounded by the distal handle 678 and a portion of the locking knob 676. Inside the proximal end of the handle body 674 is the clasp body 602, which is surrounded by the proximal end of the clasp sleeve 614. The locking washer 608 is positioned inside the clasp sleeve 614 at the distal end of the clasp body 602.

Separated at a distance from the distal end of the locking washer 608 is the rotator assembly, which, as set forth above, is longitudinally fixed to the proximal handle 678. The rotator assembly includes the pusher clasp rotator 292 surrounding the pusher clasp spring 298 and the rotator body 294. The pusher clasp body 296 is disposed on the distal end of the rotator body 294 and the crimp ring 295 secures the sheath lumen 654 on the distal projection 297 of the pusher clasp body 296.

Figure 103:
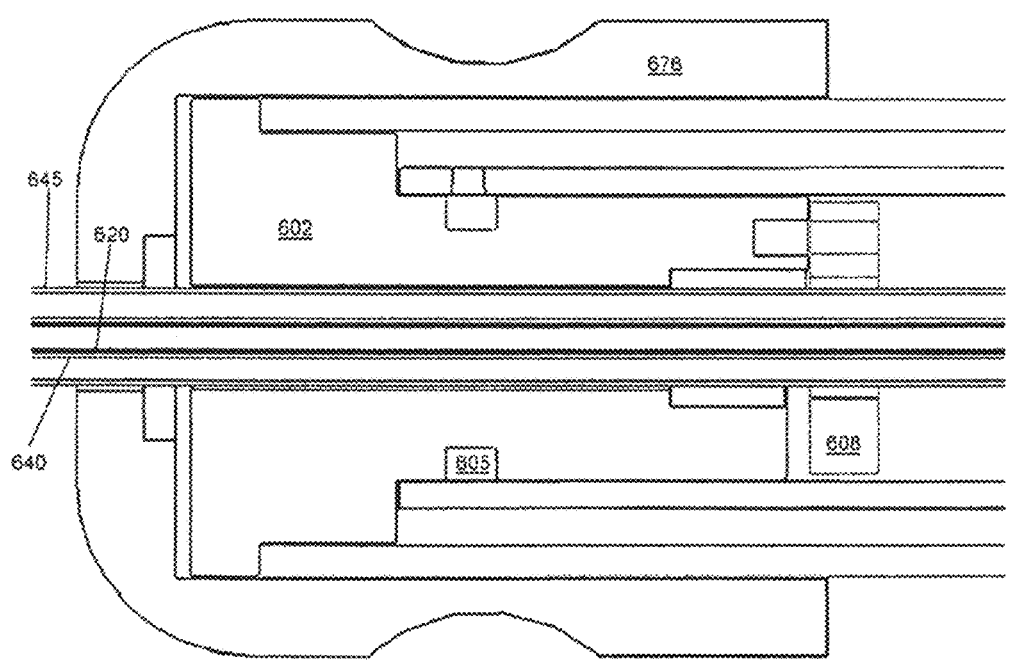
FIG. 103 is a fragmentary, enlarged, cross-sectional view of the actuation knob and clasp body assemblies of the handle assembly of FIG. 102.

FIG. 103 is an enlarged view of the proximal portion of FIG. 102 by the locking knob 676. These figures show the alignment of the bores in the clasp body 602 and the locking washer 608 so that the non-illustrated setscrew can fasten the two parts to one another. Also shown in FIG. 103 is the alignment between the groove 605 for receiving therein the setscrew 586 (see FIGS. 53 and 93) and connecting the proximal clasp assembly 604 to the clasp sleeve 614 so that the clasp sleeve 614 can still rotate around the clasp body 602. Also visible in the enlarged view of FIG. 103 is the three coaxial lumen 620, 640, 645 that pass through the clasp body 602.

Figure 104:
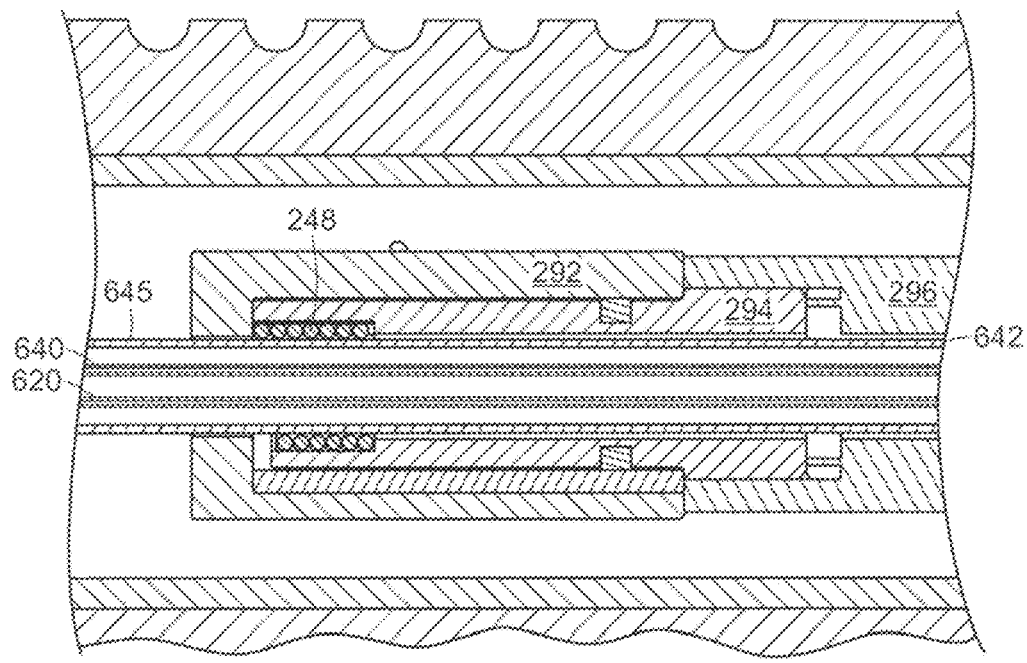
FIG. 104 is a fragmentary, enlarged, cross-sectional view of the rotator assembly of the handle assembly of FIG. 102.
Figure 105:
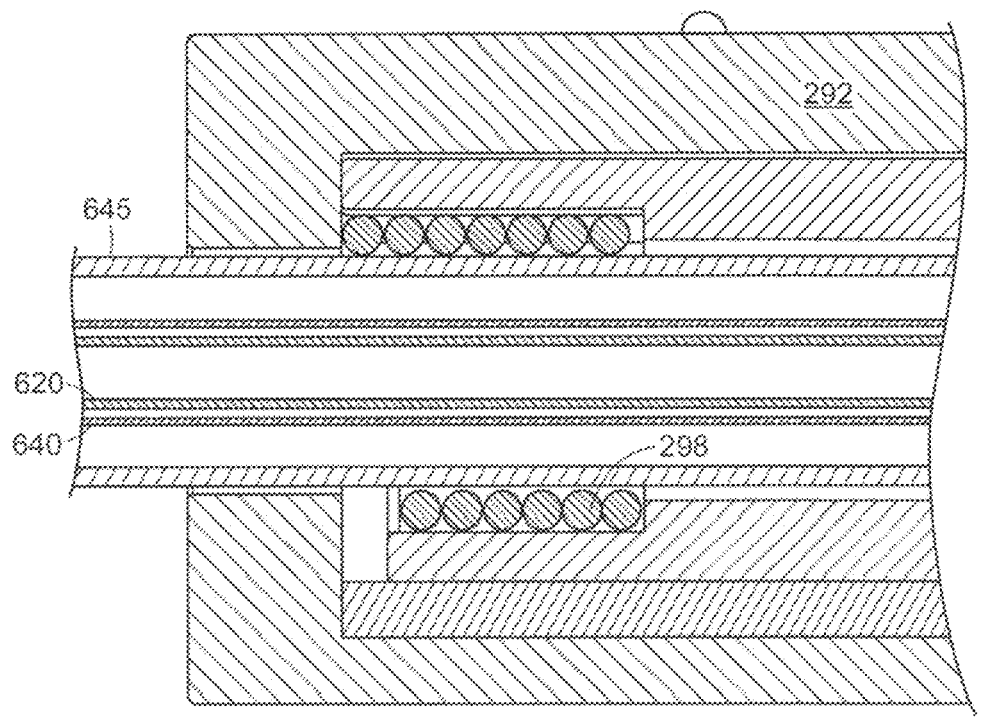
FIG. 105 is a fragmentary, further-enlarged, cross-sectional view of the rotator assembly of the handle assembly of FIG. 104.

Like FIG. 103, FIG. 104 is an enlarged view of the distal portion of the handle assembly 670 around the pusher clasp rotator 292. This view not only shows the orientations of the rotator body 294 and the pusher clasp body 296 with respect to the pusher clasp rotator 292, but the three coaxial lumen passing therethrough are also evident. The groove 2944 for receiving the non-illustrated dowels 2926 therein is also visible in this view. As can be seen, the guidewire lumen 620 and the apex release lumen 640 each pass entirely through the pusher clasp body 296 but the proximal pusher support tube 645 ends just after the distal end of the rotator body 294 for hemostasis purposes. It is at this end point that the proximal pusher support tube 645 is connected to the graft push lumen 642. This two-part structure of the proximal pusher support tube 645 and the graft push lumen 642 is, in an exemplary embodiment, a bonding of a proximal stainless steel lumen 645 and a plastic lumen 642, for example, a polyurethane-based extrusion. As set forth above, a rigid lumen 645 in the handle portion keeps rigidity there and a flexible lumen 642 distal of the distal handle sleeve 672 allows the lumen to flex as needed. The distal end of the rotator body 294 is also fluidically sealed off from the interior of the distal interior of the delivery system with a hemostasis o-ring 293. FIG. 105 is still a further enlarged view around the pusher clasp spring 298.

A transverse cross-sectional view through the handle assembly 670 is illustrative of the interaction between and relationship of various components of this assembly 670. The cross-sections shown in FIGS. 106 to 118 progress from proximal to distal.

Figure 106:
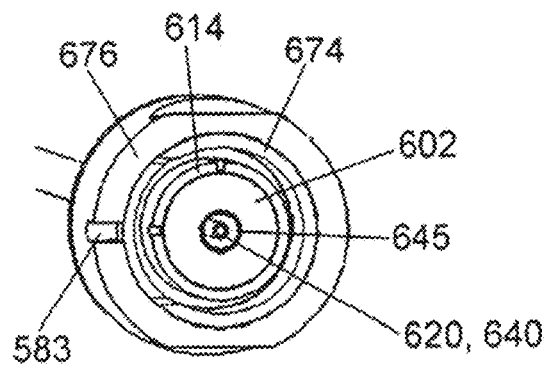
FIG. 106 is a fragmentary, transverse cross-sectional view of the handle assembly of the delivery system of FIG. 90.

A first transverse cross-section through the longitudinal slot 583 of the locking knob 676 is illustrated in FIG. 106. In this cross-sectional plane, the clasp body 602 is shown as filling up most of the interior of the clasp sleeve 614. The anchoring bore in the clasp sleeve 614 for the setscrew 585 is shown aligned with the slot 583.

Figure 107:
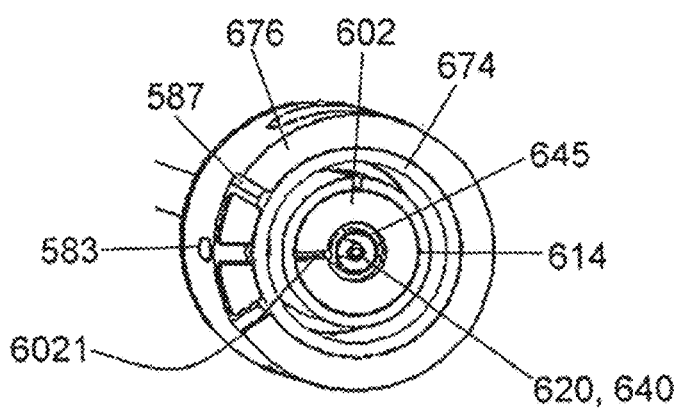
FIG. 107 is a fragmentary, transverse cross-sectional view of the handle assembly of the delivery system of FIG. 90.

A second transverse cross-section through the three-position slot 587 of the locking knob 676 is illustrated in FIG. 107. In this cross-sectional plane, the clasp body 602 still is shown as filling up most of the interior of the clasp sleeve 614. The slot 6022 of the clasp body 602 for receiving one end of the torsion spring 606 is also depicted in FIG. 107.

Figure 108:
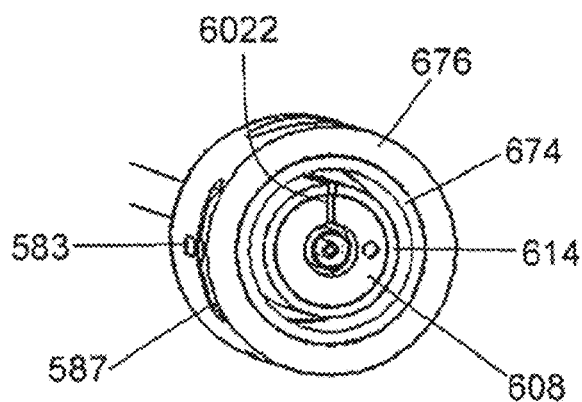
FIG. 108 is a fragmentary, transverse cross-sectional view of the handle assembly of the delivery system of FIG. 90.

A third transverse cross-section through the clasp body 602 before the locking washer 608 is illustrated in FIG. 108. In this cross-sectional plane, the slot 6022 of the clasp body 602 is aligned with a slot 6143 inside the proximal end of the clasp sleeve 614 that is not visible in FIG. 93 but is visible through the cutout in FIGS. 59 and 60. This alignment is merely shown in FIG. 108 for understanding the different depths of these slots 6022, 6143. Like the pusher clasp spring 298, the distal clasp body spring 606 has ends with different lengths. The first, shorter, end is inserted into the inner slot 6022 of the clasp body 602 and the second, longer end is inserted into the slot 6143 of the clasp sleeve 614.

Figures 109, 110, 112:
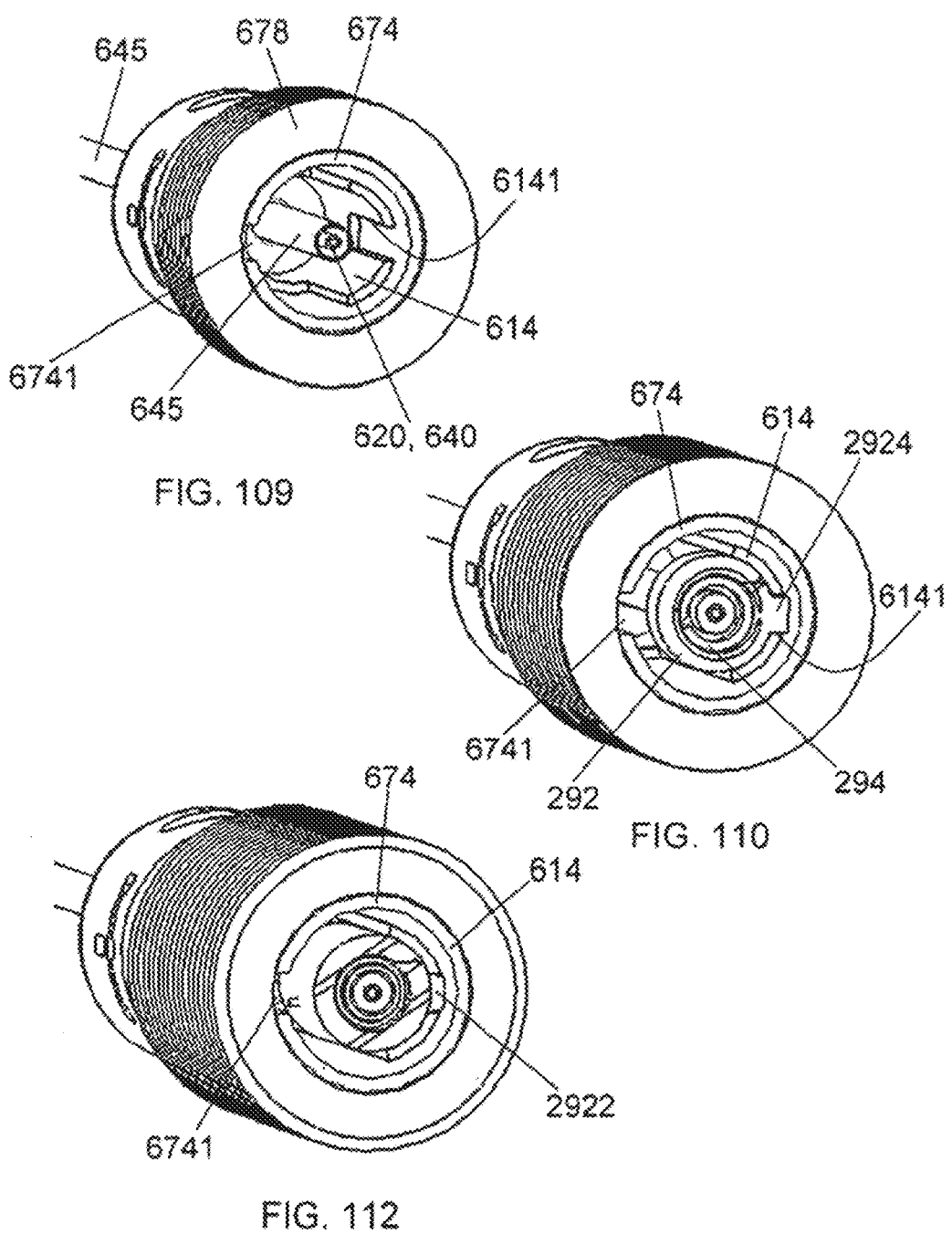
FIG. 109 is a fragmentary, transverse cross-sectional view of the handle assembly of the delivery system of FIG. 90.
FIG. 110 is a fragmentary, transverse cross-sectional view of the handle assembly of the delivery system of FIG. 90.
FIG. 112 is a fragmentary, transverse cross-sectional view of the handle assembly of the delivery system of FIG. 90.
Figure 111:
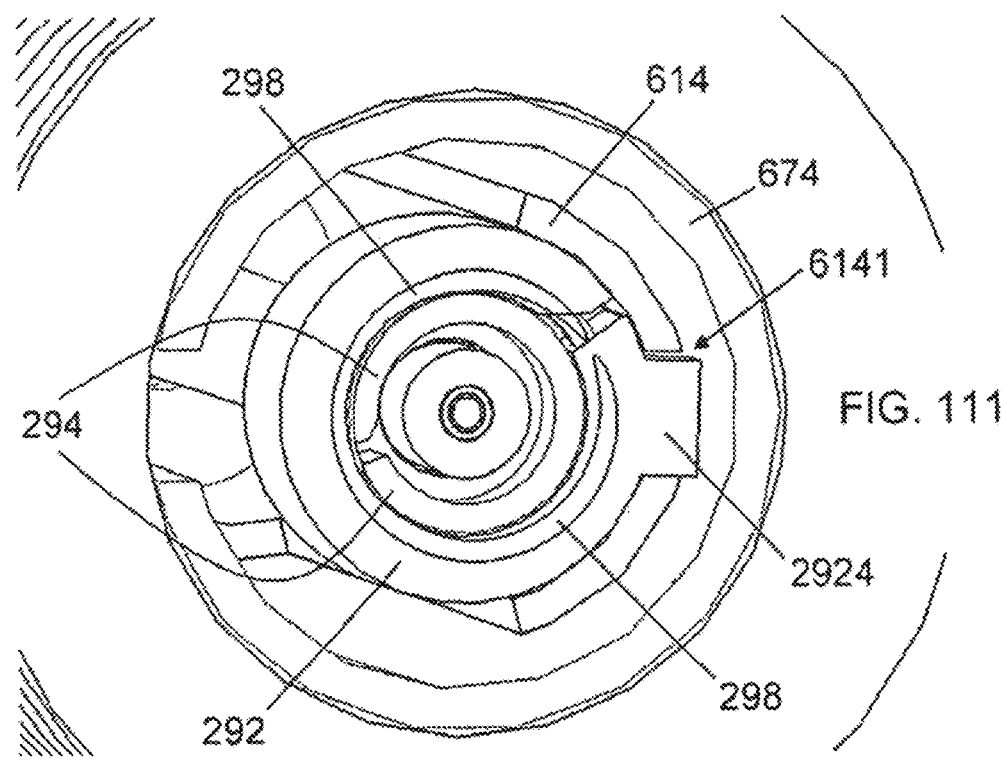
FIG. 111 is a fragmentary, enlarged, transverse cross-sectional view of the handle assembly of FIG. 110.

The fourth transverse cross-section between the proximal clasp assembly 604 and the rotator assembly shows, in FIG. 109, the spatial separation of these two assemblies that is depicted, for example, in FIGS. 101 to 102. Visible in these figures is the longitudinal slot 6141 that, as shown in the cross-sections of FIGS. 110 to 111, guides the movement of the pusher clasp rotator 292 by delimiting a space that corresponds to the width of the boss 2924 that extends out from the outer circumferences of the pusher clasp rotator 292. This slot 6141 allows the pusher clasp rotator 292 to move longitudinally freely with respect to the clasp sleeve 614; simultaneously, this connection prevents any rotation of the pusher clasp rotator 292 that is independent from rotation of the clasp sleeve 614. Accordingly, as the clasp sleeve 614 rotates about its longitudinal axis, the pusher clasp rotator 292 will rotate as well The further enlarged view of the center of the configuration illustrated in FIG. 110 is depicted in FIG. 111. Here, the rotator assembly portions are clearly shown with the pusher clasp spring 298 therebetween.

Figure 113:
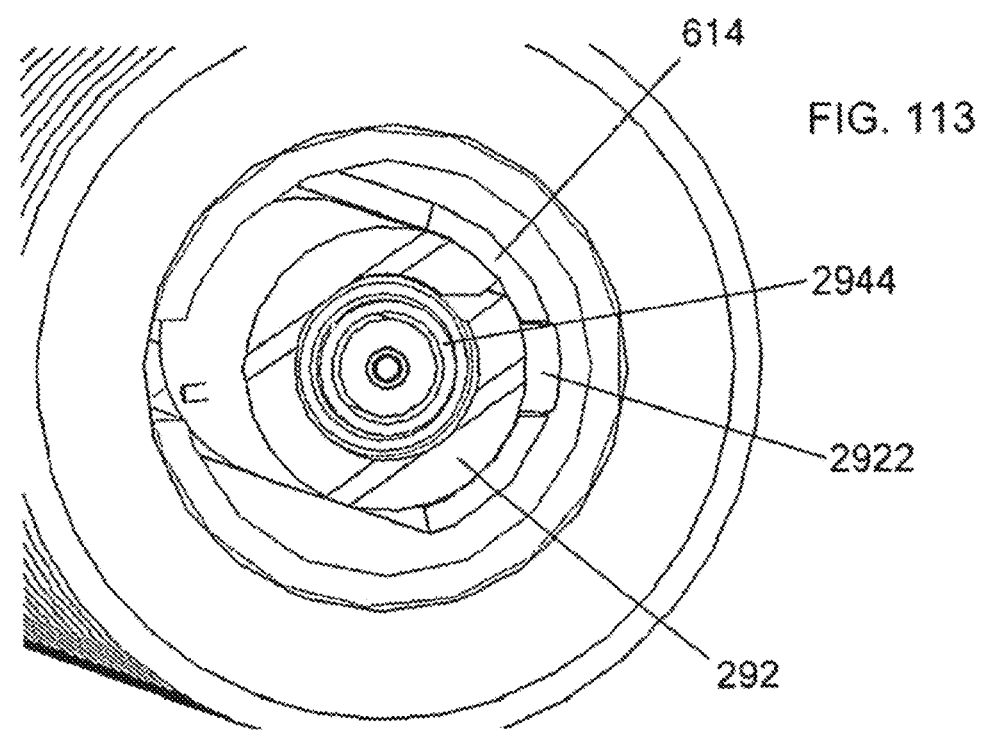
FIG. 113 is a fragmentary, enlarged transverse cross-sectional view of the handle assembly of FIG. 112.

The sixth cross-section of FIG. 112, and the enlarged view of the sixth cross-section in FIG. 113, illustrate the longitudinally fixed but rotationally free connection between the pusher clasp rotator 292 and the rotator body 294. The two bores in the pusher clasp rotator 292 for receiving the dowels 2926 (not illustrated here) are clearly shown to intersect the open space in the groove 2944 of the rotator body 294.

Figure 114:
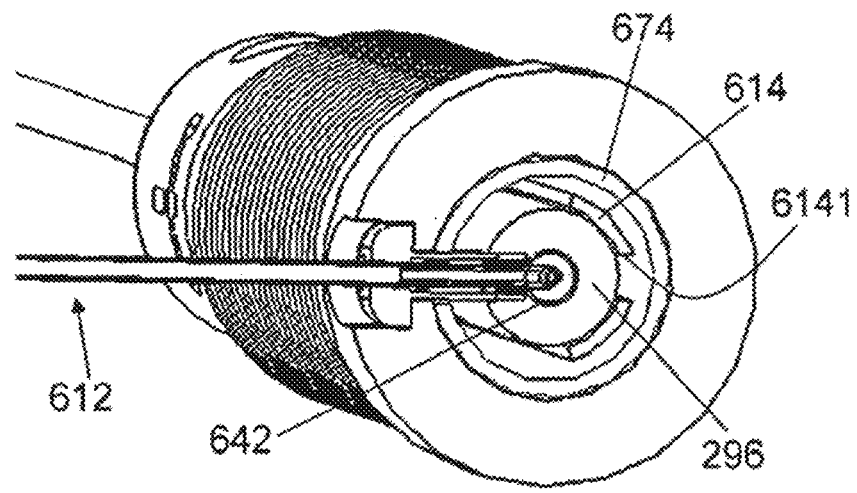
FIG. 114 is a fragmentary, transverse cross-sectional view of the handle assembly of the delivery system of FIG. 90.

A seventh cross-section in FIG. 114 shows the connection of the pusher clasp body 296 and the proximal handle 678 through the plug 2964. This view also depicts the fluid communication between the interior of the handle assembly 670 and the luer fitting 612. When the luer 612 is connected to a fluid supply, the flushing liquid enters the interior cavity distal of the rotator body 294 and sealed off by the o-ring 293 and purges all air therein at the distal end of the delivery system. FIG. 114 also shows the graft push lumen 642 extending through the handle body 674 beginning after the distal side of the o-ring 293.

Figure 115:
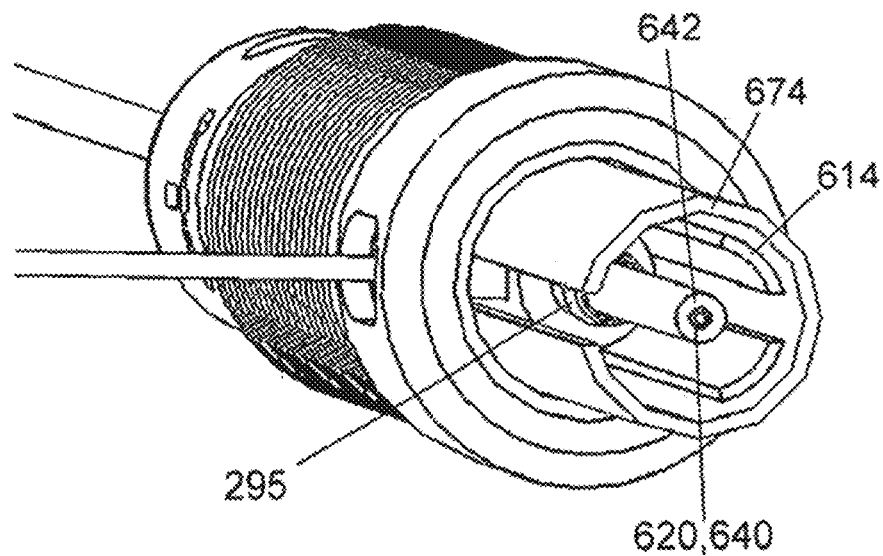
FIG. 115 is a fragmentary, transverse cross-sectional view of the handle assembly of the delivery system of FIG. 90.
Figure 116:
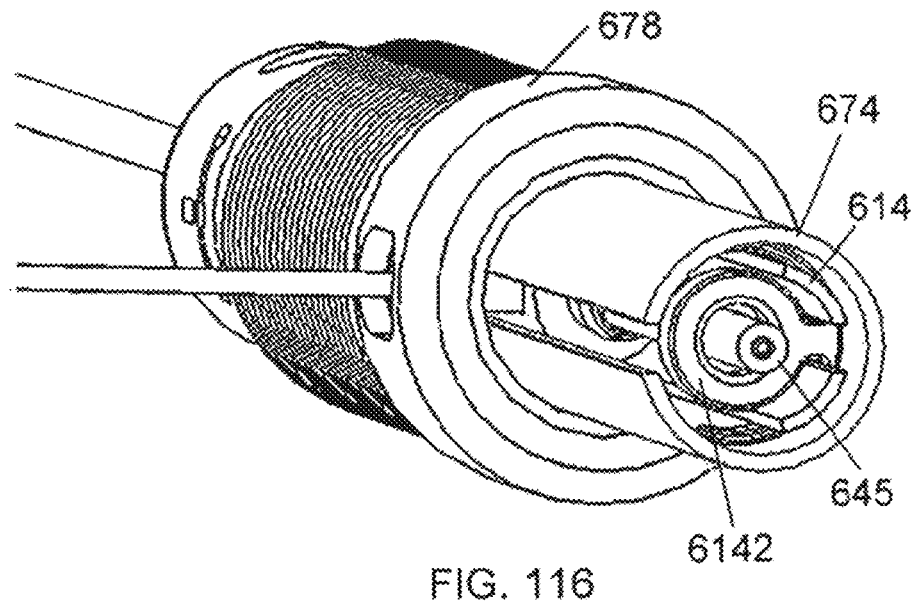
FIG. 116 is a fragmentary, transverse cross-sectional view of the handle assembly of the delivery system of FIG. 90.

The eighth cross-section of FIG. 115 illustrates the distal projection 297 at which the crimp ring 295 holds the sheath lumen 654 onto the pusher clasp body 296. This figure also illustrates the open radial space between the clasp sleeve 614 and the graft push lumen 642. To keep the relatively long extent of the flexible inner lumen 620, 640, 642 passing through the open interior of the handle body 674 from moving out of a centered orientation (i.e., from bending out from the longitudinal axis of the handle body 674, sliding spacers 6142 are periodically provided along the clasp sleeve 614 as shown in FIGS. 93 and 116 to 118. These spacers 6142 are only needed while the proximal handle 678 is moving the rotator assembly and the pusher clasp body 296 in a distal direction to prevent bending of the interior flexible lumen 620, 640, 642. Accordingly, the spacers 6142 can slide within the groove 6141 of the clasp sleeve 614 up to and over the distal end of the clasp sleeve 614 (the right side of the sleeve 614 as viewed in FIG. 93; see also FIG. 117). Each of these spacers 6142 is self secured in a slidable manner to the clasp sleeve 614.

Figure 117:
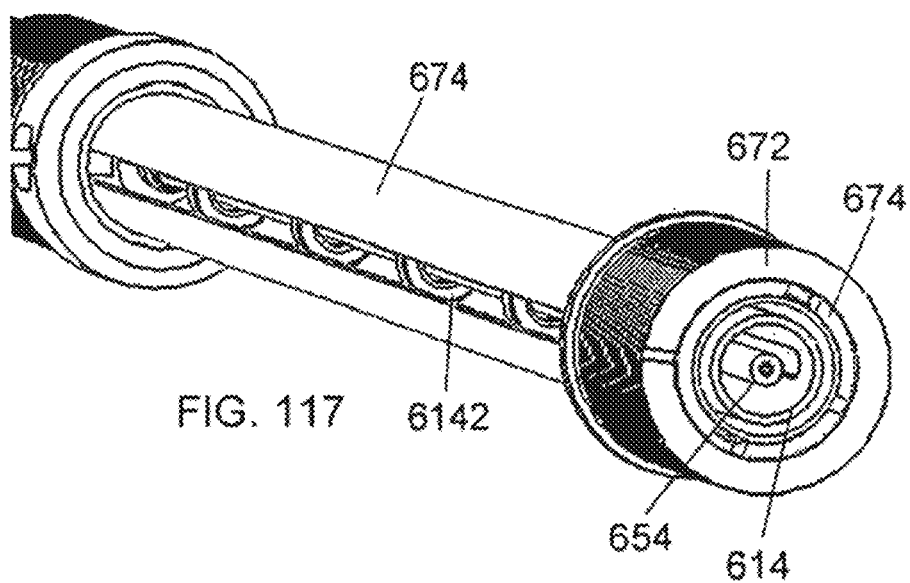
FIG. 117 is a fragmentary, transverse cross-sectional view of the handle assembly of the delivery system of FIG. 90.
Figure 118:
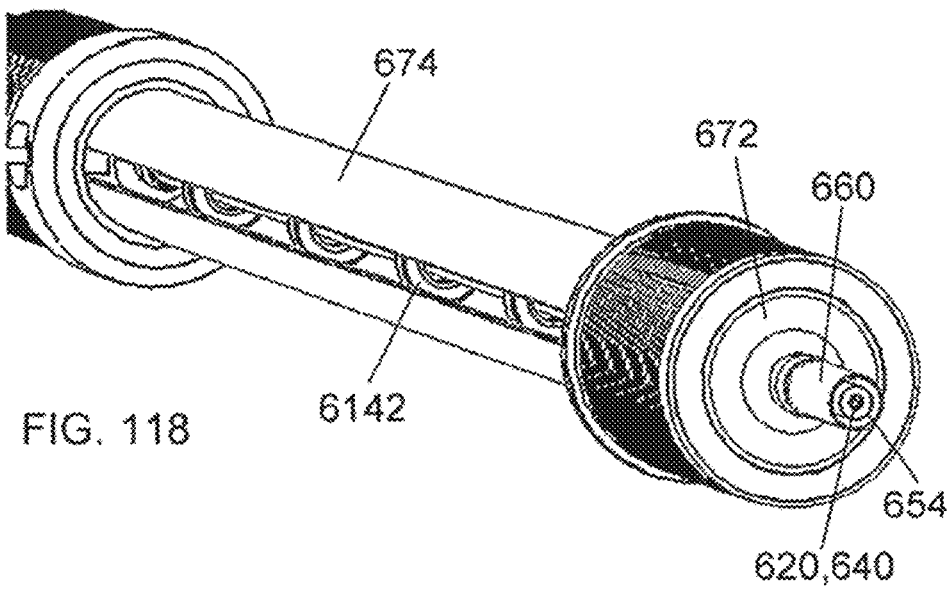
FIG. 118 is a fragmentary, transverse cross-sectional view of the handle assembly of the delivery system of FIG. 90.

FIG. 117 depicts a ninth cross-section through a distal end of the clasp sleeve 614 within the distal handle 672. The distal handle 672 freely rotates about the handle body 674 in an exemplary embodiment. In such an embodiment, the outer catheter 660 will also freely rotate about all of the lumen 620, 640, 642 therein because of the fixation between the outer catheter 660 and the distal handle 672. See FIG. 118.

Figure 119:
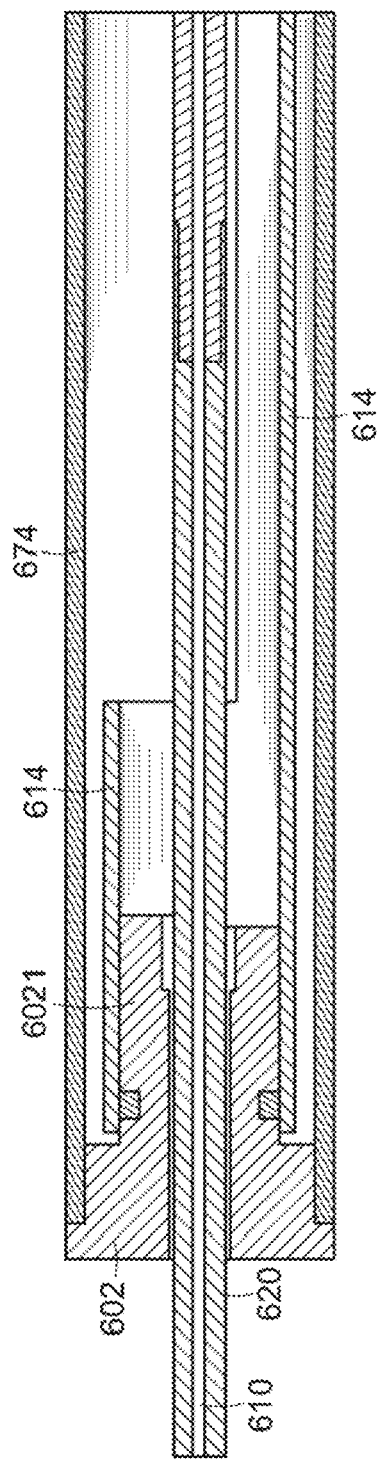

The shaded parts in FIG. 119 are provided to show portions of the features around the clasp body 602. In this view, the rotator assembly is removed.

The following text describes the four movements for implanting a prosthesis with the delivery system and the relative connections between relevant lumens when in the three different settings of the locking knob 676.

The first movement will be referred to as the advancement stage and utilizes position 1 of the locking knob 676. When in position 1, the distal spring 298 is engaged around and holds the pusher support tube 645 (and, therefore, graft push lumen 642) to the rotator assembly 292, 294. This assembly 292, 294 is fixed at the distal end of the rotator body 294 inside the pusher clasp body 296 (through a non-illustrated setscrew passing through the threaded bore 2966 shown in FIG. 98). As set forth above, the pusher clasp body 296 is fixed to the proximal handle 678 and, therefore, the pusher support tube 245 moves with the proximal handle 678 in position 1.

In this first movement, the entire distal assembly is advanced up to the implantation site using the proximal handle 678. Thus, when the handle 678 moves distally, all of the lumen, including the guidewire lumen 620, the apex release lumen 640, the graft push lumen 642/proximal pusher support tube 645, and the sheath lumen 654, are locked together and move distally with a corresponding movement of the proximal handle 678. As the outer catheter 660 is longitudinally fixed to the distal handle 672, it remains longitudinally fixed during the first movement. The lumen displacement in the advancement stage is depicted in FIGS. 19 to 21.

The second movement will be referred to as the primary deployment stage and utilizes position 2 of the locking knob 676. When in position 2, the distal spring 298 is disengaged from the pusher support tube 645 and the proximal spring 606 becomes engaged around the pusher. support tube 645 to anchor only the push rod 642 (without lumen 620, 640) to the proximal handle 678 and allow retraction of sheath lumen 654 (and, thereby, the inner sheath 652) while all other lumens are disengaged and remain stationary.

In this second movement, the inner sheath 654 needs to be moved in the proximal direction, as shown in FIGS. 22 to 24. Accordingly. when the handle 678 moves distally, only the sheath lumen 654 moves with the handle 678. Thus, in position 2 of the locking knob 676, the sheath lumen 654 is locked to the proximal handle 678 and moves proximally with a corresponding movement of the proximal handle 678; all of the other lumen, including the guidewire lumen 620, the apex release lumen 640, and the graft push lumen 642/proximal pusher support tube 645, are unlocked and remain in the distally deployed position. See FIGS. 22 to 24.

The third movement will be referred to as the final deployment stage because, in this movement, the apex capture device 634 completely releases the distal end of the prosthesis as shown in FIG. 14. Here, the apex release lumen 640 is unlocked (using the release mechanism of FIG. 91) with respect to the guidewire lumen 620 and the graft push lumen 642/645.

The fourth movement will be referred to as the extraction stage and utilizes position 4 of the locking knob (the third of the three positions in the slot 587 of the locking knob 676). When in position 4, both the distal spring 298 and the proximal spring 606 are disengaged from the pusher support tube 645 to allow the user to pull the proximal end of the pusher support tube 645 and withdraw it from the implantation site. The entire inner lumen assembly 620 and 640 travels with the proximal movement of the pusher support tube 645 because the release mechanism (see FIG. 91) is pulled with the support tube 645 as it moves proximally.

Self-Centering Tip

As set forth above, the bare stent 30 provides an outward, expanding force at the proximal end 12. The bare stent 30 and the proximal stent 23 are in a compressed state when attached to the graft sleeve 10 and also provide an outward, expanding force to the graft sleeve 10. Therefore, when implanted, these forces center the proximal end of the stent graft 1 in the vessel and press the graft sleeve 10 against the vessel wall to prevent leaks that might occur between the graft sleeve 10 and the vessel wall. Such leaks at the proximal end 12 are to be avoided in stent graft implantation.

Because some physicians are concerned that the bare stent could damage the aortic wall, especially in the case of aortic dissection, they prefer to use a stent graft without a bare stent, such as the stent graft 1100 shown in FIGS. 72 and 74 to 77. In this configuration, the proximal end 12 can travel further upstream in the aorta and, in doing so, place the graft sleeve 10 closer to the heart. Such an implantation has various advantages, such as the removal of the possibility of bare stent puncture or damage to the vessel and the ability to treat diseased portions of the aorta closer to the heart.

However, if the bare stent 30 is removed, the ability to center the proximal end 12 is affected. One deficiency of thoracic grafts not having a bare stent is a misalignment of the proximal end of the prosthesis with the aortic curvature, which leads to improper apposition of the proximal end of the graft with the aortic arch inner curvature. Proper apposition is a desirable characteristic.

Stent grafts, by their nature of replacing the through-conduit of a damaged tubular vessel, have a proximal opening 12 for receiving therein the incoming fluid previously carried by the damaged vessel. See, e.g., FIG. 1. It is desirable to directly contact the entire perimeter of this opening to the inside surface of the vessel in which the stent graft is to be placed because an opening between the proximal end of the stent graft and the vessel wall would allow a secondary flow outside and around the stent graft. This bypassing secondary flow is to be avoided when implanting stent grafts in a vessel and is particularly undesirable when implanting a stent graft in the aorta. The present invention provides a device, system and method for reducing and/or eliminating the possibility of such a bypassing flow by placing the proximal end 12 in a desired position within the vessel.

For the purposes of discussion, a few terms will be defined. The plane intersecting the proximal end opening of a stent graft is referred to herein as the inflow plane. The ring of tissue inside the vessel at which the proximal end opening is to be implanted is referred to herein as an upstream implant ring. The plane in which the upstream implant ring resides in the vessel is referred to herein as the implant plane. A longitudinal tangent is referred to herein as a line that is orthogonal to the implant plane at a point on the upstream implant ring.

A most-desirable implantation of the stent graft occurs when the inflow plane and the implant plane are co-planar. In this orientation, the longitudinal tangent of each point along the upstream implant plane is orthogonal to the inflow plane. This means that the outward force imparted by the proximal end of the stent graft is along a line that is co-planar with the implant plane, thereby insuring that the fluid-sealing force of the proximal end is maximized at the upstream implant ring.

When a stent graft is implanted in a longitudinally straight vessel, the inflow plane and the implant plane are virtually co-planar. In this orientation, a maximum outward sealing force is established at each point on the upstream implant ring, thereby maximizing the possibility of creating a permanent fluid-tight seal along the entire perimeter of the upstream implant ring. When a stent graft is to be placed in a longitudinally curved vessel, as shown in FIGS. 19 to 24 and 65 to 67, for example, co-planar alignment of the implant plane and the inflow plane does not occur naturally. In fact, prior art stent grafts and delivery systems could not establish this co-planar alignment of the implant plane and the inflow plane when the stent graft was placed in a curved vessel. As such, when the stent graft was implanted in the curved vessel, the inflow plane was left at an angle to the implant plane, which, in turn, created a gap at the inferior side of the curved vessel. In some instances, this gap allowed fluid to flow impermissibly around the implanted stent graft.

One of the primary reasons for this misalignment is due to the behavior of the guidewire within the curved portion of the vessel. The guidewire 610 does not remain centered within the vessel throughout the curved portion of the vessel—as illustrated diagrammatically in FIGS. 19 to 24 and 65 to 67. Instead, in practice, the guidewire 610 tracks toward the superior (outside) curve from approximately the center axis of the vessel until it actually contacts the interior of the superior curve at least at one point within the curved vessel. The curved guidewire, therefore, not only guides the stent graft towards the superior curve, it does so while imparting an outwardly directed force to the stent graft—a force that naturally moves the stent graft Off center in the curved vessel.

Figure 120:
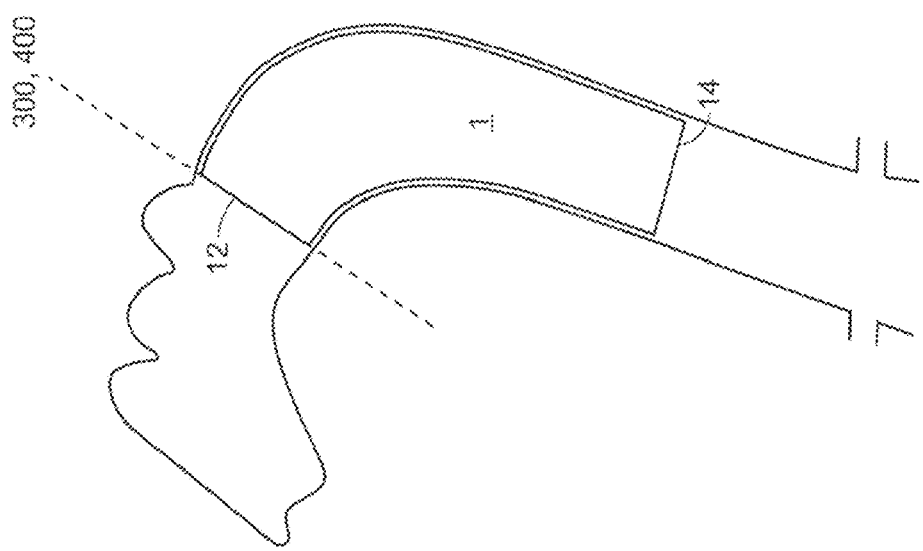
Figure 121:
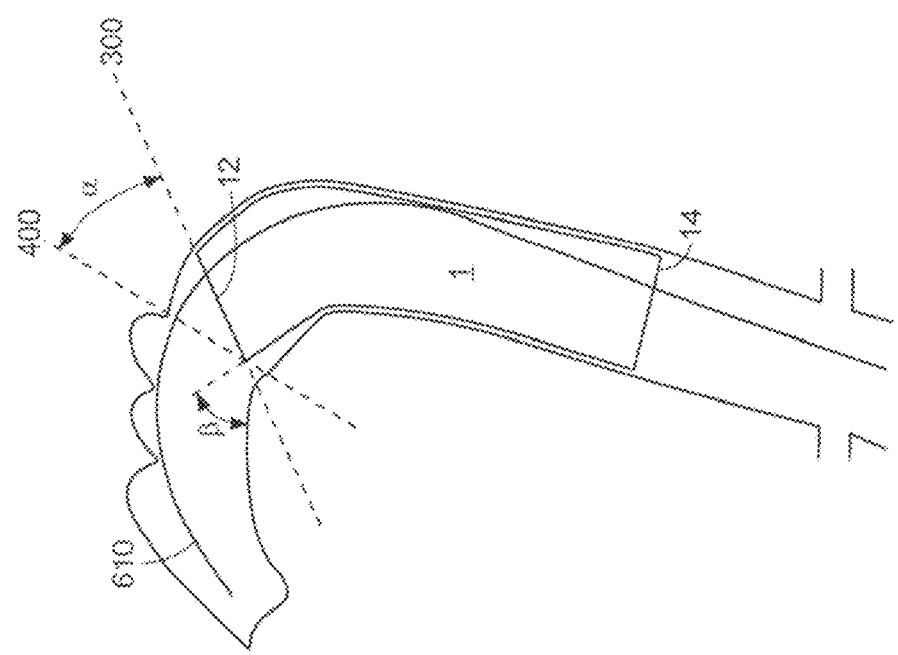

This non-axial tracking of the guidewire 610 is diagrammatically shown in FIG. 120. Here, the inflow plane 300 and the implant plane 400 are at an angle a to one another. Because the diameter of the upstream implant ring 12 has a maximum length that is defined by the opening of the graft material, an inferior gap β appears between the inferior curved vessel wall and the upstream implant ring 12. The present invention provides devices and methods for automatically centering the stent graft 1100 within the vessel and, thereby, substantially align the implant plane 400 with the inflow plane 300 as shown in FIG. 121. As used herein, substantial alignment of the implant plane 400 and the inflow plane 300 is an angular difference of less than 15 degrees between the two planes.

Figure 123:
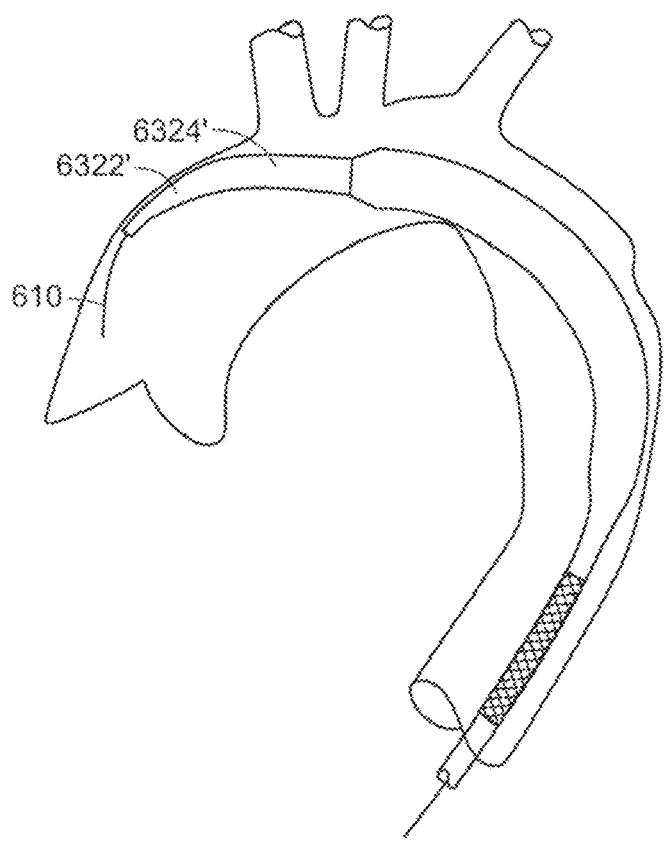
Figure 122:
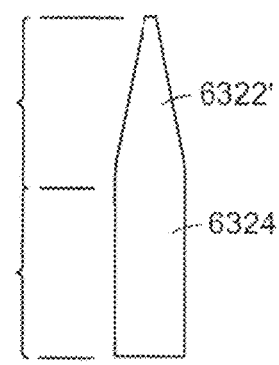

A first exemplary embodiment of the device that improves proximal end apposition when it is placed in the aortic lumen prior to deployment in curved anatomy is illustrated in FIGS. 122 and 123. The previously described tip 632 is altered as shown in FIG. 122. The new tip 632' has an overall length that is greater as compared to the tip 632. The distal section 6322' is tapered similarly to tip 632. The proximal section 6324' is straight and, hence, not bendable while tracking over the guidewire 610. This stiff proximal section 6324', along with the stiff distal and proximal clasps, produces an elongated stiff region in the nose cone assembly 630 of the delivery system 600. This stiff region does not accommodate the superior curvature of the aorta and pushes the distal end. of the delivery system down towards the inferior curvature when tracking in curved anatomies.

FIG. 123 illustrates how a modified tip pushes the proximal end of the stent graft down (as viewed in FIG. 123) towards the inferior curve of the curved aortic lumen. If the proximal end 12 of the stent graft 1100 is deployed while centered as shown, the proximal end 12 will have proper apposition with the aortic wall at the inferior curvature.

Figure 124:
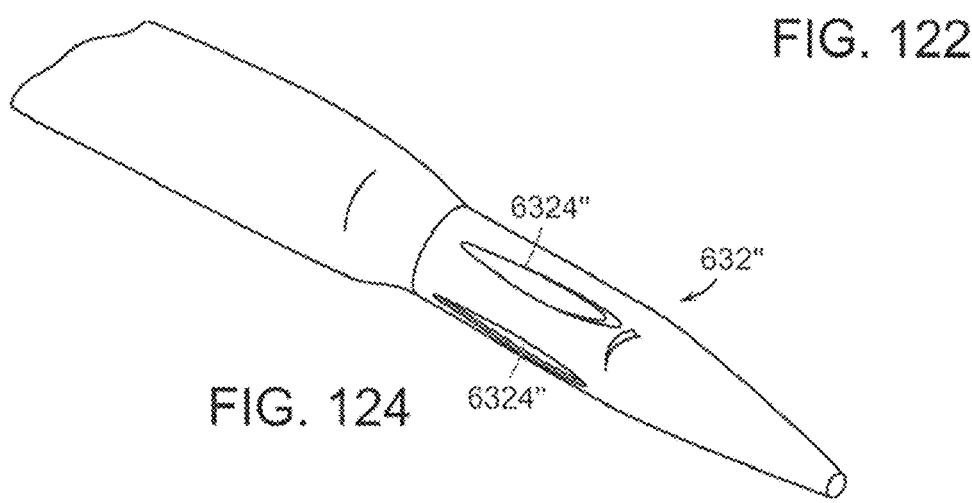
Figure 125:
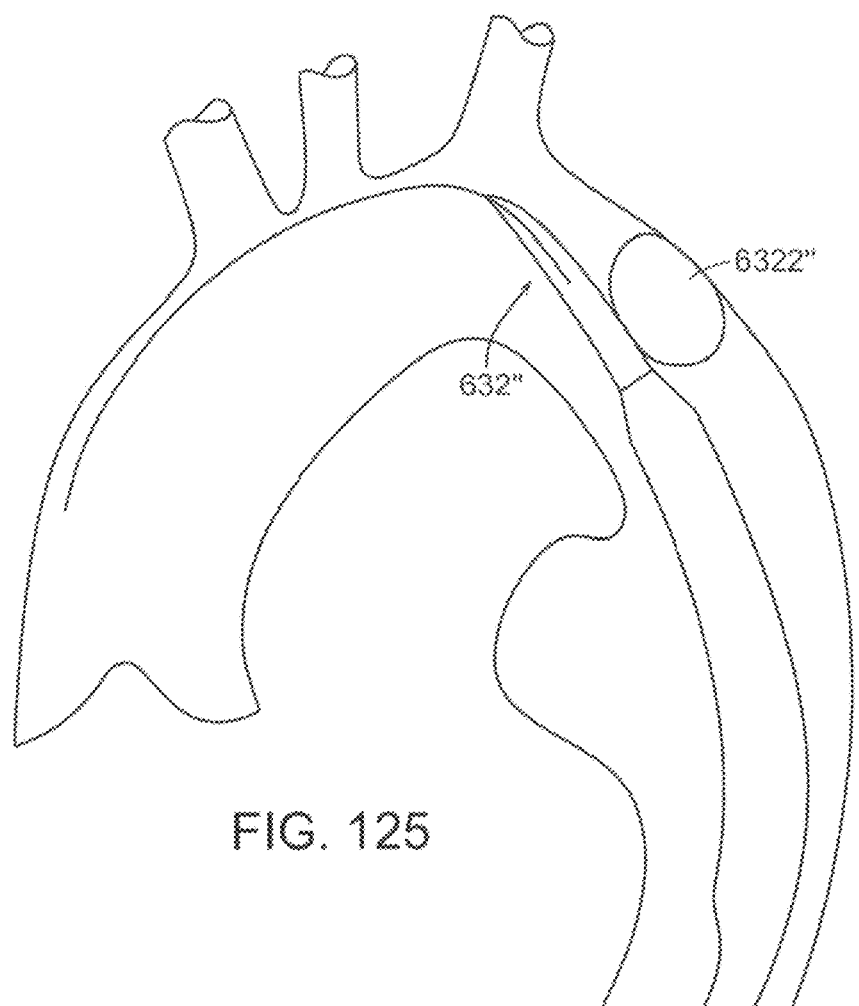
Figure 126:
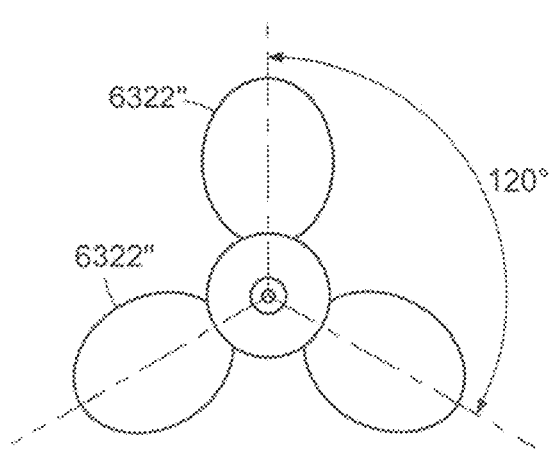

A second exemplary embodiment of the proximal end apposition improvement device is illustrated in FIGS. 124 to 126. In this embodiment, the tip 632" contains therein a set of balloons 6322" that, when inflated independently, exit and extend from a respective slit 6324". The number of balloons can be 1, 2, 3, 4, or more. In the exemplary embodiments shown, there are three balloons spaced 120 degrees apart from one another. Which balloon(s) that are inflated after the tip 632" is positioned in the curved vessel will depend upon the position of the slits 6324". As shown in FIG. 125, one balloon 6322" can be inflated to center the tip 632" or, as shown in FIG. 126, all three balloons 6322" can be inflated.

A third exemplary embodiment of the proximal end apposition improvement device takes its genesis from the bare stent 30. In all of the embodiments for improving apposition, the bare stent 30 is removed. Because some physicians are concerned that a bare stent can damage an aortic wall, especially in the case of aortic dissection, the invention proposes creating a bio-absorbable bare stent. Such a bare stent 30 dissolves over time but ensures proper alignment of the proximal end of the graft during deployment. Because the bare stent is absorbed, any potential for damaging the aortic wall is eliminated.

A fourth exemplary embodiment of the proximal end apposition improvement device is illustrated in FIGS. 127 and 128. A dual-cone 410 device centers the nose cone assembly 630 of the delivery system 600 within the lumen. Centering the nose cone assembly within the aortic lumen, in turn, will ensure that the proximal end of the stent graft 1100 is properly aligned with the aorta. The dual-cone device can be made of silicone. The bases of the two opposing conical parts are adjacent one another. when the ends of the conical parts are pressed towards one another, the diameter of the conical base increases. As the base increases in diameter, its circular expansion comes in contact with the superior curve of the aortic wall to force the nose cone assembly 630 towards the center of the aortic lumen. When fully expanded, the proximal end 13 of the stent graft 1100 is in a desired centered position and is, therefore, ready for deployment. It is noted that the shape of the conical components can be modified to allow greater expansion of the conical base at specific locations.

A fifth exemplary embodiment of the proximal end apposition improvement device is illustrated in FIGS. 129 and 130. This centering system uses a pull-wire 420 that can center the tip end of the delivery system within the aortic lumen. The pull-wire 420 resides inside the delivery system between the stent graft 1100 and inner sheath 652. One end of the pull-wire 420 can be attached to the nose cone assembly 630, for example, the proximal apex body 638 and the other end of the continuous wire is attached to a mechanism at the proximal portion of the delivery system 600, whether at the proximal end of the handle assembly 670 or at the apex release assembly 690. This mechanism, when operated, pulls the wire proximally to produce a force P having two resultant forces P' and P''' shown in FIG. 130. even though P'' is the smaller of the two resultant forces, if force P is large enough, P' will pull the tip towards the inferior curve of the aorta. FIG. 129 illustrates the distal end of the delivery system being centered by pulling on the wire 520 to create centered apposition of the proximal end 12 of the stent graft 1100.

A sixth exemplary embodiment of the proximal end apposition improvement device is illustrated in FIGS. 131 and 132. The apex clasp device 636, 638 is formed in two halves or three thirds. In this configuration, the split clasp mechanism allows angular adjustment of the proximal end of the graft within the aortic lumen to insure optimum apposition with the aortic wall as shown in the comparison of FIGS. 131 and 132. The split clasp allows the user to move forward and backward some specific apices along the proximal circumference of the stent graft 1100 which, in turn, changes the angle of the inflow plane 300 with respect to the implant plane 400. By using this process and system, the physician can adjust the orientation of the proximal end 12 to ensure proper apposition against the aortic arch inner curvature.

A seventh exemplary embodiment of the proximal end apposition improvement device is illustrated in FIGS. 133 to 135. As set forth above, the apex clasp device 636,638 uses a set of distally projecting fork tines and an internal castellated portion to create openings in which the proximal apices 32 of the bare stent 30 or the proximal apices 1132 of the clasping stent 1130 are held releasably. Instead of the apex clasp device 636, 638, each of the apices 32, 1132 are individually held with an apex capture mechanism that is shown in FIGS. 133 to 135. Pushing the wire in one of the apex capture mechanisms causes the proximal end 12 of the stent graft 1100 to move. A combination of such pushing forces on one or more of these apex capture mechanisms will cause the proximal end 12 to move into a desired apposition of the inflow plane 300 and the implant plane 400. When the wires are pulled, they move proximally and release the capture of the respective stent apex 32, 1132.

An eighth exemplary embodiment of the proximal end apposition improvement device is illustrated in FIGS. 136 to 142. Here, the tip 632 has slots through which extend loops of wires that, when extended as shown in FIGS. 137, 141, and 142, center the tip 632 within the vessel in which it is placed. The mechanism is composed of wires that are contained inside the slots in a straight configuration. Compressing the wires causes them to protrude from the slots and form loops that can press against the vessel wall, thereby centering the tip 632 within the vessel. Extension of the loops can be actuated through a single pull mechanism, for example, with a telescoping slide. Centering of the tip is actuated by pulling on a knob (for example) located at the proximal end of the delivery system. The knob is connected to the wire loops by a catheter that extends from the knob to the distal end of the loops. The loops, in turn, are fixed at their distal end. Pulling on the knob would cause the catheter to slide in a proximal direction causing a compression of the wire loops, making them protrude from the tip 632 as shown in FIGS. 137, 141, and 142. In addition, the catheter can contain a component that engages the clasp as it is moved proximally. Thus, as the catheter is moved, at approximately three-fourths of the actuation stroke; the component on the catheter engages the clasp and with the remainder of knob retraction the clasp would be released.

A ninth exemplary embodiment of the proximal end apposition improvement device is illustrated in FIG. 143. In this approach, an accessory device 430 is introduced into one or more of the contra lateral limbs of the patient or radially through the arm. Before, during or after, the delivery system is used to extend the aortic stent graft into the aortic arch for implantation. The accessory device 430 is, then, extended into the aortic arch and pressed against a portion of the delivery system. For example, as shown in FIG. 3, the accessory device 430 can be introduced through the left sub-clavian artery and used to bias the delivery catheter away from the greater curve of the arch. The accessory device 430 can have many forms. It could be a balloon, a mechanical mechanism, and a pusher from the trans-femoral approach, a balloon or a mechanical mechanism is practical. Each of these concepts can be applied in a direct approach from the left sub-clavian artery or the Brachiocephalic Trunk.

A tenth exemplary embodiment of the proximal end apposition improvement device is illustrated in FIGS. 144 to 146. In this embodiment, the properties of temperature sensitive nickel-titanium are combined with the technology of localized heating to present a controlled shape manipulation. Shape memory bends are imparted to portions of the delivery system 600 prior to incorporation in the delivery system 600. Then, the portions are placed into the desired configuration, e.g., linear, and incorporated into the delivery system 600. Heater bands 440 are distributed along the delivery system 600 adjacent the memory bends. As shown in FIGS. 144 to 146, application of heat at the memory bends will cause the adjacent portion of the delivery system 600 to bend. If the bends are coordinated, they can be made to bend the in-vivo delivery system 600 in any desired way, in particular, to center the tip in the vessel and, thereby, implant the proximal end 12 of the stent graft 1100 with a proper apposition. Alternatively, ultrasonic sensitive crystals can be used as the heater bands. Thus, when energy is applied, the crystal heat up and cause the nickel-titanium memory portion to bend into their pre-programmed memory shape.

An eleventh exemplary embodiment of the proximal end apposition improvement device is illustrated in FIGS. 147 to 151. In this embodiment, a hollow balloon delivery catheter 450 having a balloon configuration 452 is provided. The balloon delivery catheter 450 has an interior bore 454 through which the outer catheter 660, the nose cone assembly 630, and the inner sheath 652 travel. FIGS. 149 to 151 illustrate an exemplary method for using the balloon delivery catheter 450 of the present invention. First, the balloon delivery catheter 450 is inserted into at least part of the aortic arch and the balloon configuration 452 is inflated to center and hold the balloon delivery catheter 450 in position within the aorta. See FIG. 147. Then, the distal end of the delivery assembly 600 is passed through the balloon delivery catheter 450 as shown in FIG. 148. The proximal end 12 of the stent graft 1100 is deployed in the aortic arch and, after satisfactory apposition of the inflow plane 300 and the implant plane 400 is verified, the balloon configuration 452 is deflated and the balloon delivery catheter 450 can be removed. Finally, the stent graft 1100 is fully implanted as set forth above.

In the exemplary balloon configuration 652 shown in FIGS. 150A, 150B and 151, there are three balloons 452 with spaces therebetween so that blood can flow past the balloons 452 when inflated. This tri-balloon device is shown in FIGS. 150A, 150B and 151.

Alternative to the balloon delivery catheter 450, a balloon configuration 452 can be added at the distal end of the outer catheter 660. When the outer catheter 660 is at its distal-most position in the aorta, the balloon configuration 450 inflates and centers the nose cone assembly 630 within the aorta. Thus, when the inner sheath 652 containing the stent graft 1100 is extended from the outer catheter 660, the nose cone assembly 630 is centered within the aorta and the inner sheath 652 and nose cone assembly 630 can be extended within the aortic arch in a centered orientation.

A twelfth exemplary embodiment of the proximal end apposition improvement device is illustrated in FIGS. 152 to 155. In this embodiment, a balloon delivery rod 460 having a balloon configuration 462 is provided. The balloon delivery rod 460 is inserted into at least part of the aortic arch and the balloon configuration 462 is inflated at the superior curve of the aortic arch. See FIG. 152. Then, the distal end of the delivery assembly 600 is passed through the aorta and along the inflated balloon configuration 462 as shown in FIG. 153. The proximal end 12 of the stent graft 1100 is deployed in the aortic arch and, after satisfactory apposition of the inflow plane 300 and the implant plane 400 is verified, the balloon configuration 462 is deflated and the balloon delivery rod 460 can be removed. Finally, the stent graft 1100 is fully implanted as set forth above. FIG. 155 illustrates one possible cross-sectional configuration for the balloon 462 of this embodiment.

A thirteenth exemplary embodiment of the proximal end apposition improvement device is illustrated in FIGS. 156 to 158. As described above, a proximal edge 12 that is perpendicular to the longitudinal edges (see FIG. 71) will be difficult to position in a curved vessel and, in such a case, the inflow plane 300 will be at an angle to the implant plane 400 as shown in FIG. 157. To counteract this non-apposition of the proximal end 12 that does not have a bare stent, the stent graft 11 00 can be formed with a non-linear proximal end 12' as shown in FIG. 158. With this angled contour, if the shorter side (left side in FIG. 158) is positioned at the inferior curved of the vessel, the proximal end 12 will fit inside the aorta to align the inflow plane 300 and the implant plane 400 as shown in FIG. 158.

A fourteenth exemplary embodiment of the proximal end apposition improvement device is illustrated in FIG. 159. The tip 632 or the nose cone assembly 630 is configured with a symmetric dilator 470 shown in FIG. 159. This dilator 470, when closed, is merely a cylinder. However, when opened as shown in the figure, the two outer bearing surfaces 472 apply pressure to opposing sides of the vessel in which the stent graft 1100 is to be implanted, thereby centering the nose cone assembly 630 and the proximal end 12 within the vessel for implantation with apposition of the inflow plane 300 and the implant plane 400.

A fifteenth exemplary embodiment of the proximal end. apposition improvement device is illustrated in FIGS. 160 and 161. In this embodiment, a plurality (e.g., four) of wires 480 are threaded through the delivery assembly 600 and are attached to, for example, four quadrants of the apex capture device 634. At the proximal end of the delivery assembly 600 is located an actuation knob or "joystick" 482. By pulling or otherwise maneuvering the knob 482, tension is applied to one or more of the wires 480 and moves the tip 632. Such maneuvering is used to center the tip 632 as desired to ensure apposition of the inflow plane 300 and the implant plane 400.

A sixteenth exemplary embodiment of the proximal end apposition improvement device is illustrated in FIGS. 162 and 163. Because blood is flowing through an aorta in which a stent graft 1100 is to be implanted, properties of the flow can be used for making perpendicular the stent graft's proximal opening with the tangent of the aortic arch to provide an optimal proximal seal. In particular, a tapered "windsock" 490 can be incorporated into the delivery assembly 600. The proximal diameter of the windsock 490 is large enough so that, upon expansion due to the incoming blood flow, the proximal opening 492 of the windsock 490 opens and presses against the aortic wall. In such a configuration, the windsock 490 channels all blood flow therethrough and discharges the flow from a distal opening 494. The distal opening 494 is made to be smaller than the proximal opening 492. The change in opening size increases the pressure in the wind sock 490. When the blood flow is channeled into a path that is concentric within the aorta, such as through an evenly spaced set of exit orifices 494, the balanced (and centered) pressure would radially center the leading portion of the stent graft 1100 during deployment.

In one exemplary configuration shown in FIG. 162, the proximal end 492 of the windsock 490 is attached with sutures to the apex capture device 632. The distal end 492 of the windsock 490 mayor may not be attached to a portion of the delivery assembly 600 distal of the proximal end 12 of the stent graft 1100 to be deployed. Compare FIGS. 162 and 163. It is noted that having no distal attachment (FIG. 163) may be more advantageous because performance of blood flow balancing may be better than with distal attachment (FIG. 162). If the distal end 494 of the windsock 490 is attached, a break-away method for the sutures can be used along with the incorporation of blood flow ports as illustrated in FIG. 162. Performance of the windsock 490 can be evaluated with varying discharge port diameters and overall tapers.

A seventeenth exemplary embodiment of the proximal end apposition improvement device is illustrated in FIGS. 164 to 169. In this embodiment, a plurality of memory shape metal (e.g.; Nitinol) hypo-tubes 500 are attached to the delivery assembly 600 and act as a mechanism to center the tip and, therefore; the stent graft 1100 during stent graft positioning and deployment. In one exemplary embodiment, two control tubes or lumens 502, 504 are placed somewhere between, around, or over the apex release lumens 620, 640. Each of the hypo-tubes 500 is secured at its distal end 506 to the inner control tube 502 at or near the tip 632. Each of the hypo-tubes 500 is further secured at its proximal end 508 to the outer control tube 504 at a distance from the tip 632. As illustrated in the comparison of FIGS. 165 and 166, forward (advancement) motion of the outer control tube makes the hypo-tubes 500 expand into a "basket" shape that contacts the walls of the aorta and centers the proximal end 12 of the stent graft 1100 within the vessel. When in this advanced position of the outer control tube 504, as shown in FIG. 164, the hypo-tubes 500 are used to create an arc during positioning and, thereby, facilitate the centering function. Backwards (retraction) motion of the outer control tube 504 decreases the profile of the hypo-tubes 500 to lie longitudinally along the length of the inner control tube 502.

To incorporate this feature into the stent grasping device that connects with each of the proximal apices 1132 of the clasping stent 1130, each hypo-tube 500 has a small "notch" 510 (slightly larger than the diameter of the wire of the clasping stent 1130. This "notch" is located at the center of the pre-formed arc of the hypo-tubes 500 (see FIGS. 166, 167). Inside the diameter of the hollow hypo-tube 500 is a rigid release wire that acts to engage the proximal apices 1132 to attach releasably the clasping stent 1130 to the delivery system. See, e.g., FIGS. 133 to 135. The releasable clasping shown in FIGS. 168 and 169 ensures a secure lock of the stent graft 1100 to the delivery assembly 600. During attachment of the stent graft 11 00 to the delivery assembly 600, the apices 1132 of the clasping stent 1130 are positioned into each notch 510 and the rigid release wire is fed over the clasping stent 1130 to capture (secure) the clasping stent 1130 and secure it to the delivery assembly 600 (see FIG. 169). Release of the stent graft 1100 from the delivery assembly 600 is obtained by withdrawing the rigid wire within the hypo-tubes 500. Expansion of the preformed nitinol hypo-tube 500 can be performed manually (slide action) or through a self-expanding configuration.

An eighteenth exemplary embodiment of the proximal end apposition improvement device is illustrated in FIGS. 170 to 172. In this embodiment, the tip 632''' has been given expandable exterior segments 6322''', in this case, three segments. The tip 632''' also contains an interior expansion mechanism, for example, a spring actuated or pusher actuated mechanism, that extends the exterior segments 6322''' from the position shown in FIGS. 170 and 171 to the position shown in FIG. 172. When the tip 632''' is so expanded, it becomes centered within the curved vessel, thereby also centering the proximal end 12 of the stent graft 1100.

The tip-centering embodiments are not limited to the distal end of the delivery assembly 600. The guidewire 610 can also be utilized. More specifically, in a nineteenth exemplary embodiment of the proximal end apposition improvement device, the guidewire 610 can be provided with an expanding "basket" 520 at the distal end thereof as shown in FIGS. 173 to 175. This basket 520 can be either self-expanding or manually expanded and opens within the aorta when the basket 520 is just upstream of the implant plane 400. The delivery assembly 600 is, then, introduced over the guidewire 610 to the deployment site. After delivery of the stent graft 1100, the guidewire 610 is withdrawn into the guidewire lumen 620 of the delivery assembly 600 and withdrawn along with the assembly 600.

A twentieth exemplary embodiment of the proximal end apposition improvement device is illustrated in FIG. 176. This embodiment provides an alternative to the bio-absorbable bare stent 30 by including a removable bare stent 30'. Utilizing such a bare stent 30' during deployment but removing it after apposition of the inflow plane 300 and the implant plane 400 is confirmed. provides the self-centering features of the original bare stent 30 but without the detrimental affects that can be caused by the long-term exposure of the bare stent 30 to the interior wall of the vessel in which the stent graft 1100 is implanted. This removable bare stent 30' can be fixed onto or be a part of the apex capture device 634. The bare stent 30' can be fixedly secured to the proximal end of the distal apex head 636, for example, and removably secured to the proximal end 12 of the stent graft 1100. Detachment of the bare stent 30' can be accomplished in a variety of ways. One exemplary embodiment can collapse the bare stent 30' with a collection ring that slides over the bare stent 30' in a proximal direction. As the ring progresses proximally along the individual turns of the bare stent 30', a radially inward force is imparted to each proximal apex 32' sufficient to release or break the contact between the apex 32' and the stent graft 1100. Another exemplary bare stent removal device reverses the orientation of a hook that connects each apex 32' to the stent graft 1100 so that the apex capture device 634 is moved distally to release the bare stent 30' from the stent graft 1100.

It is envisioned that any of the nineteen exemplary embodiments described above can be used individually or in any combination.

FIGS. 13, 14, 29 to 32, 63, 75, 77, 91, and 100 illustrate the features that allow the bare stent 30 on the proximal end 12 of the stent graft 1 to be captured and held prior to implantation of the proximal end 12 of the stent graft 1. These features provide advantages described hereinabove.

As set forth therein, a bare stent 30 improves the sealing characteristics of the stent graft end at which it is placed. Direct control of the proximal end 12 of the stent graft 1 with the apex capture device 634 allows for better placement in the vessel and improves rotational alignment of the supporting member 40 with respect to a desired implantation orientation.

While it is beneficial to have control of the proximal end 12, it has also been found that improved control over the distal end 14 has beneficial characteristics as well, namely, it shortens the seal zone length—that is, the distance between the circumferential plane at the proximal end 12 and the circumferential plane aligned with the distal apices 34 of the bare stent 30. As can be seen from FIG. 1, the seal zone of the distal end 14 is the distance between the planes aligned with each of the two opposing apices of the distal-most stent 25. Thus, it would be desirable to not only provide a bare stent 30 at the distal end 14, but to also control its rotational alignment and, thereafter, its final placement into a vessel in which the stent graft 1 is to be implanted. Accordingly, the invention provides the stent graft 1" with a distal bare stent 30", shown in FIG. 177, having a distal (seal zone 35.

When the stent graft 1" is in place both longitudinally and circumferentially (FIG. 21), the stent graft 1" is ready to be removed from the inner sheath 652 and imp hinted in the vessel 700. Because relative movement of the stent graft 1" with respect to the vessel is no longer desired, the inner sheath 652 needs to be retracted while the stent graft 1" remains in place, i.e., no longitudinal or circumferential movement. Such immovability of the stent graft 1 is insured, first, by the distal apex capture device 634 of the nose cone assembly 630 holding the proximal end 12 of the stent graft 1" by its bare stent 30 (see FIGS. 13, 22, 23, 179 and 182), second, by the proximal apex capture device 634" holding the distal end 14 of the stent graft 1" by its bare stent 30" (see FIGS. 179 and 183), and, third, by unlocking the corresponding handle assembly control to allow the sheath lumen 654 to move independently from the guidewire lumen 620, apex release lumen 640, and graft push lumen 642. The apex capture devices 634 and 634", as shown in FIGS. 178, 179, and 182-184 (and as will be described in more detail below), is holding each individual distal apex 32, 32" of the bare stents 30, 30" in a secure manner—both rotationally and longitudinally.

Because the nose cone assembly 630 and the distal apex capture device 634 and their functions were described in detail above (and are shown in FIGS. 180 and 184), the description will not be repeated here. The proximal apex capture device 634" for the distal end 14 of the stent graft 1" is somewhat similar to the distal apex capture device 634 and is shown in FIGS. 178 and 181 to 184. First, to provide control for releasing the distal end oath bare stent 30", a proximal apex release lumen 643 is slidably disposed inside the graft push lumen 642 and about the apex release lumen 640 (which can now be referred to as a distal apex release lumen 640). Next, a fixed distal capture portion 636" of the proximal apex capture device 634" is secured to the apex release lumen 640. Finally, a movable proximal capture portion 638" (of the proximal apex capture device 634" is secured to the proximal apex release lumen 643. In such a configuration, when the proximal apex capture portion 638" is translated proximally (as shown in FIG. 181, for example), the captured distal bare stent 30" is released. Thereafter, when the apex release lumen 640 is translated proximally (as shown in FIG. 180, for example, the captured proximal bare stent 30 is released.

FIG. 182 illustrates the release of the captured distal bare stent 30" and FIG. 183 illustrates the release of the captured proximal bare stent 30. FIG. 184 shows the distal and proximal apex capture devices 634, 634", respectively, after release of both bare stents 30, 30" and after withdrawal of the lumens from within the stent graft 1" (the nose cone 632 is not illustrated in FIGS. 180 and 184 to show one exemplary embodiment for connecting the nose cone 632 to the distal apex head 636 so that the nose cone 632 can be adjusted in the proximal direction, for example, to capture therein the distal end of the inner sheath 652 as shown in FIGS. 63 and 81.) In this exemplary embodiment, the stent graft 1" need not be supported at its distal end 14 by either the graft push lumen 642 (e.g., buttress 644) or the taper 653 of the inner sheath 652. It is to be understood that the described embodiment for the apex capture devices 634, 634" can be varied. For example, the parts 636" and 638" can be reversed so that the bare stent capture tines or bucket of the second proximal capture portion 638" remains still while the bare stent capture surfaces of the distal capture portion 636" moves.

The stent graft 1" is, now, ready to be finally affixed to the vessel 700, e.g., the aorta, To perform the implantation, the bare stents 30, 30" must be released from the respective apex capture devices 634, 634". To effect this release, a relative movement of the (distal) apex release lumen 640 and the guidewire lumen 620 will separate the distal apex head 636 and the distal apex body 638 from one another to release the proximal bare stent 30 and a relative movement of the proximal apex release lumen 643 and the (distal) apex release lumen 640 will separate the fixed distal part 636" and the movable proximal apex body 638" from one another to release the distal bare stent 30". The release can occur in any order or simultaneously.

To cause such relative movement, the apex release assembly 690" has, in this exemplary embodiment, five parts: a distal release part 692; a proximal release part 694"; an intermediate disk 691"; and two removable intermediate parts 696a" and 696b" (which are shown in an exemplary form of clips in FIGS. 185 and 186). To insure that the parts 636, 638 of the distal apex capture, device 634 always remain fixed with respect to one another until the distal bare stent 30 is ready to be released and further insure that the parts 636", 638" of the proximal apex capture device 634" always remain fixed with respect to one another until the proximal bare stent 30" is ready to be released, the intermediate parts 696a" and 696b" are formed to be inserted removably between (1) the distal release part 692" and the intermediate disk 691" and (2) the intermediate disk 691" and the proximal release part 694". So, for example, if the intermediate part 696a" is removed, the distal release part 692" (which is fastened to the proximal apex release lumen 643) is free to slide towards the intermediate disk 691" to, thereby, move the movable proximal capture portion 638" of the proximal apex capture device 634" and release the distal bare stent 30". Alternatively, if the intermediate part 696b" is removed, the intermediate disk 691" (which is fastened to the (distal) apex release lumen 640), is free to slide towards the proximal release part 694" to, thereby, move the proximal capture portion 638 and release the proximal bare stent 30, Likewise, if both intermediate parts 696a" and 696b" are removed together, both lumens 640 and 643 are free to slide together and, thereby, release both the proximal and distal bare stents 30, 30". Another illustration of the proximal capture device 634" is shown in FIG. 187. This is only one exemplary embodiment for allowing separate or simultaneous release of the apex capture devices 634, 634", Of course, the apex release assembly 690" can be formed with any kind of connector that moves (1) the apex release lumen 640 and the guidewire lumen 620 relative to one another and (2) the apex release lumen 640 and the proximal apex release lumen 643 relative to one another. In another exemplary alternative embodiment, for example, the intermediate parts 696a" and 696b" can be selectable levers fixedly connected to either one of the part 691" or 692 and has a length equal to the respective widths of the clips 696a" and 696b" shown in FIGS. 185 and 186. Thus, when engaged by pivoting the levers down, for example, the parts 692" and 691" cannot move with respect to one another. When either or both of the levers are disengaged by pivoting. either one or both of the parts 691" or 692", respective lumens are free to release either or both of the bare stents 30, 30".

Just like the distal apex capture device 634, the proximal apex capture device 634" allows the longitudinal forces subjected on the stent graft 1" to be fully supported, through the bare stents 30, 30", by the guidewire lumen 620, the distal apex release lumen 640, and the proximal apex release lumen 643. Support is provided by forming the capture devices with surfaces that individually support each proximal apex 32, 32" of the bare stents 30" (see, i.e., FIG. 179). When captured, each proximal apex 32, 32" separately rests on a distal surface (see, i.e., FIGS. 30 and 31). Having these distal surfaces be the load-bearing surface of the proximal apices 32, 32" ensures expansion of each and every one of the distal apices 32, 32" when the apex release assembly 690" is actuated. Complete capture of the bare stents 30,30" fully transmits any longitudinal forces acting on the bare stents 30, 30" to the guidewire lumen 620, the apex release lumen 640, and the proximal apex release lumen 643, making the assembly much stronger. Further explanation of the capture devices can be found with regard to FIGS. 30 to 33 and the corresponding description.

Simply put, the apex capture devices 634, 634" provide support for load placed on the stent graft 1 "during advancement of the inner sheath 652 and during withdrawal of the inner sheath 652. Such a configuration benefits the apposition of the bare stents 30, 30" by releasing the bare stents 30, 30" after the entire graft sleeve 10 has been deployed, thus reducing the potential for vessel perforation at the point of initial deployment.

While exemplary embodiments of the invention have been illustrated and described, it will be clear that the invention is not so limited. Numerous modifications, changes, variations, substitutions, and equivalents will occur to those skilled in the art without departing from the spirit and scope of the present invention as defined by the appended claims.

What is claimed is:

1. A delivery system for delivering and deploying a stent graft having distal and proximal stents, comprising:
 a) a guidewire catheter having a proximal end and a distal end, and defining an interior extending along a longitudinal axis;
 b) a nose cone assembly at the distal end of the guidewire catheter, the nose cone assembly including a nose cone and a distal capture portion proximal to the nose cone, the distal capture portion being movable from a distal capture position to a distal release position by proximal movement of the distal capture portion;
 c) a proximal capture portion along the longitudinal axis and proximal to the distal capture portion of the nose cone assembly; and
 d) a stent graft including, i) a graft component having a proximal end and a distal end,
ii) a proximal stent having proximal apices at the proximal end of the graft component, and
iii) a distal stent having distal apices at the distal end of the graft component,
wherein the proximal stent is secured to the distal capture portion and releasable by proximal movement relative to the stent graft of the distal capture portion from the distal capture position to the distal release position, and wherein the distal stent is releasably secured to the proximal capture portion.

2. The delivery system of claim 1, wherein the guidewire catheter is curved.

3. The delivery system of claim 1, wherein the proximal capture portion and the distal capture portion actuate independently.

4. The delivery system of claim 1, wherein the distal stent is releasable from the proximal capture portion by proximal movement relative to the stent graft of the proximal capture portion from a proximal capture position to a proximal release position.

5. The delivery system of claim 1, wherein the proximal apices of the proximal stent extend proximally beyond the proximal end of the graft component, and the distal apices of the distal stent extend distally beyond the distal end of the graft component.

6. The delivery system of claim 5, further including an outer catheter that extends about the guidewire catheter and the stent graft, wherein the outer catheter is retractable from the stent graft.

7. The delivery system of claim 6, further including a sheath that is flexible relative to the outer catheter and that extends about the stent graft and the guidewire catheter, wherein the sheath is retractable from the stent graft.

8. The delivery system of claim 7, wherein the sheath extends between the stent graft and the outer catheter.

9. The delivery system of claim 8, wherein the proximal end of the stent graft is releasably secured to the distal apex capture portion at the proximal apices of the proximal stent, and the distal end of the stent graft is releasably secured to the proximal capture portion at the distal apices of the distal stent.

10. A delivery system for delivering and deploying a stent graft having distal and proximal stents, comprising:
    a) a curved guidewire catheter having a proximal end and a distal end, and defining an interior extending along a longitudinal axis;
    b) a nose cone assembly at the distal end of the guidewire catheter, the nose cone assembly including a nose cone and a distal capture portion proximal to the nose cone, the distal capture portion being movable from a distal capture position to a distal release position by proximal movement of the distal capture portion;
    c) a proximal capture portion along the longitudinal axis and proximal to the distal capture portion of the nose cone assembly, the proximal capture portion being movable from a proximal capture position to a proximal release position, and wherein the proximal capture portion and the distal capture portion arcuate actuate independently; and
    d) a stent graft including,
        i) a graft component having a proximal end and a distal end,
        ii) a proximal stent having proximal apices at the proximal end of the graft component, and
        iii) a distal stent having distal apices at the distal end of the graft component,
    wherein the proximal stent is releasably secured to the distal capture portion and releasable by proximal movement relative to the stent graft of the distal capture portion from the distal capture position to the distal release position, and wherein the distal stent is releasably secured to the proximal capture portion and is releasable from the proximal capture portion by proximal movement of the proximal capture portion from the proximal capture position to the proximal release position.

11. The delivery system of claim 10, wherein the proximal apices of the proximal stent extend proximally beyond the proximal end of the graft component, and the distal apices of the distal stent extend distally beyond the distal end of the graft component.

12. The delivery system of claim 11, further including an outer catheter that extends about the guidewire catheter and the stent graft, wherein the outer catheter is retractable from the stent graft.

13. The delivery system of claim 12, further including a sheath that is flexible relative to the outer catheter and that extends about the stent graft and the guidewire catheter, wherein the sheath is retractable from the stent graft.

14. The delivery system of claim 13, wherein the sheath extends between the stent graft and the outer catheter.

15. The delivery system of claim 14, wherein the proximal end of the stent graft is releasably secured to the distal apex capture portion at the proximal apices of the proximal stent, and the distal end of the stent graft is releasably secured to the proximal capture portion at the distal apices of the distal stent.

* * * * *

UNITED STATES PATENT AND TRADEMARK OFFICE
CERTIFICATE OF CORRECTION

PATENT NO. : 10,105,250 B2
APPLICATION NO. : 14/924102
DATED : October 23, 2018
INVENTOR(S) : Humberto Berra Page 1 of 1

It is certified that error appears in the above-identified patent and that said Letters Patent is hereby corrected as shown below:

In the Claims

Claim 10, Column 62, Line 10, delete the word "arcuate" before the word "actuate".

Signed and Sealed this
Second Day of April, 2019

Andrei Iancu
*Director of the United States Patent and Trademark Office*